US012215382B2

(12) United States Patent
Kathiresan et al.

(10) Patent No.: US 12,215,382 B2
(45) Date of Patent: Feb. 4, 2025

(54) LIVER PROTECTIVE MARC VARIANTS AND USES THEREOF

(71) Applicant: THE GENERAL HOSPITAL CORPORATION, Boston, MA (US)

(72) Inventors: Sekar Kathiresan, Boston, MA (US); Connor Emdin, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 480 days.

(21) Appl. No.: 16/807,125

(22) Filed: Mar. 2, 2020

(65) Prior Publication Data

US 2021/0262022 A1    Aug. 26, 2021

Related U.S. Application Data

(60) Provisional application No. 62/812,881, filed on Mar. 1, 2019.

(51) Int. Cl.
| | |
|---|---|
| *C12N 15/11* | (2006.01) |
| *A61K 31/7088* | (2006.01) |
| *A61K 31/713* | (2006.01) |
| *A61K 45/06* | (2006.01) |
| *C12Q 1/6858* | (2018.01) |

(52) U.S. Cl.
CPC ........ *C12Q 1/6858* (2013.01); *A61K 31/7088* (2013.01); *A61K 31/713* (2013.01); *A61K 45/06* (2013.01); *C12Q 2600/158* (2013.01)

(58) Field of Classification Search
CPC ............ C12Q 2600/158; C12Q 1/6883; C12Q 2600/112
See application file for complete search history.

(56) References Cited

U.S. PATENT DOCUMENTS

| | | | |
|---|---|---|---|
| 4,797,368 A | 1/1989 | Carter et al. | |
| 4,873,316 A | 10/1989 | Meade et al. | |
| 5,173,414 A | 12/1992 | Lebkowski et al. | |
| 5,543,158 A | 8/1996 | Gref et al. | |
| 5,563,055 A | 10/1996 | Townsend et al. | |
| 5,789,156 A | 8/1998 | Bujard et al. | |
| 5,814,618 A | 9/1998 | Bujard et al. | |
| 5,846,946 A | 12/1998 | Huebner et al. | |
| 5,855,913 A | 1/1999 | Hanes et al. | |
| 5,985,309 A | 11/1999 | Edwards et al. | |
| 6,007,845 A | 12/1999 | Domb et al. | |
| 6,268,490 B1 | 7/2001 | Imanishi et al. | |
| 6,479,626 B1 | 11/2002 | Kim et al. | |
| 6,525,191 B1 | 2/2003 | Ramasamy et al. | |
| 6,534,261 B1 | 3/2003 | Cox et al. | |
| 6,602,858 B2 | 8/2003 | Beigelman et al. | |
| 6,607,882 B1 | 8/2003 | Cox et al. | |
| 6,670,461 B1 | 12/2003 | Wengel et al. | |
| 6,746,838 B1 | 6/2004 | Choo et al. | |
| 6,750,059 B1 | 6/2004 | Blakesley et al. | |
| 6,794,136 B1 | 9/2004 | Eisenberg et al. | |
| 6,794,499 B2 | 9/2004 | Wengel et al. | |
| 6,824,978 B1 | 11/2004 | Cox et al. | |
| 6,866,997 B1 | 3/2005 | Choo et al. | |
| 6,903,185 B2 | 6/2005 | Kim et al. | |
| 6,933,113 B2 | 8/2005 | Case et al. | |
| 6,979,539 B2 | 12/2005 | Cox et al. | |
| 6,998,484 B2 | 2/2006 | Koch et al. | |
| 7,013,219 B2 | 3/2006 | Case et al. | |
| 7,030,215 B2 | 4/2006 | Liu et al. | |
| 7,034,133 B2 | 4/2006 | Wengel et al. | |
| 7,053,207 B2 | 5/2006 | Wengel et al. | |
| 7,084,125 B2 | 8/2006 | Wengel et al. | |
| 7,220,719 B2 | 5/2007 | Case et al. | |
| 7,241,573 B2 | 7/2007 | Choo et al. | |
| 7,241,574 B2 | 7/2007 | Choo et al. | |
| 7,259,015 B2 | 8/2007 | Kingsman et al. | |
| 7,303,910 B2 | 12/2007 | Bebbington et al. | |
| 7,351,585 B2 | 4/2008 | Mitrophanous et al. | |
| 7,399,845 B2 | 7/2008 | Seth et al. | |
| 7,427,672 B2 | 9/2008 | Imanishi et al. | |
| 7,569,686 B1 | 8/2009 | Bhat et al. | |
| 7,585,849 B2 | 9/2009 | Liu et al. | |
| 7,595,376 B2 | 9/2009 | Kim et al. | |
| 7,741,457 B2 | 6/2010 | Seth et al. | |
| 7,776,321 B2 | 8/2010 | Cascalho et al. | |
| 8,021,867 B2 | 9/2011 | Smith et al. | |
| 8,022,193 B2 | 9/2011 | Seth et al. | |

(Continued)

FOREIGN PATENT DOCUMENTS

| | | |
|---|---|---|
| EP | 0264166 A1 | 4/1988 |
| WO | 9301294 A1 | 1/1993 |

(Continued)

OTHER PUBLICATIONS

Emdin et al., A missense variant in mitochondrial amidoxime reducing component 1 gene and protection against liver disease, PLoS Genetics, vol. 16(4):e1008629, pp. 1-16. (Year: 2020).*

Janik et al., MARC1 p.A165T variant is associated with decreased markers of liver injury and enhanced antioxidant capacity in autoimmune hepatitis, Scientific Reports, vol. 11:24407, pp. 1-10. (Year: 2021).*

Sato et al., Suppressive effect of the histone deacetylase inhibitor subreroylanilide hydroxamic acid (SAHA) on hepatitis C virus replication, Journal of Cellular Biochemistry, vol. 114, pp. 1987-1996. (Year: 2013).*

Eslam et al., Genetics and epigenetics of NAFLD and NASH: Clinical impact, Journal of Hepatology, vol. 68, pp. 268-279. (Year: 2018).*

(Continued)

*Primary Examiner* — Dana H Shin
(74) *Attorney, Agent, or Firm* — Withers Bergman LLP; Christopher R. Cowles

(57) ABSTRACT

Described herein are MARC variants that associate with a risk of liver diseases or a symptom(s) thereof, such as cirrhosis, or protection against such liver diseases or symptom(s) thereof. Also described herein are compositions and formulations that can be capable of modulating MARC in a subject and/or treatment of a liver disease or a symptom thereof.

12 Claims, 8 Drawing Sheets

Specification includes a Sequence Listing.

(56) References Cited

U.S. PATENT DOCUMENTS

| | | | |
|---|---|---|---|
| 8,030,467 | B2 | 10/2011 | Seth et al. |
| 8,044,019 | B2 | 10/2011 | Uno et al. |
| 8,071,082 | B2 | 12/2011 | Zugates et al. |
| 8,097,710 | B2 | 1/2012 | Baulcombe et al. |
| 8,101,348 | B2 | 1/2012 | Tuschl et al. |
| 8,119,361 | B2 | 2/2012 | Smith et al. |
| 8,119,381 | B2 | 2/2012 | Smith et al. |
| 8,124,369 | B2 | 2/2012 | Smith et al. |
| 8,129,134 | B2 | 3/2012 | Smith et al. |
| 8,133,697 | B2 | 3/2012 | Smith et al. |
| 8,163,514 | B2 | 4/2012 | Smith et al. |
| 8,278,283 | B2 | 10/2012 | Seth et al. |
| 8,278,425 | B2 | 10/2012 | Prakash et al. |
| 8,278,426 | B2 | 10/2012 | Seth et al. |
| 8,314,227 | B2 | 11/2012 | Wengel et al. |
| 8,372,951 | B2 | 2/2013 | Chang et al. |
| 8,404,658 | B2 | 3/2013 | Hajjar et al. |
| 8,454,972 | B2 | 6/2013 | Nabel et al. |
| 8,575,305 | B2 | 11/2013 | Gait et al. |
| 8,614,194 | B1 | 12/2013 | Chen et al. |
| 8,709,843 | B2 | 4/2014 | Shakuda et al. |
| 8,945,839 | B2 | 2/2015 | Zhang et al. |
| 9,301,923 | B2 | 4/2016 | Baryza et al. |
| 10,076,536 | B2 | 9/2018 | Kole et al. |
| 10,835,581 | B2 | 11/2020 | Gladwin |
| 2002/0150626 | A1 | 10/2002 | Kohane et al. |
| 2004/0013648 | A1 | 1/2004 | Kingsman et al. |
| 2004/0142476 | A1 | 7/2004 | Evans et al. |
| 2004/0171156 | A1 | 9/2004 | Hartley et al. |
| 2004/0171570 | A1 | 9/2004 | Allerson et al. |
| 2005/0019923 | A1 | 1/2005 | Uchegbu et al. |
| 2005/0123596 | A1 | 6/2005 | Kohane et al. |
| 2005/0244858 | A1 | 11/2005 | Rossi et al. |
| 2006/0281180 | A1 | 12/2006 | Radcliffe et al. |
| 2007/0025970 | A1 | 2/2007 | Kingsman et al. |
| 2007/0054961 | A1 | 3/2007 | Maden et al. |
| 2008/0039618 | A1 | 2/2008 | Allerson et al. |
| 2008/0267903 | A1 | 10/2008 | Uchegbu et al. |
| 2009/0007284 | A1 | 1/2009 | Radcliffe et al. |
| 2009/0012281 | A1 | 1/2009 | Swayze et al. |
| 2009/0017543 | A1 | 1/2009 | Wilkes et al. |
| 2009/0111106 | A1 | 4/2009 | Mitrophanous et al. |
| 2010/0129793 | A1 | 5/2010 | Mirkin et al. |
| 2010/0317109 | A1 | 12/2010 | Maden et al. |
| 2011/0027239 | A1 | 2/2011 | Paek et al. |
| 2011/0117189 | A1 | 5/2011 | Mazzone et al. |
| 2011/0201643 | A1* | 8/2011 | Maier ............... A61P 37/06 514/307 |
| 2011/0212179 | A1 | 9/2011 | Liu et al. |
| 2011/0293571 | A1 | 12/2011 | Widdowson et al. |
| 2011/0293703 | A1 | 12/2011 | Mahon et al. |
| 2011/0313020 | A1 | 12/2011 | Templin et al. |
| 2012/0157511 | A1 | 6/2012 | Manoharan et al. |
| 2012/0295960 | A1 | 11/2012 | Palfi et al. |
| 2013/0011922 | A1 | 1/2013 | Quay et al. |
| 2013/0096289 | A1 | 4/2013 | Wengel et al. |
| 2013/0185823 | A1 | 7/2013 | Kuang et al. |
| 2013/0190383 | A1 | 7/2013 | Vaish et al. |
| 2013/0244279 | A1 | 9/2013 | De Fougerolles et al. |
| 2013/0245107 | A1 | 9/2013 | De Fougerolles et al. |
| 2013/0252281 | A1 | 9/2013 | De Fougerolles et al. |
| 2013/0302401 | A1 | 11/2013 | Ma et al. |
| 2014/0287983 | A1 | 9/2014 | Mourich et al. |
| 2014/0308304 | A1 | 10/2014 | Manoharan et al. |
| 2014/0328759 | A1 | 11/2014 | Cullis et al. |
| 2014/0348900 | A1 | 11/2014 | Zhu et al. |
| 2015/0023288 | A1 | 1/2015 | Vermani et al. |
| 2015/0071903 | A1 | 3/2015 | Liu et al. |
| 2015/0105538 | A1 | 4/2015 | Chromy et al. |
| 2015/0118216 | A1 | 4/2015 | Liu et al. |
| 2015/0140070 | A1 | 5/2015 | Heartlein et al. |
| 2015/0232883 | A1 | 8/2015 | Dahlman et al. |
| 2015/0250725 | A1 | 9/2015 | Bader et al. |
| 2015/0267202 | A1 | 9/2015 | Iversen et al. |
| 2015/0291966 | A1 | 10/2015 | Zhang et al. |
| 2016/0082126 | A1 | 3/2016 | Wang et al. |
| 2016/0174546 | A1 | 6/2016 | Berg et al. |
| 2016/0200779 | A1 | 7/2016 | Liu et al. |
| 2016/0251398 | A1 | 9/2016 | Weller et al. |
| 2016/0367686 | A1 | 12/2016 | Anderson et al. |
| 2017/0051278 | A1 | 2/2017 | Kole et al. |
| 2017/0079916 | A1 | 3/2017 | Khan et al. |
| 2017/0166903 | A1 | 6/2017 | Zhang et al. |
| 2018/0216111 | A1 | 8/2018 | Wilton et al. |
| 2018/0271893 | A1 | 9/2018 | Kole et al. |
| 2019/0015440 | A1 | 1/2019 | Passini et al. |
| 2019/0177723 | A1 | 6/2019 | Dickson et al. |
| 2019/0203212 | A1 | 7/2019 | Zhang et al. |
| 2019/0352652 | A1 | 11/2019 | Abudayyeh et al. |
| 2020/0241005 | A1* | 7/2020 | Miner ............... G01N 33/6893 |
| 2022/0062385 | A1* | 3/2022 | Gladwin ............ A61K 38/28 |

FOREIGN PATENT DOCUMENTS

| | | |
|---|---|---|
| WO | 9324641 A2 | 12/1993 |
| WO | 9405700 A3 | 8/1994 |
| WO | 9839352 A1 | 9/1998 |
| WO | 1999007409 A1 | 2/1999 |
| WO | 1999032619 A1 | 7/1999 |
| WO | 9914226 A3 | 8/1999 |
| WO | 2000001846 A2 | 1/2000 |
| WO | 0047599 A1 | 8/2000 |
| WO | 2000044895 A1 | 8/2000 |
| WO | 2000044914 A1 | 8/2000 |
| WO | 2001029058 A1 | 4/2001 |
| WO | 2001036646 A1 | 5/2001 |
| WO | 2001075164 A2 | 10/2001 |
| WO | 2004083430 A3 | 11/2004 |
| WO | 2005105152 A2 | 11/2005 |
| WO | 2006069782 A2 | 7/2006 |
| WO | 2006047842 A3 | 9/2006 |
| WO | 2007121947 A1 | 11/2007 |
| WO | 2008042156 A1 | 4/2008 |
| WO | 2008042973 A2 | 4/2008 |
| WO | 2008049078 B1 | 6/2008 |
| WO | 2010061186 A2 | 6/2010 |
| WO | 2011005861 A9 | 8/2011 |
| WO | 2011028929 A3 | 10/2011 |
| WO | 2012135025 A2 | 10/2012 |
| WO | 2013036868 A1 | 3/2013 |
| WO | 2013046247 A1 | 4/2013 |
| WO | 2013093648 A2 | 6/2013 |
| WO | 2014018423 A2 | 1/2014 |
| WO | 2014093622 A2 | 6/2014 |
| WO | 2014118272 A1 | 8/2014 |
| WO | 2014186366 A1 | 11/2014 |
| WO | 2015082080 A1 | 6/2015 |
| WO | 2015086795 A1 | 6/2015 |
| WO | 2015089419 A2 | 6/2015 |
| WO | 2016025131 A1 | 2/2016 |
| WO | 2016027264 A1 | 2/2016 |
| WO | 2016073433 A1 | 5/2016 |
| WO | 2016099887 A1 | 6/2016 |
| WO | 2016100272 A1 | 6/2016 |
| WO | 2016100562 A1 | 6/2016 |
| WO | 2016100568 A1 | 6/2016 |
| WO | 2016100571 A1 | 6/2016 |
| WO | 2016106236 A1 | 6/2016 |
| WO | 2016161516 A1 | 10/2016 |
| WO | 2017019867 A1 | 2/2017 |
| WO | 2017066175 A1 | 4/2017 |
| WO | 2017062835 A3 | 6/2017 |
| WO | 2017100158 A1 | 6/2017 |
| WO | 2017105991 A1 | 6/2017 |
| WO | 2017106414 A1 | 6/2017 |
| WO | 2018000580 A1 | 1/2018 |
| WO | 2018213708 A1 | 11/2018 |
| WO | 2018213726 A1 | 11/2018 |
| WO | 2019005884 A1 | 1/2019 |
| WO | 2019005886 A1 | 1/2019 |
| WO | 2019018423 A1 | 1/2019 |
| WO | 2019059973 A1 | 3/2019 |
| WO | 2019071048 A1 | 4/2019 |
| WO | 2019126709 A1 | 6/2019 |

(56) References Cited

FOREIGN PATENT DOCUMENTS

| | | |
|---|---|---|
| WO | 2019126716 A1 | 6/2019 |
| WO | 2019126762 A2 | 6/2019 |
| WO | 2020033601 A1 | 2/2020 |
| WO | 2020131862 A1 | 6/2020 |

OTHER PUBLICATIONS

Namjou et al., GWAS and enrichment analyses of non-alcoholic fatty liver disease identify new trait-associated genes and pathways across eMERGE network, BMC Medicine, vol. 17:135, pp. 1-19. (Year: 2019).*

Willer et al. (of Global Lipids Genetics Consortium), published in 2013, Discovery and refinement of loci associated with lipid levels, Nature Genetics 45(11):1274-1283, and supplementary information available at https://static-content.springer.com/esm/art%3A10.1038%2Fng.2797/MediaObjects/41588_2013_BFng2797_MOESM43_ESM.pdf.

Teslovich et al., published in 2010, Biological, Clinical, and Population Relevance of 95 Loci for Blood Lipids, Nature 466 (7307):707-713.

Abul-Husn et al., published in 2018, A Protein-Truncating HSD17B13 Variant and Protection from Chronic Liver Disease, The New England Journal of Medicine 378(12):1096-1106, and supplementary material available at https://www.nejm.org/doi/suppl/10.1056/NEJMoa1712191/suppl_file/nejmoa1712191_appendix.pdf.

Emdin et al., published in 2019, A missense variant in Mitochondrial Amidoxime Reducing 4 Component 1 gene and protection against liver disease, available at bioRxiv preprint doi: https//doi.org/10.1101/594523.

Wilkins et al., published in 2013, Nonalcoholic Fatty Liver Disease: Diagnosis and Management, 5 Am. Fam. Physician 88(1):35-42.

Martin et al., published in 2007, Genetic association meets RNA interference: large-scale genomic screens for causation and mechanism of complex diseases, Pharmacogenomics 8(5):455-464.

"Coding Variation in ANGPTL4, LPL, and SVEP1 and the Risk of Coronary Disease", Myocardial Infarction Genetics and CARDIoGRAM Exome Consortia Investigators, The New England Journal of Medicine, vol. 374, No. 12, Mar. 2016, 1134-1144.

Abe, et al., "The Development of CRISPR for a Mollusc Establishes the Formin Lsdia1 as the Long-Sought Gene for Snail Dextral/sinistral Coiling", Development, vol. 147, 2020, 8 pages.

About, et al., "HCV-Associated Liver Fibrosis and HSD17B13", The New England Journal of Medicine, vol. 379, No. 19, Nov. 8, 2018, 1875-1876.

Abul-Husn, et al., "A Protein-Truncating HSD17B13 Variant and Protection from Chronic Liver Disease", The New England Journal of Medicine, vol. 387, No. 12, Mar. 22, 2018, 1096-1106.

Alba, et al., "Gutless Adenovirus: Last-Generation Adenovirus for Gene Therapy", Gene Therapy, vol. 12, 2005, S18-S27.

Alhasan, "Exosome Encased Spherical Nucleic Acid Gold Nanoparticle Conjugates As Potent MicroRNA Regulation Agents", Small, vol. 10, Issue 1, Jan. 15, 2014, 14 pages.

Allart, et al., "1,5-Anhydro-2-Deoxy-D-Altritol Oligonucleotides as Conformationally Restricted Analogues of Rna", Nucleosides and Nucleotides, vol. 17, Issue 9-11, 1998, 1523-1526.

Allshire, "RNAi and Heterochromatin—a Hushed-Up Affair", Science, vol. 297, Issue 5588, 2002, 1818-1819.

Altinoglu, et al., "Intracellular Delivery of the Pten Protein Using Cationic Lipidoids for Cancer Therapy", Biomaterials Science, vol. 4, No. 12, 2016, 1773-1780.

Amalfitano, "Production and Characterization of Improved Adenovirus Vectors with the E1, E2b, and E3 Genes Deleted", Journal of Virology, vol. 72, No. 2, 1998, 926-933.

Amann, et al., "Tightly Regulated Tuc Promoter Vectors Useful For the Expression of Unfused and Fused Proteins in *Escherichia coli*", Gene, vol. 69, 1988, 301-315.

Anton, et al., "Visualization of Specific DNA Sequences in Living Mouse Embryonic Stem Cells With a Programmable Fluorescent CRISPR/Cas System", Nucleus, vol. 5, No. 2, Mar./Apr. 2014, 163-172.

Anzalone, et al., "Search-and-replace Genome Editing Without Double-Strand Breaks or Donor DNA", Nature, vol. 576, No. 7785, Dec. 5, 2019, 30 pages.

Atschul, et al., "Basic Local Alignment Search Tool", Journal of Molecular Biology, vol. 215, 1990, 403-410.

Azzouz, et al., "Multicistronic Lentiviral Vector-Mediated Striatal Gene Transfer of Aromatic L-Amino Acid Decarboxylase, Tyrosine Hydroxylase, and GTP Cyclohydrolase I Induces Sustained Transgene Expression, Dopamine Production, and Functional Improvement in a Rat Model o", The Journal of Neuroscience, vol. 22, No. 3, Dec. 1, 2002, 10302-10312.

Back, et al., "Neuron-Specific Genome Modification in the Adult Rat Brain Using CRISPR-Cas9 Transgenic Rats", Neuron, vol. 102, Apr. 3, 2019, 105-119.

Bacon, et al., "Diagnosis and Management of Hemochromatosis: 2011 Practice Guideline by the American Association for the Study of Liver Disease", Hepatology, vol. 54, No. 1, 2011, 328-343.

Bahramian, et al., "Transcriptional and Posttranscriptional Silencing of Rodent α1(I) Collagen by a Homologous Transcriptionally Self-Silenced Transgene", Molecular and Cellular Biology, vol. 19, No. 1, 1999, 274-283.

Balagaan, et al., "Stable and Efficient Intraocular Gene Transfer Using Pseudotyped EIAV Lentiviral Vectors", The Journal of Gene Medicine, vol. 8, Issue 3, Mar. 2006, 275-285.

Balaggan, et al., "Ocular Gene Delivery Using Lentiviral Vectors", Gene Therapy, vol. 19, 2012, 145-153.

Balague, et al., "Sustained High-Level Expression of Full-Length Human Factor VIII and Restoration of Clotting Activity in Hemophilic Mice Using a Minimal Adenovirus Vector", Blood, vol. 95, No. 3, 2000, 820-828.

Baldari, et al., "A Novel Leader Peptide Which Allows Efficient Secretion of a Fragment of Human Interleukin 1β In *Saccharomyces cerevisiae*", The EMBO Journal, vol. 6, No. 1, 1987, 229-234.

Banerji, et al., "A Lymphocyte-Specific Cellular Enhancer is Located Downstream of the Joining Region in Immunoglobulin Heavy Chain Genes", Cell, vol. 33, Issue 3, Jul. 1983, 729-740.

Bartlett, et al., "Impact of Tumor-Specific Targeting on The Biodistribution and Efficacy of Sirna Nanoparticles Measured by Multimodality In Vivo Imaging", Proceedings of the National Academy of Sciences, vol. 104, No. 39, Sep. 25, 2007, 15549-15554.

Bass, "Double-stranded RNA as a Template for Gene Silencing", Cell, vol. 101, No. 3, 2000, 235-238.

Bawage, et al., "Synthetic mRNA Expressed Cas13a Mitigates RNA Virus Infections", bioRxiv preprint doi: https://doi.org/10.1101/370460, Jul. 23, 2018, 9 pages.

Belhaj, et al., "Plant Genome Editing Made Easy: Targeted Mutagenesis in Model and Crop Plants Using the CRISPR/Cas System", Plant Methods, vol. 9, No. 1, Oct. 11, 2013, 1-10.

Bender, et al., "Receptor-Targeted Nipah Virus Glycoproteins Improve Cell-Type Selective Gene Delivery and Reveal a Preference for Membrane-Proximal Cell Attachment", PLoS Pathogens, vol. 12, No. 6, e1005641, 2016, 28 pages.

Bennetzen, et al., "Codon Selection in Yeast", Journal of Biological Chemistry, vol. 257, No. 6, Mar. 1982, 3026-3031.

Bernstein, et al., "Role for a Bidentate Ribonuclease in the Initiation Step of RNA Interference", Nature, vol. 409, No. 6818, 2001, 363-366.

Betchen, et al., "Future and Current Surgical Therapies in Parkinson's Disease", Current Opinion in Neurology, vol. 16, No. 4, 2003, 487-493.

Binley, et al., "Safety and Biodistribution of an Equine Infectious Anemai Virus-Based Gene Therapy, RetinoStat, for Age-Related Macular Degeneration", Human Gene Therapy, vol. 23, Sep. 2012, 980-991.

Biswas, et al., "CRISPRTarget Bioinformatic Prediction and Analysis of CrRNA Targets", RNA Biology, vol. 10, No. 5, May 2013, 817-827.

Boch, et al., "Breaking the Code of DNA Binding Specificity of TAL-type III Effectors", Science, vol. 326, No. 5959, Dec. 11, 2009, 1509-1512.

Boshart, et al., "A Very Strong Enhancer Is Located Upstream of an Immediate Early Gene of Human Cytomegalovirus", Cell, vol. 41, No. 2, Jun. 1985, 521-530.

(56) References Cited

OTHER PUBLICATIONS

Buch, et al., "A Genome-Wide Association Study Confirms PNPLA3 and Identifies TM6SF2 and MBOAT7 as Risk Loci for Alcohol-Related Cirrhosis", Nature Genetics, vol. 47, No. 12, 2015, 1443-1448.
Buchholz, et al., "Surface-Engineered Viral Vectors for Selective and Cell Type-Specific Gene Delivery", Trends in Biotechnology, vol. 33, No. 12, 2015, 777-790.
Buchschacher, et al., "Human Immunodeficiency Virus Vectors for Inducible Expression of Foreign Genes", Journal of Virology, vol. 66, No. 5, 1992, 2731-2739.
Buckholz, et al., "Yeast Systems for the Commercial Production of Heterologous Proteins", Bio/Technology, vol. 9, Nov. 1991, 1067-1072.
Byrne, et al., "Multiplex Gene Regulation: A Two-Tiered Approach to Transgene Regulation in Transgenic Mice", Proceedings of the National Academy of Sciences, vol. 86, Jul. 1989, 5473-5477.
Calame, et al., "Transcriptional Controlling Elements in the Immunoglobulin and T Cell Receptor Loci", Advances in Immunology, vol. 43, Feb. 1988, 235-275.
Campbell, "Codon Usage in Higher Plants, Green Algae, and Cyanobacteria", Plant Physiology, vol. 92, No. 1, Jan. 1990, 1-11.
Camper, et al., "Postnatal Repression of the Alpha-Fetoprotein Gene is Enhancer Independent", Genes and Development, vol. 3, 1989, 537-546.
Capone, et al., "Expression in Different Populations of Cells of the Root Meristem is Controlled by Different Domains of the rolB Promoter", Plant Molecular Biology, vol. 25, 1994, 681-691.
Carr, et al., "Genome Engineering", Nature Biotechnology, vol. 27, No. 12, Dec. 9, 2009, 1151-1162.
Casas, et al., "Transgenic Sorghum Plants via Microprojectile Bombardment", Proceedings of the National Academy of Sciences, vol. 90, Dec. 1993, 11212-11216.
Chambers, et al., "Genome-wide Association Study Identifies Loci Influencing Concentrations of Liver Enzymes in Plasma", Nature Genetics, vol. 43, No. 11, 2011, 1131-1138.
Chamoun-Emaneulli, et al., "In Vitro Incorporation of a Cell-Binding Protein to a Lentiviral Vector Using an Engineered Split Intein Enables Targeted Delivery of Genetic Cargo", Biotechnology and Bioengineering, vol. 112, No. 12, Dec. 2015, 2611-2617.
Chang, et al., "Second-generation PLINK: Rising to the Challenge of Larger and Richer Datasets", GigaScience, vol. 4, Article No. 7, 2015, 16 pages.
Chen, et al., "Dynamic Imaging of Genomic Loci in Living Human Cells by an Optimized CRISPR/Cas System", Cell, vol. 155, Issue 7, Dec. 19, 2013, 1479-1491.
Cho, et al., "Lipid-like Nanoparticles for Small Interfering RNA Delivery to Endothelial Cells", Advanced Functional Materials, vol. 19, Issue 19, Oct. 9, 2009, 15 pages.
Choi, et al., "Mechanism for the Endocytosis of Spherical Nucleic Acid Nanoparticle Conjugates", Proceedings of the National Academy of Sciences, vol. 110, No. 19, 2013, 6 pages.
Chu, et al., "Efficient Generation of Rosa26 Knock-in Mice using Crispr/cas9 in C57bl/6 Zygotes", BMC Biotechnology, vol. 16, No. 4, Jan. 16, 2016, 15 pages.
Cideciyan, et al., "Vision 1 Year after Gene Therapy for Leber's Congenital Amaurosis", The New England Journal of Medicine, vol. 361, 2009, 725-727.
Cockrell, et al., "Gene Delivery by Lentivirus Vectors", Molecular Biotechnology, vol. 36, 2007, 184-204.
Cooney, et al., "Hybrid Nonviral/Viral Vector Systems for Improved piggyBac DNA Transposon In Vivo Delivery", Molecular Therapy, vol. 23, No. 4, 2015, 667-674.
Cox, et al., "RNA Editing with CRISPR-Cas13", Science, vol. 358, No. 6366, Nov. 24, 2017, 23 pages.
Crane, et al., "Rescue Administration of a Helper-Dependent Adenovirus Vector with Long-Term Efficacy in Dogs with Glycogen Storage Disease Type Ia", Gene Therapy, vol. 9, 2012, 443-452.
Cronican, et al., "A Class of Human Proteins That Deliver Functional Proteins Into Mammalian Cells In Vitro and In Vivo", Chemistry & Biology, vol. 18, Issue 7, Jul. 29, 2011, 10 pages.
Cronican, et al., "Potent Delivery of Functional Proteins into Mammalian Cells in Vitro and in Vivo Using a Supercharged Protein", ACS Chemical Biology, vol. 5, No. 8, 2010, 747-752.
Croyle, et al., "PEGylated Helper-Dependent Adenoviral Vectors: Highly Efficient Vectors with an Enhanced Safety Profile", Gene Therapy, vol. 12, 2005, 579-587.
Cutler, et al., "Polyvalent Nucleic Acid Nanostructures", Journal of the American Chemical Society, vol. 133, Issue 24, Jun. 22, 2011, 10 pages.
Cutler, et al., "Spherical Nucleic Acids", Journal of the American Chemical Society, vol. 134, Issue 3, 2012, 1376-1391.
Dahlman, et al., "In Vivo Endothelial Sirna Delivery Using Polymeric Nanoparticles with Low Molecular Weight", Nature Nanotechnology, vol. 9, No. 8, Aug. 2014, 17 pages.
Datsomor, et al., "CRISPR/Cas9-Mediated Ablation of Elovl2 in Atlantic Salmon (*Salmo salar* L.) Inhibits Elongation of Polyunsaturated Fatty Acids and Induces Srebp-1 and Target Genes", Scientific Reports, vol. 9, Article No. 7533, 2019, 13 pages.
Davey, et al., "Direct DNA Transfer to Plant Cells", Plant Molecular Biology, vol. 13, 1989, 273-285.
Davis, et al., "Evidence of RNAi in Humans From Systemically Administered siRNA via Targeted Nanoparticles", Nature, vol. 464, No. 7291, Apr. 15, 2010, 1067-1070.
De Veylder, et al., "Herbicide Safener-Inducible Gene Expression in *Arabidopsis thaliana*", Plant and Cell Physiology, vol. 38, No. 5, May 1977, 568-577.
Denny, et al., "PheWAS: Demonstrating the Feasibility of a Phenome-Wide Scan to Discover Gene-Disease Associations", Bioinformatics, vol. 26, No. 9, 2010, 1205-1210.
Deshpande, et al., "Current Trends in the Use of Liposomes for Tumor Targeting", Nanomedicine (Lond), vol. 8, No. 9, Sep. 2013, 32 pages.
Digiusto, et al., "RNA-Based Gene Therapy for HIV with Lentiviral Vector-Modified CD34(+) Cells in Patients Undergoing Transplantation for AIDSrelated Lymphoma", Science Translational Medicine, vol. 2, Issue 36, Jun. 16, 2010, 8 pages.
Do, et al., "Exome Sequencing Identifies Rare LDLR and APOA5 Alleles Conferring Risk for Myocardial Infarction", Nature, vol. 518, No. 7537, 2015, 102-106.
Doyon, et al., "Enhancing Zinc-Finger-Nuclease Activity With Improved Obligate Heterodimeric Architectures", Nature Methods, vol. 8, No. 1, Jan. 2011, 74-79.
Duan, "CRISPR Alleviates Muscular Dystrophy in Dogs", Nature Biomedical Engineering, vol. 2, 2018, 795-796.
Durr, et al., "Carcinogenesis of Primary Liver Malignancies", Langenbeck's Archives of Surgery, vol. 385, No. 3, 2000, 154-161.
Edlund, et al., "Cell-Specific Expression of the Rat Insulin Gene: Evidence for Role of Two Distinct 5∝ Flanking Elements", Science. vol. 230, No. 4728, Nov. 22, 1985, 912-916.
Ehrhardt, et al., "Somatic Integration From an Adenoviral Hybrid Vector Into a Hot Spot in Mouse Liver Results in Persistent Transgene Expression Levels in Vivo", Molecular Therapy, vol. 15, No. 1, 2007, 146-156.
El-Andaloussi, et al., "Exosome-Mediated Delivery of siRNA in Vitro and in Vivo", Nature Protocols, vol. 7, Issue 12, Dec. 2012, 2112-2126.
Elbashir, et al., "Duplexes of 21-nucleotide RNAs Mediate RNA Interference in Cultured Mammalian Cells", Nature, vol. 411, No. 6836, 2001, 494-498.
Elbashir, et al., "Functional Anatomy of siRNAs for Mediating Efficient RNAi in *Drosophila melanogaster* Embryo Lysate", The EMBO Journal, vol. 20, No. 23, 2001, 6877-6888.
Elbashir, et al., "RNA Interference Is Mediated by 21- And 22-nucleotide RNAs", Genes Development, vol. 15, No. 2, 2001, 188-200.
Elmen, et al., "Locked Nucleic Acid (LNA) Mediated Improvements in siRNA Stability and Functionality", Nucleic Acids Research, vol. 33, Issue 1, Jan. 2005, 439-447.
Emdin, et al., "Analysis of Predicted Loss-Of-Function Variants in UK Biobank Identifies Variants Protective for Disease", Nature Communications vol. 9, Article No. 1613, 2018, 8 pages.

(56) References Cited

OTHER PUBLICATIONS

Emdin, et al., "Phenotypic Consequences of a Genetic Predisposition to Enhanced Nitric Oxide Signaling", Circulation, vol. 137, No. 3, Jan. 16, 2018, 222-232.
Enkirch, et al., "Targeted Lentiviral Vectors Pseudotyped With The Tupaia Paramyxovirus Glycoproteins", Gene Therapy vol. 20, 2013, 16-23.
Esvelt, et al., "Orthogonal Cas9 Proteins for RNA-guided Gene Regulation and Editing", Nature Methods, vol. 10, No. 11, Nov. 2013, 19 pages.
Fire, et al., "Potent and Specific Genetic Interference by Double-Stranded Rna in Caenorhabditis Elegans", Nature, vol. 391, No. 6669, Feb. 1998, 806-811.
Flotte, et al., "A Phase I Study of an Adeno-Associated virus-CFTR Gene Vector in Adult CF Patients With Mild Lung Disease", Human Gene Therapy, vol. 7, No. 9, 1996, 1145-1159.
Friedrich, et al., "DARPin-targeting of Measles Virus: Unique Bispecificity, Effective Oncolysis, and Enhanced Safety", Molecular Therapy, vol. 21, No. 4, 2013, 849-859.
Fu, et al., "Linear Transgene Constructs Lacking Vector Backbone Sequences Generate Low-Copy-Number Transgenic Plants with Simple Integration Patterns", Transgenic Research, Kluwer Academic Publishers, vol. 9, No. 1, 2000, 11-19.
Fuchsberger, et al., "The Genetic Architecture of Type 2 Diabetes", Nature, vol. 536, Aug. 4, 2016, 29 pages.
Funke, et al., "Targeted Cell Entry of Lentiviral Vectors", Molecular Therapy vol. 16 No. 8, 2008, 1427-1436.
Gallie, "Introduction of mRNA to Plant Protoplasts using Polyethylene Glycol", Plant Cell Reports, vol. 13, 1993, 119-122.
Gantz, et al., "Gene Editing Technologies and Applications for Insects", Current Opinion in Insect Science, vol. 28, Aug. 2018, 66-72.
Gao, et al., "Engineered Cpf1 Enzymes with Altered PAM Specificities", Nature Biotechnology, vol. 35, No. 8, Dec. 4, 2016, 17 pages.
Gatz, et al., "Regulation of a Modified CaMV 35S Promoter by the Tn10-Encoded Tet Repressor in Transgenic Tobacco", Molecular Genetics and Genomics, vol. 227, No. 2, 1991, 229-237.
Gaudelli, et al., "Programmable Base Editing of A•T to G•C in Genomic DNA without DNA Cleavage", Nature, vol. 551, No. 7681, Nov. 23, 2017, 37 pages.
Girard-Gagnepain, et al., "Baboon Envelope Pseudotyped LVs Outperform VSV-G-LVs for Gene Transfer Into Early-Cytokine-Stimulated And Resting HSCs", Blood, vol. 124 No. 8, Aug. 21, 2014, 1221-1231.
Gleditzsch, et al., "PAM Identification by CRISPR-Cas Effector Complexes: Diversified Mechanisms and Structures", RNA Biology, vol. 16. No. 4, 2019, 504-517.
Gorad, et al., "Liver Specific Drug Targeting Strategies: A Review", International Journal of Pharmaceutical Sciences and Research, vol. 4, No. 11, 2013, 4145-4157.
Grissa, et al., "CRISPRFinder: A Web Tool to Identify Clustered Regularly Interspaced Short Palindromic Repeats", Nucleic Acids Research, vol. 35, 2007, W52-W57.
Gruber, et al., "The Vienna RNA Websuite", Nucleic Acids Research, vol. 36, Apr. 19, 2008, W70-W74.
Gruenewald, et al., "The Fourth Molybdenum Containing Enzyme mARC: Cloning and Involvement in the Activation of N-hydroxylated Prodrugs", Journal of Medicinal Chemistry, vol. 51, No. 24, 2008, 8173-8177.
Grunweller, et al., "Comparison of Different Antisense Strategies in Mammalian Cells Using Locked Nucleic Acids, 2'-O-methyl RNA, Phosphorothioates and Small Interfering RNA", Nucleic Acids Research, vol. 31, No. 12, 2003, 3185-3193.
Gui, et al., "CRISPR/Cas9-Mediated Genome Editing and Mutagenesis of EcChi4 in Exopalaemon carinicauda", Genes Genomes Genetics (Bethesda), vol. 6, No. 11, Nov. 2016, 3757-3764.
Hall, et al., "Establishment and Maintenance of a Heterochromatin Domain", Science, vol. 297, No. 5590, 2002, 2232-2237.

Hall, et al., "Genome Editing in Mice Using CRISPR/Cas9 Technology", Current Protocols in Cell Biology, vol. 81, No. 1, 2018, 31 pages.
Hamilton, et al., "A Species of Small Antisense RNA in Post-transcriptional Gene Silencing in Plants", Science, vol. 286, No. 5441, 1999, 950-952.
Hanawa, et al., "Comparison of Various Envelope Proteins for Their Ability to Pseudotype Lentiviral Vectors and Transduce Primitive Hematopoietic Cells From Human Blood", Molecular Therapy, vol. 5, No. 3., Mar. 2002, 242-251.
Hao, et al., "Nucleic Acid-Gold Nanoparticle Conjugates as Mimics of microRNA", Small, vol. 7, Issue 22, Nov. 18, 2011, 10 pages.
Hardee, et al., "Advances in Non-Viral DNA Vectors for Gene Therapy", Genes , vol. 8, No. 2, 2017, 22 pages.
Harrison, et al., "A CRISPR View of Development", Genes & Development, vol. 28, Sep. 1, 2014, 1859-1872.
Havemeyer, et al., "Identification of the Missing Component in the Mitochondrial Benzamidoxime Prodrug-Converting System as a Novel Molybdenum Enzyme", Journal of Biological Chemistry, vol. 281, No. 46, Nov. 17, 2006, 34796-34802.
Heo, et al., "CRISPR/Cas9 Nuclease-Mediated Gene Knock-In in Bovine-Induced Pluripotent Cells", Stem Cells Development, vol. 24, No. 3, Feb. 2015, 10 pages.
Hermonat, et al., "Use of Adeno-Associated Virus as a Mammalian DNA Cloning Vector: Transduction of Neomycin Resistance into Mammalian Tissue Culture Cells", Proceedings of National Academy of Sciences, vol. 81, Oct. 1984, 6466-6470.
Hirel, et al., "Forcing Expression of a Soybean Root Glutamine Synthetase Gene in Tobacco Leaves Induces a Native Gene Encoding Cytosolic Enzyme", Plant Molecular Biology, vol. 20, 1992, 207-218.
Hutvagner, et al., "A Cellular Function for the RNA-interference Enzyme Dicer in the Maturation of the let-7 Small Temporal RNA", Science, vol. 293, No. 5531, 2001, 834-838.
Hutvagner, et al., "A MicroRNA in a Multiple-Turnover RNAi Enzyme Complex", Science, vol. 297, 5589, Oct. 2002, 2056-2060.
Ivics, et al., "Molecular Reconstruction of Sleeping Beauty, a Tc1-like Transposon From Fish, and Its Transposition in Human Cells", Cell, vol. 91, No. 4, Nov. 14, 1997, 501-510.
Jensen, et al., "Spherical Nucleic Acid Nanoparticle Conjugates as an RNAi-Based Therapy for Glioblastoma", Science Translational Medicine, vol. 5, Issue 209, Oct. 30, 2013, 12 pages.
Jensen, et al., "Unlocked Nucleic Acid (UNA) and UNA Derivatives: Thermal Denaturation Studies", Nucleic Acids Symposium Series, vol. 52, Issue No. 1, 2008, 133-134.
Jenuwein, "An RNA-Guided Pathway for the Epigenome", Science, vol. 297, Issue 5590, 2002, 2215-2218.
Ji, et al., "Genome-wide Association Study of Primary Sclerosing Cholangitis Identifies New Risk Loci and Quantifies the Genetic Relationship With Inflammatory Bowel Disease", Nature Genetics, vol. 49, No. 2, Feb. 2017, 269-273.
Jiang, et al., "RNA-Guided Editing of Bacterial Genomes Using CRISPR-Cas Systems", Nature Biotechnology, vol. 31, No. 3, Mar. 2013, 233-239.
Jin, et al., "Safe Engineering of CAR T Cells for Adoptive Cell Therapy of Cancer Using Long-term Episomal Gene Transfer", EMBO Molecular Medicine, vol. 8, No. 7, 2016, 702-711.
Johann, et al., "GLVR1, a Receptor for Gibbon Ape Leukemia Virus, is Homologous to a Phosphaate Permease of Neurospora crassa and is Expresssed at High Levels in the Brain and Thymus", Journal of Virology, vol. 66, No. 3, Mar. 1992, 1635-1640.
Kabadi, et al., "Multiplex CRISPR/Cas9-based Genome Engineering from a Single Lenttiviral Vector", Nucleic Acids Research, vol. 42, No. 19, Aug. 13, 2014, 11 pages.
Kalds, et al., "Sheep and Goat Genome Engineering: From Random Transgenesis to the CRISPR Era", Frontiers in Genetics, vol. 10, Article 750, Sep. 2019, 27 pages.
Kalimuthu, et al., "Human Mitochondrial Amidoxime Reducing Component (mARC): An Electrochemical Method for Identifying New Substrates and Inhibitors", Electrochemistry Communications, vol. 84, Nov. 2017, 90-93.

(56) References Cited

OTHER PUBLICATIONS

Kanai, et al., "Genetic Analysis of Quantitative Traits in the Japanese Population Links Cell Types to Complex Human Diseases", Nature, vol. 50, 2018, 390-400.

Karimi-Ashtiyani, et al., "Point Mutation Impairs Centromeric CENH3 Loading and Induces Haploid Plants", Proceedings of the National Academy of Sciences, vol. 112, No. 36, Sep. 8, 2015, 11211-11216.

Kasaraneni, et al., "A Simple Strategy for Retargeting Lentiviral Vectors to Desired Cell Types via a Disulfide-Bond-Forming Protein-Peptide Pair", Scientific Reports, vol. 8, No. 10990, 2018, 9 pages.

Kaufman, et al., "Translational Efficiency of Polycistronic MRNAs and their Utilization to Express Heterologous Genes in Mammalian Cells", The EMBO Journal, vol. 6, No. 1, 1987, 187-195.

Kawai, et al., "Transformation of *Saccharomyces cerevisiae* and Other Fungi", Bioengineered Bugs, vol. 1, No. 6, Nov./Dec. 2010, 395-403.

Kawamata, et al., "Temporal and Spatial Pattern of Expression of the Pea Phenylalanine Ammonia-Lyase Gene1 Promoter in Transgenic Tobacco", Plant Cell Physiology, vol. 38, No. 7, 1997, 792-803.

Kay, et al., "Evidence for Gene Transfer and Expression of Factor IX in Haemophilia B Patients Treated With an AAV Vector", Nature Genetics, vol. 24, No. 3, 2000, 257-261.

Kessel, et al., "Murine Developmental Control Genes", Science, vol. 249, No. 4967, Jul. 27, 1990, 374-379.

Khera, et al., "Association of Rare and Common Variation in the Lipoprotein Lipase Gene with Coronary Artery Disease", The Journal of the American Medical Association, vol. 317, No. 9, Mar. 7, 2017, 937-946.

Khera, et al., "Diagnostic Yield and Clinical Utility of Sequencing Familial Hypercholesterolemia Genes in Patients With Severe Hypercholesterolemia", Journal of the American College of Cardiology, vol. 67, No. 22, 2016, 2578-2589.

Kim, et al., "Chimeric Restriction Endonuclease", Proceedings of the National Academy of Sciences, vol. 91, No. 3, 1994, 883-887.

Kim, et al., "Highly Efficient Rna-guided Genome Editing in Human Cells via Delivery of Purified Cas9 Ribonucleoproteins", Genome Research, vol. 24, No. 6, Jun. 24, 2014, 1012-1019.

Kim, et al., "Hybrid Restriction Enzymes: Zinc Finger Fusions to Fok I Cleavage Domain", Proceedings of the National Academy of Sciences, vol. 93 No. 3, Feb. 1996, 1156-1160.

Klein, et al., "High-velocity Microprojectiles for Delivering Nucleic Acids into Living Cells", Nature, vol. 327, 1987, 70-73.

Klein, et al., "The Mitochondrial Amidoxime-reducing Component (mARC1) Is a Novel Signal-anchored Protein of the Outer Mitochondrial Membrane", Journal of Biological Chemistry, vol. 287, 2012, 42795-42803.

Klein, et al., "Transformation of Microbes, Plants and Animals by Particle Bombardment", Bio/Technology, vol. 10, 1992, 286-291.

Kleinstiver, et al., "Engineered Crispr-Cas9 Nucleases with Altered Pam Specificities", Nature, vol. 523, No. 7561, Jul. 23, 2015, 17 pages.

Klompe, et al., "Transposon-encoded CRISPR-Cas Systems Direct RNA-guided DNA Integration", Nature, vol. 571, Jul. 11, 2019, 24 pages.

Komor, et al., "Programmable Editing of a Target Base in Genomic DNA without Double-Stranded DNA Cleavage", Nature, vol. 533, No. 7603, May 19, 2016, 17 pages.

Koonin, et al., "Origins and Evolution of CRISPR-Cas Systems", Philosophical Transactions of the Royal Society of London, vol. 374, Issue 1772, Oct. 24, 2018, 16 pages.

Kotin, "Prospects for the Use of Adeno-Associated Virus as a Vector for Human Gene Therapy", Human Gene Therapy, vol. 5, 1994, 793-801.

Kotthaus, et al., "Reduction of Nω-Hydroxy-L-Arginine by the Mitochondrial Amidoxime Reducing Component (mARC)", Biochemical Journal, vol. 433, Issue 2, Jan. 2011, 383-391.

Kotwica-Rolinska, "CRISPR/Cas9 Genome Editing Introduction and Optimization in the Non-model Insect *Pyrrhocoris apterus*", Frontiers in Physiology, vol. 10, Article 891, Jul. 2019, 15 pages.

Kozlitina, et al., "Exome-wide Association Study Identifies a TM6SF2 Variant That Confers Susceptibility to Nonalcoholic Fatty Liver Disease", Nature Genetics, vol. 46, No. 4, 2014, 352-356.

Kubitza, et al., "Crystal Structure of Human mARC1 Reveals Its Exceptional Position Among Eukaryotic Molybdenum Enzymes", Proceedings of the National Academy of Sciences, vol. 115, No. 47, Nov. 20, 2018, 11958-11963.

Kubo, et al., "A New Hybrid System Capable of Efficient Lentiviral Vector Production and Stable Gene Transfer Mediated by a Single Helper-Dependent Adenoviral Vector", Journal of Virology, vol. 77, No. 5, Mar. 2003, 2964-2971.

Kubo, et al., "Adenovirus—Retrovirus Hybrid Vectors Achieve Highly Enhanced Tumor Transduction and Antitumor Efficacy In Vivo", Molecular Therapy, vol. 19, No. 1, 2011, 76-82.

Kurjan, et al., "Structure of A Yeast Pheromone Gene (Mfα): A Putative A-Factor Precursor Contains Four Tandem Copies of Mature A-Factor", Cell, vol. 30, No. 3, Nov. 1982, 933-943.

Kuster, et al., "The Promoter of the *Vicia faba* L. VfENOD-GRP3 Gene Encoding a Glycine-Rich Early Nodnlin Mediates a Predominant Gene Expression in the Interzone II-III Region of Transgenic Vicia Hirsuta Root Nodules", Plant Molecular Biology, vol. 29, No. 4, 1995, 759-772.

Lagauzère, "Viromer® RED, a powerful tool for transfection of keratinocytes", doi: 10.13140/RG.2.2.16993.61281, Aug. 2017, 6 pages.

Lagauzère, "Viromer® Transfection—Factbook 2018: Technology, Product Overview, Users' Data", Project: Viromer®: an innovative technology for transfection DOI: 10.13140/RG.2.2.23912.16642, 2018, 21 pages.

Lai, et al., "Adenovirus and Adeno-Associated Virus Vectors", DNA Cell Biology. vol. 21, No. 12, 2002, 895-913.

Lawrence, et al., "Supercharging Proteins Can Impart Unusual Resilience", Journal of the American Chemical Society, vol. 129, Issue 33, Aug. 1, 2007, 8 pages.

Lee, et al., "Engraftment of Human iPS Cells and Allogenic Porcine Cells into Pigs with Inactivated RAG2 and Acompanying Severe Combined Immunodeficiency", Proceedings of the National Academy of Sciences, vol. 111, No. 20, May 20, 2014, 7260-7265.

Li, et al., "Base Editing With a Cpf1-cytidine Deaminase Fusion", Nature Biotechnology, vol. 36, 2018, 324-327.

Li, et al., "piggyBac Transposase Tools for Genome Engineering", Proceedings of the National Academy of Sciences, vol. 110, No. 25, Jun. 18, 2013, E2279-E2287.

Li, et al., "Protein Transport into Chloroplasts", Annual Review of Plant Biology, vol. 61, 2010, 157-180.

Liang, et al., "CRISPR/Cas9-mediated gene editing in human tripronuclear zygotes", Protein Cell 2015, vol. 6, No. 5, Accepted Apr. 1, 2015, pp. 363-372.

Lima, et al., "Single-stranded siRNAs Activate RNAi in Animals", Cell, vol. 150, No. 3, 2012, 883-894.

Lin, et al., "Policing Rogue Genes", Nature, vol. 402, 1999, 128-129.

Liu, et al., "Exome-wide Association Study of Plasma Lipids in >300,000 Individuals", Nature Genetics, vol. 49, No. 12, Dec. 2017, 1758-1766.

Liu, et al., "Expanding the CRISPR Toolbox in Zebrafish for Studying Development and Disease", Frontiers in Cell and Developmental Biology, vol. 7, Article 13, Mar. 2019, 15 pages.

Liu, et al., "Highly Efficient RNA-Guided Base Editing in Rabbit", Nature Communications, vol. 9, Article No. 2717, 2018, 10 pages.

Liu, et al., "Multiple Homologous Genes Knockout (KO) by CRISPR/Cas9 System in Rabbit", Gene, vol. 647, Mar. 2018, 261-267.

Liu, et al., "Recombinant Human Foamy Virus, a Novel Vector for Neurological Disorders Gene Therapy, Drives Production of GAD in Cultured Astrocytes", Molecular Therapy, vol. 15, No. 10, 2007, 1834-1841.

Liu, et al., "The Effect of the TM6SF2 E167K Variant on Liver Steatosis and Fibrosis in Patients with Chronic Hepatitis C: A Meta-Analysis", Scientific Reports, vol. 7, Article No. 9273, 2017, 11 pages.

(56) References Cited

OTHER PUBLICATIONS

Liu, et al., "TM6SF2 rs58542926 Influences Hepatic Fibrosis Progression in Patients with Non-Alcoholic Fatty Liver Disease", Nature Communications, vol. 5, Article No. 4309, 2014, 6 pages.
Locke, et al., "Genetic Studies of Body Mass Index Yield New Insights for Obesity Biology", Nature, vol. 518, Feb. 2015, 197-206.
Lok, "CRISPR/Cas9 Mutagenesis and Expression of Dominant Mutant Transgenes as Functional Genomic Approaches in Parasitic Nematodes", Frontiers in Genetics, vol. 10, Article 656, Jul. 2019, 11 pages.
Lorenzer, et al., "Going Beyond the Liver: Progress and Challenges of Targeted Delivery of siRNA Therapeutics", Journal of Controlled Release, vol. 203, Apr. 2015, 1-15.
Lowder, et al., "A CRISPR/Cas9 Toolbox for Multiplexed Plant Genome Editing and Transcriptional Regulation", Plant Physiology, vol. 169, No. 2, Oct. 2015, 15 pages.
Lozano, et al., "Global and Regional Mortality From 235 Causes of Death for 20 Age Groups in 1990 and 2010: A Systematic Analysis for the Global Burden of Disease Study 2010", The Lancet, vol. 380, No. 9859, Dec. 2012, 2095-2128.
Luckow, et al., "High Level Expression of Nonfused Foreign Genes with Autographa Californica Nuclear Polyhedrosis Virus Expression Vectors", Virology, vol. 170, Issue 1, May 1989, 31-39.
Ma, et al., "A Robust CRISPR/Cas9 System for Convenient High-Efficiency Multiplex Genome Editing in Monocot and Dicot Plants", Molecular Plant, vol. 8, Aug. 2015, 1274-1284.
Macparland, et al., "Single Cell RNA Sequencing of Human Liver Reveals Distinct Intrahepatic Macrophage Populations", Nature Communications, vol. 9, Article No. 4383, 2018, 21 pages.
Makarova, et al., "Classification and Nomenclature of CRISPR-Cas Systems: Where from Here?", The CRISPR Journal, vol. 1, No. 5, 2018, 325-336.
Makarova, et al., "Evolutionary Classification of CRISPR-Cas Systems: A Burst of Class 2 and Derived Variants", Nature Reviews Microbiology, vol. 18, Feb. 2020, 67-83.
Mali, et al., "RNA-Guided Human Genome Engineering via Cas9", Science, vol. 339, No. 6121, Feb. 15, 2013, 8 pages.
Malina, et al., "Repurposing CRISPR/Cas9 for in Situ Functional Assays", Genes & Development, vol. 27, No. 23, Oct. 25, 2013, 2602-2614.
Marraffini, et al., "Self Vs. Non-Self Discrimination During CRISPR RNA-Directed Immunity", Nature, vol. 463, No. 7280, Jan. 28, 2010, 13 pages.
Mccarthy, et al., "A Reference Panel of 64,976 Haplotypes for Genotype Imputation", Nature Genetics, vol. 48, No. 10, 2016, 1279-1283.
Mclaren, et al., "Deriving the Consequences of Genomic Variants With the Ensembl API and SNP Effect Predictor", Bioinformatics, vol. 26, No. 16, 2010, 2069-2070.
Mcmanus, et al., "Gene Silencing Using micro-RNA Designed Hairpins", RNA, vol. 8, No. 6, 2002, 842-850.
Mcnaughton, et al., "Mammalian Cell Penetration, siRNA Transfection, and DNA Transfection by Supercharged Proteins", PNAS, vol. 106, No. 15, Apr. 14, 2009, 6111-6116.
Miki, et al., "Selectable Marker Genes in Transgenic Plants: Applications, Alternatives and Biosafety", Journal of Biotechnology, vol. 107, No. 3, Feb. 2004, 193-232.
Miller, et al., "Construction and Properties of Retrovirus Packaging Cells Based on Gibbon Ape Leukemia Virus", Journal of Virology, vol. 65, No. 5, May 1991, 2220-2224.
Mirkin, "Interview: An Interview with Chad Mirkin: Nanomedicine Expert", Nanomedicine, vol. 7, Issue 5, May 2012, 6 pages.
Mirkovitch, et al., "Organization of the Higher-Order Chromatin Loop: Specific DNA Attachment Sites on Nuclear Scaffold", Cell, vol. 39, 1984, 223-232.
Miskey, et al., "The Frog Prince: A Reconstructed Transposon from Rana Pipiens with High Transpositional Activity in Vertebrate Cells", Nucleic Acids Research, vol. 31, No. 23, 2003, 6873-6881.

Mojica, et al., "Short Motif Sequences Determine the Targets of the Prokaryotic CRISPR Defence System", Microbiology, vol. 155, 2009, 733-740.
Mook, et al., "Evaluation of Locked Nucleic Acid-modified Small Interfering RNA in Vitro and in Vivo", Molecular Cancer Therapeutics, vol. 6, Issue 3, Mar. 2007, 833-843.
Moore, et al., "CRISPR-Based Self-Cleaving Mechanism for Controllable Gene Delivery in Human Cells", Nucleic Acids Research, vol. 43, No. 2, 2015, 1297-1303.
Morizono, et al., "A Versatile Targeting System With Lentiviral Vectors Bearing The Biotin-Adaptor Peptide", The Journal of Gene Medicine, vol. 11 No. 8, Aug. 2009, 655-663.
Morizono, et al., "Antibody-Directed Targeting of Retroviral Vectors via Cell Surface Antigens", Journal of Virology, vol. 75, No. 17, Sep. 2001, pp. 8016-8020.
Morizono, et al., "Lentiviral Vector Retargeting to P-glycoprotein on Metastatic Melanoma Through Intravenous Injection", Nature Medicine vol. 11 No. 3, Mar. 2005, 346-352.
Morizono, et al., "Redirecting lentiviral vectors by insertion of integrin-tageting peptides into envelope proteins", The Journal of Gene Medicine, vol. 11, No. 7, Jul. 2009, 549-558.
Morizono, et al., "Redirecting Lentiviral Vectors Pseudotyped with Sindbis Virus-Derived Envelope Proteins to DC-SIGN by Modification of N-Linked Glycans of Envelope Proteins", Journal Of Virology vol. 84, No. 14, Jul. 2010, 6923-6934.
Morizono, et al., "Transient Low pH Treatment Enhances Infection of Lentiviral Vector Pseudotypes with a Targeting Sindbis Envelope", Virology 355, 2006, 71-81.
Morral, et al., "Administration of Helper-Dependent Adenoviral Vectors and Sequential Delivery of Different Vector Serotype for Long-Term Liver-Directed Gene Transfer in Baboons", Proceedings of the National Academy of Sciences, vol. 96, No. 22, 1999, 12816-12821.
Morral, et al., "High Doses of a Helper-Dependent Adenoviral Vector Yield Supraphysiological Levels of alpha1-antitrypsin With Negligible Toxicity", Human Gene Therapy, vol. 9, No. 18, 1998, 2709-2716.
Morrissey, et al., "Potent and Persistent In vivo Anti-HBV Activity of Chemically Modified siRNAs", Nature Biotechnology, vol. 23, No. 8, Aug. 2005, 6 pages.
Morton, "Selection On The Codon Bias Of Chloroplast And Cyanelle Genes In Different Plant And Algal Lineages", Journal of Molecular Evolution, vol. 46, Issue 4, Apr. 1998, 449-459.
Moscou, et al., "A Simple Cipher Governs DNA Recognition by TAL Effectors", Science, vol. 326, Issue 5959, Dec. 11, 2009, 1501 page.
Murray, et al., "Codon usage in plant genes", Nucleic Acids Research, vol. 17, No. 2, Jan. 1989, 477-498.
Muzyczka, "Adeno-Associated Virus (AAV) Vectors: Will They Work?", Journal of Clinical Investigation, vol. 94, Oct. 1994, p. 1351.
Nair, et al., "Multivalent N-Acetylgalactosamine-Conjugated siRNA Localizes in Hepatocytes and Elicits Robust RNAi-Mediated Gene Silencing", Journal of the American Chemical Society, vol. 136, No. 49, Dec. 1, 2014, 16958-16961.
Nakamura, et al., "Codon Usage Tabulated from International DNA Sequence Databases: Status for the Year 2000", Nucleic Acids Research, vol. 28, No. 1, 2000, p. 292.
Nakayama, et al., "Simple and Efficient CRISPR/Cas9-mediated Targeted Mutagenesis in Xenopus Tropicalis", Genesis, vol. 51, No. 12, Dec. 2013, 835-843.
Nehlsen, et al., "Replicating Minicircles: Generation of Nonviral Episomes for the Efficient Modification of Dividing Cells", Gene Therapy and Molecular Biology, vol. 10, 2006, 233-244.
Nishida, et al., "Targeted Nucleotide Editing Using Hybrid Prokaryotic and Vertebrate Adaptive Immune Systems", Science, vol. 353, Issue 6305, Aug. 4, 2016, 35 pages.
Nishimasu, et al., "Crystal Structure of Cas9 in Complex with Guide RNA and Target DNA", Cell, vol. 156, Feb. 27, 2014, 935-949.
Nykanen, et al., "ATP Requirements and Small Interfering RNA Structure in the RNA Interference Pathway", Cell, vol. 107, No. 3, 2001, 309-321.

(56) References Cited

OTHER PUBLICATIONS

O'Hare, et al., "Transformation of Mouse Fibroblasts to Methotrexate Resistance by A Recombinant Plasmid Expressing A Prokaryotic Dihydrofolate Reductase", Proceedings of the National Academy of Sciences, vol. 78, No. 3, Mar. 1981, 1527-1531.
Ono, et al., "Transient Assay System for the Analysis of PR-1a Gene Promoter in Tobacco BY-2 Cells", Bioscience, Biotechnology, and Biochemistry, vol. 68, No. 4, 2004, 803-807.
Ott, et al., "Functional Characterization of Protein Variants Encoded by Nonsynonymous Single Nucleotide Polymorphisms in MARC1 and MARC2 in Healthy Caucasians", Drug Metabolism and Disposition, vol. 42, No. 4, Apr. 2014, 718-725.
Paix, et al., "High Efficiency, Homology-Directed Genome Editing in Caenorhabditis Elegans using CRISPR-Cas9 Ribonucleoprotein Complexes", Genetics, vol. 201, No. 1, Sep. 2015, 47-54.
Pardridge, "Preparation of Trojan Horse Liposomes (THLs) for Gene Transfer across the Blood-Brain Barrier", Cold Spring Harbor Protocols, vol. 2010, Issue 4, Apr. 2010, 8 pages.
Pattanayak, et al., "High-Throughput Profiling of Off-Target DNA Cleavage Reveals RNA-Programmed Cas9 Nuclease Specificity", Nature biotechnology, vol. 31, No. 9, Sep. 2013, 16 pages.
Perez-Perez, et al., "Synthesis and Antiviral Activity of 2-Deoxy-1,5-Anhydro-D-Mannitol Nucleosides Containing a Pyrimidine Base Moiety", Bioorganic & Medicinal Chemistry Letters, vol. 6, Issue 13, Jul. 1996, 1457-1460.
Peters, et al., "Recruitment of CRISPR-Cas Systems by Tn7-Like Transposons", Proceedings of the National Academy of Sciences, vol. 114, No. 35, 2017, E7358-E7366.
Pinkert, et al., "An Albumin Enhancer Located 10 kb Upstream Functions Along with its Promoter to Direct Efficient, Liver-Specific Expression in Transgenic Mice", Genes and Development, vol. 1, No. 3, May 1987, 268-277.
Price, et al., "Cas9-Mediated Targeting of Viral RNA in Eukaryotic Cells", Proceedings of the National Academy of Sciences, vol. 112, No. 19, May 12, 2015, 6164-6169.
Qiu, et al., "A Genome-Wide Association Study Identifies Six Novel Risk Loci for Primary Biliary Cholangitis", Nature Communications, vol. 8, Article No. 14828, 2017, 8 pages.
Queen, et al., "Immunoglobulin Gene Transcription is Activated by Downstream Sequence Elements", Cell, vol. 33, Jul. 1983, 741-748.
Qui, et al., "Mutation Detection Using Surveyor Nuclease", Biotechniques, vol. 36, No. 4, 2004, 702-707.
Ramakrishna, et al., "Gene Disruption by Cell-Penetrating Peptide-Mediated Delivery of Cas9 Protein and Guide RNA", Genome Research, vol. 24, No. 6, Jun. 2014, 1020-1027.
Ramanan, et al., "CRISPR/Cas9 Cleavage of Viral DNA Efficiently Suppresses Hepatitis B Virus", Scientific Reports, vol. 5, Article No. 10833, Jun. 2, 2015, 9 pages.
Ramirez, et al., "Engineering Split Intein DnaE From Nostoc Punctiforme for Rapid Protein Purification", Protein Engineering, Design and Selection, vol. 26, No. 3, 2013, 215-223.
Rasys, et al., "CRISPR-Cas9 Gene Editing in Lizards through Microinjection of Unfertilized Oocytes", Cell Reports, vol. 28, No. 9, Aug. 2019, 2288-2292.
Rees, et al., "Base Editing: Precision Chemistry on the Genome and Transcriptome of Living Cells", Nature Reviews Genetics, vol. 19, 2018, 41 pages.
Reinhart, et al., "MicroRNAs in Plants", Genes & Development, vol. 16, No. 13, 2002, 1616-1626.
Reinhart, et al., "Small RNAs Correspond to Centromere Heterochromatic Repeats", Science, vol. 297, No. 5588, 2002, p. 1831.
Revilla-I-Domingo, et al., "Establishment of Transgenesis in the Demosponge Suberites domuncula", Genetics, vol. 210, No. 2, Oct. 2018, 435-443.
Rios, et al., "FcεRI Expression and Dynamics on Mast Cells", Methods in Molecular Biology, vol. 1220, 2015, 239-255.
Roereckea, et al., "Ischemic Heart Disease Mortality and Morbidity Rates in Former Drinkers: A Meta-Analysis", American Journal of Epidemiology, vol. 173, No. 3, Feb. 2011, 245-258.
Romeo, et al., "Genetic Variation in PNPLA3 Confers Susceptibility to Nonalcoholic Fatty Liver Disease", Nature Genetics, vol. 40, No. 12, Dec. 2008, 1461-1465.
Rosewell, et al., "Helper-Dependent Adenoviral Vectors", J Genet Syndr Gene Ther. , Suppl 5, 2011, 34 pages.
Rusk, et al., "Multi-Omics Single-Cell Analysis", Nature Methods, vol. 16, No. 8, Aug. 2019, 679 page.
Sainsbury, et al., "pEAQ: Versatile Expression Vectors for Easy and Quick Transient Expression of Heterologous Proteins in Plants", Plant Biotechnology Journal, vol. 7, No. 7, 2009, 682-693.
Samulski, et al., "Helper-Free Stocks of Recombinant Adeno-Associated Viruses: Normal Integration Does Not Require Viral Gene Expression", Journal of Virology, vol. 63, No. 9, Sep. 1989, 3822-3828.
Schaeffer, et al., "CRISPR/Cas9-mediated Genome Editing and Gene Replacement in Plants: Transitioning From Lab to Field", Plant Science, vol. 240, 2015, 57 pages.
Schiffelers, et al., "Cancer siRNA Therapy by Tumor Selective Delivery with Ligand-Targeted Sterically Stabilized Nanoparticle", Nucleic Acids Research, vol. 32, No. 19, e149, Nov. 1, 2004, 10 pages.
Schneider, et al., "Detoxification of Trimethylamine N-Oxide by the Mitochondrial Amidoxime Reducing Component mARC", Chemical Research in Toxicology, vol. 31, 2018, 447-453.
Scholthof, et al., "Plant Virus Gene Vectors For Transient Expression of Foreign Proteins in Plants", Annual Review of Phytopathology, vol. 34, 1996, 299-323.
Schomberg, et al., "Optimization of CRISPR/Cas9 Platform-Mediated Gene Editing of Swine Embryos for The Creation of Novel Biomedical Swine Models", The FASEB Journal, vol. 30, No. 1, Apr. 2016, Supplement 571.1.
Schroeder, et al., "Lipid-Based Nanotherapeutics for siRNA Delivery", Journal of Internal Medicine, vol. 267, No. 1, Jan. 2010, 21 pages.
Schultz, et al., "Expression and Secretion in Yeast of A 400-Kda Envelope Glycoprotein Derived from Epstein-Barr Virus", Gene, vol. 54, No. 1, 1987, 113-123.
Schuppan, et al., "Liver Cirrhosis", Lancet, vol. 371, No. 9615, Mar. 2008, 838-851.
Scott, et al., "Applications of Avian Transgenesis", ILAR Journal, vol. 51, No. 4, 2010, 353-361.
Seed, "An LFA-3 Cdna Encodes a Phospholipid-Linked Membrane Protein Homologous to its Receptor CD2", Nature, vol. 329, No. 6142, Oct. 29, 1987, 840-842.
Sharp, "RNA Interference—2001", Genes & Development, vol. 15, No. 5, 2001, 485-490.
Sharp, "RNAi and Double-strand RNA", Genes & Development, vol. 13, 1999, 139-141.
Shmakov, et al., "Discovery and Functional Characterization of Diverse Class 2 CRISPR-Cas Systems", Molecular Cell, vol. 60, No. 3, Nov. 5, 2015, 385-397.
Shungin, et al., "New Genetic Loci Link Adipose and Insulin Biology to Body Fat Distribution", Nature, vol. 518, 2015, 187-196.
Sid, et al., "Applications of Gene Editing in Chickens: A New Era Is on the Horizon", Frontiers in Genetics, vol. 9, Article 456, Oct. 2018, 12 pages.
Simonelli, et al., "Gene Therapy for Leber's Congenital Amaurosis is Safe and Effective Through 1.5 Years After Vector Administration", Molecular Therapy, vol. 18, No. 3, 2010, 643-650.
Smith, et al., "Production of Human Beta Interferon in Insect Cells Infected with a Baculovirus Expression Vector", Molecular and Cellular Biology, vol. 3, No. 12, Dec. 1983, 2156-2165.
Smith, et al., "Single-Step Purification of Polypeptides Expressed in *Escherichia coli* As Fusions with Glutathione S-Transferase", Gene, vol. 67, No. 1, Jul. 15, 1988, 31-40.
Sommerfelt, et al., "Receptor Interference Groups of 20 Retroviruses Plating on Human Cells", Virology, vol. 176, 1990, 58-69.
Soyk, et al., "Variation in the Flowering Gene Self Pruning 5G Promotes Day-Neutrality and Early Yield in Tomato", Nature Genetics, vol. 49, No. 1, 2017, 162-168.

(56) References Cited

OTHER PUBLICATIONS

Sparacino-Watkins, et al., "Nitrite Reductase and Nitric-oxide Synthase Activity of the Mitochondrial Molybdopterin Enzymes mARC1 and mARC2", Journal of Biological Chemistry, vol. 289, No. 15, Apr. 11, 2014, 10345-10358.

Speliotes, et al., "Liver Fat Is Reproducibly Measured Using Computed Tomography in the Framingham Heart Study", European Journal of Gastroenterology & Hepatology, vol. 23, No. 6, 2008, 894-899.

Speliotes, et al., "PNPLA3 Variants Specifically Confer Increased Risk for Histologic Nonalcoholic Fatty Liver Disease but Not Metabolic Disease", Hepatology, vol. 52, Issue 3, Sep. 2010, 904-912.

Spuch, et al., "Liposomes for Targeted Delivery of Active Agents against Neurodegenerative Diseases (Alzheimer's Disease and Parkinson's Disease)", Journal of Drug Delivery, vol. 2011, Article ID 469679, 2011, 12 pages.

Strecker, et al., "RNA-Guided DNA Insertion with CRiSPR-Associated Transposes", Science, 10/1126/science.aax9181, 2019, 12 pages.

Studier, et al., "Use of T7 RNA Polymerase to Direct Expression of Cloned Genes", Methods in Enzymology, vol. 185, 1990, 60-89.

Sugano, et al., "CRISPR/Cas9-Mediated Targeted Mutagenesis in the Liverwort *Marchantia polymorpha* L.", Plant and Cell Physiology, vol. 55, No. 3, Mar. 2014, 475-481.

Sun, et al., "Cocoon-like Self-Degradable Dna Nanoclew for Anticancer Drug Delivery", Journal of the American Chemical Society, vol. 136, No. 42, Oct. 13, 2014, 14722-14725.

Sun, et al., "Self-Assembled Dna Nanoclews for the Efficient Delivery of Crispr-cas9 for Genome Editing", Angewandte Chemie International Edition, vol. 54, Issue 41, Oct. 5, 2015, 12029-12033.

Tait-Burkard, et al., "Livestock 2.0—Genome Editing for Fitter, Healthier, and More Productive Farmed Animals", Genome Biology, vol. 19, Article No. 204, 2018, 11 pages.

Takebe, et al., "SRα Promoter: an Efficient and Versatile Mammalian cDNA Expression System Composed of the Simian Virus 40 Early Promoter and the R-U5 Segment of Human T-Cell Leukemia Virus Type 1 Long Terminal Repeat", Molecular and Cellular Biology, vol. 8, No. 1, Jan. 1988, 466-472.

Takeda, et al., "Synthetic and Nature-Derived Lipid Nanoparticles for Neural Regeneration", Neural Regeneration Research, vol. 10, No. 5, May 2015, 2 pages.

Tan, et al., "Efficient Nonmeiotic Allele Introgression in Livestock Using Custom Endonucleases", Proceedings of the National Academy of Sciences, vol. 110, No. 41, Oct. 2013, 16526-16531.

Teramato, et al., "Crisis of Adenoviruses in Human Gene Therapy", Lancet, vol. 355, No. 9218, 2000, 1911-1912.

Thompson, et al., "Cellular Uptake Mechanisms and Endosomal Trafficking of Supercharged Proteins", Chemistry & Biology, vol. 19, Issue 7, Jul. 27, 2012, 23 pages.

Thompson, et al., "Engineering and Identifying Supercharged Proteins for Macromolecule Delivery into Mammalian Cells", Methods in Enzymology, vol. 503, 2012, 25 pages.

Tolman, et al., "Treatment of Non-Alcoholic Fatty Liver Disease", Therapeutics and Clinical Risk Management, vol. 3, No. 6, 2007, 1153-1163.

Tratschin, et al., "A Human Parvovirus, Adeno-Associated Virus, as a Eukaryotic Vector: Transient Expression and Encapsidation of the Procaryotic Gene for Chloramphenical Acetyltansferase", Mol. Cell Biol., vol. 4, No. 10, Oct. 1984, 2072-2081.

Tratschin, et al., "Adeno-Associated Virus Vector for High-Frequency Integration, Expression, and Rescue of Genes in Mammalian Cells", Molecular and Cellular Biology, vol. 5, No. 11, Nov. 1985, 3251-3260.

Trobridge, "Foamy Virus Vectors for Gene Transfer", Expert Opinion on Biological Therapy, vol. 9, No. 11, 2009, 1427-1436.

Valenti, et al., "Patatin-Like Phospholipase Domain-containing 3 I148M Polymorphism, Steatosis, and Liver Damage in Chronic Hepatitis C", Hepatalogy, vol. 53, Issue 3, Mar. 2011, 791-799.

Verghese, et al., "S/MAR Sequence Confers Long-Term Mitotic Stability on Non-Integrating Lentiviral Vector Episomes Without Selection", Nucleic Acid Research, vol. 42, No. 7, 2014, 13 pages.

Volpe, et al., "Regulation of Heterochromatic Silencing and Histone H3 lysine-9 Methylation by RNAi", Science, vol. 297, No. 5588, Oct. 2002, 1833-1837.

Wahl, et al., "Biochemical and Spectroscopic Characterization of the Human Mitochondrial Amidoxime Reducing Components hmARC-1 and hmARC-2 Suggests the Existence of a New Molybdenum Enzyme Family in Eukaryotes", Journal of Biological Chemistry, vol. 285, No. 48, 2010, 37847-37859.

Wahlgren, et al., "Plasma Exosomes can Deliver Exogenous Short Interfering RNA to Monocytes and Lymphocytes", Nucleic Acid Research, vol. 40, No. 17, e130, May 22, 2012, 12 pages.

Waldrip, et al., "A CRISPR-based Approach for Proteomic Analysis of a Single Genomic Locus", Epigenetics, vol. 9, No. 9, Sep. 2014, 1207-1211.

Wang, et al., "A Combinatorial Library of Unsaturated Lipidoids for Efficient Intracellular Gene Delivery", ACS Synthetic Biology, vol. 1, No. 9, May 25, 2012, 403-407.

Wang, et al., "Combinatorially Designed Lipid-Like Nanoparticles for Intracellular Delivery of Cytotoxic Protein for Cancer Therapy", Angewandte Chemie, vol. 53, No. 11, Mar. 10, 2014, 2893-2898.

Wang, et al., "Efficient Delivery of Genome-Editing Proteins using Bioreducible Lipid Nanoparticles", Proceedings of the National Academy of Sciences of the United States of America, vol. 113, No. 11, Mar. 15, 2016, 2868-2873.

Wang, et al., "Enhanced Intracellular siRNA Delivery Using Bioreducible Lipid-Like Nanoparticles", Advanced Healthcare Materials, vol. 3, No. 9, 2014, 1398-1403.

Wang, et al., "Hyaluronic Acid Modification of RNase a and Its Intracellular Delivery Using Lipid-like Nanoparticles", Journal of Controlled Release, S0168-3659(17)30038-X, 2017, 22 pages.

Wang, et al., "Integrating Protein Engineering and Bioorthogonal Click Conjugation for Extracellular Vesicle Modulation and Intracellular Delivery", Plos One,, Nov. 3, 2015, 12 pages.

Wang, et al., "One-Step Generation of Mice Carrying Mutations in Multiple Genes by CRISPR/Cas-Mediated Genome Engineering", Cell, vol. 153, No. 4, May 9, 2013, 13 pages.

Wang, et al., "Optimizing Multiplex CRISPR/Cas9-Based Genome Editing for Wheat", Retrived as on Oct. 18, 2020 :-doi: http://dx.doi.org/10.1101/051342, May 12, 2016, 34 pages.

Weintraub, "The New Gold Standard", Nature, vol. 495, Mar. 14, 2013, S14-S16.

West, et al., "Gene Expression in Adeno-Associated Virus Vectors: The Effects of Chimeric Mrna Structure, Helper Virus, and Adenovirus VA, RNA", Virology, vol. 160, Issue 1, 1987, 38-47.

West, et al., "Genome Editing in Large Animals", Journal of Equine Veterinary Science, vol. 41, Jun. 2016, 1-6.

Whitworth, et al., "Gene-Edited Pigs are Protected from Porcine Reproductive and Respiratory Syndrome Virus", Nature Biotechnology, vol. 34, No. 1, Dec. 7, 2015, 20-22.

Wianny, et al., "Specific Interference with Gene Function by Double-Stranded RNA in Early Mouse Development", Nature Cell Biology, vol. 2, 2000, 70-75.

Willer, et al., "Discovery and Refinement of Loci Associated with Lipid Levels", Nature Genetics, vol. 45, No. 11, Global Lipids Genetics Consortium, Nov. 2013, 1274-1283.

Willer, et al., "METAL: Fast and Efficient Meta-Analysis of Genomewide Association Scans", Bioinformatics, vol. 26, No. 17, 2010, 2190-2191.

Wilson, et al., "Formation of Infectious Hybrid Virions with Gibbon Ape Leukemia Virus and Human T-cell Leukemia Virus Retroviral Envelope Glycoproteins and the gag and pol Proteins of Moloney Murine Leukemia Virus", Journal of Virology, vol. 63, No. 5, May 1989, 2374-2378.

Winoto, et al., "A Novel, Inducible and T Cell-Specific Enhancer Located at the 3' End of the T Cell Receptor α Locus", The EMBO Journal, vol. 8, No. 3, 1989, 729-733.

Wong, et al., "Lentivirus-Mediated Gene Transfer to the Central Nervous System: Therapeutic and Research Applications", Human Gene Therapy, vol. 17, No. 1, Jan. 2006, 1-9.

(56) References Cited

OTHER PUBLICATIONS

Wong, et al., "Sustained Expression From DNA Vectors", American Journal of Human Genetics, vol. 80, No. 1, 2015, 113-152.
Woo, et al., "DNA-Free Genome Editing in Plants with Preassembled CRISPR-Cas9 Ribonucleoproteins", Nature Biotechnology, vol. 33, No. 11, Nov. 2015, 1162-1164.
Xing, et al., "A CRISPR/Cas9 Toolkit for Multiplex Genome Editing in Plants", BMC Plant Biology, vol. 14, No. 327, 2014, 12 pages.
Xu, et al., "Non-Integrating Lentiviral Vectors Based on the Minimal S/MAR Sequence Retain Transgene Expression in Dividing Cells", Science China Life Sciences, vol. 59, Oct. 2016, 1024-1033.
Yamamoto, et al., "Light-Responsive Elements of the Tobacco PSI-D Gene are Located Both Upstream and Within the Transcribed Region", The Plant Journal, vol. 12, No. 2, 1997, 255-265.
Yin, et al., "A Geminivirus-Based Guide RNA Delivery System for CRISPR/Cas9 Mediated Plant Genome Editing", Scientific Reports, vol. 5, Article No. 14926, Oct. 9, 2015, 10 pages.
Young, et al., "Hollow Spherical Nucleic Acids for Intracellular Gene Regulation Based Upon Biocompatible Silica Shells", Nano Letters, vol. 12, Issue 7, Jul. 11, 2012, 10 pages.
Yum, et al., "Efficient Generation of Transgenic Cattle Using the DNA Transposon and Their Analysis by Next-Generation Sequencing", Scientific Reports vol. 6, Article No. 27185, 2016, 12 pages.
Yusa, et al., "A Hyperactive piggyBac Transposase for Mammalian Applications", Proceedings of the National Academy of Sciences, vol. 108, No. 4, Jan. 25, 2011, 1531-1536.
Zamore, et al., "RNAi: Double-Stranded RNA Directs the ATP-dependent Cleavage of mRNA at 21 to 23 Nucleotide Intervals", Cell, vol. 101, Issue 1, Mar. 31, 2000, 25-33.
Zetche, et al., "A Split Cas9 Architecture for Inducible Genome Editing and Transcription Modulation", Nature Biotechnology, vol. 33, No. 2, Feb. 2015, 6 pages.
Zetsche, et al., "Cpf1 is a Single RNA-Guided Endonuclease of a Class 2 CRISPR-Cas System", Cell, vol. 163, No. 3, Oct. 22, 2015, 759-771.
Zhang, et al., "A Strategy for Increasing Drug Solubility and Efficacy through Covalent Attachment to Polyvalent DNA-Nanoparticle Conjugates", ACS Nano, vol. 5, No. 9, Sep. 27, 2011, 20 pages.
Zhang, et al., "Antibody-linked Spherical Nucleic Acids for Cellular Targeting", Journal of the American Chemical Society, vol. 134, Issue 40, Oct. 10, 2012, 11 pages.
Zhang, et al., "Efficient Construction of Sequence-Specific TAL Effectors for Modulating Mammalian Transcription", Nature Biotechnology, vol. 29, No. 2, Feb. 2011, 149-153.
Zhang, et al., "Hybrid Adeno-Associated Viral Vectors Utilizing Transposase-Mediated Somatic Integration for Stable Transgene Expression in Human Cells", PLoS One, vol. 8, No. 10, e76771, Oct. 2013, 17 pages.
Zheng, et al., "Topical Delivery of siRNA-Based Spherical Nucleic Acid Nanoparticle Conjugates for Gene Regulation", Proceedings of the National Academy of Sciences, vol. 109, No. 30, Jul. 24, 2012, 11975-11980.
Zhou, et al., "Efficiently Controlling for Case-Control Imbalance and Sample Relatedness in Large-Scale Genetic Association Studies", Nature Genetics, vol. 50, No. 9, Sep. 2018, 1335-1341.
Zhou, et al., "Exploiting SNPs for Biallelic CRISPR Mutations in the Outcrossing Woody Perennial Populus Reveals 4-coumarate:CoA ligase Specificity and Redundancy", New Phytologist, vol. 208, Oct. 2015, 298-301.
Zhou, et al., "Fine Tuning of Electrostatics Around the Internucleotidic Phosphate Through Incorporation of Modified 2',4'-carbocyclic-LNAs and -ENAs Leads to Significant Modulation of Antisense Properties", The Journal of Organic Chemistry, vol. 74, No. 1, 2009, 118-134.
Zou, et al., "Generation of Gene-Target Dogs Using CRISPR/Cas9 System", Journal of Molecular Cell Biology, vol. 7, Issue 6, Oct. 12, 2015, 580-583.
Zuker, et al., "Optimal Computer Folding of Large RNA Sequences Using Thermodynamics and Auxiliary Information", Nucleic Acids Research, vol. 9, No. 1, 1981, 133-148.
Bondensgaard, et al. "Structural Studies of LNA:RNA Duplexes by NMR: Conformations and Implications for RNase H Activity**," Chem. Eur. J., vol. 6, No. 15, pp. 2687-2695, 2000.
Braasch, et al., "Locked nucleic acid (LNA): ¢ne-tuning the recognition of DNA and RNA," Chemistry & Biology, No. 8, pp. 1-7, First published online Dec. 19, 2000.
Kurreck, et al., "Design of antisense oligonucleotides stabilized by locked nucleic acids," Nucleic Acids Research, vol. 30, No. 9, pp. 1911-1918, Revised and Accepted Mar. 5, 2002.
Leenay, et al., "Identifying and Visualizing Functional PAM Diversity across CRISPR-Cas Systems," Molecular Cell, vol. 62, pp. 137-147, Apr. 7, 2016.
Wahlestedt, et al., "Potent and nontoxic antisense oligonucleotides containing locked nucleic acids," PNAS, vol. 97, No. 10, pp. 5633-5638, May 9, 2000.

\* cited by examiner

A. Cirrhosis

B. Fatty Liver
*Hepatic Fat On CT Imaging*

*Physician-Diagnosed Fatty Liver*

SEQUENCE LISTING

<160> NUMBER OF SEQ ID NOS: 50

<210> SEQ ID NO 1
<211> LENGTH: 337
<212> TYPE: PRT
<213> ORGANISM: Homo sapiens

<400> SEQUENCE: 1

Met Gly Ala Ala Gly Ser Ser Ala Leu Ala Arg Phe Val Leu Leu Ala
1               5                   10                  15

Gln Ser Arg Pro Gly Trp Leu Gly Val Ala Ala Leu Gly Leu Thr Ala
            20                  25                  30

Val Ala Leu Gly Ala Val Ala Trp Arg Arg Ala Trp Pro Thr Arg Arg
        35                  40                  45

Arg Arg Leu Leu Gln Gln Val Gly Thr Val Ala Gln Leu Trp Ile Tyr
    50                  55                  60

Pro Val Lys Ser Cys Lys Gly Val Pro Val Ser Glu Ala Glu Cys Thr
65                  70                  75                  80

Ala Met Gly Leu Arg Ser Gly Asn Leu Arg Asp Arg Phe Trp Leu Val
                85                  90                  95

Ile Asn Gln Glu Gly Asn Met Val Thr Ala Arg Gln Glu Pro Arg Leu
            100                 105                 110

Val Leu Ile Ser Leu Thr Cys Asp Gly Asp Thr Leu Thr Leu Ser Ala
        115                 120                 125

Ala Tyr Thr Lys Asp Leu Leu Leu Pro Ile Lys Thr Pro Thr Thr Asn
    130                 135                 140

Ala Val His Lys Cys Arg Val His Gly Leu Glu Ile Glu Gly Arg Asp
145                 150                 155                 160

Cys Gly Glu Ala Thr Ala Gln Trp Ile Thr Ser Phe Leu Lys Ser Gln
                165                 170                 175

Pro Tyr Arg Leu Val His Phe Glu Pro His Met Arg Pro Arg Arg Pro
            180                 185                 190

His Gln Ile Ala Asp Leu Phe Arg Pro Lys Asp Gln Ile Ala Tyr Ser
        195                 200                 205

Asp Thr Ser Pro Phe Leu Ile Leu Ser Glu Ala Ser Leu Ala Asp Leu
    210                 215                 220

Asn Ser Arg Leu Glu Lys Lys Val Lys Ala Thr Asn Phe Arg Pro Asn
225                 230                 235                 240

Ile Val Ile Ser Gly Cys Asp Val Tyr Ala Glu Asp Ser Trp Asp Glu
                245                 250                 255

Leu Leu Ile Gly Asp Val Glu Leu Lys Arg Val Met Ala Cys Ser Arg
            260                 265                 270

Cys Ile Leu Thr Thr Val Asp Pro Asp Thr Gly Val Met Ser Arg Lys
        275                 280                 285

Glu Pro Leu Glu Thr Leu Lys Ser Tyr Arg Gln Cys Asp Pro Ser Glu
    290                 295                 300

Arg Lys Leu Tyr Gly Lys Ser Pro Leu Phe Gly Gln Tyr Phe Val Leu
305                 310                 315                 320

Glu Asn Pro Gly Thr Ile Lys Val Gly Asp Pro Val Tyr Leu Leu Gly
                325                 330                 335

Gln

<210> SEQ ID NO 2
<211> LENGTH: 1150
<212> TYPE: DNA

<213> ORGANISM: Homo sapiens

<400> SEQUENCE: 2

```
cttgccgccg ccacctcgcg gagaagccag ccatgggcgc cgccggctcc tccgcgctgg      60
cgcgctttgt cctcctcgcg caatcccggc ccgggtggct cggggttgcc gcgctgggcc     120
tgaccgcggt ggcgctgggg gctgtcgcct ggcgccgcgc atgcccacg cggcgccggc     180
ggctgctgca gcaggtgggc acagtggcgc agctctggat ctaccctgtg aaatcctgca     240
aggggggtgcc ggtgagcgag gcggagtgca cggccatggg gctgcgcagc ggcaacctgc     300
gggacaggtt ttggcttgtg atcaaccagg agggaaacat ggttactgct cgccaggaac     360
ctcgcctggt cctgatttcc ctgacctgcg atggtgacac cctgactctc agtgcagcct     420
acacaaagga cctactactg cctatcaaaa cgcccaccac aaatgcagtg cacaagtgca     480
gagtgcacgg cctggagata gagggcaggg actgtggcga ggccaccgcc cagtggataa     540
ccagcttcct gaagtcacag ccctaccgcc tggtgcactt cgagcctcac atgcgaccga     600
gacgtcctca tcaaatagca gacttgttcc gacccaagga ccagattgct tactcagaca     660
ccagcccatt cttgatcctt tctgaggcgt cgctggcgga tctcaactcc aggctagaga     720
agaaagttaa agcaaccaac ttcaggccca atattgtaat ttcaggatgc gatgtctatg     780
cagaggattc ttgggatgag cttcttattg gtgacgtgga actgaaaagg gtgatggctt     840
gttccagatg cattttaacc acagtggacc cagacaccgg tgtcatgagc aggaaggaac     900
cgctggaaac actgaagagt tatcgccagt gtgacccttc agaacgaaag ttatatggaa     960
aatcaccact ctttgggcag tattttgtgc tggaaaaccc agggaccatc aaagtgggag    1020
accctgtgta cctgctgggc cagtaatggg aaccgtatgt cctggaatat tagatgcctt    1080
ttaaaaatgt tctcaaaaat gacaacactt gaagcatggt gtttcagaac tgagacctct    1140
acattttctt                                                            1150
```

<210> SEQ ID NO 3
<211> LENGTH: 2146
<212> TYPE: DNA
<213> ORGANISM: Homo sapiens

<400> SEQUENCE: 3

```
cattaccgcg caggcttggt caccgcatta aggcattccc gctctccgcg gaactgctct      60
gccgtctcgg cggtgaaagt gtgagagggt ccgtagttgg gtcaactttg actcctctcg     120
cctgcccgga tccttaaggg cctcctcgtc ctcccggtct ccggtcgctg ccgggtctgt     180
gcgccggtcc gcgcccgccc tcgctctgcc atgggcgctt ccagctcctc cgcgctggcc     240
cgcctcggcc tccagcccg gcctggccc aggtggctcg gggtcgccgc gctaggactg     300
gccgccgtgg ccctggggac tgtcgcctgg cgccgcgcat gcccaggcg cgccggcgg     360
ctgcagcagg tggcaccgt ggcgaagctc tggatctacc cggtgaaatc ctgcaaaggg     420
gtgccggtga gcgaggctga gtgcacggcc atgggctgc gcagcggcaa cctgcgggac     480
aggttttggc tggtgattaa ggaagatgga cacatggtca ctgcccgaca ggagcctcgc     540
ctcgtgctca tctccatcat ttatgagaat aactgcctga tcttcaggg tccagacatg     600
gaccagctgg ttttgcctag caagcagcct tcctcaaaca aactccacaa ctgcaggata     660
tttggccttg acattaaagg cagagactgt ggcaatgagg cagctaagtg gttcaccaac     720
ttcttgaaaa ctgaagcgta tagattggtt caatttgaga caaacatgaa gggaagaaca     780
tcaagaaaac ttctccccac tcttgatcag aatttccagg tggcctaccc agactactgc     840
```

```
ccgctcctga tcatgacaga tgcctccctg gtagatttga ataccaggat ggagaagaaa      900
atgaaaatgg agaatttcag gccaaatatt gtggtgaccg gctgtgatgc ttttgaggag      960
gatacctggg atgaactcct aattggtagt gtagaagtga aaaaggtaat ggcatgcccc     1020
aggtgtattt tgacaacggt ggacccagac actggagtca tagacaggaa acagccactg     1080
gacaccctga agagctaccg cctgtgtgat ccttctgaga gggaattgta caagttgtct     1140
ccactttttg ggatctatta ttcagtggaa aaaattggaa gcctgagagt tggtgaccct     1200
gtgtatcgga tggtgtagtg atgagtgatg gatccactag ggtgatatgg cttcagcaac     1260
caggagggat tgactgagat cttaacaaca gcagcaacga tacatcagca aatccttatt     1320
atccagcctt caactatctt taccctggaa aacaatctcg attttttgact tttcaaagtt     1380
gtgtatgctc caggttaatg caaggaaagt attagagggg ggaatatgaa agtatatata     1440
taaattttag gtactgaagg ctttaaaaat aattaagatc atcaaaaatg ctattttgaa     1500
tgttatcatg gctattacac ttttacttcc tgactttaat attgatgaat aaagcaagtt     1560
taatgaatca actaaaaagc tgcaaaaatg ttttttaaaat gtgtgccttt tattacctat     1620
cagtctatgt tttgggagaa atgggaagca acagatcact gtgtcctgat gtgcaggacg     1680
catgttacca cactcacaaa tgcctaatat tggtctttat gtggccattg agtcctgttg     1740
actttccact catgtgcttt ttactctagc attatggaat ctgggctgta cttgagtatg     1800
gaaattctct tatagactta gttttagtac tctattacac ctttactaag ccacataaaa     1860
gtaatctgtt tgtgtgtaac tgccagatat accacctgga attccaagta agataaggaa     1920
gaggatgaca tttaaaagag aatggaattt tgagagtagg aatgcaagga agacagcatg     1980
aacatatttt tttcagtgca ataattttt tcgtaacaaa gaaacgaaca actttggtat     2040
gatcttaagc aaaaatactc actgaaatag tatgtggatg aattcaccta cttacaattt     2100
tatggtttct ttgtaaataa taaatgtgaa tctcaatcct gcttta                   2146
```

<210> SEQ ID NO 4
<211> LENGTH: 335
<212> TYPE: PRT
<213> ORGANISM: Homo sapiens

<400> SEQUENCE: 4

```
Met Gly Ala Ser Ser Ser Ala Leu Ala Arg Leu Gly Leu Pro Ala
1               5                  10                  15

Arg Pro Trp Pro Arg Trp Leu Gly Val Ala Ala Leu Gly Leu Ala Ala
            20                  25                  30

Val Ala Leu Gly Thr Val Ala Trp Arg Arg Ala Trp Pro Arg Arg
        35                  40                  45

Arg Arg Leu Gln Gln Val Gly Thr Val Ala Lys Leu Trp Ile Tyr Pro
    50                  55                  60

Val Lys Ser Cys Lys Gly Val Pro Val Ser Glu Ala Glu Cys Thr Ala
65                  70                  75                  80

Met Gly Leu Arg Ser Gly Asn Leu Arg Asp Arg Phe Trp Leu Val Ile
                85                  90                  95

Lys Glu Asp Gly His Met Val Thr Ala Arg Gln Glu Pro Arg Leu Val
            100                 105                 110

Leu Ile Ser Ile Ile Tyr Glu Asn Asn Cys Leu Ile Phe Arg Ala Pro
        115                 120                 125

Asp Met Asp Gln Leu Val Leu Pro Ser Lys Gln Pro Ser Ser Asn Lys
    130                 135                 140
```

```
Leu His Asn Cys Arg Ile Phe Gly Leu Asp Ile Lys Gly Arg Asp Cys
145                 150                 155                 160

Gly Asn Glu Ala Ala Lys Trp Phe Thr Asn Phe Leu Lys Thr Glu Ala
                165                 170                 175

Tyr Arg Leu Val Gln Phe Glu Thr Asn Met Lys Gly Arg Thr Ser Arg
            180                 185                 190

Lys Leu Leu Pro Thr Leu Asp Gln Asn Phe Gln Val Ala Tyr Pro Asp
        195                 200                 205

Tyr Cys Pro Leu Leu Ile Met Thr Asp Ala Ser Leu Val Asp Leu Asn
210                 215                 220

Thr Arg Met Glu Lys Lys Met Lys Met Glu Asn Phe Arg Pro Asn Ile
225                 230                 235                 240

Val Val Thr Gly Cys Asp Ala Phe Glu Glu Asp Thr Trp Asp Glu Leu
                245                 250                 255

Leu Ile Gly Ser Val Glu Val Lys Lys Val Met Ala Cys Pro Arg Cys
            260                 265                 270

Ile Leu Thr Thr Val Asp Pro Asp Thr Gly Val Ile Asp Arg Lys Gln
        275                 280                 285

Pro Leu Asp Thr Leu Lys Ser Tyr Arg Leu Cys Asp Pro Ser Glu Arg
        290                 295                 300

Glu Leu Tyr Lys Leu Ser Pro Leu Phe Gly Ile Tyr Tyr Ser Val Glu
305                 310                 315                 320

Lys Ile Gly Ser Leu Arg Val Gly Asp Pro Val Tyr Arg Met Val
                325                 330                 335

<210> SEQ ID NO 5
<211> LENGTH: 1992
<212> TYPE: DNA
<213> ORGANISM: Homo sapiens

<400> SEQUENCE: 5
acctgtagac caggaatact gggccagaag aaaaaaatac tgtctagttt agcaaattgc      60
agaatggaca gcactgaatg ttggaacata aaatttttaa aaggttttgg cttgtgatca     120
accaggaggg aaacatggtt actgctcgcc aggaacctcg cctggtcctg atttccctga     180
cctgcgatgg tgacaccctg actctcagtg cagcctacac aaaggaccta ctactgccta     240
tcaaaacgcc caccacaaat gcagtgcaca agtgcagagt gcacggcctg agatagagg      300 gcagggactg tggcgaggcc accgcccagt ggataaccag cttcctgaag tcacagccct     360
accgcctggt gcacttcgag cctcacatgc gaccgagacg tcctcatcaa atagcagact     420
tgttccgacc caaggaccag attgcttact cagacaccag cccattcttg atcctttctg     480
aggcgtcgct ggcggatctc aactccaggc tagagaagaa agttaaagca accaacttca     540
ggcccaatat tgtaatttca ggatgcgatg tctatgcaga ggtaacacta tgcccctttg     600
gatctttcct tggatttgac ttctttttta agatttattc agcacttaat aagtgcagac     660
ttctgtgtgg aggatacaaa tgttgatggg tcagagactg tcatcaagga ggcagttcag     720
tatctaaggc ttctaaggag aattctgagt tgacaggatt cttgggatga gcttcttatt     780
ggtgacgtgg aactgaaaag ggtgatggct tgttccagat gcattttaac acagtggac      840 ccagacaccg tgtcatgag caggaaggaa ccgctggaaa cactgaagag ttatcgccag      900
tgtgacccct tcagaacgaaa gttatatgga aaatcaccac tctttgggca gtattttgtg    960
ctggaaaacc cagggaccat caaagtggga gaccctgtgt acctgctggg ccagtaatgg   1020
```

```
gaaccgtatg tcctggaata ttagatgcct tttaaaaatg ttctcaaaaa tgacaacact   1080
tgaagcatgg tgtttcagaa ctgagacctc tacattttct ttaaatttgt gattttcaca   1140
tttttcgtct tttggacttc tggtgtctca atgcttcaat gtcccagtgc aaaaagtaaa   1200
gaaatatagt ctcaataact tagtaggact tcagtaagtc acttaaatga caagacagga   1260
ttctgaaaac tccccgttta actgattatg gaatagttct ttctcctgct tctccgttta   1320
tctaccaaga gcgcagactt gcatcctgtc actaccactc gttagagaaa gagaagaaga   1380
gaaagaggaa gagtgggtgg gctggaagaa tatcctagaa tgtgttattg cccctgttca   1440
tgaggtacgc aatgaaaatt aaattgcacc ccaaatatgg ctggaatgcc acttcccttt   1500
tcttctcaag ccccgggcta gcttttgaaa tggcataaag actgaggtga ccttcaggaa   1560
gcactgcaga tattaatttt ccatagatct ggatctggcc ctgctgcttc tcagacagca   1620
ttggatttcc taaaggtgct caggaggatg gttgtgtagt catggaggac ccctggatcc   1680
ttgccattcc cctcagctaa tgacggagtg ctccttctcc agttccgggt gaaaaagttc   1740
tgaattctgt ggaggagaag aaaagtgatt cagtgatttc agatagacta ctgaaaacct   1800
ttaaaggggg aaaaggaaag catatgtcag ttgtttaaaa cccaatatct atttttaac   1860 tgattgtata actctaagat ctgatgaagt atatttttta ttgccatttt gtcctttgat   1920
tatattggga agttgactaa acttgaaaaa tgttttaaaa actgtgaata aatggaagct   1980
actttgacta gt                                                       1992
```

<210> SEQ ID NO 6
<211> LENGTH: 202
<212> TYPE: PRT
<213> ORGANISM: Homo sapiens

<400> SEQUENCE: 6

Met Leu Glu His Lys Ile Phe Lys Arg Phe Trp Leu Val Ile Asn Gln
1               5                   10                  15

Glu Gly Asn Met Val Thr Ala Arg Gln Glu Pro Arg Leu Val Leu Ile
            20                  25                  30

Ser Leu Thr Cys Asp Gly Asp Thr Leu Thr Leu Ser Ala Ala Tyr Thr
        35                  40                  45

Lys Asp Leu Leu Leu Pro Ile Lys Thr Pro Thr Thr Asn Ala Val His
    50                  55                  60

Lys Cys Arg Val His Gly Leu Glu Ile Glu Gly Arg Asp Cys Gly Glu
65                  70                  75                  80

Ala Thr Ala Gln Trp Ile Thr Ser Phe Leu Lys Ser Gln Pro Tyr Arg
                85                  90                  95

Leu Val His Phe Glu Pro His Met Arg Pro Arg Pro His Gln Ile
            100                 105                 110

Ala Asp Leu Phe Arg Pro Lys Asp Gln Ile Ala Tyr Ser Asp Thr Ser
        115                 120                 125

Pro Phe Leu Ile Leu Ser Glu Ala Ser Leu Ala Asp Leu Asn Ser Arg
    130                 135                 140

Leu Glu Lys Lys Val Lys Ala Thr Asn Phe Arg Pro Asn Ile Val Ile
145                 150                 155                 160

Ser Gly Cys Asp Val Tyr Ala Glu Val Thr Leu Cys Pro Phe Gly Ser
                165                 170                 175

Phe Leu Gly Phe Asp Phe Phe Phe Lys Ile Tyr Ser Ala Leu Asn Lys
            180                 185                 190

Cys Arg Leu Leu Cys Gly Gly Tyr Lys Cys

<210> SEQ ID NO 7
<211> LENGTH: 1876
<212> TYPE: DNA
<213> ORGANISM: Homo sapiens

<400> SEQUENCE: 7

```
cttcaggcca gcctcgggtc ttattgtgag gctgcacttg aaactccttt ccagagcagc      60
cctcgcagtt cagcaagtaa cacaggacta atgggagctg taacctttct cctaccagct     120
ccccagacag agggcaattc atgacatagt tgaaaggttt tggcttgtga tcaaccagga     180
gggaaacatg gttactgctc gccaggaacc tcgcctggtc ctgatttccc tgacctgcga     240
tggtgacacc ctgactctca gtgcagccta cacaaaggac ctactactgc ctatcaaaac     300
gcccaccaca aatgcagtgc acaagtgcag agtgcacggc ctggagatag agggcaggga     360
ctgtggcgag gccaccgccc agtggataac cagcttcctg aagtcacagc cctaccgcct     420
ggtgcacttc gagcctcaca tgcgaccgag acgtcctcat caaatagcag acttgttccg     480
acccaaggac cagattgctt actcagacac cagcccattc ttgatccttt ctgaggcgtc     540
gctgcggat ctcaactcca ggctagaaa gaaagttaaa gcaaccaact tcaggcccaa     600
tattgtaatt tcaggatgcg atgtctatgc agaggattct gggatgagc ttcttattgg     660
tgacgtgaa ctgaaaaggg tgatggcttg ttccagatgc attttaacca cagtggaccc     720
agacaccggt gtcatgagca ggaaggaacc gctggaaaca ctgaagagtt atcgccagtg     780
tgacccttca gaacgaaagt tatatggaaa atcaccactc tttgggcagt attttgtgct     840
ggaaaaccca gggaccatca agtgggaga ccctgtgtac ctgctgggcc agtaatggga     900
accgtatgtc ctggaatatt agatgccttt taaaaatgtt ctcaaaaatg acaacacttg     960
aagcatggtg tttcagaact gagacctcta catttcttt aaatttgtga ttttcacatt    1020
tttcgtcttt tggacttctg gtgtctcaat gcttcaatgt cccagtgcaa aaagtaaaga    1080
aatatagtct caataactta gtaggacttc agtaagtcac ttaaatgaca agacaggatt    1140
ctgaaaactc cccgtttaac tgattatgga atagttcttt ctcctgcttc tccgtttatc    1200
taccaagagc gcagacttgc atcctgtcac taccactcgt tagagaaaga gaagaagaga    1260
aagaggaaga gtgggtgggc tggaagaata tcctagaatg tgttattgcc cctgttcatg    1320
aggtacgcaa tgaaaattaa attgcacccc aaatatggct ggaatgccac ttcccttttc    1380
ttctcaagcc ccgggctagc ttttgaaatg gcataaagac tgaggtgacc ttcaggaagc    1440
actgcagata ttaattttcc atagatctgg atctggccct gctgcttctc agacagcatt    1500
ggatttccta aggtgctca ggaggatggt tgtgtagtca tggaggaccc ctggatcctt    1560
gccattcccc tcagctaatg acggagtgct ccttctccag ttcgggtga aaaagttctg    1620
aattctgtgg aggagaagaa aagtgattca gtgatttcag atagactact gaaaaccttt    1680
aaaggggaa aaggaaagca tatgtcagtt gtttaaaacc caatatctat tttttaactg    1740
attgtataac tctaagatct gatgaagtat attttttatt gccattttgt cctttgatta    1800
tattgggaag ttgactaaac ttgaaaaatg ttttaaaac tgtgaataaa tggaagctac    1860
tttgactagt ttcaga                                                   1876
```

<210> SEQ ID NO 8
<211> LENGTH: 235
<212> TYPE: PRT
<213> ORGANISM: Homo sapiens

<400> SEQUENCE: 8

```
Met Val Thr Ala Arg Gln Glu Pro Arg Leu Val Leu Ile Ser Leu Thr
1               5                   10                  15
Cys Asp Gly Asp Thr Leu Thr Leu Ser Ala Ala Tyr Thr Lys Asp Leu
            20                  25                  30
Leu Leu Pro Ile Lys Thr Pro Thr Thr Asn Ala Val His Lys Cys Arg
        35                  40                  45
Val His Gly Leu Glu Ile Gly Arg Asp Cys Gly Glu Ala Thr Ala
    50                  55                  60
Gln Trp Ile Thr Ser Phe Leu Lys Ser Gln Pro Tyr Arg Leu Val His
65                  70                  75                  80
Phe Glu Pro His Met Arg Pro Arg Pro His Gln Ile Ala Asp Leu
            85                  90                  95
Phe Arg Pro Lys Asp Gln Ile Ala Tyr Ser Asp Thr Ser Pro Phe Leu
            100                 105                 110
Ile Leu Ser Glu Ala Ser Leu Ala Asp Leu Asn Ser Arg Leu Glu Lys
            115                 120                 125
Lys Val Lys Ala Thr Asn Phe Arg Pro Asn Ile Val Ile Ser Gly Cys
130                 135                 140
Asp Val Tyr Ala Glu Asp Ser Trp Asp Glu Leu Leu Ile Gly Asp Val
145                 150                 155                 160
Glu Leu Lys Arg Val Met Ala Cys Ser Arg Cys Ile Leu Thr Thr Val
            165                 170                 175
Asp Pro Asp Thr Gly Val Met Ser Arg Lys Glu Pro Leu Glu Thr Leu
            180                 185                 190
Lys Ser Tyr Arg Gln Cys Asp Pro Ser Glu Arg Lys Leu Tyr Gly Lys
            195                 200                 205
Ser Pro Leu Phe Gly Gln Tyr Phe Val Leu Glu Asn Pro Gly Thr Ile
            210                 215                 220
Lys Val Gly Asp Pro Val Tyr Leu Leu Gly Gln
225                 230                 235
```

<210> SEQ ID NO 9
<211> LENGTH: 1947
<212> TYPE: DNA
<213> ORGANISM: Homo sapiens

<400> SEQUENCE: 9

```
ttgtcctctt tagggtctgg cttcaggcca gcctcgggtc ttattgtgag gctgcacttg      60
aaactccttt ccagagcagc cctcgcagtt cagcaagtaa cacaggacta atgggagctg     120
taacctttct cctaccagct ccccagacag agggcaattc atgacatagt tgaaaggttt     180
tggcttgtga tcaaccagga gggaaacatg gttactgctc gccaggaacc tcgcctggtc     240
ctgatttccc tgacctgcga tggtgacacc ctgactctca gtgcagccta cacaaaggac     300
ctactactgc ctatcaaaac gcccaccaca aatgcagtgc acaagtgcag agtgcacggc     360
ctggagatag agggcaggga ctgtggcgag gccaccgccc agtggataac cagcttcctg     420
aagtcacagc cctaccgcct ggtgcacttc gagcctcaca tgcgaccgag acgtcctcat     480
caaatagcag acttgttccg acccaaggac cagattgctt actcagacac cagcccattc     540
ttgatccttt ctgaggcgtc gctggcggat ctcaactcca ggctagagaa gaaagttaaa     600
gcaaccaact tcaggcccaa tattgtaatt tcaggatgcg atgtctatgc agaggtaaca     660
ctatgccccct ttggatcttt ccttggattt gacttctttt ttaaggattc ttgggatgag     720
```

-continued

```
cttcttattg gtgacgtgga actgaaaagg gtgatggctt gttccagatg cattttaacc     780
acagtggacc cagacaccgg tgtcatgagc aggaaggaac cgctggaaac actgaagagt     840
tatcgccagt gtgaccctc agaacgaaag ttatatggaa atcaccact ctttgggcag      900
tattttgtgc tggaaaaccc agggaccatc aaagtgggag accctgtgta cctgctgggc     960
cagtaatggg aaccgtatgt cctggaatat tagatgcctt ttaaaaatgt tctcaaaaat    1020
gacaacactt gaagcatggt gtttcagaac tgagacctct acattttctt taaatttgtg    1080
attttcacat ttttcgtctt ttggacttct ggtgtctcaa tgcttcaatg tcccagtgca    1140
aaaagtaaag aaatatagtc tcaataactt agtaggactt cagtaagtca cttaaatgac    1200
aagacaggat tctgaaaact ccccgtttaa ctgattatgg aatagttctt tctcctgctt    1260
ctccgtttat ctaccaagag cgcagacttg catcctgtca ctaccactcg ttagagaaag    1320
agaagaagag aaagaggaag agtgggtggg ctggaagaat atcctagaat gtgttattgc    1380
ccctgttcat gaggtacgca atgaaaatta aattgcaccc caaatatggc tggaatgcca    1440
cttccctttt cttctcaagc cccgggctag cttttgaaat ggcataaaga ctgaggtgac    1500
cttcaggaag cactgcagat attaattttc catagatctg gatctggccc tgctgcttct    1560
cagacagcat tggatttcct aaaggtgctc aggaggatgg ttgtgtagtc atggaggacc    1620
cctggatcct tgccattccc ctcagctaat gacggagtgc tccttctcca gttccgggtg    1680
aaaaagttct gaattctgtg gaggagaaga aaagtgattc agtgatttca gatagactac    1740
tgaaaacctt taaggggga aaaggaaagc atatgtcagt tgtttaaaac ccaatatcta    1800
ttttttaact gattgtataa ctctaagatc tgatgaagta tattttttat tgccattttg    1860
tcctttgatt atattgggaa gttgactaaa cttgaaaaat gttttaaaa ctgtgaataa    1920
atggaagcta ctttgactag tttcaga                                       1947
```

<210> SEQ ID NO 10
<211> LENGTH: 252
<212> TYPE: PRT
<213> ORGANISM: Homo sapiens

<400> SEQUENCE: 10

```
Met Val Thr Ala Arg Gln Glu Pro Arg Leu Val Leu Ile Ser Leu Thr
1               5                   10                  15

Cys Asp Gly Asp Thr Leu Thr Leu Ser Ala Ala Tyr Thr Lys Asp Leu
                20                  25                  30

Leu Leu Pro Ile Lys Thr Pro Thr Thr Asn Ala Val His Lys Cys Arg
            35                  40                  45

Val His Gly Leu Glu Ile Glu Gly Arg Asp Cys Gly Glu Ala Thr Ala
        50                  55                  60

Gln Trp Ile Thr Ser Phe Leu Lys Ser Gln Pro Tyr Arg Leu Val His
65                  70                  75                  80

Phe Glu Pro His Met Arg Pro Arg Arg Pro His Gln Ile Ala Asp Leu
                85                  90                  95

Phe Arg Pro Lys Asp Gln Ile Ala Tyr Ser Asp Thr Ser Pro Phe Leu
            100                 105                 110

Ile Leu Ser Glu Ala Ser Leu Ala Asp Leu Asn Ser Arg Leu Glu Lys
        115                 120                 125

Lys Val Lys Ala Thr Asn Phe Arg Pro Asn Ile Val Ile Ser Gly Cys
    130                 135                 140

Asp Val Tyr Ala Glu Val Thr Leu Cys Pro Phe Gly Ser Phe Leu Gly
```

```
                145                 150                 155                 160
           Phe Asp Phe Phe Phe Lys Asp Ser Trp Asp Glu Leu Leu Ile Gly Asp
                           165                 170                 175

Val Glu Leu Lys Arg Val Met Ala Cys Ser Arg Cys Ile Leu Thr Thr
                       180                 185                 190

Val Asp Pro Asp Thr Gly Val Met Ser Arg Lys Glu Pro Leu Glu Thr
                       195                 200                 205

Leu Lys Ser Tyr Arg Gln Cys Asp Pro Ser Arg Lys Leu Tyr Gly
               210                 215                 220

Lys Ser Pro Leu Phe Gly Gln Tyr Phe Val Leu Glu Asn Pro Gly Thr
           225                 230                 235                 240

Ile Lys Val Gly Asp Pro Val Tyr Leu Leu Gly Gln
                               245                 250

<210> SEQ ID NO 11
<211> LENGTH: 1150
<212> TYPE: DNA
<213> ORGANISM: Homo sapiens

<400> SEQUENCE: 11
cttgccgccg ccacctcgcg gagaagccag ccatgggcgc cgccggctcc tccgcgctgg        60
cgcgctttgt cctcctcgcg caatcccggc ccgggtggct cggggttgcc gcgctgggcc       120
tgaccgcggt ggcgctgggg gctgtcgcct ggcgccgcg  atgcccacg cggcgccggc       180 ggctgctgca gcaggtgggc acagtggcgc agctctggat ctaccctgtg aaatcctgca       240 aggggggtgcc ggtgagcgag gcggagtgca cggccatggg gctgcgcagc ggcaacctgc      300
gggacaggtt ttggcttgtg atcaaccagg agggaaacat ggttactgct cgccaggaac      360
ctcgcctggt cctgatttcc ctgacctgcg atggtgacac cctgactctc agtgcagcct      420
acacaaagga cctactactg cctatcaaaa cgcccaccac aaatgcagtg cacaagtgca      480
gagtgcacgg cctggagata gagggcaggg actgtggcga ggccaccgcc cagtggataa      540
ccagcttcct gaagtcacag ccctaccgcc tggtgcactt cgagcctcac atgcgaccga      600
gacgtcctca tcaaatagca gacttgttcc gacccaagga ccagattgct tactcagaca      660
ccagcccatt cttgatcctt tctgaggcgt cgctggcgga tctcaactcc aggctagaga      720
agaaagttaa agcaaccaac ttcaggccca atattgtaat ttcaggatgc gatgtctatg      780
cagaggattc ttgggatgag cttcttattg gtgacgtgga actgaaaagg gtgatggctt      840
gttccagatg cattttaacc acagtggacc cagacaccgg tgtcatgagc aggaaggaac      900
cgctggaaac actgaagagt tatcgccagt gtgacccttc agaacgaaag ttatatggaa      960
aatcaccact ctttgggcag tattttgtgc tggaaaaccc agggaccatc aaagtgggag     1020
accctgtgta cctgctgggc cagtaatggg aaccgtatgt cctggaatat agatgccttt     1080 taaaaatgt tctcaaaaat gacaacactt gaagcatggt gtttcagaac tgagacctct     1140
acatttctt                                                            1150

<210> SEQ ID NO 12
<211> LENGTH: 254
<212> TYPE: PRT
<213> ORGANISM: Homo sapiens

<400> SEQUENCE: 12

Met Leu Glu His Lys Ile Phe Lys Arg Phe Trp Leu Val Ile Asn Gln
1               5                   10                  15
```

Glu Gly Asn Met Val Thr Ala Arg Gln Glu Pro Arg Leu Val Leu Ile
            20                  25                  30

Ser Leu Thr Cys Asp Gly Asp Thr Leu Thr Leu Ser Ala Ala Tyr Thr
        35                  40                  45

Lys Asp Leu Leu Leu Pro Ile Lys Thr Pro Thr Thr Asn Ala Val His
    50                  55                  60

Lys Cys Arg Val His Gly Leu Glu Ile Glu Gly Arg Asp Cys Gly Glu
65                  70                  75                  80

Ala Thr Ala Gln Trp Ile Thr Ser Phe Leu Lys Ser Gln Pro Tyr Arg
                85                  90                  95

Leu Val His Phe Glu Pro His Met Arg Pro Arg Pro His Gln Ile
            100                 105                 110

Ala Asp Leu Phe Arg Pro Lys Asp Gln Ile Ala Tyr Ser Asp Thr Ser
        115                 120                 125

Pro Phe Leu Ile Leu Ser Glu Ala Ser Leu Ala Asp Leu Asn Ser Arg
    130                 135                 140

Leu Glu Lys Lys Val Lys Ala Thr Asn Phe Arg Pro Asn Ile Val Ile
145                 150                 155                 160

Ser Gly Cys Asp Val Tyr Ala Glu Asp Ser Trp Asp Glu Leu Leu Ile
                165                 170                 175

Gly Asp Val Glu Leu Lys Arg Val Met Ala Cys Ser Arg Cys Ile Leu
            180                 185                 190

Thr Thr Val Asp Pro Asp Thr Gly Val Met Ser Arg Lys Glu Pro Leu
        195                 200                 205

Glu Thr Leu Lys Ser Tyr Arg Gln Cys Asp Pro Ser Glu Arg Lys Leu
    210                 215                 220

Tyr Gly Lys Ser Pro Leu Phe Gly Gln Tyr Phe Val Leu Glu Asn Pro
225                 230                 235                 240

Gly Thr Ile Lys Val Gly Asp Pro Val Tyr Leu Leu Gly Gln
                245                 250

<210> SEQ ID NO 13
<211> LENGTH: 2670
<212> TYPE: DNA
<213> ORGANISM: Homo sapiens

<400> SEQUENCE: 13

```
ttctctgttg atggacactc gggctgttac tacttttttca gcattttgat taaagctgca      60
ataaacattg atacacaaat gtctgtttga gttcctgttt tcagttcttt ggggtctata     120
cgtaggagtg tgctaggtat tttatgtttt atatatattt tactgcaatt aaaaaataaa     180
tatataaaag actggcctgt gtgaagacct cgggaggtaa gaatggctgg agcaacagct     240
ggatcatgaa gggctgggca cgccttgtt taggagttgg ttttatcctg aaagcaggaa      300
ccatggaggg attttgaatg aggggtcat aaagttagat ttgcatttta gagcgatgta      360
aactgccatt accaggaaga atattagaca gaatattcac ctgctagtcc caaggatttg     420
ggtcagggca ggcctctgtc tgtgcagaaa caaagtctgg taaaagggca gttacggaaa     480
gggcttatac taagcatatt tttctagtgt agctgaacaa ctcaaccatg ataacctgct     540
ggaagtgatg caagaaatat cttgaacgac ctaaagtacc ggccatattt ttttcttatg     600
tctggaaatc tcaaaagcac atgctcactt ctataattgt aatcatttga tcagtgtgta     660
ctgtaaggat tgaaatgcca atatgttttg cttccttggt agctgagaga taacctgcaa     720
aaacatgttg ttcttgttct ggaaatggct ctttctatta cctttatttc tccatttatc     780
```

```
ttttttttcta ggaagtacct gtagaccagg aatactgggc cagaagaaaa aaatactgtc    840
tagtttagca aattgcagaa tggacagcac tgaatgttgg aacataaaat ttttaaaagg    900
ttttggcttg tgatcaacca ggagggaaac atggttactg ctcgccagga acctcgcctg    960
gtcctgattt ccctgacctg cgatggtgac accctgactc tcagtgcagc ctacacaaag   1020
gacctactac tgcctatcaa acgcccacc acaaatgcag tgcacaagtg cagagtgcac    1080
ggcctggaga tagagggcag ggactgtggc gaggccaccg cccagtggat aaccagcttc   1140
ctgaagtcac agccctaccg cctggtgcac ttcgagcctc acatgcgacc gagacgtcct   1200
catcaaatag cagacttgtt ccgacccaag gaccagattg cttactcaga caccagccca   1260
ttcttgatcc tttctgaggc gtcgctggcg atctcaact ccaggctaga aagaaagtt    1320 aaagcaacca acttcaggcc caatattgta atttcaggat gcgatgtcta tgcagaggta   1380
acactatgcc cctttggatc tttccttgga tttgacttct tttttaagga ttcttgggat   1440
gagcttctta ttggtgacgt ggaactgaaa agggtgatgg cttgttccag atgcatttta   1500
accacagtgg acccagacac cggtgtcatg agcaggaagg aaccgctgga acactgaag   1560 agttatcgcc agtgtgaccc ttcagaacga aagttatatg gaaaatcacc actctttggg   1620
cagtattttg tgctggaaaa cccagggacc atcaaagtgg agaccctgt gtacctgctg    1680 ggccagtaat gggaaccgta tgtcctggaa tattagatgc cttttaaaaa tgttctcaaa   1740
aatgacaaca cttgaagcat ggtgtttcag aactgagacc tctacatttt ctttaaattt   1800
gtgattttca cattttcgt cttttggact tctggtgtct caatgcttca atgtcccagt    1860
gcaaaaagta aagaaatata gtctcaataa cttagtagga cttcagtaag tcacttaaat   1920
gacaagacag gattctgaaa actccccgtt taactgatta tggaatagtt ctttctcctg   1980
cttctccgtt tatctaccaa gagcgcagac ttgcatcctg tcactaccac tcgttagaga   2040
aagagaagaa gagaaagagg aagagtgggt gggctggaag aatatcctag aatgtgttat   2100
tgcccctgtt catgaggtac gcaatgaaaa ttaaattgca ccccaaatat ggctggaatg   2160
ccacttccct tttcttctca gccccgggc tagcttttga aatggcataa agactgaggt    2220
gaccttcagg aagcactgca gatattaatt ttccatagat ctggatctgg ccctgctgct   2280
tctcagacag cattggattt cctaaaggtg ctcaggagga tggttgtgta gtcatggagg   2340
acccctggat ccttgccatt cccctcagct aatgacggag tgctccttct ccagttccgg   2400
gtgaaaaagt tctgaattct gtggaggaga agaaagtga ttcagtgatt tcagatagac    2460
tactgaaaac ctttaaaggg ggaaaaggaa agcatatgtc agttgtttaa acccaatat    2520 ctattttta actgattgta taactctaag atctgatgaa gtatatttt tattgccatt    2580 ttgtcctttg attatattgg gaagttgact aaacttgaaa aatgttttta aaactgtgaa   2640
taaatggaag ctactttgac tagtttcaga                                    2670
```

<210> SEQ ID NO 14
<211> LENGTH: 271
<212> TYPE: PRT
<213> ORGANISM: Homo sapiens

<400> SEQUENCE: 14

```
Met Leu Glu His Lys Ile Phe Lys Arg Phe Trp Leu Val Ile Asn Gln
1               5                   10                  15

Glu Gly Asn Met Val Thr Ala Arg Gln Glu Pro Arg Leu Val Leu Ile
            20                  25                  30

Ser Leu Thr Cys Asp Gly Asp Thr Leu Thr Leu Ser Ala Ala Tyr Thr
```

```
                35                  40                  45
Lys Asp Leu Leu Leu Pro Ile Lys Thr Pro Thr Thr Asn Ala Val His
 50                  55                  60

Lys Cys Arg Val His Gly Leu Glu Ile Glu Gly Arg Asp Cys Gly Glu
 65                  70                  75                  80

Ala Thr Ala Gln Trp Ile Thr Ser Phe Leu Lys Ser Gln Pro Tyr Arg
                 85                  90                  95

Leu Val His Phe Glu Pro His Met Arg Pro Arg Pro His Gln Ile
                100                 105                 110

Ala Asp Leu Phe Arg Pro Lys Asp Gln Ile Ala Tyr Ser Asp Thr Ser
                115                 120                 125

Pro Phe Leu Ile Leu Ser Glu Ala Ser Leu Ala Asp Leu Asn Ser Arg
        130                 135                 140

Leu Glu Lys Lys Val Lys Ala Thr Asn Phe Arg Pro Asn Ile Val Ile
145                 150                 155                 160

Ser Gly Cys Asp Val Tyr Ala Glu Val Thr Leu Cys Pro Phe Gly Ser
                165                 170                 175

Phe Leu Gly Phe Asp Phe Phe Lys Asp Ser Trp Asp Glu Leu Leu
                180                 185                 190

Ile Gly Asp Val Glu Leu Lys Arg Val Met Ala Cys Ser Arg Cys Ile
        195                 200                 205

Leu Thr Thr Val Asp Pro Asp Thr Gly Val Met Ser Arg Lys Glu Pro
210                 215                 220

Leu Glu Thr Leu Lys Ser Tyr Arg Gln Cys Asp Pro Ser Glu Arg Lys
225                 230                 235                 240

Leu Tyr Gly Lys Ser Pro Leu Phe Gly Gln Tyr Phe Val Leu Glu Asn
                245                 250                 255

Pro Gly Thr Ile Lys Val Gly Asp Pro Val Tyr Leu Leu Gly Gln
                260                 265                 270
```

<210> SEQ ID NO 15
<211> LENGTH: 1236
<212> TYPE: DNA
<213> ORGANISM: Homo sapiens

<400> SEQUENCE: 15

| | | | | |
|---|---|---|---|---|
| acagcgccct gcagcgcagg cgacggaagg ttgcagaggc agtggggcgc cgaccaagtg | 60 |
| gaagctgagc caccacctcc cactcccgc gccgcccccc agaaggacgc actgctctga | 120 |
| ttggcccgga agggttcagg agctgcccag cctttgggct cggggccaaa ggccgcacct | 180 |
| tcccccagcg gccccgggcg accagcgcgc tccggccttg ccgccgccac ctcgcggaga | 240 |
| agccagccat gggcgccgcc ggctcctccg cgctggcgcg cttttgtcctc ctcgcgcaat | 300 |
| cccggcccgg gtggctcggg gttgccgcgc tgggcctgac cgcggtggcg ctggggctg | 360 |
| tcgcctggcg ccgcgcatgg cccacgcggc gccggcggct gctgcagcag gtgggcacag | 420 |
| tggcgcagct ctggatctac cctgtgaaat cctgcaaggg ggtgccggtg agcgaggcgg | 480 |
| agtgcacggc catggggctg cgcagcggca acctgcggga caggttttgg cttgtgatca | 540 |
| accaggaggg aaacatggtt actgctcgcc aggaacctcg cctggtcctg atttccctga | 600 |
| cctgcgatgg tgacaccctg actctcagtg cagcctacac aaaggaccta ctactgccta | 660 |
| tcaaaacgcc caccacaaat gcagtgcaca agtgcagagt gcacggcctg agatagagg | 720 |
| gcagggactg tggcgaggcc accgcccagt ggataaccag cttcctgaag tcacagccct | 780 |
| accgcctggt gcacttcgag cctcacatgc gaccgagacg tcctcatcaa atagcagact | 840 |

```
tgttccgacc caaggaccag attgcttact cagacaccag cccattcttg atcctttctg      900
aggcgtcgct ggcggatctc aactccaggc tagagaagaa agttaaagca accaacttca      960
ggcccaatat tgtaatttca ggatgcgatg tctatgcaga ggtaacacta tgcccctttg     1020
gatctttcct tggatttgac ttcttttta agatttattc agcacttaat aagtgcagac      1080
ttctgtgtgg aggatacaaa tgttgatggg tcagagactg tcatcaagga ggcagttcag     1140
tatctaaggc ttctaaggag aattctgagt tgacaggatt cttgggatga gcttcttatt     1200
ggtgacgtgg aactgaaaag ggtgatggct tgttcc                              1236
```

<210> SEQ ID NO 16
<211> LENGTH: 285
<212> TYPE: PRT
<213> ORGANISM: Homo sapiens

<400> SEQUENCE: 16

```
Met Gly Ala Ala Gly Ser Ser Ala Leu Ala Arg Phe Val Leu Leu Ala
1               5                   10                  15

Gln Ser Arg Pro Gly Trp Leu Gly Val Ala Ala Leu Gly Leu Thr Ala
            20                  25                  30

Val Ala Leu Gly Ala Val Ala Trp Arg Arg Ala Trp Pro Thr Arg Arg
        35                  40                  45

Arg Arg Leu Leu Gln Gln Val Gly Thr Val Ala Gln Leu Trp Ile Tyr
    50                  55                  60

Pro Val Lys Ser Cys Lys Gly Val Pro Val Ser Glu Ala Glu Cys Thr
65                  70                  75                  80

Ala Met Gly Leu Arg Ser Gly Asn Leu Arg Asp Arg Phe Trp Leu Val
                85                  90                  95

Ile Asn Gln Glu Gly Asn Met Val Thr Ala Arg Gln Glu Pro Arg Leu
            100                 105                 110

Val Leu Ile Ser Leu Thr Cys Asp Gly Asp Thr Leu Thr Leu Ser Ala
        115                 120                 125

Ala Tyr Thr Lys Asp Leu Leu Leu Pro Ile Lys Thr Pro Thr Thr Asn
    130                 135                 140

Ala Val His Lys Cys Arg Val His Gly Leu Glu Ile Glu Gly Arg Asp
145                 150                 155                 160

Cys Gly Glu Ala Thr Ala Gln Trp Ile Thr Ser Phe Leu Lys Ser Gln
                165                 170                 175

Pro Tyr Arg Leu Val His Phe Glu Pro His Met Arg Pro Arg Arg Pro
            180                 185                 190

His Gln Ile Ala Asp Leu Phe Arg Pro Lys Asp Gln Ile Ala Tyr Ser
        195                 200                 205

Asp Thr Ser Pro Phe Leu Ile Leu Ser Glu Ala Ser Leu Ala Asp Leu
    210                 215                 220

Asn Ser Arg Leu Glu Lys Lys Val Lys Ala Thr Asn Phe Arg Pro Asn
225                 230                 235                 240

Ile Val Ile Ser Gly Cys Asp Val Tyr Ala Glu Val Thr Leu Cys Pro
                245                 250                 255

Phe Gly Ser Phe Leu Gly Phe Asp Phe Phe Lys Ile Tyr Ser Ala
            260                 265                 270

Leu Asn Lys Cys Arg Leu Leu Cys Gly Gly Tyr Lys Cys
    275                 280                 285
```

<210> SEQ ID NO 17

<211> LENGTH: 1534
<212> TYPE: DNA
<213> ORGANISM: Homo sapiens

<400> SEQUENCE: 17

| | | | | | |
|---|---|---|---|---|---|
| acagcgccct | gcagcgcagg | cgacggaagg | ttgcagaggc | agtggggcgc | cgaccaagtg | 60 |
| gaagctgagc | caccacctcc | cactcccgc | gccgcccccc | agaaggacgc | actgctctga | 120 |
| ttggcccgga | agggttcagg | agctgccag | cctttgggct | cggggccaaa | ggccgcacct | 180 |
| tcccccagcg | gccccgggcg | accagcgcgc | tccggccttg | ccgccgccac | ctcgcggaga | 240 |
| agccagccat | gggcgccgcc | ggctcctccg | cgctggcgcg | ctttgtcctc | ctcgcgcaat | 300 |
| cccggcccgg | gtggctcggg | gttgccgcgc | tgggcctgac | cgccgtggcg | ctggggctg | 360 |
| tcgcctggcg | ccgcgcatgg | cccacgcggc | gccggcggct | gctgcagcag | gtgggcacag | 420 |
| tggcgcagct | ctggatctac | cctgtgaaat | cctgcaaggg | ggtgccggtg | agcgaggcgg | 480 |
| agtgcacggc | catggggctg | cgcagcggca | acctgcggga | caggttttgg | cttgtgatca | 540 |
| accaggaggg | aaacatggtt | actgctcgcc | aggaaccctcg | cctggtcctg | atttccctga | 600 |
| cctgcgatgg | tgacaccctg | actctcagtg | cagcctacac | aaaggaccta | ctactgccta | 660 |
| tcaaaacgcc | caccacaaat | gcagtgcaca | agtgcagagt | gcacggcctg | agatagagg | 720 |
| gcagggactg | tggcgaggcc | accgcccagt | ggataaccag | cttcctgaag | tcacagccct | 780 |
| accgcctggt | gcacttcgag | cctcacatgc | gaccgagacg | tcctcatcaa | atagcagact | 840 |
| tgttccgacc | caaggaccag | attgcttact | cagacaccag | cccattcttg | atcctttctg | 900 |
| aggcgtcgct | ggcggatctc | aactccaggc | tagagaagaa | agttaaagca | accaacttca | 960 |
| ggcccaatat | tgtaatttca | ggatgcgatg | tctatgcaga | ggtaacacta | tgccccttg | 1020 |
| gatctttcct | tggatttgac | ttcttttta | agatttattc | agcacttaat | aagtgcagac | 1080 |
| ttctgtgtgg | aggatacaaa | tgttgatggg | tcagagactg | tcatcaagga | ggcagttcag | 1140 |
| tatctaaggc | ttctaaggag | aattctgagt | tgacagggaa | aaatggaatc | aaagcaattg | 1200 |
| agttttaacc | ttttatcctc | agaggagcca | attatattct | tcacttttgc | tgtacggagg | 1260 |
| caaaactatg | ctgaaagaga | ataatctaa | gaatttgatt | cccacattca | aaccagaaga | 1320 |
| tgtgacggct | ggtttcagct | tctgcactgg | cttctgcatg | actttgagca | gccccgctaa | 1380 |
| gtcccattta | ccttgcctga | caatgagat | gatcatattt | ctgcctaggg | ttaccttaag | 1440 |
| ggtctgttga | agggtcagtt | tggataatgt | aatttatgag | atgtataaaa | gcaatatcaa | 1500 |
| tcgatggagg | ataataaaag | tacgcccaaa | tcca | | | 1534 |

<210> SEQ ID NO 18
<211> LENGTH: 285
<212> TYPE: PRT
<213> ORGANISM: Homo sapiens

<400> SEQUENCE: 18

Met Gly Ala Ala Gly Ser Ser Ala Leu Ala Arg Phe Val Leu Leu Ala
1               5                   10                  15

Gln Ser Arg Pro Gly Trp Leu Gly Val Ala Ala Leu Gly Leu Thr Ala
            20                  25                  30

Val Ala Leu Gly Ala Val Ala Trp Arg Arg Ala Trp Pro Thr Arg Arg
        35                  40                  45

Arg Arg Leu Leu Gln Gln Val Gly Thr Val Ala Gln Leu Trp Ile Tyr
    50                  55                  60

Pro Val Lys Ser Cys Lys Gly Val Pro Val Ser Glu Ala Glu Cys Thr

```
              65                  70                  75                  80
Ala Met Gly Leu Arg Ser Gly Asn Leu Arg Asp Arg Phe Trp Leu Val
                    85                  90                  95
Ile Asn Gln Glu Gly Asn Met Val Thr Ala Arg Gln Glu Pro Arg Leu
                100                 105                 110
Val Leu Ile Ser Leu Thr Cys Asp Gly Asp Thr Leu Thr Leu Ser Ala
                115                 120                 125
Ala Tyr Thr Lys Asp Leu Leu Leu Pro Ile Lys Thr Pro Thr Thr Asn
130                 135                 140
Ala Val His Lys Cys Arg Val His Gly Leu Glu Ile Glu Gly Arg Asp
145                 150                 155                 160
Cys Gly Glu Ala Thr Ala Gln Trp Ile Thr Ser Phe Leu Lys Ser Gln
                165                 170                 175
Pro Tyr Arg Leu Val His Phe Glu Pro His Met Arg Pro Arg Arg Pro
                180                 185                 190
His Gln Ile Ala Asp Leu Phe Arg Pro Lys Asp Gln Ile Ala Tyr Ser
                195                 200                 205
Asp Thr Ser Pro Phe Leu Ile Leu Ser Glu Ala Ser Leu Ala Asp Leu
                210                 215                 220
Asn Ser Arg Leu Glu Lys Lys Val Lys Ala Thr Asn Phe Arg Pro Asn
225                 230                 235                 240
Ile Val Ile Ser Gly Cys Asp Val Tyr Ala Glu Val Thr Leu Cys Pro
                245                 250                 255
Phe Gly Ser Phe Leu Gly Phe Asp Phe Phe Phe Lys Ile Tyr Ser Ala
                260                 265                 270
Leu Asn Lys Cys Arg Leu Leu Cys Gly Gly Tyr Lys Cys
                275                 280                 285

<210> SEQ ID NO 19
<211> LENGTH: 2294
<212> TYPE: DNA
<213> ORGANISM: Homo sapiens

<400> SEQUENCE: 19
acagcgccct gcagcgcagg cgacggaagg ttgcagaggc agtggggcgc cgaccaagtg      60
gaagctgagc caccacctcc cactccccgc gccgccccc  agaaggacgc actgctctga     120
ttggcccgga agggttcagg agctgccccag cctttgggct cggggccaaa ggccgcacct    180
tcccccagcg gccccgggcg accagcgcgc tccggccttg ccgccgccac ctcgcggaga     240
agccagccat gggcgccgcc ggctcctccg cgctggcgcg ctttgtcctc ctcgcgcaat     300
cccggcccgg gtggctcggg gttgccgcgc tgggcctgac cgcggtggcg ctggggctg     360 tcgcctggcg ccgcgcatgg cccacgcggc gccggcggct gctgcagcag gtgggcacag    420
tggcgcagct ctggatctac cctgtgaaat cctgcaaggg ggtgccggtg agcgaggcgg    480
agtgcacggc catggggctg cgcagcggca acctgcggga caggttttgg cttgtgatca    540
accaggaggg aaacatggtt actgctcgcc aggaacctcg cctggtcctg atttccctga    600
cctgcgatgg tgacaccctg actctcagtg cagcctacac aaaggaccta ctactgccta    660
tcaaaacgcc caccacaaat gcagtgcaca agtgcagagt gcacggcctg gagatagagg    720
gcagggactg tggcgaggcc accgcccagt ggataaccag cttcctgaag tcacagccct    780
accgcctggt gcacttcgag cctcacatgc gaccgagacg tcctcatcaa atagcagact    840
tgttccgacc caaggaccag attgcttact cagacaccag cccattcttg atcctttctg    900
```

```
aggcgtcgct ggcggatctc aactccaggc tagagaagaa agttaaagca accaacttca    960
ggcccaatat tgtaatttca ggatgcgatg tctatgcaga ggtaacacta tgcccctttg   1020
gatctttcct tggatttgac ttcttttta aggattcttg ggatgagctt cttattggtg   1080
acgtggaact gaaagggtg atggcttgtt ccagatgcat tttaaccaca gtggacccag   1140
acaccggtgt catgagcagg aaggaaccgc tggaaacact gaagagttat cgccagtgtg   1200
acccttcaga acgaaagtta tatggaaaat caccactctt tgggcagtat tttgtgctgg   1260
aaaacccagg gaccatcaaa gtgggagacc ctgtgtacct gctgggccag taatgggaac   1320
cgtatgtcct ggaatattag atgccttta aaaatgttct caaaaatgac aacacttgaa   1380
gcatggtgtt tcagaactga gacctctaca ttttctttaa atttgtgatt ttcacatttt   1440
tcgtctttg gacttctggt gtctcaatgc ttcaatgtcc cagtgcaaaa agtaaagaaa   1500
tatagtctca ataacttagt aggacttcag taagtcactt aaatgacaag acaggattct   1560
gaaaactccc cgtttaactg attatggaat agttctttct cctgcttctc cgtttatcta   1620
ccaagagcgc agacttgcat cctgtcacta ccactcgtta gagaaagaga agaagagaaa   1680
gaggaagagt gggtgggctg gaagaatatc ctagaatgtg ttattgcccc tgttcatgag   1740
gtacgcaatg aaaattaaat tgcacccccaa atatggctgg aatgccactt cccttttctt   1800
ctcaagcccc gggctagctt ttgaaatggc ataaagactg aggtgacctt caggaagcac   1860
tgcagatatt aattttccat agatctggat ctggccctgc tgcttctcag acagcattgg   1920
atttcctaaa ggtgctcagg aggatggttg tgtagtcatg gaggacccct ggatccttgc   1980
cattccctc agctaatgac ggagtgctcc ttctccagtt ccgggtgaaa aagttctgaa   2040
ttctgtggag gagaagaaaa gtgattcagt gatttcagat agactactga aaacctttaa   2100
agggggaaaa ggaaagcata tgtcagttgt ttaaaaccca atatctattt tttaactgat   2160
tgtataactc taagatctga tgaagtatat tttttattgc cattttgtcc tttgattata   2220
ttgggaagtt gactaaactt gaaaaatgtt tttaaaactg tgaataaatg gaagctactt   2280
tgactagttt caga                                                    2294
```

<210> SEQ ID NO 20
<211> LENGTH: 354
<212> TYPE: PRT
<213> ORGANISM: Homo sapiens

<400> SEQUENCE: 20

```
Met Gly Ala Ala Gly Ser Ser Ala Leu Ala Arg Phe Val Leu Leu Ala
1               5                   10                  15

Gln Ser Arg Pro Gly Trp Leu Gly Val Ala Ala Leu Gly Leu Thr Ala
            20                  25                  30

Val Ala Leu Gly Ala Val Ala Trp Arg Arg Ala Trp Pro Thr Arg Arg
        35                  40                  45

Arg Arg Leu Leu Gln Gln Val Gly Thr Val Ala Gln Leu Trp Ile Tyr
    50                  55                  60

Pro Val Lys Ser Cys Lys Gly Val Pro Val Ser Glu Ala Glu Cys Thr
65                  70                  75                  80

Ala Met Gly Leu Arg Ser Gly Asn Leu Arg Asp Arg Phe Trp Leu Val
                85                  90                  95

Ile Asn Gln Glu Gly Asn Met Val Thr Ala Arg Gln Glu Pro Arg Leu
            100                 105                 110

Val Leu Ile Ser Leu Thr Cys Asp Gly Asp Thr Leu Thr Leu Ser Ala
        115                 120                 125
```

```
Ala Tyr Thr Lys Asp Leu Leu Leu Pro Ile Lys Thr Pro Thr Thr Asn
    130                 135                 140

Ala Val His Lys Cys Arg Val His Gly Leu Glu Ile Glu Gly Arg Asp
145                 150                 155                 160

Cys Gly Glu Ala Thr Ala Gln Trp Ile Thr Ser Phe Leu Lys Ser Gln
                165                 170                 175

Pro Tyr Arg Leu Val His Phe Glu Pro His Met Arg Pro Arg Arg Pro
            180                 185                 190

His Gln Ile Ala Asp Leu Phe Arg Pro Lys Asp Gln Ile Ala Tyr Ser
        195                 200                 205

Asp Thr Ser Pro Phe Leu Ile Leu Ser Glu Ala Ser Leu Ala Asp Leu
    210                 215                 220

Asn Ser Arg Leu Glu Lys Lys Val Lys Ala Thr Asn Phe Arg Pro Asn
225                 230                 235                 240

Ile Val Ile Ser Gly Cys Asp Val Tyr Ala Glu Val Thr Leu Cys Pro
                245                 250                 255

Phe Gly Ser Phe Leu Gly Phe Asp Phe Phe Lys Asp Ser Trp Asp
            260                 265                 270

Glu Leu Leu Ile Gly Asp Val Glu Leu Lys Arg Val Met Ala Cys Ser
    275                 280                 285

Arg Cys Ile Leu Thr Thr Val Asp Pro Asp Thr Gly Val Met Ser Arg
290                 295                 300

Lys Glu Pro Leu Glu Thr Leu Lys Ser Tyr Arg Gln Cys Asp Pro Ser
305                 310                 315                 320

Glu Arg Lys Leu Tyr Gly Lys Ser Pro Leu Phe Gly Gln Tyr Phe Val
                325                 330                 335

Leu Glu Asn Pro Gly Thr Ile Lys Val Gly Asp Pro Val Tyr Leu Leu
            340                 345                 350

Gly Gln

<210> SEQ ID NO 21
<211> LENGTH: 4013
<212> TYPE: DNA
<213> ORGANISM: Homo sapiens

<400> SEQUENCE: 21
cattaccgcg caggcttggt caccgcatta aggcattccc gctctccgcg gaactgctct      60
gccgtctcgg cggtgaaagt gtgagagggt ccgtagttgg gtcaactttg actcctctcg     120
cctgcccgga tccttaaggg cctcctcgtc ctcccggtct ccggtcgctg ccgggtctgt     180
gcgccggtcc gcgcccgccc tcgctctgcc atgggcgctt ccagctcctc cgcgctggcc     240
cgcctcggcc tccagcccg gcctggccc aggtggctcg gggtcgccgc gctaggactg      300
gccgccgtgg ccctggggac tgtcgcctgg cgccgcgcat ggcccaggcg cgccggcgg     360 ctgcagcagg tgggcaccgt ggcgaagctc tggatctacc cggtgaaatc ctgcaaaggg     420
gtgccggtga gcgaggctga gtcacggcc atggggctgc gcagcggcaa cctgcgggac     480
aggttttggc tggtgattaa ggaagatgga cacatggtca ctgcccgaca ggagcctcgc     540
ctcgtgctca tctccatcat ttatgagaat aactgcctga tcttcaggc tccagacatg      600 gaccagctgg ttttgcctag caagcagcct tcctcaaaca aactccacaa ctgcaggata     660
tttggccttg acattaaagg cagagactgt ggcaatgagg cagctaagtg gttcaccaac     720
ttcttgaaaa ctgaagcgta tagattggtt caatttgaga caaacatgaa gggaagaaca     780
```

```
tcaagaaaac ttctccccac tcttgatcag aatttccagg tggcctaccc agactactgc    840
ccgctcctga tcatgacaga tgcctccctg gtagatttga ataccaggat ggagaagaaa    900
atgaaaatgg agaatttcag gccaaatatt gtggtgaccg gctgtgatgc ttttgaggag    960
gatacctggg atgaactcct aattggtagt gtagaagtga aaaaggtaat ggcatgcccc   1020
aggtgtattt tgacaacggt ggacccagac actggagtca tagacaggaa acagccactg   1080
gacaccctga agagctaccg cctgtgtgat ccttctgaga gggaattgta caagttgtct   1140
ccacttttg ggatctatta ttcagtggaa aaaattggaa gcctgagagt tggtgaccct   1200
gtgtatcgga tggtgtagtg atgagtgatg gatccactag ggtgatatgg taaagggctt   1260
cagcaaccag gagggattga ctgagatctt aacaacagca gcaacgatac atcagcaaat   1320
ccttattatc cagccttcaa ctatctttac cctggaaaac aatctcgatt tttgactttt   1380
caaagttgtg tatgctccag gttaatgcaa ggaaagtatt agagggggga atatgaaagt   1440
atatatataa attttaggta ctgaaggctt taaaaataat taagatcatc aaaaatgcta   1500
ttttgaatgt tatcatggct attacacttt tacttcctga ctttaatatt gatgaataaa   1560
gcaagtttaa tgaatcaact aaaaagctgc aaaaatgttt ttaaaatgtg tgcctttat   1620
tacctatcag tctatgtttt gggagaaatg gaagcaaca gatcactgtg tcctgatgtg   1680
caggacgcat gttaccacac tcacaaatgc ctaatattgg tctttatgtg gccattgagt   1740
cctgttgact ttccactcat gtgcttttta ctctagcatt atggaatctg gctgtactt   1800
gagtatggaa attctcttat agacttagtt ttagtactct attacaccctt tactaagcca   1860
cattaccgcg caggcttggt caccgcatta aggcattccc gctctccgcg gaactgctct   1920
gccgtctcgg cggtgaaagt gtgagagggt ccgtagttgg gtcaactttg actcctctcg   1980
cctgcccgga tccttaaggg cctcctcgtc ctcccggtct ccggtcgctg ccgggtctgt   2040
gcgccggtcc gcgcccgccc tcgctctgcc atgggcgctt ccagctcctc cgcgctggcc   2100
cgcctcggcc tcccagcccg gccctggccc aggtggctcg gggtcgccgc gctaggactg   2160
gccgccgtgg ccctggggac tgtcgcctgg cgccgcgcat ggcccaggcg cgccggcgg   2220
ctgcagcagg tgggcaccgt ggcgaagctc tggatctacc cggtgaaatc ctgcaaaggg   2280
gtgccggtga gcgaggctga gtgcacggcc atggggctgc gcagcggcaa cctgcgggac   2340
aggttttggc tggtgattaa ggaagatgga cacatggtca ctgcccgaca ggagcctcgc   2400
ctcgtgctca tctccatcat ttatgagaat aactgcctga tcttcagggc tccagacatg   2460
gaccagctgt ttttgcctag caagcagcct tcctcaaaca aactccacaa ctgcaggata   2520
tttggccttg acattaaagg cagagactgt ggcaatgagg cagctaagtg gttcaccaac   2580
ttcttgaaaa ctgaagcgta tagattggtt caatttgaga caaacatgaa gggaagaaca   2640
tcaagaaaac ttctccccac tcttgatcag aatttccagg tggcctaccc agactactgc   2700
ccgctcctga tcatgacaga tgcctccctg gtagatttga ataccaggat ggagaagaaa   2760
atgaaaatgg agaatttcag gccaaatatt gtggtgaccg gctgtgatgc ttttgaggag   2820
gatacctggg atgaactcct aattggtagt gtagaagtga aaaaggtaat ggcatgcccc   2880
aggtgtattt tgacaacggt ggacccagac actggagtca tagacaggaa acagccactg   2940
gacaccctga agagctaccg cctgtgtgat ccttctgaga gggaattgta caagttgtct   3000
ccacttttg ggatctatta ttcagtggaa aaaattggaa gcctgagagt tggtgaccct   3060
gtgtatcgga tggtgtagtg atgagtgatg gatccactag ggtgatatgg taaagggctt   3120
cagcaaccag gagggattga ctgagatctt aacaacagca gcaacgatac atcagcaaat   3180
```

-continued

```
cccttattatc cagccttcaa ctatctttac cctggaaaac aatctcgatt tttgacttttt    3240 caaagttgtg tatgctccag gttaatgcaa ggaaagtatt agaggggga atatgaaagt      3300 atatatataa attttaggta ctgaaggctt taaaaataat taagatcatc aaaaatgcta     3360
ttttgaatgt tatcatggct attacacttt tacttcctga ctttaatatt gatgaataaa     3420
gcaagtttaa tgaatcaact aaaaagctgc aaaaatgttt ttaaaatgtg tgccttttat     3480
tacctatcag tctatgtttt gggagaaatg ggaagcaaca gatcactgtg tcctgatgtg    3540
caggacgcat gttaccacac tcacaaatgc ctaatattgg tctttatgtg gccattgagt    3600
cctgttgact ttccactcat gtgcttttta ctctagcatt atggaatctg ggctgtactt    3660
gagtatggaa attctcttat agacttagtt ttagtactct attacaccctt tactaagcca   3720 cataaaagta atctgtttgt gtgtaactgc cagatatacc acctggaatt ccaagtaaga   3780
taaggaagag gatgacattt aaaagagaat ggaattttga gagtaggaat gcaaggaaga   3840
cagcatgaac atatttttttt cagtgcaaat aattttttcg taacaaagaa acgaacaact   3900
ttggtatgat cttaagcaaa aatactcact gaaatagtat gtggatgaat tcacctactt   3960
acaattttat ggtttctttg taaataataa atgtgaatct caatcctgct tta          4013
```

<210> SEQ ID NO 22
<211> LENGTH: 335
<212> TYPE: PRT
<213> ORGANISM: Homo sapiens

<400> SEQUENCE: 22

```
Met Gly Ala Ser Ser Ser Ala Leu Ala Arg Leu Gly Leu Pro Ala
1               5                   10                  15

Arg Pro Trp Pro Arg Trp Leu Gly Val Ala Ala Leu Gly Leu Ala Ala
            20                  25                  30

Val Ala Leu Gly Thr Val Ala Trp Arg Arg Ala Trp Pro Arg Arg
        35                  40                  45

Arg Arg Leu Gln Gln Val Gly Thr Val Ala Lys Leu Trp Ile Tyr Pro
    50                  55                  60

Val Lys Ser Cys Lys Gly Val Pro Val Ser Glu Ala Glu Cys Thr Ala
65                  70                  75                  80

Met Gly Leu Arg Ser Gly Asn Leu Arg Asp Arg Phe Trp Leu Val Ile
                85                  90                  95

Lys Glu Asp Gly His Met Val Thr Ala Arg Gln Glu Pro Arg Leu Val
            100                 105                 110

Leu Ile Ser Ile Ile Tyr Glu Asn Asn Cys Leu Ile Phe Arg Ala Pro
        115                 120                 125

Asp Met Asp Gln Leu Val Leu Pro Ser Lys Gln Pro Ser Ser Asn Lys
    130                 135                 140

Leu His Asn Cys Arg Ile Phe Gly Leu Asp Ile Lys Gly Arg Asp Cys
145                 150                 155                 160

Gly Asn Glu Ala Ala Lys Trp Phe Thr Asn Phe Leu Lys Thr Glu Ala
                165                 170                 175

Tyr Arg Leu Val Gln Phe Glu Thr Asn Met Lys Gly Arg Thr Ser Arg
            180                 185                 190

Lys Leu Leu Pro Thr Leu Asp Gln Asn Phe Gln Val Ala Tyr Pro Asp
        195                 200                 205

Tyr Cys Pro Leu Leu Ile Met Thr Asp Ala Ser Leu Val Asp Leu Asn
    210                 215                 220
```

```
Thr Arg Met Glu Lys Lys Met Lys Met Glu Asn Phe Arg Pro Asn Ile
225                 230                 235                 240

Val Val Thr Gly Cys Asp Ala Phe Glu Glu Asp Thr Trp Asp Glu Leu
            245                 250                 255

Leu Ile Gly Ser Val Glu Val Lys Lys Val Met Ala Cys Pro Arg Cys
                260                 265                 270

Ile Leu Thr Thr Val Asp Pro Asp Thr Gly Val Ile Asp Arg Lys Gln
            275                 280                 285

Pro Leu Asp Thr Leu Lys Ser Tyr Arg Leu Cys Asp Pro Ser Glu Arg
        290                 295                 300

Glu Leu Tyr Lys Leu Ser Pro Leu Phe Gly Ile Tyr Tyr Ser Val Glu
305                 310                 315                 320

Lys Ile Gly Ser Leu Arg Val Gly Asp Pro Val Tyr Arg Met Val
                325                 330                 335
```

<210> SEQ ID NO 23
<211> LENGTH: 1857
<212> TYPE: DNA
<213> ORGANISM: Homo sapiens

<400> SEQUENCE: 23

| | | |
|---|---|---|
| cattaccgcg caggcttggt caccgcatta aggcattccc gctctccgcg gaactgctct | 60 |
| gccgtctcgg cggtgaaagt gtgagagggt ccgtagttgg gtcaactttg actcctctcg | 120 |
| cctgcccgga tccttaaggg cctcctcgtc ctcccggtct ccggtcgctg ccgggtctgt | 180 |
| gcgccggtcc gcgcccgccc tcgctctgcc atgggcgctt ccagctcctc cgcgctggcc | 240 |
| cgcctcggcc tcccagcccg gccctggccc aggtggctcg gggtcgccgc gctaggactg | 300 |
| gccgccgtgg ccctggggac tgtcgcctgg cgccgcgcat ggcccaggcg cgcgcggcgg | 360 |
| ctgcagcagg tgggcaccgt ggcgaagctc tggatctacc cggtgaaatc ctgcaaaggg | 420 |
| gtgccggtga gcgaggctga gtgcacggcc atgggctgc gcagcggcaa cctgcgggac | 480 |
| aggttttggc tggtgattaa ggaagatgga cacatggtca ctgcccgaca ggagcctcgc | 540 |
| ctcgtgctca tctccatcat ttatgagaat aactgcctga tcttcagggc tccagacatg | 600 |
| gaccagctgg ttttgcctag caagcagcct tcctcaaaca aactccacaa ctgcaggata | 660 |
| tttggccttg acattaaagg cagagactgt ggcaatgagg cagctaagtg gttcaccaac | 720 |
| ttcttgaaaa ctgaagcgta tagattggtt caatttgaga caaacatgaa gggaagaaca | 780 |
| tcaagaaaac ttctccccac tcttgatcag aatttccagg tggcctaccc agactactgc | 840 |
| ccgctcctga tcatgacaga tgcctccctg gtagatttga ataccaggat ggagaagaaa | 900 |
| atgaaaatgg agaatttcag gccaaatatt gtggtgaccg gctgtgatgc ttttgaggag | 960 |
| gcttcagcaa ccaggaggga ttgactgaga tcttaacaac agcagcaacg atacatcagc | 1020 |
| aaatccttat tatccagcct tcaactatct ttaccctgga aaacaatctc gattttgac | 1080 |
| ttttcaaagt tgtgtatgct ccaggttaat gcaaggaaag tattagaggg gggaatatga | 1140 |
| aagtatatat ataaatttta ggtactgaag gctttaaaaa taattaagat catcaaaaat | 1200 |
| gctattttga atgttatcat ggctattaca cttttacttc ctgactttaa tattgatgaa | 1260 |
| taaagcaagt ttaatgaatc aactaaaaag ctgcaaaaat gttttaaaa tgtgtgcctt | 1320 |
| ttattaccta tcagtctatg ttttgggaga atgggaagc aacagatcac tgtgtcctga | 1380 |
| tgtgcaggac gcatgttacc acactcacaa atgcctaata ttggtcttta tgtggccatt | 1440 |
| gagtcctgtt gactttccac tcatgtgctt tttactctag cattatggaa tctgggctgt | 1500 |

```
acttgagtat ggaaattctc ttatagactt agttttagta ctctattaca cctttactaa    1560
gccacataaa agtaatctgt ttgtgtgtaa ctgccagata taccacctgg aattccaagt    1620
aagataagga agaggatgac atttaaaaga gaatggaatt ttgagagtag gaatgcaagg    1680
aagacagcat gaacatattt ttttcagtgc aaataatttt ttcgtaacaa agaaacgaac    1740
aactttggta tgatcttaag caaaaatact cactgaaata gtatgtggat gaattcacct    1800
acttacaatt ttatggtttc tttgtaaata ataaatgtga atctcaatcc tgcttta      1857
```

<210> SEQ ID NO 24
<211> LENGTH: 257
<212> TYPE: PRT
<213> ORGANISM: Homo sapiens

<400> SEQUENCE: 24

```
Met Gly Ala Ser Ser Ser Ala Leu Ala Arg Leu Gly Leu Pro Ala
1               5                  10                  15

Arg Pro Trp Pro Arg Trp Leu Gly Val Ala Ala Leu Gly Leu Ala Ala
            20                  25                  30

Val Ala Leu Gly Thr Val Ala Trp Arg Arg Ala Trp Pro Arg Arg Arg
        35                  40                  45

Arg Arg Leu Gln Gln Val Gly Thr Val Ala Lys Leu Trp Ile Tyr Pro
    50                  55                  60

Val Lys Ser Cys Lys Gly Val Pro Val Ser Glu Ala Glu Cys Thr Ala
65                  70                  75                  80

Met Gly Leu Arg Ser Gly Asn Leu Arg Asp Arg Phe Trp Leu Val Ile
                85                  90                  95

Lys Glu Asp Gly His Met Val Thr Ala Arg Gln Glu Pro Arg Leu Val
            100                 105                 110

Leu Ile Ser Ile Ile Tyr Glu Asn Asn Cys Leu Ile Phe Arg Ala Pro
        115                 120                 125

Asp Met Asp Gln Leu Val Leu Pro Ser Lys Gln Pro Ser Ser Asn Lys
    130                 135                 140

Leu His Asn Cys Arg Ile Phe Gly Leu Asp Ile Lys Gly Arg Asp Cys
145                 150                 155                 160

Gly Asn Glu Ala Ala Lys Trp Phe Thr Asn Phe Leu Lys Thr Glu Ala
                165                 170                 175

Tyr Arg Leu Val Gln Phe Glu Thr Asn Met Lys Gly Arg Thr Ser Arg
            180                 185                 190

Lys Leu Leu Pro Thr Leu Asp Gln Asn Phe Gln Val Ala Tyr Pro Asp
        195                 200                 205

Tyr Cys Pro Leu Leu Ile Met Thr Asp Ala Ser Leu Val Asp Leu Asn
    210                 215                 220

Thr Arg Met Glu Lys Lys Met Lys Met Glu Asn Phe Arg Pro Asn Ile
225                 230                 235                 240

Val Val Thr Gly Cys Asp Ala Phe Glu Glu Ala Ser Ala Thr Arg Arg
                245                 250                 255

Asp
```

<210> SEQ ID NO 25
<211> LENGTH: 2153
<212> TYPE: DNA
<213> ORGANISM: Homo sapiens

<400> SEQUENCE: 25

```
cattaccgcg caggcttggt caccgcatta aggcattccc gctctccgcg gaactgctct    60
```

```
gccgtctcgg cggtgaaagt gtgagagggt ccgtagttgg gtcaactttg actcctctcg      120
cctgcccgga tccttaaggg cctcctcgtc ctcccggtct ccggtcgctg ccgggtctgt      180
gcgccggtcc gcgcccgccc tcgctctgcc atgggcgctt ccagctcctc cgcgctggcc      240
cgcctcggcc tcccagcccg gccctggccc aggtggctcg gggtcgccgc gctaggactg      300
gccgccgtgg ccctggggac tgtcgcctgg cgccgcgcat ggcccaggcg gcgccggcgg      360
ctgcagcagg tgggcaccgt ggcgaagctc tggatctacc cggtgaaatc ctgcaaaggg      420
gtgccggtga gcgaggctga gtcacggcc atggggctgc gcagcggcaa cctgcgggac       480
aggttttggc tggtgattaa ggaagatgga cacatggtca ctgcccgaca ggagcctcgc      540
ctcgtgctca tctccatcat ttatgagaat aactgcctga tcttcagggc tccagacatg      600
gaccagctgt ttttgcctag caagcagcct tcctcaaaca aactccacaa ctgcaggata      660
tttggccttg acattaaagg cagagactgt ggcaatgagg cagctaagtg gttcaccaac      720
ttcttgaaaa ctgaagcgta tagattggtt caatttgaga caaacatgaa gggaagaaca      780
tcaagaaaac ttctccccac tcttgatcag aatttccagg tggcctaccc agactactgc      840
ccgctcctga tcatgacaga tgcctccctg gtagatttga ataccaggat ggagaagaaa      900
atgaaaatgg agaatttcag gccaaatatt gtggtgaccg gctgtgatgc ttttgaggag      960
gatacctggg atgaactcct aattggtagt gtagaagtaa aaaaggtaat ggcatgcccc     1020
aggtgtattt tgacaacggt ggacccagac actggagtca tagacaggaa acagccactg     1080
gacaccctga gagctaccg cctgtgtgat ccttctgaga gggaattgta caagttgtct      1140 ccacttttg ggatctatta ttcagtggaa aaaattggaa gcctgagagt tggtgaccct      1200
gtgtatcgga tggtgtagtg atgagtgatg gatccactag ggtgatatgg taaagggctt     1260
cagcaaccag gagggattga ctgagatctt aacaacagca gcaacgatac atcagcaaat     1320
ccttattatc cagccttcaa ctatctttac cctggaaaac aatctcgatt tttgacttt      1380 caaagttgtg tatgctccag gttaatgcaa ggaaagtatt agagggggga atatgaaagt     1440
atatatataa attttaggta ctgaaggctt taaaaataat taagatcatc aaaaatgcta     1500
ttttgaatgt tatcatggct attacacttt tacttcctga ctttaatatt gatgaataaa     1560
gcaagtttaa tgaatcaact aaaaagctgc aaaaatgttt ttaaaatgtg tgccttttat     1620
tacctatcag tctatgtttt gggagaaatg ggaagcaaca gatcactgtg tcctgatgtg     1680
caggacgcat gttaccacac tcacaaatgc ctaatattgg tctttatgtg gccattgagt     1740
cctgttgact ttccactcat gtgcttttta ctctagcatt atggaatctg gctgtactt      1800 gagtatggaa attctcttat agacttagtt ttagtactct attacacctt tactaagcca     1860
cataaaagta atctgtttgt gtgtaactgc cagatatacc acctggaatt ccaagtaaga     1920
taaggaagag gatgacattt aaaagagaat ggaattttga gagtaggaat gcaaggaaga     1980
cagcatgaac atattttttt cagtgcaaat aattttttcg taacaaagaa acgaacaact     2040
ttggtatgat cttaagcaaa aatactcact gaaatagtat gtggatgaat tcacctactt     2100
acaattttat ggtttctttg taaataataa atgtgaatct caatcctgct tta            2153
```

<210> SEQ ID NO 26
<211> LENGTH: 335
<212> TYPE: PRT
<213> ORGANISM: Homo sapiens

<400> SEQUENCE: 26

Met Gly Ala Ser Ser Ser Ala Leu Ala Arg Leu Gly Leu Pro Ala
1               5                   10                  15

Arg Pro Trp Pro Arg Trp Leu Gly Val Ala Ala Leu Gly Leu Ala Ala
            20                  25                  30

Val Ala Leu Gly Thr Val Ala Trp Arg Ala Trp Pro Arg Arg Arg
            35                  40                  45

Arg Arg Leu Gln Gln Val Gly Thr Val Ala Lys Leu Trp Ile Tyr Pro
    50                  55                  60

Val Lys Ser Cys Lys Gly Val Pro Val Ser Glu Ala Glu Cys Thr Ala
65                  70                  75                  80

Met Gly Leu Arg Ser Gly Asn Leu Arg Asp Arg Phe Trp Leu Val Ile
                85                  90                  95

Lys Glu Asp Gly His Met Val Thr Ala Arg Gln Glu Pro Arg Leu Val
                100                 105                 110

Leu Ile Ser Ile Ile Tyr Glu Asn Asn Cys Leu Ile Phe Arg Ala Pro
            115                 120                 125

Asp Met Asp Gln Leu Val Leu Pro Ser Lys Gln Pro Ser Ser Asn Lys
    130                 135                 140

Leu His Asn Cys Arg Ile Phe Gly Leu Asp Ile Lys Gly Arg Asp Cys
145                 150                 155                 160

Gly Asn Glu Ala Ala Lys Trp Phe Thr Asn Phe Leu Lys Thr Glu Ala
                165                 170                 175

Tyr Arg Leu Val Gln Phe Glu Thr Asn Met Lys Gly Arg Thr Ser Arg
            180                 185                 190

Lys Leu Leu Pro Thr Leu Asp Gln Asn Phe Gln Val Ala Tyr Pro Asp
    195                 200                 205

Tyr Cys Pro Leu Leu Ile Met Thr Asp Ala Ser Leu Val Asp Leu Asn
210                 215                 220

Thr Arg Met Glu Lys Lys Met Lys Met Glu Asn Phe Arg Pro Asn Ile
225                 230                 235                 240

Val Val Thr Gly Cys Asp Ala Phe Glu Glu Asp Thr Trp Asp Glu Leu
                245                 250                 255

Leu Ile Gly Ser Val Glu Val Lys Lys Val Met Ala Cys Pro Arg Cys
            260                 265                 270

Ile Leu Thr Thr Val Asp Pro Asp Thr Gly Val Ile Asp Arg Lys Gln
        275                 280                 285

Pro Leu Asp Thr Leu Lys Ser Tyr Arg Leu Cys Asp Pro Ser Glu Arg
    290                 295                 300

Glu Leu Tyr Lys Leu Ser Pro Leu Phe Gly Ile Tyr Tyr Ser Val Glu
305                 310                 315                 320

Lys Ile Gly Ser Leu Arg Val Gly Asp Pro Val Tyr Arg Met Val
                325                 330                 335

<210> SEQ ID NO 27
<211> LENGTH: 1857
<212> TYPE: DNA
<213> ORGANISM: Homo sapiens

<400> SEQUENCE: 27
cattaccgcg caggcttggt caccgcatta aggcattccc gctctccgcg gaactgctct    60
gccgtctcgg cggtgaaagt gtgagagggt ccgtagttgg gtcaactttg actcctctcg   120
cctgcccgga tccttaaggg cctcctcgtc ctcccggtct ccggtcgctg ccgggtctgt   180
gcgccggtcc gcgcccgccc tcgctctgcc atgggcgctt ccagctcctc cgcgctggcc   240

```
cgcctcggcc tcccagcccg ccctggccc aggtggctcg gggtcgccgc gctaggactg    300
gccgccgtgg ccctggggac tgtcgcctgg cgccgcgcat ggcccaggcg cgcccggcgg    360
ctgcagcagg tgggcaccgt ggcgaagctc tggatctacc cggtgaaatc ctgcaaaggg    420
gtgccggtga gcgaggctga gtgcacggcc atggggctgc gcagcggcaa cctgcgggac    480
aggttttggc tggtgattaa ggaagatgga cacatggtca ctgcccgaca ggagcctcgc    540
ctcgtgctca tctccatcat ttatgagaat aactgcctga tcttcagggc tccagacatg    600
gaccagctgg ttttgcctag caagcagcct tcctcaaaca aactccacaa ctgcaggata    660
tttggccttg acattaaagg cagagactgt ggcaatgagg cagctaagtg gttcaccaac    720
ttcttgaaaa ctgaagcgta tagattggtt caatttgaga caaacatgaa gggaagaaca    780
tcaagaaaac ttctccccac tcttgatcag aatttccagg tggcctaccc agactactgc    840
ccgctcctga tcatgacaga tgcctccctg gtagatttga ataccaggat ggagaagaaa    900
atgaaaatgg agaatttcag gccaaatatt gtggtgaccg gctgtgatgc ttttgaggag    960
gcttcagcaa ccaggaggga ttgactgaga tcttaacaac agcagcaacg atacatcagc   1020
aaatccttat tatccagcct tcaactatct ttaccctgga aacaatctc gattttgac    1080 ttttcaaagt tgtgtatgct ccaggttaat gcaaggaaaa tattagaggg gggaatatga   1140
aagtatatat ataaatttta ggtactgaag gctttaaaaa taattaagat catcaaaaat   1200
gctattttga atgttatcat ggctattaca cttttacttc ctgactttaa tattgatgaa   1260
taaagcaagt ttaatgaatc aactaaaaag ctgcaaaaat gttttaaaa tgtgtgcctt    1320 ttattaccta tcagtctatg ttttgggaga atgggaagc aacagatcac tgtgtcctga   1380
tgtgcaggac gcatgttacc acactcacaa atgcctaata ttggtcttta tgtggccatt   1440
gagtcctgtt gactttccac tcatgtgctt tttactctag cattatgaa tctgggctgt    1500 acttgagtat ggaaattctc ttatagactt agttttagta ctctattaca cctttactaa   1560
gccacataaa agtaatctgt tgtgtgtaa ctgccagata taccacctgg aattccaagt   1620
aagataagga agaggatgac atttaaaaga gaatggaatt ttgagagtag gaatgcaagg   1680
aagacagcat gaacatattt ttttcagtgc aaataatttt ttcgtaacaa agaaacgaac   1740
aactttggta tgatcttaag caaaaatact cactgaaata gtatgtggat gaattcacct   1800
acttacaatt ttatggtttc tttgtaaata ataaatgtga atctcaatcc tgcttta      1857
```

<210> SEQ ID NO 28
<211> LENGTH: 257
<212> TYPE: PRT
<213> ORGANISM: Homo sapiens

<400> SEQUENCE: 28

Met Gly Ala Ser Ser Ser Ala Leu Ala Arg Leu Gly Leu Pro Ala
1               5                   10                  15

Arg Pro Trp Pro Arg Trp Leu Gly Val Ala Ala Leu Gly Leu Ala Ala
            20                  25                  30

Val Ala Leu Gly Thr Val Ala Trp Arg Arg Ala Trp Pro Arg Arg Arg
        35                  40                  45

Arg Arg Leu Gln Gln Val Gly Thr Val Ala Lys Leu Trp Ile Tyr Pro
    50                  55                  60

Val Lys Ser Cys Lys Gly Val Pro Val Ser Glu Ala Glu Cys Thr Ala
65                  70                  75                  80

Met Gly Leu Arg Ser Gly Asn Leu Arg Asp Arg Phe Trp Leu Val Ile
                85                  90                  95

```
Lys Glu Asp Gly His Met Val Thr Ala Arg Gln Glu Pro Arg Leu Val
            100                 105                 110

Leu Ile Ser Ile Ile Tyr Glu Asn Asn Cys Leu Ile Phe Arg Ala Pro
        115                 120                 125

Asp Met Asp Gln Leu Val Leu Pro Ser Lys Gln Pro Ser Ser Asn Lys
130                 135                 140

Leu His Asn Cys Arg Ile Phe Gly Leu Asp Ile Lys Gly Arg Asp Cys
145                 150                 155                 160

Gly Asn Glu Ala Ala Lys Trp Phe Thr Asn Phe Leu Lys Thr Glu Ala
                165                 170                 175

Tyr Arg Leu Val Gln Phe Glu Thr Asn Met Lys Gly Arg Thr Ser Arg
                180                 185                 190

Lys Leu Leu Pro Thr Leu Asp Gln Asn Phe Gln Val Ala Tyr Pro Asp
            195                 200                 205

Tyr Cys Pro Leu Leu Ile Met Thr Asp Ala Ser Leu Val Asp Leu Asn
210                 215                 220

Thr Arg Met Glu Lys Lys Met Lys Met Glu Asn Phe Arg Pro Asn Ile
225                 230                 235                 240

Val Val Thr Gly Cys Asp Ala Phe Glu Glu Ala Ser Ala Thr Arg Arg
                245                 250                 255

Asp

<210> SEQ ID NO 29
<211> LENGTH: 3227
<212> TYPE: DNA
<213> ORGANISM: Homo sapiens

<400> SEQUENCE: 29
aaacagattt tactcagtaa ctacttacag taggagaaaa agctgatcat tctcatttgt      60
gcatagcaga atgggcgttt taaagggtga aggagagaat agggccggga agctagcagg     120
ggatcaagtg aaaaatcatg aagggcggt cagtattaat gacgggcagc tgtgcctgga      180
gctggccgtt atgaagctgg gattctatcc tcccacagag actggggac agaggcctat      240 cctccccatg actgcatttc agagcaatgg ctttcaggtc cttgagaaag acacttctga     300
ggtgtaggcg atacatatac atctcaaagc aacagagaaa ggattcacag ttgtaagccc     360
ttttaagaaa atatcctaaa aaaggaggt caggggcttt accatcgggt gttggctaga      420
ataaacgggg aattctcctg gctgccttga gctttctcgg aagacattt tactggggtc      480 gaggttaggc ggcagcggag ggtgggggac cttgagtcat gctcctataa gccacgctag     540
agttcctcgt ctttgagtgc agaggtttag actgtgtctt tgtgtgcaga aagtcctgca     600
gttctcacag cgacctgcca gaaaaagtcg ttcccaaatg tttgtaaatc ctccgttggg     660
caacccgcct tcacgttctg cggtgatctt gtcgagcgac taagcgtgca gtattagcag     720
agaagggggt ggcagagtgc tggcgctgaa ggtcatgttg catgggtaac tgtcgtgttg     780
taggggcggg gaagagggag gagacactga ccaccccaga ggccgcccca ttagctcgct     840
tgctttgggc ggcgtcgctc ccacggcgcc cagggtaccc cgccgctgt ctgcctgtct      900 tcctccatta ccgcgcaggc ttggtcaccg cattaaggca tttcccgctct ccgcggaact    960 gctctgccgt ctcggcggtg aaagtgtgag agggtccgta gttgggtcaa ctttgactcc   1020
tctcgcctgc ccgatccctt aagggcctcc tcgtcctccc ggtctccggt cgctgccggg   1080
tctgtgcgcc ggtccgcgcc cgccctcgct ctgccatggg cgcttccagc tcctccgcgc   1140
```

-continued

```
tggcccgcct cggcctccca gcccggccct ggcccaggtg gctcggggtc gccgcgctag    1200
gactggccgc cgtggccctg gggactgtcg cctggcgccg cgcatggccc aggcggcgcc    1260
ggcggctgca gcaggtgggc accgtggcga agctctggat ctacccggtg aaatcctgca    1320
aaggggtgcc ggtgagcgag gctgagtgca cggccatggg gctgcgcagc ggcaacctgc    1380
gggacaggtt ttggctggtg attaaggaag atggacacat ggtcactgcc cgacaggagc    1440
ctcgcctcgt gctcatctcc atcatttatg agaataactg cctgatcttc agggctccag    1500
acatggacca gctggttttg cctagcaagc agccttcctc aaacaaactc cacaactgca    1560
ggatatttgg ccttgacatt aaaggcgaga actgtggcaa tgaggcagct aagtggttca    1620
ccaacttctt gaaaactgaa gcgtatagat tggttcaatt tgagacaaac atgaagggaa    1680
gaacatcaag aaaacttctc cccactcttg atcagaattt ccaggtggcc tacccagact    1740 actgccgct cctgatcatg acagatgcct ccctggtaga tttgaatacc aggatggaga    1800
agaaaatgaa aatggagaat tcaggccaa atattgtggt gaccggctgt gatgcttttg    1860
aggagaccaa ggaggaagtg tgtcttcaga cggtggtg cgcggtattc ccctcgagtg    1920
agtgtgatac gtgaacgcac gcttatcgat cccttgtaag gagaggtcat tcactttaca    1980
atgctaccca agagacaagc ccttcaaata cagatgttgg agtagagacg gcagagtgga    2040
ggatacctgg gatgaactcc taattggtag tgtagaagtg aaaaaggtaa tggcatgccc    2100
caggtgtatt ttgacaacgg tggacccaga cactggagtc atagacagga aacagccact    2160
ggacaccctg aagagctacc gcctgtgtga tccttctgag agggaattgt acaagttgtc    2220 tccactttt gggatctatt attcagtgga aaaaattgga agcctgagag ttggtgaccc    2280
tgtgtatcgg atggtgtagt gatgagtgat ggatccacta gggtgatatg gcttcagcaa    2340
ccaggaggga ttgactgaga tcttaacaac agcagcaacg atacatcagc aaatccttat    2400
tatccagcct tcaactatct ttaccctgga aaacaatctc gattttgac ttttcaaagt    2460 tgtgtatgct ccaggttaat gcaaggaaag tattagaggg gggaatatga agtatatat    2520 ataaattta ggtactgaag gctttaaaaa taattaagat catcaaaaat gctattttga    2580
atgttatcat ggctattaca cttttacttc ctgactttaa tattgatgaa taaagcaagt    2640
ttaatgaatc aactaaaaag ctgcaaaaat gttttaaaa tgtgtgcctt ttattaccta    2700
tcagtctatg ttttgggaga atgggaagc aacagatcac tgtgtcctga tgtgcaggac    2760
gcatgttacc acactcacaa atgcctaata ttggtcttta tgtggccatt gagtcctgtt    2820
gactttccac tcatgtgctt tttactctag cattatggaa tctgggctgt acttgagtat    2880
ggaaattctc ttatagactt agttttagta ctctattaca cctttactaa gccacataaa    2940
agtaatctgt ttgtgtgtaa ctgccagata taccacctgg aattccaagt aagataagga    3000
agaggatgac atttaaaaga gaatggaatt ttgagagtag gaatgcaagg aagacagcat    3060
gaacatattt ttttcagtgc aaataatttt ttcgtaacaa agaaacgaac aactttggta    3120
tgatcttaag caaaaatact cactgaaata gtatgtggat gaattcacct acttacaatt    3180
ttatggtttc tttgtaaata ataaatgtga atctcaatcc tgcttta              3227
```

<210> SEQ ID NO 30
<211> LENGTH: 272
<212> TYPE: PRT
<213> ORGANISM: Homo sapiens

<400> SEQUENCE: 30

Met Gly Ala Ser Ser Ser Ser Ala Leu Ala Arg Leu Gly Leu Pro Ala

```
              1               5              10              15
            Arg Pro Trp Pro Arg Trp Leu Gly Val Ala Ala Leu Gly Leu Ala Ala
                             20                  25                  30

Val Ala Leu Gly Thr Val Ala Trp Arg Arg Ala Trp Pro Arg Arg Arg
                             35                  40                  45

Arg Arg Leu Gln Gln Val Gly Thr Val Ala Lys Leu Trp Ile Tyr Pro
                     50                  55                  60

Val Lys Ser Cys Lys Gly Val Pro Val Ser Glu Ala Glu Cys Thr Ala
            65                  70                  75                  80

Met Gly Leu Arg Ser Gly Asn Leu Arg Asp Arg Phe Trp Leu Val Ile
                             85                  90                  95

Lys Glu Asp Gly His Met Val Thr Ala Arg Gln Glu Pro Arg Leu Val
                            100                 105                 110

Leu Ile Ser Ile Ile Tyr Glu Asn Asn Cys Leu Ile Phe Arg Ala Pro
                            115                 120                 125

Asp Met Asp Gln Leu Val Leu Pro Ser Lys Gln Pro Ser Ser Asn Lys
                        130                 135                 140

Leu His Asn Cys Arg Ile Phe Gly Leu Asp Ile Lys Gly Arg Asp Cys
            145                 150                 155                 160

Gly Asn Glu Ala Ala Lys Trp Phe Thr Asn Phe Leu Lys Thr Glu Ala
                                165                 170                 175

Tyr Arg Leu Val Gln Phe Glu Thr Asn Met Lys Gly Arg Thr Ser Arg
                            180                 185                 190

Lys Leu Leu Pro Thr Leu Asp Gln Asn Phe Gln Val Ala Tyr Pro Asp
                        195                 200                 205

Tyr Cys Pro Leu Leu Ile Met Thr Asp Ala Ser Leu Val Asp Leu Asn
                    210                 215                 220

Thr Arg Met Glu Lys Lys Met Lys Met Glu Asn Phe Arg Pro Asn Ile
            225                 230                 235                 240

Val Val Thr Gly Cys Asp Ala Phe Glu Glu Thr Lys Glu Val Cys
                                245                 250                 255

Leu Gln Arg Arg Trp Cys Ala Val Phe Pro Ser Ser Glu Cys Asp Thr
                        260                 265                 270

<210> SEQ ID NO 31
<211> LENGTH: 1746
<212> TYPE: DNA
<213> ORGANISM: Homo sapiens

<400> SEQUENCE: 31
attcggtgcc tggtgcagtt gctgggaggg cgtgcttgtc ctccctgacc ttggaaatct     60
ctgctctcct tagcagccat atgttttggc tggtgattaa ggaagatgga cacatggtca    120
ctgcccgaca ggagcctcgc ctcgtgctca tctccatcat ttatgagaat aactgcctga    180
tcttcagggc tccagacatg gaccagctgg ttttgcctag caagcagcct tcctcaaaca    240
aactccacaa ctgcaggata tttggccttg acattaaagg cagagactgt ggcaatgagg    300
cagctaagtg gttcaccaac ttcttgaaaa ctgaagcgta tagattggtt caatttgaga    360
caaacatgaa gggaagaaca tcaagaaaac ttctccccac tcttgatcag aatttccagg    420
tggcctaccc agactactgc cgctcctga tcatgacaga tgcctccctg gtagatttga    480
ataccaggat ggagaagaaa atgaaaatgg agaatttcag gccaaatatt gtggtgaccg    540
gctgtgatgc ttttgaggag gatacctggg atgaactcct aattggtagt gtagaagtga    600
aaaaggtaat ggcatgcccc aggtgtattt tgacaacggt ggacccagac actggagtca    660
```

-continued

```
tagacaggaa acagccactg gacaccctga agagctaccg cctgtgtgat ccttctgaga    720
gggaattgta caagttgtct ccacttttg ggatctatta ttcagtggaa aaaattggaa    780
gcctgagagt tggtgaccct gtgtatcgga tggtgtagtg atgagtgatg gatccactag    840
ggtgatatgg cttcagcaac caggagggat tgactgagat cttaacaaca gcagcaacga    900
tacatcagca atccttatt atccagcctt caactatctt taccctggaa acaatctcg     960 atttttgact tttcaaagtt gtgtatgctc caggttaatg caaggaaagt attagagggg   1020
ggaatatgaa agtatatata taaattttag gtactgaagg ctttaaaaat aattaagatc   1080
atcaaaaatg ctattttgaa tgttatcatg gctattacac ttttacttcc tgactttaat   1140
attgatgaat aaagcaagtt taatgaatca actaaaaagc tgcaaaaatg ttttttaaaat 1200 gtgtgccttt tattacctat cagtctatgt tttgggagaa atgggaagca acagatcact   1260
gtgtcctgat gtgcaggacg catgttacca cactcacaaa tgcctaatat tggtctttat   1320
gtggccattg agtcctgttg actttccact catgtgcttt ttactctagc attatggaat   1380
ctgggctgta cttgagtatg gaaattctct tatagactta gttttagtac tctattacac   1440
ctttactaag ccacataaaa gtaatctgtt tgtgtgtaac tgccagatat accacctgga   1500
attccaagta agataaggaa gaggatgaca tttaaaagag aatggaattt tgagagtagg   1560
aatgcaagga agacagcatg aacatatttt tttcagtgca ataatttttt tcgtaacaaa   1620
gaaacgaaca actttggtat gatcttaagc aaaaatactc actgaaatag tatgtggatg   1680
aattcaccta cttacaattt tatggtttct ttgtaaataa taaatgtgaa tctcaatcct   1740
gcttta                                                              1746
```

<210> SEQ ID NO 32
<211> LENGTH: 245
<212> TYPE: PRT
<213> ORGANISM: Homo sapiens

<400> SEQUENCE: 32

```
Met Phe Trp Leu Val Ile Lys Glu Asp Gly His Met Val Thr Ala Arg
1               5                   10                  15

Gln Glu Pro Arg Leu Val Leu Ile Ser Ile Ile Tyr Glu Asn Asn Cys
            20                  25                  30

Leu Ile Phe Arg Ala Pro Asp Met Asp Gln Leu Val Leu Pro Ser Lys
        35                  40                  45

Gln Pro Ser Ser Asn Lys Leu His Asn Cys Arg Ile Phe Gly Leu Asp
    50                  55                  60

Ile Lys Gly Arg Asp Cys Gly Asn Glu Ala Ala Lys Trp Phe Thr Asn
65                  70                  75                  80

Phe Leu Lys Thr Glu Ala Tyr Arg Leu Val Gln Phe Glu Thr Asn Met
                85                  90                  95

Lys Gly Arg Thr Ser Arg Lys Leu Leu Pro Thr Leu Asp Gln Asn Phe
            100                 105                 110

Gln Val Ala Tyr Pro Asp Tyr Cys Pro Leu Leu Ile Met Thr Asp Ala
        115                 120                 125

Ser Leu Val Asp Leu Asn Thr Arg Met Glu Lys Met Lys Met Glu
    130                 135                 140

Asn Phe Arg Pro Asn Ile Val Val Thr Gly Cys Asp Ala Phe Glu Glu
145                 150                 155                 160

Asp Thr Trp Asp Glu Leu Leu Ile Gly Ser Val Glu Val Lys Lys Val
                165                 170                 175
```

-continued

```
Met Ala Cys Pro Arg Cys Ile Leu Thr Thr Val Asp Pro Asp Thr Gly
            180                 185                 190

Val Ile Asp Arg Lys Gln Pro Leu Asp Thr Leu Lys Ser Tyr Arg Leu
        195                 200                 205

Cys Asp Pro Ser Glu Arg Glu Leu Tyr Lys Leu Ser Pro Leu Phe Gly
210                 215                 220

Ile Tyr Tyr Ser Val Glu Lys Ile Gly Ser Leu Arg Val Gly Asp Pro
225                 230                 235                 240

Val Tyr Arg Met Val
                245

<210> SEQ ID NO 33
<211> LENGTH: 356
<212> TYPE: PRT
<213> ORGANISM: Homo sapiens

<400> SEQUENCE: 33

Met Gly Ser Gly Gly Gly Ser Glu Gly Ala Pro Lys Lys Lys Arg
1               5                   10                  15

Lys Val Gly Ser Ser Leu Gly Thr Gly Asn Arg Cys Val Lys Gly Asp
            20                  25                  30

Ser Leu Ser Leu Lys Gly Glu Thr Val Asn Asp Cys His Ala Glu Ile
        35                  40                  45

Ile Ser Arg Arg Gly Phe Ile Arg Phe Leu Tyr Ser Glu Leu Met Lys
    50                  55                  60

Tyr Asn Ser Gln Thr Ala Lys Asp Ser Ile Phe Glu Pro Ala Lys Gly
65                  70                  75                  80

Gly Glu Lys Leu Gln Ile Lys Lys Thr Val Ser Phe His Leu Tyr Ile
                85                  90                  95

Ser Thr Ala Pro Cys Gly Asp Gly Ala Leu Phe Asp Lys Ser Cys Ser
            100                 105                 110

Asp Arg Ala Met Glu Ser Thr Glu Ser Arg His Tyr Pro Val Phe Glu
        115                 120                 125

Asn Pro Lys Gln Gly Lys Leu Arg Thr Lys Val Glu Asn Gly Gln Gly
    130                 135                 140

Thr Ile Pro Val Glu Ser Ser Asp Ile Val Pro Thr Trp Asp Gly Ile
145                 150                 155                 160

Arg Leu Gly Glu Arg Leu Arg Thr Met Ser Cys Ser Asp Lys Ile Leu
                165                 170                 175

Arg Trp Asn Val Leu Gly Leu Gln Gly Ala Leu Leu Thr His Phe Leu
            180                 185                 190

Gln Pro Ile Tyr Leu Lys Ser Val Thr Leu Gly Tyr Leu Phe Ser Gln
        195                 200                 205

Gly His Leu Thr Arg Ala Ile Cys Cys Arg Val Thr Arg Asp Gly Ser
    210                 215                 220

Ala Phe Glu Asp Gly Leu Arg His Pro Phe Ile Val Asn His Pro Lys
225                 230                 235                 240

Val Gly Arg Val Ser Ile Tyr Asp Ser Lys Arg Gln Ser Gly Lys Thr
                245                 250                 255

Lys Glu Thr Ser Val Asn Trp Cys Leu Ala Asp Gly Tyr Asp Leu Glu
            260                 265                 270

Ile Leu Asp Gly Thr Arg Gly Thr Val Asp Gly Pro Arg Asn Glu Leu
        275                 280                 285

Ser Arg Val Ser Lys Lys Asn Ile Phe Leu Leu Phe Lys Lys Leu Cys
```

```
            290                 295                 300
Ser Phe Arg Tyr Arg Asp Leu Leu Arg Leu Ser Tyr Gly Glu Ala
305                 310                 315                 320

Lys Lys Ala Ala Arg Asp Tyr Glu Thr Ala Lys Asn Tyr Phe Lys Lys
                325                 330                 335

Gly Leu Lys Asp Met Gly Tyr Gly Asn Trp Ile Ser Lys Pro Gln Glu
                340                 345                 350

Glu Lys Asn Phe
        355

<210> SEQ ID NO 34
<211> LENGTH: 229
<212> TYPE: PRT
<213> ORGANISM: Rattus rattus

<400> SEQUENCE: 34

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
                20                  25                  30

Arg Lys Glu Thr Cys Leu Leu Tyr Glu Ile Asn Trp Gly Gly Arg His
            35                  40                  45

Ser Ile Trp Arg His Thr Ser Gln Asn Thr Asn Lys His Val Glu Val
50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
            100                 105                 110

Phe Ile Tyr Ile Ala Arg Leu Tyr His His Ala Asp Pro Arg Asn Arg
        115                 120                 125

Gln Gly Leu Arg Asp Leu Ile Ser Ser Gly Val Thr Ile Gln Ile Met
130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Phe Phe Thr Ile
        195                 200                 205

Ala Leu Gln Ser Cys His Tyr Gln Arg Leu Pro Pro His Ile Leu Trp
210                 215                 220

Ala Thr Gly Leu Lys
225

<210> SEQ ID NO 35
<211> LENGTH: 236
<212> TYPE: PRT
<213> ORGANISM: Homo sapiens

<400> SEQUENCE: 35

Met Thr Ser Glu Lys Gly Pro Ser Thr Gly Asp Pro Thr Leu Arg Arg
1               5                   10                  15

Arg Ile Glu Pro Trp Glu Phe Asp Val Phe Tyr Asp Pro Arg Glu Leu
```

```
            20                  25                  30
Arg Lys Glu Ala Cys Leu Leu Tyr Glu Ile Lys Trp Gly Met Ser Arg
        35                  40                  45
Lys Ile Trp Arg Ser Ser Gly Lys Asn Thr Thr Asn His Val Glu Val
    50                  55                  60
Asn Phe Ile Lys Lys Phe Thr Ser Glu Arg Asp Phe His Pro Ser Met
65                  70                  75                  80
Ser Cys Ser Ile Thr Trp Phe Leu Ser Trp Ser Pro Cys Trp Glu Cys
                85                  90                  95
Ser Gln Ala Ile Arg Glu Phe Leu Ser Arg His Pro Gly Val Thr Leu
            100                 105                 110
Val Ile Tyr Val Ala Arg Leu Phe Trp His Met Asp Gln Gln Asn Arg
        115                 120                 125
Gln Gly Leu Arg Asp Leu Val Asn Ser Gly Val Thr Ile Gln Ile Met
    130                 135                 140
Arg Ala Ser Glu Tyr Tyr His Cys Trp Arg Asn Phe Val Asn Tyr Pro
145                 150                 155                 160
Pro Gly Asp Glu Ala His Trp Pro Gln Tyr Pro Pro Leu Trp Met Met
                165                 170                 175
Leu Tyr Ala Leu Glu Leu His Cys Ile Ile Leu Ser Leu Pro Pro Cys
            180                 185                 190
Leu Lys Ile Ser Arg Arg Trp Gln Asn His Leu Thr Phe Phe Arg Leu
        195                 200                 205
His Leu Gln Asn Cys His Tyr Gln Thr Ile Pro Pro His Ile Leu Leu
    210                 215                 220
Ala Thr Gly Leu Ile His Pro Ser Val Ala Trp Arg
225                 230                 235

<210> SEQ ID NO 36
<211> LENGTH: 325
<212> TYPE: PRT
<213> ORGANISM: Homo sapiens

<400> SEQUENCE: 36

Met Glu Leu Lys Tyr His Pro Glu Met Arg Phe Phe His Trp Phe Ser
1               5                   10                  15
Lys Trp Arg Lys Leu His Arg Asp Gln Glu Tyr Glu Val Thr Trp Tyr
            20                  25                  30
Ile Ser Trp Ser Pro Cys Thr Lys Cys Thr Arg Asp Met Ala Thr Phe
        35                  40                  45
Leu Ala Glu Asp Pro Lys Val Thr Leu Thr Ile Phe Val Ala Arg Leu
    50                  55                  60
Tyr Tyr Phe Trp Asp Pro Asp Tyr Gln Glu Ala Leu Arg Ser Leu Cys
65                  70                  75                  80
Gln Lys Arg Asp Gly Pro Arg Ala Thr Met Lys Ile Met Asn Tyr Asp
                85                  90                  95
Glu Phe Gln His Cys Trp Ser Lys Phe Val Tyr Ser Gln Arg Glu Leu
            100                 105                 110
Phe Glu Pro Trp Asn Asn Leu Pro Lys Tyr Tyr Ile Leu Leu His Ile
        115                 120                 125
Met Leu Gly Glu Ile Leu Arg His Ser Met Asp Pro Pro Thr Phe Thr
    130                 135                 140
Phe Asn Phe Asn Asn Glu Pro Trp Val Arg Gly Arg His Glu Thr Tyr
145                 150                 155                 160
```

```
Leu Cys Tyr Glu Val Glu Arg Met His Asn Asp Thr Trp Val Leu Leu
            165                 170                 175

Asn Gln Arg Arg Gly Phe Leu Cys Asn Gln Ala Pro His Lys His Gly
        180                 185                 190

Phe Leu Glu Gly Arg His Ala Glu Leu Cys Phe Leu Asp Val Ile Pro
            195                 200                 205

Phe Trp Lys Leu Asp Leu Asp Gln Asp Tyr Arg Val Thr Cys Phe Thr
    210                 215                 220

Ser Trp Ser Pro Cys Phe Ser Cys Ala Gln Met Ala Lys Phe Ile
225                 230                 235                 240

Ser Lys Asn Lys His Val Ser Leu Cys Ile Phe Thr Ala Arg Ile Tyr
                245                 250                 255

Asp Asp Gln Gly Arg Cys Gln Glu Gly Leu Arg Thr Leu Ala Glu Ala
            260                 265                 270

Gly Ala Lys Ile Ser Ile Met Thr Tyr Ser Glu Phe Lys His Cys Trp
        275                 280                 285

Asp Thr Phe Val Asp His Gln Gly Cys Pro Phe Gln Pro Trp Asp Gly
    290                 295                 300

Leu Asp Glu His Ser Gln Asp Leu Ser Gly Arg Leu Arg Ala Ile Leu
305                 310                 315                 320

Gln Asn Gln Glu Asn
                325

<210> SEQ ID NO 37
<211> LENGTH: 208
<212> TYPE: PRT
<213> ORGANISM: Petromyzon marinus

<400> SEQUENCE: 37

Met Thr Asp Ala Glu Tyr Val Arg Ile His Glu Lys Leu Asp Ile Tyr
1               5                   10                  15

Thr Phe Lys Lys Gln Phe Phe Asn Asn Lys Lys Ser Val Ser His Arg
            20                  25                  30

Cys Tyr Val Leu Phe Glu Leu Lys Arg Arg Gly Glu Arg Arg Ala Cys
        35                  40                  45

Phe Trp Gly Tyr Ala Val Asn Lys Pro Gln Ser Gly Thr Glu Arg Gly
    50                  55                  60

Ile His Ala Glu Ile Phe Ser Ile Arg Lys Val Glu Glu Tyr Leu Arg
65                  70                  75                  80

Asp Asn Pro Gly Gln Phe Thr Ile Asn Trp Tyr Ser Ser Trp Ser Pro
                85                  90                  95

Cys Ala Asp Cys Ala Glu Lys Ile Leu Glu Trp Tyr Asn Gln Glu Leu
            100                 105                 110

Arg Gly Asn Gly His Thr Leu Lys Ile Trp Ala Cys Lys Leu Tyr Tyr
        115                 120                 125

Glu Lys Asn Ala Arg Asn Gln Ile Gly Leu Trp Asn Leu Arg Asp Asn
    130                 135                 140

Gly Val Gly Leu Asn Val Met Val Ser Glu His Tyr Gln Cys Cys Arg
145                 150                 155                 160

Lys Ile Phe Ile Gln Ser Ser His Asn Gln Leu Asn Glu Asn Arg Trp
                165                 170                 175

Leu Glu Lys Thr Leu Lys Arg Ala Glu Lys Arg Arg Ser Glu Leu Ser
            180                 185                 190

Ile Met Ile Gln Val Lys Ile Leu His Thr Thr Lys Ser Pro Ala Val
        195                 200                 205
```

<210> SEQ ID NO 38
<211> LENGTH: 200
<212> TYPE: PRT
<213> ORGANISM: Homo sapiens

<400> SEQUENCE: 38

```
Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Tyr Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu Leu Asp
        195                 200
```

<210> SEQ ID NO 39
<211> LENGTH: 181
<212> TYPE: PRT
<213> ORGANISM: Homo sapiens

<400> SEQUENCE: 39

```
Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125
```

```
Leu His Arg Ala Gly Val Gln Ile Ala Ile Met Thr Phe Lys Asp Tyr
        130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu
            180

<210> SEQ ID NO 40
<211> LENGTH: 12
<212> TYPE: DNA
<213> ORGANISM: Artificial Sequence
<220> FEATURE:
<223> OTHER INFORMATION: Synthetic

<400> SEQUENCE: 40
acttgtttaa gt                                                    12

<210> SEQ ID NO 41
<211> LENGTH: 16
<212> TYPE: DNA
<213> ORGANISM: Artificial Sequence
<220> FEATURE:
<223> OTHER INFORMATION: Synthethic

<400> SEQUENCE: 41
ggcaccgagt cggtgc                                                16

<210> SEQ ID NO 42
<211> LENGTH: 15
<212> TYPE: PRT
<213> ORGANISM: Artificial Sequence
<220> FEATURE:
<223> OTHER INFORMATION: Synthetic

<400> SEQUENCE: 42

Gly Gly Gly Gly Ser Gly Gly Gly Gly Ser Gly Gly Gly Gly Ser
1               5                   10                  15

<210> SEQ ID NO 43
<211> LENGTH: 30
<212> TYPE: PRT
<213> ORGANISM: Artificial Sequence
<220> FEATURE:
<223> OTHER INFORMATION: Synthetic

<400> SEQUENCE: 43

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 44
<211> LENGTH: 45
<212> TYPE: PRT
<213> ORGANISM: Artificial Sequence
<220> FEATURE:
<223> OTHER INFORMATION: Synthetic

<400> SEQUENCE: 44

Gly Gly Gly Gly Ser Gly Gly Gly Gly Ser Gly Gly Gly Gly Ser Gly
1               5                   10                  15
```

```
Gly Gly Gly Ser Gly Gly Gly Ser Gly Gly Gly Ser Gly Gly
            20                  25                  30

Gly Gly Ser Gly Gly Gly Ser Gly Gly Gly Ser
        35                  40                  45

<210> SEQ ID NO 45
<211> LENGTH: 5
<212> TYPE: PRT
<213> ORGANISM: Artificial Sequence
<220> FEATURE:
<223> OTHER INFORMATION: Synthetic

<400> SEQUENCE: 45

Gly Gly Gly Gly Ser
1               5

<210> SEQ ID NO 46
<211> LENGTH: 288
<212> TYPE: PRT
<213> ORGANISM: Artificial Sequence
<220> FEATURE:
<223> OTHER INFORMATION: Synthetic

<400> SEQUENCE: 46

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Thr Met Arg Val Ala Val Thr Ala Ala
        115                 120                 125

Arg Pro Pro Arg Ala Lys Pro Ala Pro Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
    210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270
```

Glu Ala Val His Ala Trp Arg Asn Ala Leu Thr Gly Ala Pro Leu Asn
        275                 280                 285

<210> SEQ ID NO 47
<211> LENGTH: 183
<212> TYPE: PRT
<213> ORGANISM: Artificial Sequence
<220> FEATURE:
<223> OTHER INFORMATION: Synthetic

<400> SEQUENCE: 47

Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
        35                  40                  45

Pro Ala Leu Ile Lys Arg Thr Asn Arg Ile Pro Glu Arg Thr Ser
    50                  55                  60

His Arg Val Ala Asp His Ala Gln Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180

<210> SEQ ID NO 48
<211> LENGTH: 15
<212> TYPE: PRT
<213> ORGANISM: Artificial Sequence
<220> FEATURE:
<223> OTHER INFORMATION: Synthetic

<400> SEQUENCE: 48

Gly Gly Gly Gly Ser Gly Gly Gly Gly Ser Gly Gly Gly Gly Ser
1               5                   10                  15

<210> SEQ ID NO 49
<211> LENGTH: 30
<212> TYPE: PRT
<213> ORGANISM: Artificial Sequence
<220> FEATURE:
<223> OTHER INFORMATION: Synthetic

<400> SEQUENCE: 49

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

```
<210> SEQ ID NO 50
<211> LENGTH: 45
<212> TYPE: PRT
<213> ORGANISM: Artificial Sequence
<220> FEATURE:
<223> OTHER INFORMATION: Synthetic

<400> SEQUENCE: 50

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser
            35                  40                  45
```

LIVER PROTECTIVE MARC VARIANTS AND USES THEREOF

CROSS-REFERENCE TO RELATED APPLICATIONS

This application claims the benefit of U.S. Provisional Application No. 62/812,881, filed Mar. 1, 2019. The entire contents of the above-identified applications are hereby fully incorporated herein by reference.

STATEMENT REGARDING FEDERALLY SPONSORED RESEARCH

This invention was made with government support under Grant No.(s) HL127564 awarded by the National Institutes of Health. The government has certain rights in the invention.

TECHNICAL FIELD

The subject matter disclosed herein is generally relates generally to genetic basis of hereditary disposition to liver disease, diagnosis, prophylaxis and treatment.

BACKGROUND

The liver is a vital organ and diseases of the liver result in significant morbidity and mortality worldwide. Indeed, liver cirrhosis is a leading cause of illness and death in the United States. The most common causes of cirrhosis are excess alcohol use and chronic infection with hepatitis viruses (such as hepatitis B and hepatitis C). Cirrhosis can be caused by other conditions including fatty liver disease, inherited disorders, drug-induced injury, bile duct disorders, and autoimmune diseases. A large number of patients (up to 20%) do not have an identifiable cause for cirrhosis. This is known as cryptogenic cirrhosis. As such, there exists a need for treatments for and prevention of liver diseases, such as cirrhosis.

Citation or identification of any document in this application is not an admission that such a document is available as prior art to the present invention.

SUMMARY

In certain example embodiments, described herein are methods of treating or preventing a liver disease or a symptom thereof in a subject in need thereof comprising: detecting a MARC1 risk allele, a MARC2 risk allele, or both in the subject in need thereof, wherein the presence of a MARC1 risk allele, a MARC2 risk allele, or both indicates that the subject in need thereof has an increased risk of liver disease; and administering, to the subject in need thereof, an amount of a treatment or preventative effective to reduce the amount of, activity of, or both of MARC1, MARC2, or both in the subject in need thereof.

In certain example embodiments, the liver disease or symptom thereof comprises liver cirrhosis.

In certain example embodiments, the liver disease or symptom thereof comprises alcoholic cirrhosis, non-alcoholic cirrhosis, a hepatitis-related cirrhosis, hepatic steatosis, alcohol-related fatty liver disease (ALD), or nonalcoholic fatty liver disease (NAFLD).

In certain example embodiments, the MARC1 risk allele encodes an alanine at amino acid position 165 of SEQ ID NO: 1 or at a position equivalent to amino acid position 165 of SEQ ID NO: 1 and wherein the MARC2 risk allele encodes an alanine at a position in the MARC2 that is equivalent to amino acid position 165 of SEQ ID NO: 1.

In certain example embodiments, the treatment or preventative effective to reduce the amount of, activity of, or both of MARC1, MARC2, or both comprises a MARC1-specific RNAi molecule, a MARC2-specific RNAi molecule, a small molecule agent, a MARC1-specific gene modifying agent, a MARC2-specific gene modifying agent, or a combination thereof.

In certain example embodiments, the MARC1- or MARC2-specific gene modifying agent is capable of modifying a polynucleotide encoding an alanine at position 165 of SEQ ID NO: 1 or equivalent position in the MARC1 or MARC2 to a polynucleotide encoding a threonine in a cell in the subject in need thereof.

In certain example embodiments, the subject in need thereof has an elevated amount, activity of, or both of or one or more of aminotransferase (ALT), triglyceride (TG), alkaline phosphatase (ALP), total cholesterol, low-density lipoprotein (LDL) cholesterol, or a combination thereof prior to administration.

In certain example embodiments, administering the amount of a treatment or preventative effective to reduce the amount of, activity of, or both of MARC1, MARC2, or both reduces the amount of, activity of, or both of aminotransferase (ALT), triglyceride (TG), alkaline phosphatase (ALP), total cholesterol, low-density lipoprotein (LDL) cholesterol, or a combination thereof.

In certain example embodiments, administering the amount of a treatment or preventative effective to reduce the amount of, activity of, or both of MARC1, MARC2, or both reduces the level of total cholesterol, low-density lipoprotein (LDL) cholesterol, triglycerides, or a combination thereof in the subject in need thereof.

In certain example embodiments, the subject in need thereof is
  a) heterozygous for the high-risk MARC1 allele;
  b) homozygous for the high-risk MARC1 allele;
  c) heterozygous for the high-risk MARC2 allele;
  d) heterozygous for the high-risk MARC1 allele;
  e) or any permissible combination thereof.

In certain example embodiments, described herein are methods of reducing total cholesterol, low-density lipoprotein, or a combination thereof in a subject in need thereof, comprising: administering, to the subject in need thereof, an amount of a treatment effective to reduce the amount of, activity of, or both of MARC1, MARC2, or both in the subject in need thereof.

In certain example embodiments, the subject in need thereof has a MARC1 risk allele, a MARC2 risk allele, or both.

In certain example embodiments, the subject in need thereof is
  a) heterozygous for the high-risk MARC1 allele;
  b) homozygous for the high-risk MARC1 allele;
  c) heterozygous for the high-risk MARC2 allele;
  d) heterozygous for the high-risk MARC1 allele;
  e) or any permissible combination thereof.

In certain example embodiments, the MARC1 risk allele encodes an alanine at amino acid position 165 of SEQ ID NO: 1 or at a position equivalent to amino acid position 165 of SEQ ID NO: 1 and wherein the MARC2 risk allele encodes an alanine at a position in the MARC2 that is equivalent to amino acid position 165 of SEQ ID NO: 1.

In certain example embodiments, the treatment or preventative effective to reduce the amount of, activity of, or both of MARC1, MARC2, or both comprises a MARC1-specific RNAi molecule, a MARC2-specific RNAi molecule, a small molecule agent, a MARC1-specific gene modifying agent, a MARC2-specific gene modifying agent, or a combination thereof.

In certain example embodiments, the MARC1- or MARC2-specific gene modifying agent is capable of modifying a polynucleotide encoding an alanine at position 165 of SEQ ID NO: 1 or equivalent position in the MARC1 or MARC2 to a polynucleotide encoding a threonine in a cell in the subject in need thereof.

In certain example embodiments, the subject in need thereof has an elevated amount, activity of, or both of or one or more of aminotransferase (ALT), triglyceride (TG), alkaline phosphatase (ALP), or a combination thereof prior to administration.

In certain example embodiments, the subject in need thereof has a liver disease or a symptom thereof, wherein the liver disease is selected from the group consisting of: alcoholic cirrhosis, non-alcoholic cirrhosis, a hepatitis-related cirrhosis, hepatic steatosis, alcohol-related fatty liver disease (ALD), or nonalcoholic fatty liver disease (NAFLD).

In certain example embodiments, described herein are agent(s) that is/are effective to reduce an amount of, activity of, or both of MARC1, MARC2, or both or effective to treat a liver disease or a symptom thereof, or both, comprising:
  comprises a MARC1-specific RNAi molecule, a MARC2-specific RNAi molecule, a small molecule agent, a MARC1-specific gene modifying agent, a MARC2-specific gene modifying agent, or a combination thereof,
  wherein the agent is produced by a method comprising administering an amount of a test agent to a subject; and determining
    a) the level or modulation thereof of a MARC1 in the subject;
    b) the level or modulation thereof of a MARC2 in the subject;
    c) the level of alanine transaminase (ALT) in the plasma of the subject;
    d) the level of aspartate transaminase (AST) in the plasma of the subject;
    e) the level of alkaline phosphatase (ALP) in the plasma of the subject;
    f) the level of the total cholesterol in the subject;
    g) the level of low-density lipoprotein (LDL) cholesterol in the subject;
    h) the level of high-density lipoprotein (HDL) cholesterol in the subject;
    i) the level of triglycerides in the subject; or
    j) a combination thereof,
  wherein the agent effective to reduce an amount of, activity of, or both of MARC1, MARC2, or both or effective to treat a liver disease or a symptom thereof, or both, is effective to a) reduce the amount, activity, or both of the MARC1 in the subject;
    b) reduce the amount, activity, or both of the MARC2 in the subject;
    c) reduce the level of ALT in the plasma of the subject;
    d) reduce the level of AST in the plasma of the subject;
    e) reduce the level of ALP in the plasma of the subject;
    f) reduce the level of total cholesterol in the subject;
    g) reduce the level of LDL cholesterol in the subject;
    h) reduce the level of HDL cholesterol in the subject;
    i) reduce the level of triglycerides in the subject; or
    j) any combination thereof.

In certain example embodiments, the MARC1- or MARC2-specific gene modifying agent is capable of modifying a polynucleotide encoding an alanine at position 165 of SEQ ID NO: 1 or equivalent position in the MARC1 or MARC2 to a polynucleotide encoding a threonine in a cell in the subject in need thereof.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which.

Figure 1:
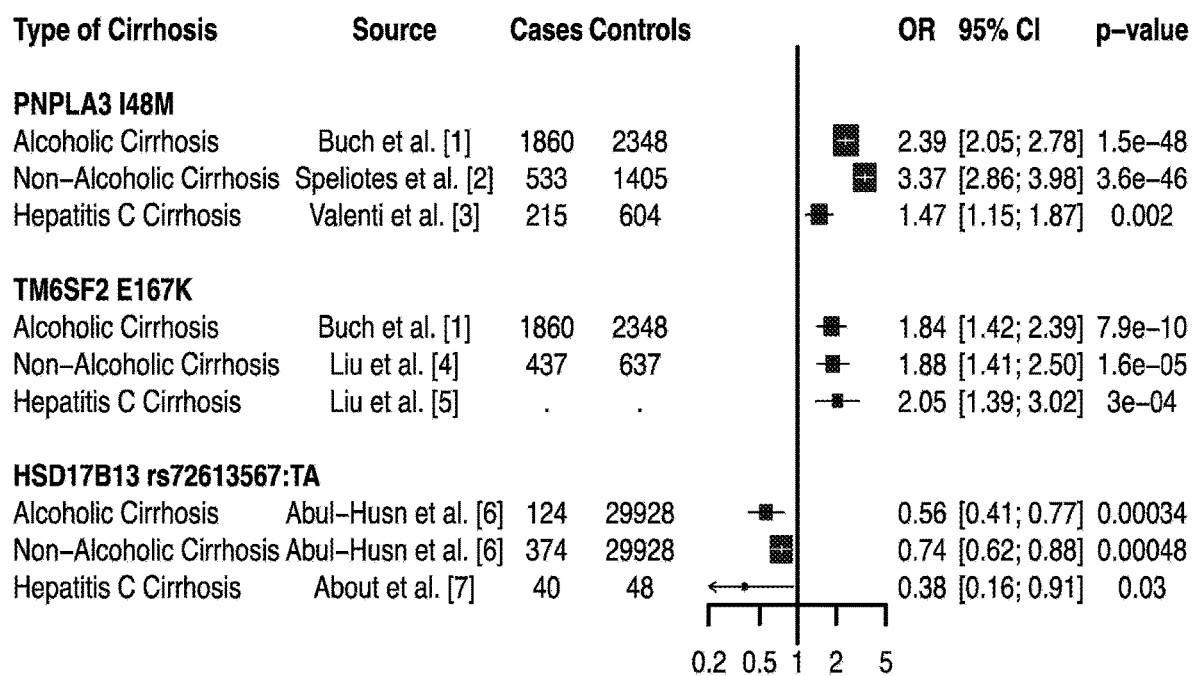
FIG. 1—Risk of alcoholic, non-alcoholic and hepatitis C cirrhosis associated with PNPLA3 I48M, TM6SF2 E40K and HSD17B13 from a recessive model.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N. Y. 1994), March, Advanced Organic Chemistry Reactions, Mechanisms and Structure 4th ed., John Wiley & Sons (New York, N. Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, and cell cultures from bodily fluids. Bodily fluids may be obtained from a mammal organism, for example, by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

The liver is the largest organ of the body, weighing about 1 to 1.5 kg and representing 1.5 to 2.5% of the lean body mass. The size and shape of the liver vary and generally match the general body shape long and lean or squat and square. The liver is located in the right upper quadrant of the abdomen under the right lower rib cage against the diaphragm and projects for a variable extent into the left upper quadrant. The liver is held in place by ligamentous attachments to the diaphragm, peritoneum, great vessels, and upper gastrointestinal organs. It receives a dual blood supply; approximately 20% of the blood flow is oxygen-rich blood from the hepatic artery, and 80% is nutrient-rich blood from the portal vein arising from the stomach, intestines, pancreas, and spleen. The majority of cells in the liver are hepatocytes, which constitute two-thirds of the mass of the liver. The remaining cell types are Kupffer cells (members of the reticuloendothelial system), stellate (Ito or fat-storing) cells, endothelial cells and blood vessels, bile ductular cells, and supporting structures. Gorad et al., "Liver Specific Drug Targeting Strategies: A Review," International Journal of Pharmaceutical Sciences and Research, 2013; 4 (11): 4145-57. doi: 10.13040/IJPSR. 0975-8232.4 (11).4145-57.

The mitochondrial amidoxime-reducing component-1 (MARC1) and -2 (MARC2) are involved in various metabolic activities. They have been reported to catalyze the reduction of N-oxygenated molecules and can act as a counterpart of cytochrome P450 and flavin-containing monooxygenases in metabolic cycles (see e.g., Gruenewald et al. 2008, J. Med. Chem. 51:8173-8177; Kotthaus et al., 2011. Biochem. J. 433:383-391; Kubitza et al., 2018. Proc. Natl. Acad. Sci. USA. 11958-11963). They have also been reported to be a component of the pro-drug converting system and can reduce a multitude of N-hydroxylated prodrugs, particularly amidoximes, leading to increased drug bioavailability (see e.g., Gruenewald et al., 2008. J. Med. Chem. 51:8173-8177). MARC1 and MARC2 have also been proposed to be involved in mitochondrial N (omega)-hydroxyl-L-arginine (NOHA) reduction, regulating endogenous nitric oxide levels and biosynthesis (see e.g., Kotthaus et al., 2011. Biochem. J. 433:383-391), and are believed to be involved in the N—OH bond of N-hydroxylated substrates in concert with electron transfer from NADH to cytochrome B5 reductase then to cytochrome b5, which is the ultimate electron donor that primes the active site for substrate reduction (See e.g., Kotthaus et al., 2011. Biochem. J. 433:383-391 and Gruenewald et al., 2008. J. Med. Chem. 51:8173-8177). The mARC N-reductive enzyme system is a highly effective counterpart to one of the most prominent biotransformation enzymes, CYP450, and is involved in activation of amidoxime prodrugs as well as inactivation of other drugs containing N-hydroxylated functional groups. The crystal structure of human mARC1 illuminates is function. Kubitza et al., Proc. Natl. Acad. Sci. USA, Nov. 20, 2018, Vol. 115, pp. 11958-11963.

Diseases of the liver are a significant cause of mortality and morbidity worldwide. Such diseases include, but are not limited to, cirrhosis, nonalcoholic fatty liver disease (NAFLD), alcoholic liver disease, hepatic steatosis, liver fibrosis, cholestatic liver diseases, and inherited liver diseases (e.g., alpha-1 antitrypsin deficiency, cystic fibrosis (CF), Wilson disease, hereditary hemochromatosis, and type I tyrosinemia). As such, there exists a need for improved understanding of liver diseases, identification of at-risk and affected individuals, and treatments for liver diseases.

Embodiments disclosed herein provide assays and methods capable of detecting, measuring, or otherwise identifying a mutation in the MARC gene, which is associated with and can confer protection against some liver diseases.

Embodiments disclosed herein provide treatments, which can reduce the expression of a MARC gene (e.g., MARC 1 or MARC 2) and/or reduce the amount of a MARC gene product.

In certain example embodiments, described herein are methods of treating or preventing a liver disease or a symptom thereof in a subject in need thereof comprising: detecting a MARC1 risk allele, a MARC2 risk allele, or both in the subject in need thereof, wherein the presence of a MARC1 risk allele, a MARC2 risk allele, or both indicates that the subject in need thereof has an increased risk of liver disease; and administering, to the subject in need thereof, an amount of a treatment or preventative effective to reduce the amount of, activity of, or both of MARC1, MARC2, or both in the subject in need thereof.

In certain example embodiments, the liver disease or symptom thereof comprises liver cirrhosis.

In certain example embodiments, the liver disease or symptom thereof comprises alcoholic cirrhosis, non-alcoholic cirrhosis, a hepatitis-related cirrhosis, hepatic steatosis, alcohol-related fatty liver disease (ALD), or nonalcoholic fatty liver disease (NAFLD).

In certain example embodiments, the MARC1 risk allele encodes an alanine at amino acid position 165 of SEQ ID NO: 1 or at a position equivalent to amino acid position 165 of SEQ ID NO: 1 and wherein the MARC2 risk allele encodes an alanine at a position in the MARC2 that is equivalent to amino acid position 165 of SEQ ID NO: 1.

In certain example embodiments, the treatment or preventative effective to reduce the amount of, activity of, or both of MARC1, MARC2, or both comprises a MARC1-specific RNAi molecule, a MARC2-specific RNAi molecule, a small molecule agent, a MARC1-specific gene modifying agent, a MARC2-specific gene modifying agent, or a combination thereof.

In certain example embodiments, the MARC1- or MARC2-specific gene modifying agent is capable of modifying a polynucleotide encoding an alanine at position 165 of SEQ ID NO: 1 or equivalent position in the MARC1 or MARC2 to a polynucleotide encoding a threonine in a cell in the subject in need thereof.

In certain example embodiments, the subject in need thereof has an elevated amount, activity of, or both of or one or more of aminotransferase (ALT), triglyceride (TG), alkaline phosphatase (ALP), total cholesterol, low-density lipoprotein (LDL) cholesterol, or a combination thereof prior to administration.

In certain example embodiments, administering the amount of a treatment or preventative effective to reduce the amount of, activity of, or both of MARC1, MARC2, or both reduces the amount of, activity of, or both of aminotransferase (ALT), triglyceride (TG), alkaline phosphatase (ALP), total cholesterol, low-density lipoprotein (LDL) cholesterol, or a combination thereof.

In certain example embodiments, administering the amount of a treatment or preventative effective to reduce the amount of, activity of, or both of MARC1, MARC2, or both reduces the level of total cholesterol, low-density lipoprotein (LDL) cholesterol, triglycerides, or a combination thereof in the subject in need thereof.

In certain example embodiments, the subject in need thereof is
a) heterozygous for the high-risk MARC1 allele;
b) homozygous for the high-risk MARC1 allele;
c) heterozygous for the high-risk MARC2 allele;
d) heterozygous for the high-risk MARC1 allele;
e) or any permissible combination thereof.

In certain example embodiments, described herein are methods of reducing total cholesterol, low-density lipoprotein, or a combination thereof in a subject in need thereof, comprising: administering, to the subject in need thereof, an amount of a treatment effective to reduce the amount of, activity of, or both of MARC1, MARC2, or both in the subject in need thereof.

In certain example embodiments, the subject in need thereof has a MARC1 risk allele, a MARC2 risk allele, or both.

In certain example embodiments, the subject in need thereof is
a) heterozygous for the high-risk MARC1 allele;
b) homozygous for the high-risk MARC1 allele;
c) heterozygous for the high-risk MARC2 allele;
d) heterozygous for the high-risk MARC1 allele;
e) or any permissible combination thereof.

In certain example embodiments, the MARC1 risk allele encodes an alanine at amino acid position 165 of SEQ ID NO: 1 or at a position equivalent to amino acid position 165 of SEQ ID NO: 1 and wherein the MARC2 risk allele encodes an alanine at a position in the MARC2 that is equivalent to amino acid position 165 of SEQ ID NO: 1.

In certain example embodiments, the treatment or preventative effective to reduce the amount of, activity of, or both of MARC1, MARC2, or both comprises a MARC1-specific RNAi molecule, a MARC2-specific RNAi molecule, a small molecule agent, a MARC1-specific gene modifying agent, a MARC2-specific gene modifying agent, or a combination thereof.

In certain example embodiments, the MARC1- or MARC2-specific gene modifying agent is capable of modifying a polynucleotide encoding an alanine at position 165 of SEQ ID NO: 1 or equivalent position in the MARC1 or MARC2 to a polynucleotide encoding a threonine in a cell in the subject in need thereof.

In certain example embodiments, the subject in need thereof has an elevated amount, activity of, or both of or one or more of aminotransferase (ALT), triglyceride (TG), alkaline phosphatase (ALP), or a combination thereof prior to administration.

In certain example embodiments, the subject in need thereof has a liver disease or a symptom thereof, wherein the liver disease is selected from the group consisting of: alcoholic cirrhosis, non-alcoholic cirrhosis, a hepatitis-related cirrhosis, hepatic steatosis, alcohol-related fatty liver disease (ALD), or nonalcoholic fatty liver disease (NAFLD).

In certain example embodiments, described herein are agent(s) that is/are effective to reduce an amount of, activity of, or both of MARC1, MARC2, or both or effective to treat a liver disease or a symptom thereof, or both, comprising:
 comprises a MARC1-specific RNAi molecule, a MARC2-specific RNAi molecule, a small molecule agent, a MARC1-specific gene modifying agent, a MARC2-specific gene modifying agent, or a combination thereof,
 wherein the agent is produced by a method comprising administering an amount of a test agent to a subject; and determining
  a) the level or modulation thereof of a MARC1 in the subject;
  b) the level or modulation thereof of a MARC2 in the subject;
  c) the level of alanine transaminase (ALT) in the plasma of the subject;
  d) the level of aspartate transaminase (AST) in the plasma of the subject;
  e) the level of alkaline phosphatase (ALP) in the plasma of the subject;
  f) the level of the total cholesterol in the subject;
  g) the level of low-density lipoprotein (LDL) cholesterol in the subject;
  h) the level of high-density lipoprotein (HDL) cholesterol in the subject;
  i) the level of triglycerides in the subject; or
  j) a combination thereof,
 wherein the agent effective to reduce an amount of, activity of, or both of MARC1, MARC2, or both or effective to treat a liver disease or a symptom thereof, or both, is effective to a) reduce the amount, activity, or both of the MARC1 in the subject;
  b) reduce the amount, activity, or both of the MARC2 in the subject;
  c) reduce the level of ALT in the plasma of the subject;
  d) reduce the level of AST in the plasma of the subject;
  e) reduce the level of ALP in the plasma of the subject;
  f) reduce the level of total cholesterol in the subject;
  g) reduce the level of LDL cholesterol in the subject;
  h) reduce the level of HDL cholesterol in the subject;
  i) reduce the level of triglycerides in the subject; or
  j) any combination thereof.

In certain example embodiments, the MARC1- or MARC2-specific gene modifying agent is capable of modifying a polynucleotide encoding an alanine at position 165 of SEQ ID NO: 1 or equivalent position in the MARC1 or MARC2 to a polynucleotide encoding a threonine in a cell in the subject in need thereof.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description and be within the scope of the present disclosure.

Liver Protective Marc Variants

Described herein are variants of the mitochondrial amidoxime reducing component (MARC) that are associated with a protective effect against a liver disease, such as cirrhosis. In some embodiments, the variant(s) can have a protective effect against a cause of a liver disease, such as cirrhosis. In some embodiments, the MARC variant has reduced or complete loss of MARC function and/or activity. In some embodiments, the MARC variant contains a nonsense mutation that results in early termination of MARC1, frameshift mutations due to indels, and/or splice variants resulting from splice-site mutations. In some embodiments, the MARC variant is associated with a reduced risk of a liver disease, such as cirrhosis.

MARC and MARC Variants

There are two known isoforms of mitochondrial amidoxime reducing component (mARC): mARC-1 and mARC-2. These isoforms are encoded by two genes (MARC1, NM_022746.4, and MARC2, NM_017898.5), which are located on chromosome 1 (1q41) in a tandem arrangement. Their sequences are also shown in Table 1. Their sequences show 66% identity and 80% similarity (Wahl et al., "Biochemical and spectroscopic characterization of the human mitochondrial amidoxime reducing components hmARC-1 and hmARC-2 suggests the existence of a new molybdenum enzyme family in eukaryotes," J. Biol. Chem., 2010, Vol. 285 pp. 37847-37859). As previously discussed both MARC isoforms are involved in various metabolic activities (see e.g., Kubitza et al., 2018. Proc. Natl. Acad. Sci. USA. 11958-11963, Kotthaus et al., 2011. Biochem. J. 433:383-391, and Gruenewald et al. 2008. J. Med. Chem. 51:8173-8177).

The crystal structure of MARC1 revealed that amino acid residue 165 resides in the N-terminal domain (Kubitza et al. 2018. PNAS US. 115 (47): 11958-11963). The N-terminal domain variants at this position exist (Ott et al. 2014. Drug Metab Dispos. 42:718-725). One such variant has a threonine at residue 165 and one variant has an alanine at residue 165. Id. Table 1 below shows MARC1 and MARC2 reference nucleotide and amino acid sequences. In Table 1, the ATG start codon at position 33 and ACC codon at position 525 of the MARC1 transcript are underlined. This encodes threonine at position 165 of the polypeptide encoded by the transcript, which is underlined in Table 1. In other words, the reference sequence provided is an example of the MARC1 variant having threonine at position 165.

As demonstrated in at least the Working Examples elsewhere herein, the variant having threonine at position 165 of MARC1 is the higher frequency variant in the population and is encoded by the higher frequency allele at rs2642438. The lower frequency variant has alanine at position 165 of the MARC1. In the lower frequency allele (about 25% as demonstrated in the Working Examples herein), the codon at position 525 of MARC1 is GCC (encoding alanine). See also Table 8 in Example 1.

Other variants of MARC1 and MARC2 have been identified, and these are shown in Table 2. Where amino acid sequences were not known for a corresponding DNA or RNA sequence, open reading frames were translated. The longest translated polypeptide for each was aligned with MARC1 or MARC2 polypeptide sequences shown in Table 1 to confirm the variant using the Translate tool available from ExPASy at web.expasy.org and a pairwise sequence alignment tool that is based on the Needleman-Wunsch algorithm available at ebi.ac.uk/Tools/emboss/. The position aligned with amino acid residue 165 of the MARC1 reference sequence in each polypeptide of MARC1 or MARC2 variant in Table 2 is underlined. As is shown in the Table 2 below, some variants have A and some have T at position 165 or the position corresponding to position 165 of the reference MARC1 polypeptide.

TABLE 1

MARC1 and MARC 2 reference sequences.

| | |
|---|---|
| MARC1 partial transcript NM_022746. 4 (SEQ ID NO: 2) | cttgccgccg ccacctcgcg gagaagccag ccatgggcgc cgccggctcc tccgcgctgg cgcgctttgt cctcctcgcg caatcccggc ccgggtggct cggggttgcc gcgctgggcc tgaccgcggt ggcgctgggg gctgtcgcct ggcgccgcgc atggcccacg cggcgcgggc ggctgctgca gcaggtgggc acagtggcgc agctctggat ctaccctgtg aaatcctgca aggggggtgcc ggtgagcgag gcggagtgca cggccatggg gctgcgcagc ggcaacctgc gggacaggtt ttggcttgtg atcaaccagg agggaaacat ggttactgct cgccaggaac ctcgcctggt cctgatttcc ctgacctgcg atggtgacac cctgactctc agtgcagcct acacaaagga cctactactg cctatcaaaa cgcccaccac aaatgcagtg cacaagtgca gagtgcacgg cctggagata gagggcaggg actgtgcga ggccaccgcc cagtggataa ccagcttcct gaagtcacag ccctaccgcc tggtgcactt cgagcctcac atgcgaccga gacgtcctca tcaaatagca gacttgttcc gacccaagga ccagattgct tactcagaca ccagcccatt cttgatcctt tctgaggcgt cgctggcgga tctcaactcc aggctagaga agaaagttaa agcaaccaac ttcaggccca atattgtaat ttcaggatgc gatgtctatg cagaggattc ttgggatgag cttcttattg gtgacgtgga actgaaaagg gtgatggctt gttccagatg catttttaacc acagtggacc cagacaccgg tgtcatgagc aggaaggaac cgctggaaac actgaagagt tatcgccagt gtgacccttc agaacgaaag ttatatggaa aatcaccact ctttgggcag tatttttgtc tggaaaaccc agggaccatc aaagtgggag accctgtgta cctgctgggc cagtaatggg aaccgtatgt cctggaatat tagatgcctt ttaaaaatgt tctcaaaaat gacaaacactt gaagcatggg gtttcagaac tgagacctct acatttctt |
| mARC1 polypeptide SEQ ID NO: 1 | MGAAGSSALA RFVLLAQSRP GWLGVAALGL TAVALGAVAW RRAWPTRRRR LLQQVGTVAQ LWIYPVKSCK GVPVSEAECT AMGLRSGNLR DREWLVINQE GNMVTARQEP RLVLISLTCD GDTLTLSAAY TKDLLLPIKT PTTNAVHKCR VHGLEIEGRD CGEATAQWIT SFLKSQPYRL VHFEPHMRPR RPHQIADLER PKDQIAYSDT SPPLILSEAS LADLNSRLEK KVKATNFRPN IVISGCDVYA EDSWDELLIG DVELKRVMAC SRCILTTVDP DTGVMSRKEP LETLKSYRQC DPSERKLYGK SPLFGQYFVL ENPGTIKVGD PVYLLGQ |
| MARC2 NM_017898.5 (SEQ ID NO: 3) | CATTACCGCGCAGGCTTGGTCACCGCATTAAGGCATTCCCGCTCTCCGCGGAACTGCTCTGCCGTCTCGG CGGTGAAAGTGTGAGAGGGTCCGTAGTTGGGTCAACTTTGACTCCTCTCGCCTGCCCGGATCCTTAAGGG CCTCCTCGTCCTCCCGGTCTCCGGTCGCTGCCCGGGTCTGTGCGCCGGTCCGCGCCCGCCCTCGCTCTGCC ATGGGCGCTTCCAGCTCCTCCGCGCTGGCCCGCCTCGGCCTCCCAGCCCGGCCTGGCCCAGGTGGCTCG GGGTCGCCGCGCTAGGACTGGCCGCCGTGGCCCTGGGGACTGTCGCCTGGCGCCGCGCATGGCCCAGGCG GCGCCGGCGGCTGCAGCAGGTGGGCACCGTGGCGAAGCTCTGGATCTACCCGGTGAAATCCTGCAAAGGG GTGCCGGTGAGCGAGGCTGAGTGCACGGCCATGGGGCTGCGCAGCGGCAACCTGCGGGACAGGTTTTGGC TGGTGATTAAGGAAGATGGACACATGGTCACTGCCCGACAGGAGCCTCGCCTCGTCGTCATCTCCATCAT TTATGAGAATAACTGCCTGATCTTCAGGGCTCCAGACATGGACCAGCTGGTTTTGCCTAGCAAGCAGCCT TCCTCAAACAAACTTCCACAACTGCAGGATATTTGGCCTTGACATTAAAGGCAGAGACTGTGGCAATGAGG CAGCTAAGTGGTTCACCAACTTCTTGAAAACTGAAGCGTATAGATTGGTTCAATTTGAGACAAACATGAA GGGAAGAACATCAAGAAAACTTCTCCCCACTCTTGATCAGAATTTCCAGGTGGCCTACCCAGACTACTGC CCGCTCCTGATCATGACAGATGCCTCCCTGGTAGATTTGAATACCAGGATGGAGAAGAAAATGAAAATGG AGAATTTCAGGCCAAATATTGTGGTGACCGGCTGTGATGCTTTTGAGGAGGATACCTGGGATGAACTCCT AATTGGTAGTGTAGAAGTGAAAAAGGTAATGGCATGCCCCAGGTGTATTTTGACAACGGTGGACCCAGAC ACTGGAGTCATAGACAGGAAACAGCCACTGGACACCCTGAAGAGCTACCGCCTGTGTGATCCTTCTGAGA GGGAATTGTACAAGTTGTCTCCACTTTTTGGGATCTATTATTCAGTGGAAAAAATTGGAAGCCTGAGAGT TGGTGACCCTGTGTATCGGATGGTGTAGTGATGAGTGATGGATCCACTAGGGTGATATGGCTTCAGCAAC CAGGAGGGATTGACTGAGATCTTAACAACAGCAGCAACGATACATCAGCAAATCCTTATTATCCAGCCTT CAACTATCTTTACCCTGGAAAACAATCTCGATTTTTGACTTTTCAAAGTTGTGTATGCTCCAGGTTAATG CAAGGAAAGTATTAGAGGGGGGAATATGAAAGTATATATATAAATTTTAGGTACTGAAGGCTTTAAAAAT AATTAAGATCATCAAAAATGCTATTTTGAATGTTATCATGGCTATTACACTTTTACTTCCTGACTTTAAT ATTGATGAATAAAGCAAGTTTAATGAATCAACTAAAAAGCTGCAAAAATGTTTTTAAAATGTGTGCCTTT TATTACCTATCAGTCTATGTTTGGGAGAAATGGGAAGCAACAGATCACTGTGTCCTGATGTGCAGGACG CATGTTACCACACTCACAAATGCCTAATATTGGTCTTTATGTGGCCATTGAGTCCTGTTGACTTTCCACT CATGTGCTTTTTACTCTAGCATTATGGAATCTGGGCTGTACTGGATGGAAATTCTCTTATAGACTTA GTTTTAGTACTCTATTACACCTTTACTAAGCCACATAAAAGTAATCTGTTTGTGTGTAACTGCCAGATAT ACCACCTGGAATTCCAAGTAAGATAAGGAAGAGGATGACATTTAAAAGAGAATGGAATTTTGAGAGTAGG AATGCAAGGAAGACAGCATGAACATATTTTTTTCAGTGCAAATAATTTTTTCGTAACAAAGAAACGAACA ACTTTGGTATGATCTTAAGCAAAAATACTCACTGAAATAGTATGTGGATGAATTCACCTACTTACAATTT TATGGTTTCTTTGTAAATAATAAATGTGAATCTCAATCCTGCTTTA |
| MARC2 NM_017898.5 (SEQ ID NO: 4) | MGASSSSALARLGLPARPWPRWLGVAALGLAAVALGTVAWRRAWPRRRRRLQ QVGTVAKLWIYPVKSCKGVPVSEAECTAMGLRSGNLRDRFWLVIKEDGHMVTA RQEPRLVLISIIYENNCLIFRAPDMDQLVLPSKQPSSNKLHNCRIFGLDIKGRDCGN EAAKWFTNPLKTEAYRLVQFETNMKGRTSRKLLPTLDQNFQVAYPDYCPLLIMT DASLVDLNTRMEKKMKMENFRPNIVVTGCDAFEEDTWDELLIGSVEVKKVMAC PRCILTTVDPDTGVIDRKQPLDTLKSYRLCDPSERELYKLSPLFGIYYSVEKIGSLR VGDPVYRMV |

TABLE 2

MARC1 and MARC2 variants

| GenBank Accession No. | Variant Name | RNA or Polypeptide | SEQ ID NO: | Sequence (underlined is position aligned with AA 165 or nucleotide 525 of GenBank Accession NM_022746.4) |
|---|---|---|---|---|
| XR_002957377.1 | MARC1 transcript variant X8 | RNA/cDNA | 5 | ACCTGTAGACCAGGAATACTGGGCCAGAAGAAAAAAA<br>TACTGTCTAGTTTAGCAAATTGCAGAATGGACA<br>GCACTGAATGTTGGAACATAAAATTTTTAAAAGGTTTT<br>GGCTTGTGATCAACCAGGAGGGAAACATGGTT<br>ACTGCTCGCCAGGAACCTCGCCTGGTCCTGATTTCCCTG<br>ACCTGCGATGGTGACACCCTGACTCTCAGTG<br>CAGCCTACACAAAGGACCTACTACTGCCTATCAAAACG<br>CCCACCACAAATGCAGTGCACAAGTGCAGAGT<br>GCACGGCCTGGAGATAGAGGGCAGGGACTGTGGCGAG<br>GCCACCGCCCAGTGGATAACCAGCTTCCTGAAG<br>TCACAGCCCTACCGCCTGGTGCACTTCGAGCCTCACAT<br>GCGACCGAGACGTCCTCATCAAATAGCAGACT<br>TGTTCCGACCCAAGGACCAGATTGCTTACTCAGACACC<br>AGCCCATTCTTGATCCTTTCTGAGGCGTCGCT<br>GGCGGATCTCAACTCCAGGCTAGAGAAGAAAGTTAAA<br>GCAACCAACTTCAGGCCCAATATTGTAATTTCA<br>GGATGCGATGTCTATGCAGAGGTAACACTATGCCCCTT<br>TGGATCTTTCCTTGGATTTGACTTCTTTTTTA<br>AGATTTATTCAGCACTTAATAAGTGCAGACTTCTGTGTG<br>GAGGATACAAATGTTGATGGGTCAGAGACTG<br>TCATCAAGGAGGCAGTTCAGTATCTAAGGCTTCTAAGG<br>AGAATTCTGAGTTGACAGGATTCTTGGGATGA<br>GCTTCTTATTGGTGACGTGGAACTGAAAAGGGTGATGG<br>CTTGTTCCAGATGCATTTTAACCACAGTGGAC<br>CCAGACACCGGTGTCATGAGCAGGAAGGAACCGCTGG<br>AAACACTGAAGAGTTATCGCCAGTGTGACCCTT<br>CAGAACGAAAGTTATATGGAAAATCACCACTCTTTGGG<br>CAGTATTTTGTGCTGGAAAACCCAGGGACCAT<br>CAAAGTGGGAGACCCTGTGTACCTGCTGGGCCAGTAAT<br>GGGAACCGTATGTCCTGGAATATTAGATGCCT<br>TTTAAAAATGTTCTCAAAAATGACAACACTTGAAGCAT<br>GGTGTTTCAGAACTGAGACCTCTACATTTTCT<br>TTAAATTTGTGATTTTCACATTTTTCGTCTTTTGGACTTC<br>TGGTGTCTCAATGCTTCAATGTCCCAGTGC<br>AAAAAGTAAAGAAATATAGTCTCAATAACTTAGTAGGA<br>CTTCAGTAAGTCACTTAAATGACAAGACAGGA<br>TTCTGAAAACTCCCCGTTTAACTGATTATGGAATAGTTC<br>TTTCTCCTGCTTCTCCGTTTATCTACCAAGA<br>GCGCAGACTTGCATCCTGTCACTACCACTCGTTAGAGA<br>AAGAGAAGAGAAAGAGGAAGAGTGGGTGG<br>GCTGGAAGAATATCCTAGAATGTGTTATTGCCCCTGTTC<br>ATGAGGTACGCAATGAAAATTAAATTGCACC<br>CCAAATATGGCTGGAATGCCACTTCCCTTTTCTTCTCAA<br>GCCCCGGGCTAGCTTTTGAAATGGCATAAAG<br>ACTGAGGTGACCTTCAGGAAGCACTGCAGATATTAATT<br>TTCCATAGATCTGGATCTGGCCCTGCTGCTTC<br>TCAGACAGCATTGGATTTCCTAAAGGTGCTCAGGAGGA<br>TGGTTGTGTAGTCATGGAGGACCCCTGGATCC<br>TTGCCATTCCCCTCAGCTAATGACGGAGTGCTCCTTCTC<br>CAGTTCCGGGTGAAAAAGTTCTGAATTCTGT<br>GGAGGAGAAGAAAAGTGATTCAGTGATTTCAGATAGA<br>CTACTGAAAACCTTTAAAGGGGGAAAAGGAAAG<br>CATATGTCAGTTGTTTAAAACCCAATATCTATTTTTTAA<br>CTGATTGTATAACTCTAAGATCTGATGAAGT<br>ATATTTTTATTGCCATTTTGTCCTTTGATTATATTGGGA<br>AGTTGACTAAACTTGAAAAATGTTTTTAAA<br>ACTGTGAATAAATGGAAGCTACTTTGACTAGT |
| None, translated in silico from XR_002957377.1 | MARC1 variant X8 | polypeptide | 6 | MLEHKIFKRFWLVINQEGNMVTARQEPRLVLISLTCDGDT<br>LTLSAAYTKDLLLPIKTPTTNAVHKCRVHGLEIEGRDCGE<br>ATAQWITSFLKSQPYRLVHFEPHMRPRRPHQIADLFRPKD<br>QIAYSDTSPFLILSEASLADLNSRLEKKVKATNFRPNIVISG<br>CDVYAEVTLCPFGSFLGFDFFFKIYSALNKCRLLCGGYKC |
| XM_017002097.2 | MARC1 variant X7 | RNA/cDNA | 7 | CTTCAGGCCAGCCTCGGGTCTTATTGTGAGGCTGCACTT<br>GAAACTCCTTTCCAGAGCAGCCCTCGCAGTT<br>CAGCAAGTAACACAGGACTAATGGGAGCTGTAACCTTT<br>CTCCTACCAGCTCCCCAGACAGAGGGCAATTC<br>ATGACATAGTTGAAAGGTTTTGGCTTGTGATCAACCAG<br>GAGGGAAACATGGTTACTGCTCGCCAGGAACC<br>TCGCCTGGTCCTGATTTCCCTGACCTGCGATGGTGACAC<br>CCTGACTCTCAGTGCAGCCTACACAAAGGAC<br>CTACTACTGCCTATCAAAACGCCCACCACAAATGCAGT<br>GCACAAGTGCAGAGTGCACGGCCTGGAGATAG |

TABLE 2-continued

MARC1 and MARC2 variants

| GenBank Accession No. | Variant Name | RNA or Polypeptide | SEQ ID NO: | Sequence (underlined is position aligned with AA 165 or nucleotide 525 of GenBank Accession NM_022746.4) |
|---|---|---|---|---|
| | | | | AGGGCAGGGACTGTGGCGAGGCCACCGCCCAGTGGAT<br>AACCAGCTTCCTGAAGTCACAGCCCTACCGCCT<br>GGTGCACTTCGAGCCTCACATGCGACCGAGACGTCCTC<br>ATCAAATAGCAGACTTGTTCCGACCCAAGGAC<br>CAGATTGCTTACTCAGACACCAGCCCATTCTTGATCCTT<br>TCTGAGGCGTCGCTGGCGGATCTCAACTCCA<br>GGCTAGAGAAGAAAGTTAAAGCAACCAACTTCAGGCC<br>CAATATTGTAATTTCAGGATGCGATGTCTATGC<br>AGAGGATTCTTGGGATGAGCTTCTTATTGGTGACGTGG<br>AACTGAAAAGGGTGATGGCTTGTTCCAGATGC<br>ATTTTAACCACAGTGGACCCAGACACCGGTGTCATGAG<br>CAGGAAGGAACCGCTGGAAACACTGAAGAGTT<br>ATCGCCAGTGTGACCCTTCAGAACGAAAGTTATATGGA<br>AAATCACCACTCTTTGGGCAGTATTTTGTGCT<br>GGAAAACCCAGGGACCATCAAAGTGGGAGACCCTGTG<br>TACCTGCTGGGCCAGTAATGGGAACCGTATGTC<br>CTGGAATATTAGATGCCTTTTAAAAATGTTCTCAAAAA<br>TGACAACACTTGAAGCATGGTGTTTCAGAACT<br>GAGACCTCTACATTTTCTTTAAATTTGTGATTTTCACAT<br>TTTTCGTCTTTTGGACTTCTGGTGTCTCAAT<br>GCTTCAATGTCCCAGTGCAAAAAGTAAAGAAATATAGT<br>CTCAATAACTTAGTAGGACTTCAGTAAGTCAC<br>TTAAATGACAAGACAGGATTCTGAAAACTCCCCGTTTA<br>ACTGATTATGGAATAGTTCTTTCTCCTGCTTC<br>TCCGTTTATCTACCAAGAGCGCAGACTTGCATCCTGTCA<br>CTACCACTCGTTAGAGAAAGAGAAGAAGAGA<br>AAGAGGAAGAGTGGGTGGGCTGGAAGAATATCCTAGA<br>ATGTGTTATTGCCCCTGTTCATGAGGTACGCAA<br>TGAAAATTAAATTGCACCCCAAATATGGCTGGAATGCC<br>ACTTCCCTTTTCTTCTCAAGCCCCGGGCTAGC<br>TTTTGAAATGGCATAAAGACTGAGGTGACCTTCAGGAA<br>GCACTGCAGATATTAATTTTCATAGATCTGG<br>ATCTGGCCCTGCTGCTTCTCAGACAGCATTGGATTTCCT<br>AAAGGTGCTCAGGAGGATGGTTGTGTAGTCA<br>TGGAGGACCCCTGGATCCTTGCCATTCCCCTCAGCTAAT<br>GACGGAGTGCTCCTTCTCCAGTTCCGGGTGA<br>AAAAGTTCTGAATTCTGTGGAGGAGAAGAAAAGTGATT<br>CAGTGATTTCAGATAGACTACTGAAAACCTTT<br>AAAGGGGGAAAAGGAAAGCATATGTCAGTTGTTTAAA<br>ACCCAATATCTATTTTTTAACTGATTGTATAAC<br>TCTAAGATCTGATGAAGTATATTTTTTATTGCCATTTTG<br>TCCTTTGATTATATTGGGAAGTTGACTAAAC<br>TTGAAAAATGTTTTTAAAACTGTGAATAAATGGAAGCT<br>ACTTTGACTAGTTTCAGA |
| XM_017002097.2 | MARC1 variant X7 | Polypeptide | 8 | MVTARQEPRLVLISLTCDGDTLTLSAAYTKDLLLPIKTPTT<br>NAVHKCRVHGLEIEGRDCGEATAQWITSFLKSQPYRLVH<br>FEPHMRPRRPHQIADLFRPKDQIAYSDTSPFLILSEASLADL<br>NSRLEKKVKATNFRPNIVISGCDVYAEDSWDELLIGDVEL<br>KRVMACSRCILTTVDPDTGVMSRKEPLETLKSYRQCDPSE<br>RKLYGKSPLFGQYFVLENPGTIKVGDPVYLLGQ |
| XM_011509904.3 | MARC1 variant X6 | RNA/cDNA | 9 | TTGTCCTCTTTAGGGTCTGGCTTCAGGCCAGCCTCGGGT<br>CTTATTGTGAGGCTGCACTTGAAACTCCTTT<br>CCAGAGCAGCCCTCGCAGTTCAGCAAGTAACACAGGAC<br>TAATGGGAGCTGTAACCTTTCTCCTACCAGCT<br>CCCCAGACAGAGGGCAATTCATGACATAGTTGAAAGGT<br>TTTGGCTTGTGATCAACCAGGAGGGAAACATG<br>GTTACTGCTCGCCAGGAACCTCGCCTGGTCCTGATTTCC<br>CTGACCTGCGATGGTGACACCCTGACTCTCA<br>GTGCAGCCTACACAAAGGACCTACTACTGCCTATCAAA<br>ACGCCCACCACAAATGCAGTGCACAAGTGCAG<br>AGTGCACGGCCTGGAGATAGAGGGCAGGGACTGTGGC<br>GAGGCCACCGCCCAGTGGATAACCAGCTTCCTG<br>AAGTCACAGCCCTACCGCCTGGTGCACTTCGAGCCTCA<br>CATGCGACCGAGACGTCCTCATCAAATAGCAG<br>ACTTGTTCCGACCCAAGGACCAGATTGCTTACTCAGAC<br>ACCAGCCCATTCTTGATCCTTTCTGAGGCGTC<br>GCTGGCGGATCTCAACTCCAGGCTAGAGAAGAAAGTTA<br>AAGCAACCAACTTCAGGCCCAATATTGTAATT<br>TCAGGATGCGATGTCTATGCAGAGGTAACACTATGCCC<br>CTTTGGATCTTTCCTTGGATTTGACTTCTTTT<br>TTAAGGATTCTTGGGATGAGCTTCTTATTGGTGACGTGG<br>AACTGAAAAGGGTGATGGCTTGTTCCAGATG |

TABLE 2-continued

MARC1 and MARC2 variants

| GenBank Accession No. | Variant Name | RNA or Polypeptide | SEQ ID NO: | Sequence (underlined is position aligned with AA 165 or nucleotide 525 of GenBank Accession NM_022746.4) |
|---|---|---|---|---|
| | | | | CATTTTAACCACAGTGGACCCAGACACCGGTGTCATGA<br>GCAGGAAGGAACCGCTGGAAACACTGAAGAGT<br>TATCGCCAGTGTGACCCTTCAGAACGAAAGTTATATGG<br>AAAATCACCACTCTTTGGGCAGTATTTTGTGC<br>TGGAAAACCCAGGGACCATCAAAGTGGGAGACCCTGT<br>GTACCTGCTGGGCCAGTAATGGGAACCGTATGT<br>CCTGGAATATTAGATGCCTTTTAAAAATGTTCTCAAAA<br>ATGACAACACTTGAAGCATGGTGTTTCAGAAC<br>TGAGACCTCTACATTTTCTTTAAATTTGTGATTTTCACA<br>TTTTTCGTCTTTTGGACTTCTGGTGTCTCAA<br>TGCTTCAATGTCCCAGTGCAAAAAGTAAAGAAATATAG<br>TCTCAATAACTTAGTAGGACTTCAGTAAGTCA<br>CTTAAATGACAAGACAGGATTCTGAAAACTCCCCGTTT<br>AACTGATTATGGAATAGTTCTTTCTCCTGCTT<br>CTCCGTTTATCTACCAAGAGCGCAGACTTGCATCCTGTC<br>ACTACCACTCGTTAGAGAAAGAGAAGAAGAG<br>AAAGAGGAAGAGTGGGTGGGCTGGAAGAATATCCTAG<br>AATGTGTTATTGCCCCTGTTCATGAGGTACGCA<br>ATGAAAATTAAATTGCACCCCAAATATGGCTGGAATGC<br>CACTTCCCTTTTCTTCTCAAGCCCCGGGCTAG<br>CTTTTGAAATGGCATAAAGACTGAGGTGACCTTCAGGA<br>AGCACTGCAGATATTAATTTTCCATAGATCTG<br>GATCTGGCCCTGCTGCTTCTCAGACAGCATTGGATTTCC<br>TAAAGGTGCTCAGGAGGATGGTTGTGTAGTC<br>ATGGAGGACCCCTGGATCCTTGCCATTCCCCTCAGCTA<br>ATGACGAGTGCTCCTTCTCCAGTTCCGGGTG<br>AAAAAGTTCTGAATTCTGTGGAGGAGAAGAAAAGTGA<br>TTCAGTGATTTCAGATAGACTACTGAAAACCTT<br>TAAAGGGGGAAAAGGAAAGCATATGTCAGTTGTTTAA<br>AACCCAATATCTATTTTTTAACTGATTGTATAA<br>CTCTAAGATCTGATGAAGTATATTTTTTATTGCCATTTT<br>GTCCTTTGATTATATTGGGAAGTTGACTAAA<br>CTTGAAAAATGTTTTTAAAACTGTGAATAAATGGAAGC<br>TACTTTGACTAGTTTCAGA |
| XM_011509904.3 | MARC1 variant X6 | Polypeptide | 10 | MVTARQEPRLVLISLTCDGDTLTLSAAYTKDLLLPIKTPTT<br>NAVHKCRVHGLEIEGRDCGEATAQWITSFLKSQPYRLVH<br>FEPHMRPRRPHQIADLFRPKDQIAYSDTSPFLILSEASLADL<br>NSRLEKKVKATNFRPNIVISGCDVYAEVTLCPFGSFLGFDF<br>FFKDSWDELLIGDVELKRVMACSRCILTTVDPDTGVMSR<br>KEPLETLKSYRQCDPSERKLYGKSPLFGQYFVLENPGTIK<br>VGDPVYLLGQ |
| XM_017002096.2 | MARC1 variant X5 | RNA/cDNA | 11 | cttgccgccg ccacctcgcg gagaagccag ccatgggcgc cgccggctcc<br>tccgcgctgg cgcgctttgt cctcctcgcg caatcccggc ccgggtggct<br>cggggttgcc gcgctgggcc tgaccgcggt ggcgctgggg gctgtcgcct<br>ggcgccgcgc atgcccacg cggcgccggc ggctgctgca gcaggtgggc<br>acagtggcgc agctctggat ctaccctgtg aaatcctgca aggggtgcc<br>ggtgagcgag gcggagtgca cggccatggg gctgcgcagc ggcaacctgc<br>gggacaggtt ttggcttgtg atcaaccagg agggaaacat ggttactgct<br>cgccaggaac ctcgcctggt cctgatttcc ctgacctgcg atggtgacac<br>cctgactctc agtgcagcct acacaaagga cctactactg cctatcaaaa<br>cgcccaccac aaatgcagtg cacaagtgca ggtgcacgg cctggagata<br>gagggcaggg actgtggcga ggccaccgcc cagtggataa ccagcttcct<br>gaagtcacag ccctaccgcc tggtgcactt cgagcctcac atgcgaccga<br>gacgtcctca tcaaatagca gacttgttcc gacccaagga ccagattgct<br>tactcagaca ccagcccatt cttgatcctt tctgaggcgt cgctggcgga<br>tctcaactcc aggctagaga agaaagttaa agcaaccaac ttcaggccca<br>atattgtaat ttcaggatgc gatgtctatg cagaggattc ttgggatgag<br>cttcttattg gtgacgtgga actgaaaagg gtgatggctt gttccagatg<br>catttaacc acagtggacc cagacaccgg tgtcatgagc aggaaggaac<br>cgctggaaac actgaagagt tatcgccagt gtgacccttc agaacgaaag<br>ttatatggaa aatcaccact ctttgggcag tattttgtgc tggaaaaccc<br>agggaccatc aaagtgggag accctgtgta cctgctgggc cagtaatggg<br>aaccgtatgt cctggaatat tagatgcctt ttaaaaatgt tctcaaaaat<br>gacaacactt gaagcatggt gtttcagaac tgagacctct acattttctt |
| XM_017002096.2 | MARC1 variant X5 | Polypeptide | 12 | MLEHKIFKRFWLVINQEGNMVTARQEPRLVLISLTCDGDT<br>LTLSAAYTKDLLLPIKTPTTNAVHKCRVHGLEIEGRDCGE<br>ATAQWITSFLKSQPYRLVHFEPHMRPRRPHQIADLFRPKD<br>QIAYSDTSPFLILSEASLADLNSRLEKKVKATNFRPNIVISG<br>CDVYAEDSWDELLIGDVELKRVMACSRCILTTVDPDTGV<br>MSRKEPLETLKSYRQCDPSERKLYGKSPLFGQYFVLENPG<br>TIKVGDPVYLLGQ |

TABLE 2-continued

MARC1 and MARC2 variants

| GenBank Accession No. | Variant Name | RNA or Polypeptide | SEQ ID NO: | Sequence (underlined is position aligned with AA 165 or nucleotide 525 of GenBank Accession NM_022746.4) |
|---|---|---|---|---|
| XM_011509903.3 | MARC1 variant X4 | RNA/cDNA | 13 | TTCTCTGTTGATGGACACTCGGGCTGTTACTACTTTTTC<br>AGCATTTTGATTAAAGCTGCAATAAACATTG<br>ATACACAAATGTCTGTTTGAGTTCCTGTTTTCAGTTCTT<br>TGGGGTCTATACGTAGGAGTGTGCTAGGTAT<br>TTTATGTTTTATATATATTTTACTGCAATTAAAAAATAA<br>ATATATAAAAGACTGGCCTGTGTGAAGACCT<br>CGGGAGGTAAGAATGGCTGGAGCAACAGCTGGATCAT<br>GAAGGGCTGGGCACGCCCTTGTTTAGGAGTTGG<br>TTTTATCCTGAAAGCAGGAACCATGGAGGGATTTTGAA<br>TGAGGGGGTCATAAAGTTAGATTTGCATTTTA<br>GAGCGATGTAAACTGCCATTACCAGGAAGAATATTAGA<br>CAGAATATTCACCTGCTAGTCCCAAGGATTTG<br>GGTCAGGGCAGGCCTCTGTCTGTGCAGAAACAAAGTCT<br>GGTAAAAGGGCAGTTACGGAAAGGGCTTATAC<br>TAAGCATATTTTTCTAGTGTAGCTGAACAACTCAACCAT<br>GATAACCTGCTGGAAGTGATGCAAGAAATAT<br>CTTGAACGACCTAAAGTACCGGCCATATTTTTTTCTTAT<br>GTCTGGAAATCTCAAAAGCACATGCTCACTT<br>CTATAATTGTAATCATTTGATCAGTGTGTACTGTAAGGA<br>TTGAAATGCCAATATGTTTTGCTTCCTTGGT<br>AGCTGAGAGATAACCTGCAAAAACATGTTGTTCTTGTT<br>CTGGAAATGGCTCTTTCTATTACCTTTATTTC<br>TCCATTTATCTTTTTTTCTAGGAAGTACCTGTAGACCAG<br>GAATACTGGGCCAGAAGAAAAAAAATACTGTC<br>TAGTTTAGCAAATTGCAGAATGGACAGCACTGAATGTT<br>GGAACATAAAATTTTTAAAAGGTTTTGGCTTG<br>TGATCAACCAGGAGGGAAACATGGTTACTGCTCGCCAG<br>GAACCTCGCCTGGTCCTGATTTCCCTGACCTG<br>CGATGGTGACACCCTGACTCTCAGTGCAGCCTACACAA<br>AGGACCTACTACTGCCTATCAAAACGCCCACC<br>ACAAATGCAGTGCACAAGTGCAGAGTGCACGGCCTGG<br>AGATAGAGGGCAGGGACTGTGGCGAGGCCACCG<br>CCCAGTGGATAACCAGCTTCCTGAAGTCACAGCCCTAC<br>CGCCTGGTGCACTTCGAGCCTCACATGCGACC<br>GAGACGTCCTCATCAAATAGCAGACTTGTTCCGACCCA<br>AGGACCAGATTGCTTACTCAGACACCAGCCCA<br>TTCTTGATCCTTTCTGAGGCGTCGCTGGCGGATCTCAAC<br>TCCAGGCTAGAGAAGAAAGTTAAAGCAACCA<br>ACTTCAGGCCCAATATTGTAATTTCAGGATGCGATGTCT<br>ATGCAGAGGTAACACTATGCCCCTTTGGATC<br>TTTCCTTGGATTTGACTTCTTTTTTTAAGGATTCTTGGGAT<br>GAGCTTCTTATTGGTGACGTGGAACTGAAA<br>AGGGTGATGGCTTGTTCCAGATGCATTTTAACCACAGT<br>GGACCCAGACACCGGTGTCATGAGCAGGAAGG<br>AACCGCTGGAAACACTGAAGAGTTATCGCCAGTGTGAC<br>CCTTCAGAACGAAAGTTATATGGAAAATCACC<br>ACTCTTTGGGCAGTATTTTGTGCTGGAAAACCCAGGGA<br>CCATCAAAGTGGGAGACCCTGTGTACCTGCTG<br>GGCCAGTAATGGGAACCGTATGTCCTGGAATATTAGAT<br>GCCTTTTAAAAATGTTCTCAAAAATGACAACA<br>CTTGAAGCATGGTGTTTCAGAACTGAGACCTCTACATTT<br>TCTTTAAATTTGTGATTTTCACATTTTTCGT<br>CTTTTGGACTTCTGGTGTCTCAATGCTTCAATGTCCCAG<br>TGCAAAAAGTAAAGAAATATAGTCTCAATAA<br>CTTAGTAGGACTTCAGTAAGTCACTTAAATGACAAGAC<br>AGGATTCTGAAAACTCCCCGTTTAACTGATTA<br>TGGAATAGTTCTTTCTCCTGCTTCTCCGTTTATCTACCA<br>AGAGCGCAGACTTGCATCCTGTCACTACCAC<br>TCGTTAGAGAAAGAGAAGAAGAGAAAGAGGAAGAGTG<br>GGTGGGCTGGAAGAATATCCTAGAATGTGTTAT<br>TGCCCCTGTTCATGAGGTACGCAATGAAAATTAAATTG<br>CACCCCAAATATGGCTGGAATGCCACTTCCCT<br>TTTCTTCTCAAGCCCCGGGCTAGCTTTTGAAATGGCATA<br>AAGACTGAGGTGACCTTCAGGAAGCACTGCA<br>GATATTAATTTTCCATAGATCTGGATCTGGCCCTGCTGC<br>TTCTCAGACAGCATTGGATTTCCTAAGGGTG<br>CTCAGGAGGATGGTTGTGTAGTCATGGAGGACCCCTGG<br>ATCCTTGCCATTCCCCTCAGCTAATGACGGAG<br>TGCTCCTTCTCCAGTTCCGGGTGAAAAAGTTCTGAATTC<br>TGTGGAGGAGAAGAAAAGTGATTCAGTGATT<br>TCAGATAGACTACTGAAAACCTTTAAAGGGGGAAAAG<br>GAAAGCATATGTCAGTTGTTTAAAACCCAATAT<br>CTATTTTTTAACTGATTGTATAACTCTAAGATCTGATGA |

TABLE 2-continued

MARC1 and MARC2 variants

| GenBank Accession No. | Variant Name | RNA or Polypeptide | SEQ ID NO: | Sequence (underlined is position aligned with AA 165 or nucleotide 525 of GenBank Accession NM_022746.4) |
|---|---|---|---|---|
| | | | | AGTATATTTTTTATTGCCATTTTGTCCTTTG ATTATATTGGGAAGTTGACTAAACTTGAAAAATGTTTTT AAAACTGTGAATAAATGGAAGCTACTTTGAC TAGTTTCAGA |
| XM_011509903.3 | MARC1 variant X4 | Polypeptide | 14 | MLEHKIFKRFWLVINQEGNMVTARQEPRLVLISLTCDGDT LTLSAAYTKDLLLPIKTPTTNAVHKCRVHGLEIEGRDCGE ATAQWITSFLKSQPYRLVHFEPHMRPRRPHQIADLFRPKD QIAYSDTSPFLILSEASLADLNSRLEKKVKATNFRPNIVISG CDVYAEVTLCPFGSFLGFDFFFKDSWDELLIGDVELKRVM ACSRCILTTVDPDTGVMSRKEPLETLKSYRQCDPSERKLY GKSPLFGQYFVLENPGTIKVGDPVYLLGQ |
| XR_001737362.1 | MARC1 variant X3 | RNA/cDNA | 15 | acagcgccctgcagcgcaggcgacggaaggttgcagaggcagtggggcgccgaccaa gtggaagctgagccaccacctcccactcccgcgccgcccccagaaggacgcactg ctctgattggcccggaagggttcaggagctgcccagcctttgggctcggggccaaag gccgcaccttcccccagcggcccggggcgaccagcgcgctccgccttgccgccgcc acctcgcggagaagccagccatgggcgccgccggctcctccgcgctggcgcgctttg tcctcctcgcgcaatcccggcccgggtggctcggggttgccgcgctgggcctgaccg cggtggcgctgggggctgtcgcctggcgccgcgcatggcccacgcggcgccggcggc tgctgcagcaggtgggcacagtggcgcagctctggatctaccctgtgaaatcctgca aggggtgccggtgagcgaggcggagtgcacggccatgggcgctgcgcagcggcaacc tgcgggacaggttttggcttgtgatcaaccaggagggaaacatggttactgctcgcc aggaacctcgcctggtcctgatttccctgacctgcgatggtgacaccctgactctca gtgcagcctacacaaaggacctactactgcctatcaaaacgcccaccacaaatgcag tgcacaagtgcagagtgcacggcctggagatagagggcagggactgtggcgaggcca ccgcccagtggataaccagcttcctgaagtcacagccctaccgcctggtgcacttcg agcctcacatgcgaccgagacgtcctcatcaaatagcagacttgttccgacccaagg accagattgcttactcagacaccagcccattcttgatcctttctgaggcgtcgctgg cggatctcaactccaggctagagaagaaagttaaagcaaccaacttcaggcccaata ttgtaatttcaggatgcgatgtctatgcagaggtaacactatgccccttggatctt tccttggatttgacttcttttttaagatttattcagcacttaataagtgcagcttc tgtgtggaggatacaaatgttgatgggtcagagactgtcatcaaggaggcagttcag tatctaaggcttctaaggagaattctgagttgacaggattcttgggatgagcttctt attggtgacgtggaactgaaaagggtgatggcttgttcc |
| None, translated in silico from XR_001737362.1 | MARC1 variant X3 | Polypeptide | 16 | MGAAGSSALARFVLLAQSRPGWLGVAALGLTAVALGAV AWRRAWPTRRRRLLQQVGTVAQLWIYPVKSCKGVPVSE AECTAMGLRSGNLRDRFWLVINQEGNMVTARQEPRLVLI SLTCDGDTLTLSAAYTKDLLLPIKTPTTNAVHKCRVHGLE IEGRDCGEATAQWITSFLKSQPYRLVHFEPHMRPRRPHQI ADLFRPKDQIAYSDTSPFLILSEASLADLNSRLEKKVKATN FRPNIVISGCDVYAEVTLCPFGSFLGFDFFFKIYSALNKCRL LCGGYKC |
| XR_921908.1 | MARC1 variant X2 | RNA/cDNA | 17 | acagcgccctgcagcgcaggcgacggaaggttgcagaggcagtggggcgccgaccaa gtggaagctgagccaccacctcccactcccgcgccgcccccagaaggacgcactg ctctgattggcccggaagggttcaggagctgcccagcctttgggctcggggccaaag gccgcaccttcccccagcggcccggggcgaccagcgcgctccgccttgccgccgcc acctcgcggagaagccagccatgggcgccgccggctcctccgcgctggcgcgctttg tcctcctcgcgcaatcccggcccgggtggctcggggttgccgcgctgggcctgaccg cggtggcgctgggggctgtcgcctggcgccgcgcatggcccacgcggcgccggcggc tgctgcagcaggtgggcacagtggcgcagctctggatctaccctgtgaaatcctgca aggggtgccggtgagcgaggcggagtgcacggccatgggcgctgcgcagcggcaacc tgcgggacaggttttggcttgtgatcaaccaggagggaaacatggttactgctcgcc aggaacctcgcctggtcctgatttccctgacctgcgatggtgacaccctgactctca gtgcagcctacacaaaggacctactactgcctatcaaaacgcccaccacaaatgcag tgcacaagtgcagagtgcacggcctggagatagagggcagggactgtggcgaggcca ccgcccagtggataaccagcttcctgaagtcacagccctaccgcctggtgcacttcg agcctcacatgcgaccgagacgtcctcatcaaatagcagacttgttccgacccaagg accagattgcttactcagacaccagcccattcttgatcctttctgaggcgtcgctgg cggatctcaactccaggctagagaagaaagttaaagcaaccaacttcaggcccaata ttgtaatttcaggatgcgatgtctatgcagaggtaacactatgccccttggatctt tccttggatttgacttcttttttaagatttattcagcacttaataagtgcagcttc tgtgtggaggatacaaatgttgatgggtcagagactgtcatcaaggaggcagttcag tatctaaggcttctaaggagaattctgagttgacaggaaaatggaatcaaagcaa ttgagttttaacctttatcctcagaggagccaattatattcttcacttttgctgta cggaggcaaaactatgctgaaagagaaataatctaagaaatttgattcccacattcaa accagaagatgtgacggctggttttcagcttctgcactggcttctgcatgactttgag cagcccgctaagtcccatttaccttgcctgaacaatgagatgatcatatttctgcc tagggttaccttaagggtctgttgaagggtcagtttggataatgtaatttatgagat gtataaaagcaatatcaatcgatggaggataataaaagtacgcccaaatcca TABLE 2-continued MARC1 and MARC2 variants

| GenBank Accession No. | Variant Name | RNA or Polypeptide | SEQ ID NO: | Sequence (underlined is position aligned with AA 165 or nucleotide 525 of GenBank Accession NM_022746.4) |
|---|---|---|---|---|
| None, translated in silico from XR_921908.1 | MARC1 variant X2 | Polypeptide | 18 | MGAAGSSALARFVLLAQSRPGWLGVAALGLTAVALGAV AWRRAWPTRRRRLLQQVGTVAQLWIYPVKSCKGVPVSE AECTAMGLRSGNLRDRFWLVINQEGNMVTARQEPRLVLI SLTCDGDTLTLSAAYTKDLLLPIKTPTTNAVHKCRVHGLE IEGRDCGEATAQWITSFLKSQPYRLVHFEPHMRPRRPHQI ADLFRPKDQ<u>I</u>AYSDTSPFLILSEASLADLNSRLEKKVKATN FRPNIVISGCDVYAEVTLCPFGSFLGFDFFFKIYSALNKCRL LCGGYKC |
| XM_011509900.3 | MARC1 variant X1 | RNA/cDNA | 19 | ACAGCGCCCTGCAGCGCAGGCGACGGAAGGTTGCAGA GGCAGTGGGGCGCCGACCAAGTGGAAGCTGAGC CACCCACCTCCCACTCCCCGCGCCGCCCCCAGAAGGAC GCACTGCTCTGATTGGCCCGGAAGGGTTCAGG AGCTGCCCAGCCTTTGGGCTCGGGGCCAAAGGCCGCAC CTTCCCCCAGCGGCCCCGGGCGACCAGCGCGC TCCGGCCTTGCCGCCGCCACCTCGCGGAGAAGCCAGCC ATGGGCGCCGCCGGCTCCTCCGCGCTGGCGCG CTTTGTCCTCCTCGCGCAATCCCGGCCCGGGTGGCTCGG GGTTGCCGCGCTGGGCCTGACCGCGGTGGCG CTGGGGGCTGTCGCCTGGCGCCGCGCATGGCCCACGCG GCGCCGGCGGCTGCTGCAGCAGGTGGGCACAG TGGCGCAGCTCTGGATCTACCCTGTGAAATCCTGCAAG GGGGTGCCGGTGAGCGAGGCGGAGTGCACGGC CATGGGGCTGCGCAGCGGCAACCTGCGGGACAGGTTTT GGCTTGTGATCAACCAGGAGGGAAACATGGTT ACTGCTCGCCAGGAACCTCGCCTGGTCCTGATTTCCCTG ACCTGCGATGGTGACACCCTGACTCTCAGTG CAGCCTACACAAAGGACCTACTACTGCCTATCAAAACG CCCACCACAAATGCAGTGCACAAGTGCAGAGT GCACGGCCTGGAGATAGAGGGCAGGGACTGTGGCGAG GCCACCGCCCAGTGGATAACCAGCTTCCTGAAG TCACAGCCCTACCGCCTGGTGCACTTCGAGCCTCACAT GCGACCGAGACGTCCTCATCAAATAGCAGACT TGTTCCGACCCAAGGACCAGATTGCTTACTCAGACACC AGCCCATTCTTGATCCTTTCTGAGGCGTCGCT GGCGGATCTCAACTCCAGGCTAGAGAAGAAAGTTAAA GCAACCAACTTCAGGCCCAATATTGTAATTTCA GGATGCGATGTCTATGCAGAGGTAACACTATGCCCCTT TGGATCTTTCCTTGGATTTGACTTCTTTTTTA AGGATTCTTGGGATGAGCTTCTTATTGGTGACGTGGAA CTGAAAAGGGTGATGGCTTGTTCCAGATGCAT TTTAACCACAGTGTGGACCCAGACACCGGTGTCATGAGCA GGAAGGAACCGCTGGAAACACTGAAGAGTTAT CGCCAGTGTGACCCTTCAGAACGAAAGTTATATGGAAA ATCACCACTCTTTGGGCAGTATTTTGTGCTGG AAAAACCCAGGGACCATCAAAGTGGGAGACCCTGTGTA CCTGCTGGGCCAGTAATGGGAACCGTATGTCCT GGAATATTAGATGCCTTTTAAAAATGTTCTCAAAAATG ACAACACTTGAAGCATGGTGTTTCAGAACTGA GACCTCTACATTTTCTTTAAATTTGTGATTTTCACATTTT TCGTCTTTTGGACTTCTGGTGTCTCAATGC TTCAATGTCCCAGTGCAAAAAGTAAAGAAATATAGTCT CAATAACTTAGTAGGACTTCAGTAAGTCACTT AAATGACAAGACAGGATTCTGAAAACTCCCCGTTTAAC TGATTATGGAATAGTTCTTTCTCCTGCTTCTC CGTTTATCTACCAAGAGCGCAGACTTGCATCCTGTCACT ACCACTCGTTAGAGAAAGAGAAGAAGAGAAA GAGGAAGAGTGGGTGGGCTGGAAGAATATCCTAGAAT GTGTTATTGCCCCTGTTCATGAGGTACGCAATG AAAATTAAATTGCACCCCAAATATGGCTGGAATGCCAC TTCCCTTTTCTTCTCAAGCCCCGGGCTAGCTT TTGAAATGGCATAAAGACTGAGGTGACCTTCAGGAAGC ACTGCAGATATTAATTTTCCATAGATCTGGAT CTGGCCCTGCTGCTTCTCAGACAGCATTGGATTTCCTAA AGGTGCTCAGGAGGATGGTTGTGTAGTCATG GAGGACCCCTGGATCCTTGCCATTCCCCTCAGCTAATG ACGGAGTGCTCCTTCTCCAGTTCCGGGTGAAA AAGTTCTGAATTCTGTGGAGGAGAAGAAAAGTGATTCA GTGATTTCAGATAGACTACTGAAAACCTTTAA AGGGGGAAAGGAAAGCATATGTCAGTTGTTTAAAAC CCAATATCTATTTTTTAACTGATTGTATAACTC TAAGATCTGATGAAGTATATTTTTTATTGCCATTTTGTC CTTTGATTATATTGGGAAGTTGACTAAACTT |

TABLE 2-continued

MARC1 and MARC2 variants

| GenBank Accession No. | Variant Name | RNA or Polypeptide | SEQ ID NO: | Sequence (underlined is position aligned with AA 165 or nucleotide 525 of GenBank Accession NM_022746.4) |
|---|---|---|---|---|
| | | | | GAAAAATGTTTTTAAAACTGTGAATAAATGGAAGCTAC TTTGACTAGTTTCAGA |
| XM_011509900.3 | MARC1 variant X1 | Polypeptide | 20 | MGAAGSSALARFVLLAQSRPGWLGVAALGLTAVALGAV AWRRAWPTRRRRLLQQVGTVAQLWIYPVKSCKGVPVSE AECTAMGLRSGNLRDRFWLVINQEGNMVTARQEPRLVLI SLTCDGDTLTLSAAYTKDLLLPIKTPTTNAVHKCRVHGLE IEGRDCGEATAQWITSFLKSQPYRLVHFEPHMRPRRPHQI ADLFRPKDQIAYSDTSPFLILSEASLADLNSRLEKKVKATN FRPNIVISGCDVYAEVTLCPFGSFLGFDFFFKDSWDELLIG DVELKRVMACSRCILTTVDPDTGVMSRKEPLETLKSYRQ CDPSERKLYGKSPLFGQYFVLENPGTIKVGDPVYLLGQ |
| NM_001317338 | MARC1 variant 1 | RNA/cDNA | 21 | CATTACCGCGCAGGCTTGGTCACCGCATTAAGGCATTC CCGCTCTCCGCGGAACTGCTCTGCCGTCTCGG CGGTGAAAGTGTGAGAGGGTCCGTAGTTGGGTCAACTT TGACTCCTCTCGCCTGCCCGGATCCTTAAGGG CCTCCTCGTCCTCCCGGTCTCCGGTCGCTGCCGGGTCTG TGCGCCGGTCCGCGCCCGCCCTCGCTCTGCC ATGGGCGCTTCCAGCTCCTCCGCGCTGGCCCGCCTCGG CCTCCCAGCCCGGCCCTGGCCCAGGTGGCTCG GGGTCGCCGCGCTAGGACTGGCCGCCGTGGCCCTGGGG ACTGTCGCCTGGCGCCGCGCATGGCCCAGGCG GCGCCGGCGGCTGCAGCAGGTGGGCACCGTGGCGAAG CTCTGGATCTACCCGGTGAAATCCTGCAAAGGG GTGCCGGTGAGCGAGGCTGAGTGCACGGCCATGGGGCT GCGCAGCGGCAACCTGCGGGACAGGTTTTGGC TGGTGATTAAGGAAGATGGACACATGGTCACTGCCCGA CAGGAGCCTCGCCTCGTGCTCATCTCCATCAT TTATGAGAATAACTGCCTGATCTTCAGGGCTCCAGACA TGGACCAGCTGGTTTTGCCTAGCAAGCAGCCT TCCTCAAACAAACTCCACAACTGCAGGATATTTGGCCT TGACATTAAAGGCAGAGACTGTGGCAATGAGG CAGCTAAGTGGTTCACCAACTTCTTGAAAACTGAAGCG TATAGATTGGTTCAATTTGAGACAAACATGAA GGGAAGAACATCAAGAAACTTCTCCCCACTCTTGATC AGAATTTCCAGGTGGCCTACCCAGACTACTGC CCGCTCCTGATCATGACAGATGCCTCCCTGGTAGATTTG AATACCAGGATGGAGAAGAAAATGAAAATGG AGAATTTCAGGCCAAATATTGTGGTGACCGGCTGTGAT GCTTTTGAGGAGGATACCTGGGATGAACTCCT AATTGGTAGTGTAGAAGTGAAAAAGGTAATGGCATGCC CCAGGTGTATTTTGACAACGGTGGACCCAGAC ACTGGAGTCATAGACAGGAAACAGCCACTGGACACCCT GAAGAGCTACCGCCTGTGTGATCCTTCTGAGA GGGAATTGTACAAGTTGTCTCCACTTTTTGGGATCTATT ATTCAGTGGAAAAAATTGGAAGCCTGAGAGT TGGTGACCCTGTGTATCGGATGGTGTAGTGATGAGTGA TGGATCCACTAGGGTGATATGGTAAAGGGCTT CAGCAACCAGGAGGGATTGACTGAGATCTTAACAACA GCAGCAACGATACATCAGCAAATCCTTATTATC CAGCCTTCAACTATCTTTACCCTGGAAAACAATCTCGAT TTTTGACTTTTCAAAGTTGTGTATGCTCCAG GTTAATGCAAGGAAAGTATTAGAGGGGGGAATATGAA AGTATATATATAAATTTTAGGTACTGAAGGCTT TAAAAATAATTAAGATCATCAAAAATGCTATTTTGAAT GTTATCATGGCTATTACACTTTTACTTCCTGA CTTTAATATTGATGAATAAAGCAAGTTTAATGAATCAA CTAAAAAGCTGCAAAATGTTTTTAAAATGTG TGCCTTTTATTACCTATCAGTCTATGTTTTGGGAGAAAT GGGAAGCAACAGATCACTGTGTCCTGATGTG CAGGACGCATGTTACCACACTCACAAATGCCTAATATT GGTCTTTATGTGGCCATTGAGTCCTGTTGACT TTCCACTCATGTGCTTTTTACTCTAGCATTATGGAATCT GGGCTGTACTTGAGTATGGAAATTCTCTTAT AGACTTAGTTTTAGTACTCTATTACACCTTTACTAAGCC ACATAAAAGTAATCTGTTTGTGTGTAACTGC CAGATATACCACCTGGAATTCCAAGTAAGATAAGGAAG AGGATGACATTTAAAAGAGAATGGAATTTTGA GAGTAGGAATGCAAGGAAGACAGCATGAACATATTTTT TTCAGTGCAAATAATTTTTTCGTAACAAAGAA ACGAACAACTTTGGTATGATCTTAAGCAAAAATACTCA CTGAAATAGTATGTGGATGAATTCACCTACTT |

TABLE 2-continued

MARC1 and MARC2 variants

| GenBank Accession No. | Variant Name | RNA or Polypeptide | SEQ ID NO: | Sequence (underlined is position aligned with AA 165 or nucleotide 525 of GenBank Accession NM_022746.4) |
|---|---|---|---|---|
| | | | | ACAATTTTATGGTTTCTTTGTAAATAATAAATGTGAATC<br>TCAATCCTGCTTTA |
| NM001317338 | MARC1 variant 1 | polypeptide | 22 | MGASSSSALARLGLPARPWPRWLGVAALGLAAVALGTV<br>AWRRAWPRRRRRLQQVGTVAKLWIYPVKSCKGVPVSEA<br>ECTAMGLRSGNLRDRFWLVIKEDGHMVTARQEPRLVLISI<br>IYENNCLIFRAPDMDQLVLPSKQPSSNKLHNCRIFGLDIKG<br>RDCGNEAAKWFTNFLKTEAYRLVQFETNMKGRTSRKLLP<br>TLDQNFQVAYPDYCPLLIMTDASLVDLNTRMEKKMKME<br>NFRPNIVVTGCDAFEEDTWDELLIGSVEVKKVMACPRCIL<br>TTVDPDTGVIDRKQPLDTLKSYRLCDPSERELYKLSPLFGI<br>YYSVEKIGSLRVGDPVYRMV |
| NM_001331042.2 | MARC1 variant 3 | RNA/cDNA | 23 | CATTACCGCGCAGGCTTGGTCACCGCATTAAGGCATTC<br>CCGCTCTCCGCGGAACTGCTCTGCCGTCTCGG<br>CGGTGAAAGTGTGAGAGGGTCCGTAGTTGGGTCAACTT<br>TGACTCCTCTCGCCTGCCCGGATCCTTAAGGG<br>CCTCCTCGTCCTCCCGGTCTCCGGTCGCTGCCGGGTCTG<br>TGCGCCGGTCCGCGCCCGCCCTCGCTCTGCC<br>ATGGGCGCTTCCAGCTCCTCCGCGCTGGCCCGCCTCGG<br>CCTCCCAGCCCGGCCCTGGCCCAGGTGGCTCG<br>GGGTCGCCGCGCTAGGACTGGCCGCCGTGGCCCTGGGG<br>ACTGTCGCCTGGCGCCGCGCATGGGCCCAGGCG<br>GCGCCGGCGGCTGCAGCAGGTGGGCACCGTGGCGAAG<br>CTCTGGATCTACCCGGTGAAATCCTGCAAAGGG<br>GTGCCGGTGAGCGAGGCTGAGTGCACGGCCATGGGGCT<br>GCGCAGCGGCAACCTGCGGGACAGGTTTTGGC<br>TGGTGATTAAGGAAGATGGACACATGGTCACTGCCCGA<br>CAGGAGCCTCGCCTCGTGCTCATCTCCATCAT<br>TTATGAGAATAACTGCCTGATCTTCAGGGCTCCAGACA<br>TGGACCAGCTGGTTTTGCCTAGCAAGCAGCCT<br>TCCTCAAACAAACTCCACAACTGCAGGATATTTGGCCT<br>TGACATTAAAGGCAGAGACTGTGGCAATGAGG<br>CAGCTAAGTGGTTCACCAACTTCTTGAAAACTGAAGCG<br>TATAGATTGGTTCAATTTGAGACAAACATGAA<br>GGGAAGAACATCAAGAAAACTTCTCCCCACTCTTGATC<br>AGAATTTCCAGGTGGCCTACCCAGACTACTGC<br>CCGCTCCTGATCATGACAGATGCCTCCCTGGTAGATTTG<br>AATACCAGGATGGAGAAGAAAATGAAAATGG<br>AGAATTTCAGGCCAAATATTGTGGTGACCGGCTGTGAT<br>GCTTTTGAGGAGGCTTCAGCAACCAGGAGGGA<br>TTGACTGAGATCTTAACAACAGCAGCAACGATACATCA<br>GCAAATCCTTATTATCCAGCCTTCAACTATCT<br>TTACCCTGGAAAACAATCTCGATTTTTGACTTTTCAAAG<br>TTGTGTATGCTCCAGGTTAATGCAAGGAAAG<br>TATTAGAGGGGGGAATATGAAAGTATATATATAAATTT<br>TAGGTACTGAAGGCTTTAAAAATAATTAAGAT<br>CATCAAAAATGCTATTTTGAATGTTATCATGGCTATTAC<br>ACTTTTACTTCCTGACTTTAATATTGATGAA<br>TAAAGCAAGTTTAATGAATCAACTAAAAAGCTGCAAAA<br>ATGTTTTTAAAATGTGTGCCTTTTATTACCTA<br>TCAGTCTATGTTTTGGGAGAAATGGGAAGCAACAGATC<br>ACTGTGTCCTGATGTGCAGGACGCATGTTACC<br>ACACTCACAAATGCCTAATATTGGTCTTTATGTGGCCAT<br>TGAGTCCTGTTGACTTTCCACTCATGTGCTT<br>TTTACTCTAGCATTATGGAATCTGGGCTGTACTTGAGTA<br>TGGAAATTCTCTTATAGACTTAGTTTTAGTA<br>CTCTATTACACCTTTACTAAGCCACATAAAAGTAATCTG<br>TTTGTGTGTAACTGCCAGATATACCACCTGG<br>AATTCCAAGTAAGATAAGGAAGAGGATGACATTTAAA<br>AGAGAATGGAATTTTGAGAGTAGGAATGCAAGG<br>AAGACAGCATGAACATATTTTTTTCAGTGCAAATAATT<br>TTTTCGTAACAAAGAAACGAACAACTTTGGTA<br>TGATCTTAAGCAAAAATACTCACTGAAATAGTATGTGG<br>ATGAATTCACCTACTTACAATTTTATGGTTTC<br>TTTGTAAATAATAAATGTGAATCTCAATCCTGCTTTA |
| NM_001331042.2 | MARC1 variant 3 | polypeptide | 24 | MGASSSSALARLGLPARPWPRWLGVAALGLAAVALGTV<br>AWRRAWPRRRRRLQQVGTVAKLWIYPVKSCKGVPVSEA<br>ECTAMGLRSGNLRDRFWLVIKEDGHMVTARQEPRLVLISI<br>IYENNCLIFRAPDMDQLVLPSKQPSSNKLHNCRIFGLDIKG<br>RDCGNEAAKWFTNFLKTEAYRLVQFETNMKGRTSRKLLP<br>TLDQNFQVAYPDYCPLLIMTDASLVDLNTRMEKKMKME<br>NFRPNIVVTGCDAFEEASATRRD |

TABLE 2-continued

MARC1 and MARC2 variants

| GenBank Accession No. | Variant Name | RNA or Polypeptide | SEQ ID NO: | Sequence (underlined is position aligned with AA 165 or nucleotide 525 of GenBank Accession NM_022746.4) |
|---|---|---|---|---|
| NM_001317338.2 | MARC2 variant 1 | RNA/cDNA | 25 | CATTACCGCGCAGGCTTGGTCACCGCATTAAGGCATTC CCGCTCTCCGCGGAACTGCTCTGCCGTCTCGG CGGTGAAAGTGTGAGAGGGTCCGTAGTTGGGTCAACTT TGACTCCTCTCGCCTGCCCGGATCCTTAAGGG CCTCCTCGTCCTCCCGGTCTCCGGTCGCTGCCGGGTCTG TGCGCCGGTCCGCGCCCGCCCTCGCTCTGCC ATGGGCGCTTCCAGCTCCTCCGCGCTGGCCCGCCTCGG CCTCCCAGCCCGGCCCTGGCCCAGGTGGCTCG GGGTCGCCGCGCTAGGACTGGCCGCCGTGGCCCTGGGG ACTGTCGCCTGGCGCCGCGCATGGCCCAGGCG GCGCCGGCGGCTGCAGCAGGTGGGCACCGTGGCGAAG CTCTGGATCTACCCGGTGAAATCCTGCAAAGGG GTGCCGGTGAGCGAGGCTGAGTGCACGGCCATGGGGCT GCGCAGCGGCAACCTGCGGGACAGGTTTTGGC TGGTGATTAAGGAAGATGGACACATGGTCACTGCCCGA CAGGAGCCTCGCCTCGTGCTCATCTCCATCAT TTATGAGAATAACTGCCTGATCTTCAGGGCTCCAGACA TGGACCAGCTGGTTTTGCCTAGCAAGCAGCCT TCCTCAAACAAACTCCACAACTGCAGGATATTTGGCCT TGACATTAAAGGCAGAGACTGTGGCAATGAGG CAGCTAAGTGGTTCACCAACTTCTTGAAAACTGAAGCG TATAGATTGGTTCAATTTGAGACAAACATGAA GGGAAGAACATCAAGAAAACTTCTCCCCACTCTTGATC AGAATTTCCAGGTGGCCTACCCAGACTACTGC CCGCTCCTGATCATGACAGATGCCTCCCTGGTAGATTTG AATACCAGGATGGAGAAGAAAATGAAAATGG AGAATTTCAGGCCAAATATTGTGGTGACCGGCTGTGAT GCTTTTGAGGAGGATACCTGGGATGAACTCCT AATTGGTAGTGTAGAAGTGAAAAAGGTAATGGCATGCC CCAGGTGTATTTTGACAACGGTGGACCCAGAC ACTGGAGTCATAGACAGGAAACAGCCACTGGACACCCT GAAGAGCTACCGCCTGTGTGATCCTTCTGAGA GGGAATTGTACAAGTTGTCTCCACTTTTTGGGATCTATT ATTCAGTGGAAAAAATTGGAAGCCTGAGAGT TGGTGACCCTGTGTATCGGATGGTGTAGTGATGAGTGA TGGATCCACTAGGGTGATATGGTAAAGGGCTT CAGCAACCAGGAGGGATTGACTGAGATCTTAACAACA GCAGCAACGATACATCAGCAAATCCTTATTATC CAGCCTTCAACTATCTTTACCCTGGAAAACAATCTCGAT TTTTGACTTTTCAAAGTTGTGTATGCTCCAG GTTAATGCAAGGAAAGTATTAGAGGGGGGAATATGAA AGTATATATATAAATTTTAGGTACTGAAGGCTT TAAAAATAATTAAGATCATCAAAAATGCTATTTTGAAT GTTATCATGGCTATTACACTTTTACTTCCTGA CTTTAATATTGATGAATAAAGCAAGTTTAATGAATCAA CTAAAAAGCTGCAAAAATGTTTTTAAAATGTG TGCCTTTTATTACCTATCAGTCTATGTTTTGGGAGAAAT GGGAAGCAACAGATCACTGTGTCCTGATGTG CAGGACGCATGTTACCACACTCACAAATGCCTAATATT GGTCTTTATGTGGCCATTGAGTCCTGTTGACT TTCCACTCATGTGCTTTTTACTCTAGCATTATGGAATCT GGGCTGTACTTGAGTATGGAAATTCTCTTAT AGACTTAGTTTTAGTACTCTATTACACCTTTACTAAGCC ACATAAAAGTAATCTGTTTGTGTGTAACTGC CAGATATACCACCTGGAATTCCAAGTAAGATAAGGAAG AGGATGACATTTAAAAGAGAATGGAATTTTGA GAGTAGGAATGCAAGGAAGACAGCATGAACATATTTTT TTCAGTGCAAATAATTTTTTCGTAACAAAGAA ACGAACAACTTTGGTATGATCTTAAGCAAAAATACTCA CTGAAATAGTATGTGGATGAATTCACCTACTT ACAATTTTATGGTTTCTTTGTAAATAATAAATGTGAATC TCAATCCTGCTTTA |
| NM_001317338.2 | MARC2 variant 1 | polypeptide | 26 | MGASSSSALARLGLPARPWPRWLGVAALGLAAVALGTV AWRRAWPRRRRRLQQVGTVAKLWIYPVKSCKGVPVSEA ECTAMGLRSGNLRDRFWLVIKEDGHMVTARQEPRLVLISI IYENNCLIFRAPDMDQLVLPSKQPSSNKLHNCRIFGLDIKG RDC GNEAAKWFTNFLKTEAYRLVQFETNMKGRTSRKLLPTLD QNF<u>Q</u>VAYPDYCPLLIMTDASLVDLNTRMEKKMKMENFR PNIVVTGCDAFEEDTWDELLIGSVEVKKVMACPRCILTTV DPDTGVIDRKQPLDTLKSYRLCDPSERELYKLSPLFGIYYS VEKIGSLRVGDPVYRMV |

TABLE 2-continued

MARC1 and MARC2 variants

| GenBank Accession No. | Variant Name | RNA or Polypeptide | SEQ ID NO: | Sequence (underlined is position aligned with AA 165 or nucleotide 525 of GenBank Accession NM_022746.4) |
|---|---|---|---|---|
| NM_001331042.2 | MARC2 variant 3 | RNA/cDNA | 27 | CATTACCGCGCAGGCTTGGTCACCGCATTAAGGCATTC CCGCTCTCCGCGGAACTGCTCTGCCGTCTCGG CGGTGAAAGTGTGAGAGGGTCCGTAGTTGGGTCAACTT TGACTCCTCTCGCCTGCCCGGATCCTTAAGGG CCTCCTCGTCCTCCCGGTCTCCGGTCGCTGCCGGGTCTG TGCGCCGGTCCGCGCCCGCCCTCGCTCTGCC ATGGGCGCTTCCAGCTCCTCCGCGCTGGCCCGCCTCGG CCTCCCAGCCCGGCCCTGGCCCAGGTGGCTCG GGGTCGCCGCGCTAGGACTGGCCGCCGTGGCCCTGGGG ACTGTCGCCTGGCGCCGCGCATGGCCCAGGCG GCGCCGGCGGCTGCAGCAGGTGGGCACCGTGGCGAAG CTCTGGATCTACCCGGTGAAATCCTGCAAAGGG GTGCCGGTGAGCGAGGCTGAGTGCACGGCCATGGGGCT GCGCAGCGGCAACCTGCGGGACAGGTTTTGGC TGGTGATTAAGGAAGATGGACACATGGTCACTGCCCGA CAGGAGCCTCGCCTCGTGCTCATCTCCATCAT TTATGAGAATAACTGCCTGATCTTCAGGGCTCCAGACA TGGACCAGCTGGTTTTGCCTAGCAAGCAGCCT TCCTCAAACAAACTCCACAACTGCAGGATATTTGGCCT TGACATTAAAGGCAGAGACTGTGGCAATGAGG CAGCTAAGTGGTTCACCAACTTCTTGAAAACTGAAGCG TATAGATTGGTTCAATTTGAGACAAACATGAA GGGAAGAACATCAAGAAAACTTCTCCCCACTCTTGATC AGAATTTCCAGGTGGCCTACCCAGACTACTGC CCGCTCCTGATCATGACAGATGCCTCCCTGGTAGATTTG AATACCAGGATGGAGAAGAAAATGAAAATGG AGAATTTCAGGCCAAATATTGTGGTGACCGGCTGTGAT GCTTTTGAGGAGGCTTCAGCAACCAGGAGGGA TTGACTGAGATCTTAACAACAGCAGCAACGATACATCA GCAAATCCTTATTATCCAGCCTTCAACTATCT TTACCCTGGAAAACAATCTCGATTTTTGACTTTTCAAAG TTGTGTATGCTCCAGGTTAATGCAAGGAAAG TATTAGAGGGGGGAATATGAAAGTATATATATAAATTT TAGGTACTGAAGGCTTTAAAAATAATTAAGAT CATCAAAAATGCTATTTTGAATGTTATCATGGCTATTAC ACTTTTACTTCCTGACTTTAATATTGATGAA TAAAGCAAGTTTAATGAATCAACTAAAAAGCTGCAAAA ATGTTTTTAAAATGTGTGCCTTTTATTACCTA TCAGTCTATGTTTTGGGAGAAATGGGAAGCAACAGATC ACTGTGTCCTGATGTGCAGGACGCATGTTACC ACACTCACAAATGCCTAATATTGGTCTTTATGTGGCCAT TGAGTCCTGTTGACTTTCCACTCATGTGCTT TTTACTCTAGCATTATGGAATCTGGGCTGTACTTGAGTA TGGAAATTCTCTTATAGACTTAGTTTTAGTA CTCTATTACACCTTTACTAAGCCACATAAAAGTAATCTG TTTGTGTGTAACTGCCAGATATACCACCTGG AATTCCAAGTAAGATAAGGAAGAGGATGACATTTAAA AGAGAATGGAATTTTGAGAGTAGGAATGCAAGG AAGCACAGCATGAACATATTTTTTCAGTGCAAATAATT TTTTCGTAACAAAGAAACGAACAACTTTGGTA TGATCTTAAGCAAAAATACTCACTGAAATAGTATGTGG ATGAATTCACCTACTTACAATTTTATGGTTTC TTTGTAAATAATAAATGTGAATCTCAATCCTGCTTTA |
| NM_001331042.2 | MARC2 variant 3 | polypeptide | 28 | MGASSSSALARLGLPARPWPRWLGVAALGLAAVALGTV AWRRAWPRRRRRLQQVGTVAKLWIYPVKSCKGVPVSEA ECTAMGLRSGNLRDRFWLVIKEDGHMVTARQEPRLVLISI IYENNCLIFRAPDMDQLVLPSKQPSSNKLHNCRIFGLDIKG RDCGNEAAKWFTNFLKTEAYRLVQFETNMKGRTSRKLLP TLDQNFQVAYPDYCPLLIMTDASLVDLNTRMEKKMKME NFRPNIVVTGCDAFEEASATRRD |
| XR_247029.5 | MARC2 variant X1 | RNA/cDNA | 29 | AAACAGATTTTACTCAGTAACTACTTACAGTAGGAGAA AAAGCTGATCATTCTCATTTGTGCATAGCAGA ATGGGCGTTTTAAAGGGTGAAGGAGAGAATAGGGCCG GGAAGCTAGCAGGGGATCAAGTGAAAAATCATG AAGGGGCGGTCAGTATTAATGACGGGCAGCTGTGCCTG GAGCTGGCCGTTATGAAGCTGGGATTCTATCC TCCCACAGAGACTGGGGGACAGAGGCCTATCCTCCCCA TGACTGCATTTCAGAGCAATGGCTTTCAGGTC CTTGAGAAAGACACTTCTGAGGTGTAGGCGATACATAT ACATCTCAAAGCAACAGAGAAAGGATTCACAG TTGTAAGCCCTTTTAAGAAAATATCCTAAAAAAGGGAG |

TABLE 2-continued

MARC1 and MARC2 variants

| GenBank Accession No. | Variant Name | RNA or Polypeptide | SEQ ID NO: | Sequence (underlined is position aligned with AA 165 or nucleotide 525 of GenBank Accession NM_022746.4) |
|---|---|---|---|---|
| | | | | GTCAGGGGCTTTACCATCGGGTGTTGGCTAGA<br>ATAAACGGGGAATTCTCCTGGCTGCCTTGAGCTTTCTCG<br>GGAAGACATTTTACTGGGGTCGAGGTTAGGC<br>GGCAGCGGAGGGTGGGGGACCTTGAGTCATGCTCCTAT<br>AAGCCACGCTAGAGTTCCTCGTCTTTGAGTGC<br>AGAGGTTTAGACTGTGTCTTTGTGTGCAGAAAGTCCTG<br>CAGTTCTCACAGCGACCTGCCAGAAAAAGTCG<br>TTCCCAAATGTTTGTAAATCCTCCGTTGGGCAACCCGCC<br>TTCACGTTCTGCGGTGATCTTGTCGAGCGAC<br>TAAGCGTGCAGTATTAGCAGAGAAGGGGGTGGCAGAG<br>TGCTGGCGCTGAAGGTCATGTTGCATGGGTAAC<br>TGTCGTGTTGTAGGGGGGGGGAAGAGGGAGGAGACAC<br>TGACCACCCCAGAGGCCGCCCCATTAGCTCGCT<br>TGCTTTGGGCGGCGTCGCTCCCACGGCGCCCAGGGTAC<br>CCCCGCCGCTGTCTGCCTGTCTTCCTCCATTA<br>CCGCGCAGGCTTGGTCACCGCATTAAGGCATTCCCGCT<br>CTCCGCGGAACTGCTCTGCCGTCTCGGCGGTG<br>AAAGTGTGAGAGGGTCCGTAGTTGGGTCAACTTTGACT<br>CCTCTCGCCTGCCCGGATCCTTAAGGGCCTCC<br>TCGTCCTCCCGGTCTCCGGTCGCTGCCGGGTCTGTGCGC<br>CGGTCCGCGCCCGCCCTCGCTCTGCCATGGG<br>CGCTTCCAGCTCCTCCGCGCTGGCCCGCCTCGGCCTCCC<br>AGCCCGGCCCTGGCCCAGGTGGCTCGGGGTC<br>GCCGCGCTAGGACTGGCCGCCGTGGCCCTGGGGACTGT<br>CGCCTGGCGCCGCGCATGGCCCAGGCGGCGCC<br>GGCGGCTGCAGCAGGTGGGCACCGTGGCGAAGCTCTG<br>GATCTACCCGGTGAAATCCTGCAAAGGGGTGCC<br>GGTGAGCGAGGCTGAGTGCACGGCCATGGGCTGCGC<br>AGCGGCAACCTGCGGGACAGGTTTTGGCTGGTG<br>ATTAAGGAAGATGGACACATGGTCACTGCCCGACAGG<br>AGCCTCGCCTCGTGCTCATCTCCATCATTTATG<br>AGAATAACTGCCTGATCTTCAGGGCTCCAGACATGGAC<br>CAGCTGGTTTTGCCTAGCAAGCAGCCTTCCTC<br>AAACAAACTCCACAACTGCAGGATATTTGGCCTTGACA<br>TTAAAGGCAGAGACTGTGGCAATGAGGCAGCT<br>AAGTGGTTCACCAACTTCTTGAAAACTGAAGCGTATAG<br>ATTGGTTCAATTTGAGACAAACATGAAGGGAA<br>GAACATCAAGAAAACTTCTCCCCACTCTTGATCAGAAT<br>TTCCAGGTGGCCTACCCAGACTACTGCCCGCT<br>CCTGATCATGACAGATGCCTCCCTGGTAGATTTGAATA<br>CCAGGATGGAGAAGAAAATGAAAATGGAGAAT<br>TTCAGGCCAAATATTGTGGTGACCGGCTGTGATGCTTTT<br>GAGGAGACCAAGGAGGAAGTGTGTCTTCAGA<br>GACGGTGGTGCGCGGTATTCCCCTCGAGTGAGTGTGAT<br>ACGTGAACGCACGCTTATCGATCCCTTGTAAG<br>GAGAGGTCATTCACTTTACAATGCTACCCAAGAGACAA<br>GCCCTTCAAATACAGATGTTGGAGTAGAGACG<br>GCAGAGTGGAGGATACCTGGGATGAACTCCTAATTGGT<br>AGTGTAGAAGTGAAAAAGGTAATGGCATGCCC<br>CAGGTGTATTTTGACAACGGTGGACCCAGACACTGGAG<br>TCATAGACAGGAAACAGCCACTGGACACCCTG<br>AAGAGCTACCGCCTGTGTGATCCTTCTGAGAGGGAATT<br>GTACAAGTTGTCTCCACTTTTTGGGATCTATT<br>ATTCAGTGGAAAAAATTGGAAGCCTGAGAGTTGGTGAC<br>CCTGTGTATCGGATGGTGTAGTGATGAGTGAT<br>GGATCCACTAGGGTGATATGGCTTCAGCAACCAGGAGG<br>GATTGACTGAGATCTTAACAACAGCAGCAACG<br>ATACATCAGCAAATCCTTATTATCCAGCCTTCAACTATC<br>TTTACCCTGGAAAACAATCTCGATTTTTGAC<br>TTTTCAAAGTTGTGTATGCTCCAGGTTAATGCAAGGAA<br>AGTATTAGAGGGGGGAATATGAAAGTATATAT<br>ATAAATTTTAGGTACTGAAGGCTTTAAAAATAATTAAG<br>ATCATCAAAAATGCTATTTTGAATGTTATCAT<br>GGCTATTACACTTTTACTTCCTGACTTTAATATTGATGA<br>ATAAAGCAAGTTTAATGAATCAACTAAAAAG<br>CTGCAAAAATGTTTTTAAAATGTGTGCCTTTTATTACCT<br>ATCAGTCTATGTTTTGGGAGAAATGGGAAGC<br>AACAGATCACTGTGTCCTGATGTGCAGGACGCATGTTA<br>CCACACTCACAAATGCCTAATATTGGTCTTTA<br>TGTGGCCATTGAGTCCTGTTGACTTTCCACTCATGTGCT<br>TTTTACTCTAGCATTATGGAATCTGGGCTGT<br>ACTTGAGTATGGAAATTCTCTTATAGACTTAGTTTTAGT<br>ACTCTATTACACCTTTACTAAGCCACATAAA<br>AGTAATCTGTTTGTGTGTAACTGCCAGATATACCACCTG |

TABLE 2-continued

MARC1 and MARC2 variants

| GenBank Accession No. | Variant Name | RNA or Polypeptide | SEQ ID NO: | Sequence (underlined is position aligned with AA 165 or nucleotide 525 of GenBank Accession NM_022746.4) |
|---|---|---|---|---|
| | | | | GAATTCCAAGTAAGATAAGGAAGAGGATGAC<br>ATTTAAAAGAGAATGGAATTTTGAGAGTAGGAATGCAA<br>GGAAGACAGCATGAACATATTTTTTCAGTGC<br>AAATAATTTTTTCGTAACAAAGAAACGAACAACTTTGG<br>TATGATCTTAAGCAAAAATACTCACTGAAATA<br>GTATGTGGATGAATTCACCTACTTACAATTTTATGGTTT<br>CTTTGTAAATAATAAATGTGAATCTCAATCC<br>TGCTTTA |
| None, translated in silico from XR_247029.5 | MARC2 variant X1 (largest ORF translated) | polypeptide | 30 | MGASSSSALARLGLPARPWPRWLGVAALGLAAVALGTV<br>AWRRAWPRRRRRLQQVGTVAKLWIYPVKSCKGVPVSEA<br>ECTAMGLRSGNLRDRFWLVIKEDGHMVTARQEPRLVLISI<br>IYENNCLIFRAPDMDQLVLPSKQPSSNKLHNCRIFGLDIKG<br>RDCGNEA<u>A</u>KWFTNFLKTEAYRLVQFETNMKGRTSRKLLP<br>TLDQNFQVAYPDYCPLLIMTDASLVDLNTRMEKKMKME<br>NFRPNIVVTGCDAFEETKEEVCLQRRWCAVFPSSECDT |
| XM_011509684.1 | MARC2 variant X2 | RNA/cDNA | 31 | ATTCGGTGCCTGGTGCAGTTGCTGGGAGGGCGTGCTTG<br>TCCTCCCTGACCTTGGAAATCTCTGCTCCT<br>TAGCAGCCATATGTTTTGGCTGGTGATTAAGGAAGATG<br>GACACATGGTCACTGCCCGACAGGAGCCTCGC<br>CTCGTGCTCATCTCCATCATTTATGAGAATAACTGCCTG<br>ATCTTCAGGGCTCCAGACATGGACCAGCTGG<br>TTTTGCCTAGCAAGCAGCCTTCCTCAAACAAACTCCAC<br>AACTGCAGGATATTTGGCCTTGACATTAAAGG<br>CAGAGACTGTGGCAATGAGGCAGCTAAGTGGTTCACCA<br>ACTTCTTGAAAACTGAAGCGTATAGATTGGTT<br>CAATTTGAGACAAACATGAAGGGAAGAACATCAAGAA<br>AACTTCTCCCCACTCTTGATCAGAATTTCCAGG<br>TGGCCTACCCAGACTACTGCCCGCTCCTGATCATGACA<br>GATGCCTCCCTGGTAGATTTGAATACCAGGAT<br>GGAGAAGAAAATGAAAATGGAGAATTTCAGGCCAAAT<br>ATTGTGGTGACCGGCTGTGATGCTTTTGAGGAG<br>GATACCTGGGATGAACTCCTAATTGGTAGTGTAGAAGT<br>GAAAAAGGTAATGGCATGCCCCAGGTGTATTT<br>TGACAACGGTGGACCCAGACACTGGAGTCATAGACAG<br>GAAACAGCCACTGGACACCCTGAAGAGCTACCG<br>CCTGTGTGATCCTTCTGAGAGGGAATTGTACAAGTTGT<br>CTCCACTTTTTGGGATCTATTATTCAGTGGAA<br>AAAATTGGAAGCCTGAGAGTTGGTGACCCTGTGTATCG<br>GATGGTGTAGTGATGAGTGATGGATCCACTAG<br>GGTGATATGGCTTCAGCAACCAGGAGGGATTGACTGAG<br>ATCTTAACAACAGCAGCAACGATACATCAGCA<br>AATCCTTATTATCCAGCCTTCAACTATCTTTACCCTGGA<br>AAACAATCTCGATTTTTGACTTTTCAAAGTT<br>GTGTATGCTCCAGGTTAATGCAAGGAAAGTATTAGAGG<br>GGGGAATATGAAAGTATATATATAAATTTTAG<br>GTACTGAAGGCTTTAAAAATAATTAAGATCATCAAAAA<br>TGCTATTTTGAATGTTATCATGGCTATTACAC<br>TTTTACTTCCTGACTTTAATATTGATGAATAAAGCAAGT<br>TTAATGAATCAACTAAAAAGCTGCAAAAATG<br>TTTTTAAAATGTGTGCCTTTTATTACCTATCAGTCTATG<br>TTTTGGGAGAAATGGGAAGCAACAGATCACT<br>GTGTCCTGATGTGCAGGACGCATGTTACCACACTCACA<br>AATGCCTAATATTGGTCTTTATGTGGCCATTG<br>AGTCCTGTTGACTTTCCACTCATGTGCTTTTTACTCTAG<br>CATTATGGAATCTGGGCTGTACTTGAGTATG<br>GAAATTCTCTTATAGACTTAGTTTTAGTACTCTATTACA<br>CCTTTACTAAGCCACATAAAAGTAATCTGTT<br>TGTGTGTAACTGCCAGATATACCACCTGGAATTCCAAG<br>TAAGATAAGGAAGAGGATGACATTTAAAAGAG<br>AATGGAATTTTGAGAGTAGGAATGCAAGGAAGACAGC<br>ATGAACATATTTTTTCAGTGCAAATAATTTTT<br>TCGTAACAAAGAAACGAACAACTTTGGTATGATCTTAA<br>GCAAAAATACTCACTGAAATAGTATGTGGATG<br>AATTCACCTACTTACAATTTTATGGTTTCTTTGTAAATA<br>ATAAATGTGAATCTCAATCCTGCTTTA |
| XM_011509684.1 | MARC2 variant X2 | polypeptide | 32 | MFWLVIKEDGHMVTARQEPRLVLISIIYENNCLIFRAPDM<br>DQLVLPSKQPSSNKLHNCRIFGLDIKGRDCGNEA<u>A</u>KWFTN<br>FLKTEAYRLVQFETNMKGRTSRKLLPTLDQNFQVAYPDY<br>CPLLIMTDASLVDLNTRMEKKMKMENFRPNIVVTGCDAF<br>EEDTWDELLIGSVEVKKVMACPRCILTTVDPDTGVIDRKQ |

TABLE 2-continued

MARC1 and MARC2 variants

| GenBank Accession No. | Variant Name | RNA or Polypeptide | SEQ Sequence (underlined is position aligned with ID AA 165 or nucleotide 525 of GenBank NO: Accession NM_022746.4) |
|---|---|---|---|
| | | | PLDTLKSYRLCDPSERELYKLSPLFGIYYSVEKIGSLRVGD PVYRMV |

Protective and Risk MARC Variants

As previously discussed, MARC1 and MARC2 can have variants. In some embodiments, the variant(s) can have a protective effect against a cause of a liver disease, such as cirrhosis. In some embodiments, the protective MARC variant has reduced or complete measurable loss of MARC function and/or activity as compared to a MARC when compared to a risk MARC variant. In some embodiments, the protective MARC variant has a threonine at amino acid position 165 or equivalent position within the MARC variant. In some embodiments, the risk MARC variant has an alanine at amino acid position 165 or equivalent position within the MARC variant. It will be appreciated that the genomic DNA of the protective MARC variant will have the appropriate three-nucleotide bases that can form a codon for a threonine at position 165 or equivalent position in the polypeptide at the corresponding position within the genomic DNA. It will be appreciated that the transcript of the protective MARC variant will have the appropriate codon for a threonine at position 165 or equivalent position in the polypeptide at the corresponding position within the transcript. It will be appreciated that the genomic DNA of the risk MARC variant will have the appropriate three-nucleotide bases that can form a codon for a alanine at position 165 or equivalent position in the polypeptide at the corresponding position within the genomic DNA. It will be appreciated that the transcript of the risk MARC variant will have the appropriate codon for an alanine at position 165 or equivalent position in the polypeptide at the corresponding position within the transcript. Such sequences are described elsewhere herein.

In some embodiments, MARC function and/or activity in the MARC variant is reduced by about 1% to 100%, such as by about 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, including any value or range of values therein. In some embodiments, MARC function and/or activity in the MARC variant is reduced by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

In some embodiments, the MARC1 variant has reduced or complete measurable loss of MARC1 function and/or activity. In some embodiments, MARC1 function and/or activity in the MARC1 variant is reduced by about 1% to 100%, such as by about 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, including any value or range of values therein. In some embodiments, MARC1 function and/or activity in the MARC1 variant is reduced by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

In some embodiments, the MARC2 variant has reduced or complete measurable loss of MARC2 function and/or activity. In some embodiments, MARC2 function and/or activity in the MARC2 variant is reduced by about 1% to 100%, such as by about 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, including any value or range of values therein. In some embodiments, MARC2 function and/or activity in the MARC2 variant is reduced by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

In some embodiments, the MARC gene variant contains a nonsense mutation that results in early termination of MARC transcript and/or polypeptide, a frameshift mutation due to one or more indels and/or splice-site mutation(s), resulting in a MARC transcript and/or polypeptide splice variant. In some embodiments, the MARC1 gene variant contains a nonsense mutation that results in early termination of MARC1 transcript and/or polypeptide, a frameshift mutation due to one or more indels, and/or splice-site mutation(s), resulting in a MARC1 transcript and/or polypeptide splice variant. In some embodiments, the MARC2 gene variant contains a nonsense mutation that results in early termination of MARC2 transcript and/or polypeptide, a frameshift mutation due to one or more indels, and/or splice-site mutation(s) resulting in a MARC2 transcript and/or polypeptide splice variant. In some embodiments, the MARC (e.g., MARC1 or MARC2) gene or transcript variant can yield a MARC polypeptide with reduced function and/or activity.

Methods of measuring MARC activity include without limitation, enzyme activity assays, PCR-based methods to measure expression, protein expression techniques (e.g., ELISA, Western blotting, HPLC, mass spec, etc.) and the like, all of which are generally known in the art. Biomarkers associated with MARC activity and/or liver function can also be used to indirectly assess MARC activity. Such markers and techniques are described in greater detail elsewhere herein.

Modified MARC

In some embodiments, a MARC gene or transcript, such as one that is a risk variant, can be modified to be a protective MARC variant, described elsewhere herein, and/or produces a gene or transcript product that is a protective MARC variant. In some embodiments, a MARC gene or transcript can be modified to possess a DNA-triplet or codon that can be transcribed and/or translated to a threonine at position 165 of the reference MARC1 (SEQ ID NO: 1, see also Table 1) or a threonine in a position of a MARC (e.g., a MARC1 or MARC2) gene or transcript, where the position of the MARC gene or transcript modified is equivalent or homologous to position 165 of the reference MARC1 (SEQ ID NO: 1, see also Table 1). DNA-triplets and codons for Alanine include CGA, CGG, CGT, CGC (DNA-triplets) and GCU, GCC, GCA, GCG (codons).

Methods of Modifying MARC

The MARC gene or transcript can be modified using any suitable polynucleotide modification technique including, but not limited to, traditional targeted insertion techniques reliant upon homologous recombination, as well as nuclease-based methods (e.g., CRISPR-Cas systems, TALE nucleases (TALENs), and Zinc Finger nucleases). Generally, a polynucleotide to be modified can be in a cell. A modifying agent, such as any of those described herein or those generally known to one of ordinary skill in the art, can be exposed, contacted with, or otherwise associated with the polynucleotide to be modified. The modifying agent(s) can be delivered to the cell and/or polynucleotide by any suitable delivery method. Delivery methods are described in greater detail elsewhere herein. The modifying agent(s) can be included in a vector, virus particle, or other delivery agent. Vectors and delivery agents are described in greater detail elsewhere herein.

CRISPR-Cas Modification

In some embodiments, a polynucleotide of the present invention described elsewhere herein (e.g., a MARC1 and/or MARC2 gene or transcript) can be modified using a CRISPR-Cas and/or Cas-based system.

In general, a CRISPR-Cas or CRISPR system as used herein and in other documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g., CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOI: dx.doi.org/10.1016/j.molcel.2015.10.008.

CRISPR-Cas systems can generally fall into two classes based on their architectures of their effector molecules, which are each further subdivided by type and subtype. The two class are Class 1 and Class 2. Class 1 CRISPR-Cas systems have effector modules composed of multiple Cas proteins, some of which form crRNA-binding complexes, while Class 2 CRISPR-Cas systems include a single, multi-domain crRNA-binding protein.

In some embodiments, the CRISPR-Cas system that can be used to modify a polynucleotide of the present invention described herein can be a Class 1 CRISPR-Cas system. In some embodiments, the CRISPR-Cas system that can be used to modify a polynucleotide of the present invention described herein can be a Class 2 CRISPR-Cas system.

Class 1 CRISPR-Cas Systems

In some embodiments, the CRISPR-Cas system that can be used to modify a polynucleotide of the present invention described herein can be a Class 1 CRISPR-Cas system. Class 1 CRISPR-Cas systems are divided into types I, II, and IV. Makarova et al. 2020. Nat. Rev. 18:67-83, particularly as described in FIG. 1. Type I CRISPR-Cas systems are divided into 9 subtypes (I-A, I-B, I-C, I-D, I-E, I-F1, I-F2, I-F3, and IG). Makarova et al., 2020. Class 1, Type I CRISPR-Cas systems can contain a Cas3 protein that can have helicase activity. Type III CRISPR-Cas systems are divided into 6 subtypes (III-A, III-B, III-C, III-D, III-E, and III-F). Type III CRISPR-Cas systems can contain a Cas 10 that can include an RNA recognition motif called Palm and a cyclase domain that can cleave polynucleotides. Makarova et al., 2020. Type IV CRISPR-Cas systems are divided into 3 subtypes. (IV-A, IV-B, and IV-C). Makarova et al., 2020. Class 1 systems also include CRISPR-Cas variants, including Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems. Peters et al., PNAS 114 (35) (2017); DOI: 10.1073/pnas. 1709035114; see also, Makarova et al. 2018. The CRISPR Journal, v. 1, n5, Figure 5.

The Class 1 systems typically use a multi-protein effector complex, which can, in some embodiments, include ancillary proteins, such as one or more proteins in a complex referred to as a CRISPR-associated complex for antiviral defense (Cascade), one or more adaptation proteins (e.g., Cas1, Cas2, RNA nuclease), and/or one or more accessory proteins (e.g., Cas 4, DNA nuclease), CRISPR associated Rossman fold (CARF) domain containing proteins, and/or RNA transcriptase.

The backbone of the Class 1 CRISPR-Cas system effector complexes can be formed by RNA recognition motif domain-containing protein(s) of the repeat-associated mysterious proteins (RAMPs) family subunits (e.g., Cas 5, Cas6, and/or Cas7). RAMP proteins are characterized by having one or more RNA recognition motif domains. In some embodiments, multiple copies of RAMPs can be present. In some embodiments, the Class I CRISPR-Cas system can include 1, 2, 3, 4, 5, 6, 7, 8, 9, 10, 11, 12 or more Cas5, Cas6, and/or Cas 7 proteins. In some embodiments, the Cas6 protein is an RNAse, which can be responsible for pre-crRNA processing. When present in a Class 1 CRISPR-Cas system, Cas6 can be optionally physically associated with the effector complex.

Class 1 CRISPR-Cas system effector complexes can, in some embodiments, also include a large subunit. The large subunit can be composed of or include a Cas8 and/or Cas10 protein. See, e.g., Figures 1 and 2. Koonin E V, Makarova K S. 2019. Phil. Trans. R. Soc. B 374:20180087, DOI: 10.1098/rstb.2018.0087 and Makarova et al. 2020.

Class 1 CRISPR-Cas system effector complexes can, in some embodiments, include a small subunit (for example, Cas11). See, e.g., Figures 1 and 2. Koonin E V, Makarova K S. 2019 Origins and Evolution of CRISPR-Cas systems. Phil. Trans. R. Soc. B 374:20180087, DOI: 10.1098/rstb.2018.0087.

In some embodiments, the Class 1 CRISPR-Cas system can be a Type I CRISPR-Cas system. In some embodiments, the Type I CRISPR-Cas system can be a subtype I-A CRISPR-Cas system. In some embodiments, the Type I CRISPR-Cas system can be a subtype I-B CRISPR-Cas system. In some embodiments, the Type I CRISPR-Cas system can be a subtype I-C CRISPR-Cas system. In some embodiments, the Type I CRISPR-Cas system can be a subtype I-D CRISPR-Cas system. In some embodiments, the Type I CRISPR-Cas system can be a subtype I-E CRISPR-Cas system. In some embodiments, the Type I CRISPR-Cas system can be a subtype I-F1 CRISPR-Cas system. In some embodiments, the Type I CRISPR-Cas system can be a subtype I-F2 CRISPR-Cas system. In some embodiments, the Type I CRISPR-Cas system can be a subtype I-F3 CRISPR-Cas system. In some embodiments, the Type I CRISPR-Cas system can be a subtype I-G CRISPR-Cas system. In some embodiments, the Type I CRISPR-Cas system can be a CRISPR Cas variant, such as a Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems as previously described.

In some embodiments, the Class 1 CRISPR-Cas system can be a Type III CRISPR-Cas system. In some embodiments, the Type III CRISPR-Cas system can be a subtype III-A CRISPR-Cas system. In some embodiments, the Type III CRISPR-Cas system can be a subtype III-B CRISPR-Cas system. In some embodiments, the Type III CRISPR-Cas system can be a subtype III-C CRISPR-Cas system. In some embodiments, the Type III CRISPR-Cas system can be a subtype III-D CRISPR-Cas system. In some embodiments, the Type III CRISPR-Cas system can be a subtype III-E CRISPR-Cas system. In some embodiments, the Type III CRISPR-Cas system can be a subtype III-F CRISPR-Cas system.

In some embodiments, the Class 1 CRISPR-Cas system can be a Type IV CRISPR-Cas-system. In some embodiments, the Type IV CRISPR-Cas system can be a subtype IV-A CRISPR-Cas system. In some embodiments, the Type IV CRISPR-Cas system can be a subtype IV-B CRISPR-Cas system. In some embodiments, the Type IV CRISPR-Cas system can be a subtype IV-C CRISPR-Cas system.

The effector complex of a Class 1 CRISPR-Cas system can, in some embodiments, include a Cas3 protein that is optionally fused to a Cas2 protein, a Cas4, a Cas5, a Cas6, a Cas7, a Cas8, a Cas10, a Cas11, or a combination thereof. In some embodiments, the effector complex of a Class 1 CRISPR-Cas system can have multiple copies, such as 1, 2, 3, 4, 5, 6, 7, 8, 9, 10, 11, 12, 13, or 14, of any one or more Cas proteins.

Class 2 CRISPR-Cas Systems

The compositions, systems, and methods described in greater detail elsewhere herein can be designed and adapted for use with Class 2 CRISPR-Cas systems. Thus, in some embodiments, the CRISPR-Cas system is a Class 2 CRISPR-Cas system. Class 2 systems are distinguished from Class 1 systems in that they have a single, large, multi-domain effector protein. In certain example embodiments, the Class 2 system can be a Type II, Type V, or Type VI system, which are described in Makarova et al. "Evolutionary classification of CRISPR-Cas systems: a burst of class 2 and derived variants" Nature Reviews Microbiology, 18:67-81 (February 2020), incorporated herein by reference. Each type of Class 2 system is further divided into subtypes. See Markova et al. 2020, particularly at Figure. 2. Class 2, Type II systems can be divided into 4 subtypes: II-A, II-B, II-C1, and II-C2. Class 2, Type V systems can be divided into 17 subtypes: V-A, V-B1, V-B2, V-C, V-D, V-E, V-F1, V-F1 (V-U3), V-F2, V-F3, V-G, V-H, V-I, V-K (V-U5), V-U1, V-U2, and V-U4. Class 2, Type IV systems can be divided into 5 subtypes: VI-A, VI-B1, VI-B2, VI-C, and VI-D.

The distinguishing feature of these types is that their effector complexes consist of a single, large, multi-domain protein. Type V systems differ from Type II effectors (e.g., Cas9), which contain two nuclear domains that are each responsible for the cleavage of one strand of the target DNA, with the HNH nuclease inserted inside the RuvC-like nuclease domain sequence. The Type V systems (e.g., Cas12) only contain a RuvC-like nuclease domain that cleaves both strands. Type VI (Cas13) are unrelated to the effectors of Type II and V systems and contain two HEPN domains and target RNA. Cas13 proteins also display collateral activity that is triggered by target recognition. Some Type V systems have also been found to possess this collateral activity with two single-stranded DNA in in vitro contexts.

In some embodiments, the Class 2 system is a Type II system. In some embodiments, the Type II CRISPR-Cas system is a II-A CRISPR-Cas system. In some embodiments, the Type II CRISPR-Cas system is a II-B CRISPR-Cas system. In some embodiments, the Type II CRISPR-Cas system is a II-C1 CRISPR-Cas system. In some embodiments, the Type II CRISPR-Cas system is a II-C2 CRISPR-Cas system. In some embodiments, the Type II system is a Cas9 system. In some embodiments, the Type II system includes a Cas9.

In some embodiments, the Class 2 system is a Type V system. In some embodiments, the Type V CRISPR-Cas system is a V-A CRISPR-Cas system. In some embodiments, the Type V CRISPR-Cas system is a V-B1 CRISPR-Cas system. In some embodiments, the Type V CRISPR-Cas system is a V-B2 CRISPR-Cas system. In some embodiments, the Type V CRISPR-Cas system is a V-C CRISPR-Cas system. In some embodiments, the Type V CRISPR-Cas system is a V-D CRISPR-Cas system. In some embodiments, the Type V CRISPR-Cas system is a V-E CRISPR-Cas system. In some embodiments, the Type V CRISPR-Cas system is a V-F1 CRISPR-Cas system. In some embodiments, the Type V CRISPR-Cas system is a V-F1 (V-U3) CRISPR-Cas system. In some embodiments, the Type V CRISPR-Cas system is a V-F2 CRISPR-Cas system. In some embodiments, the Type V CRISPR-Cas system is a V-F3 CRISPR-Cas system. In some embodiments, the Type V CRISPR-Cas system is a V-G CRISPR-Cas system. In some embodiments, the Type V CRISPR-Cas system is a V-H CRISPR-Cas system. In some embodiments, the Type V CRISPR-Cas system is a V-I CRISPR-Cas system. In some embodiments, the Type V CRISPR-Cas system is a V-K (V-U5) CRISPR-Cas system. In some embodiments, the Type V CRISPR-Cas system is a V-U1 CRISPR-Cas system. In some embodiments, the Type V CRISPR-Cas system is a V-U2 CRISPR-Cas system. In some embodiments, the Type V CRISPR-Cas system is a V-U4 CRISPR- Cas system. In some embodiments, the Type V CRISPR-Cas system includes a Cas12a (Cpf1), Cas12b (C2c1), Cas12c (C2c3), CasX, and/or Cas14.

In some embodiments the Class 2 system is a Type VI system. In some embodiments, the Type VI CRISPR-Cas system is a VI-A CRISPR-Cas system. In some embodiments, the Type VI CRISPR-Cas system is a VI-B1 CRISPR-Cas system. In some embodiments, the Type VI CRISPR-Cas system is a VI-B2 CRISPR-Cas system. In some embodiments, the Type VI CRISPR-Cas system is a VI-C CRISPR-Cas system. In some embodiments, the Type VI CRISPR-Cas system is a VI-D CRISPR-Cas system. In some embodiments, the Type VI CRISPR-Cas system includes a Cas13a (C2c2), Cas13b (Group 29/30), Cas13c, and/or Cas13d.

Specialized Cas-Based Systems

In some embodiments, the system is a Cas-based system that is capable of performing a specialized function or activity. For example, the Cas protein may be fused, operably coupled to, or otherwise associated with to one or more functionals domains. In certain example embodiments, the Cas protein may be a catalytically dead Cas protein ("dCas") and/or have nickase activity. A nickase is a Cas protein that cuts only one strand of a double stranded target. In such embodiments, the dCas or nickase provide a sequence specific targeting functionality that delivers the functional domain to or proximate a target sequence. Example functional domains that may be fused to, operably coupled to, or otherwise associated with a Cas protein can be or include, but are not limited to, an HPEN domain or a catalytically active domain that is homologous to an HPEN domain, a nuclear localization signal (NLS) domain, a nuclear export signal (NES) domain, a translational activation domain, a transcriptional activation domain (e.g. VP64, p65, MyoD1, HSF1, RTA, and SET7/9), a translation initiation domain, a transcriptional repression domain (e.g., a KRAB domain, NuE domain, NcoR domain, and a SID domain such as a SID4X domain), a nuclease domain (e.g., FokI), a histone modification domain (e.g., a histone acetyltransferase), a light inducible/controllable domain, a chemically inducible/controllable domain, a transposase domain, a homologous recombination machinery domain, a recombinase domain, an integrase domain, and combinations thereof.

In some embodiments, the functional domains can have one or more of the following activities: methylase activity, demethylase activity, translation activation activity, translation initiation activity, translation repression activity, transcription activation activity, transcription repression activity, transcription release factor activity, histone modification activity, nuclease activity, single-strand RNA cleavage activity, double-strand RNA cleavage activity, single-strand DNA cleavage activity, double-strand DNA cleavage activity, molecular switch activity, chemical inducibility, light inducibility, and nucleic acid binding activity. In some embodiments, the one or more functional domains may comprise epitope tags or reporters. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporters include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP).

The one or more functional domain(s) may be positioned at, near, and/or in proximity to a terminus of the effector protein (e.g., a Cas protein). In embodiments having two or more functional domains, each of the two can be positioned at or near or in proximity to a terminus of the effector protein (e.g., a Cas protein). In some embodiments, such as those where the functional domain is operably coupled to the effector protein, the one or more functional domains can be tethered or linked via a suitable linker (including, but not limited to, GlySer linkers) to the effector protein (e.g., a Cas protein). When there is more than one functional domain, the functional domains can be same or different. In some embodiments, all the functional domains are the same. In some embodiments, all of the functional domains are different from each other. In some embodiments, at least two of the functional domains are different from each other. In some embodiments, at least two of the functional domains are the same as each other.

Other suitable functional domains can be found, for example, in International Application Publication No. WO 2019/018423.

Split CRISPR-Cas Systems

In some embodiments, the CRISPR-Cas system is a split CRISPR-Cas system. See e.g., Zetche et al., 2015. Nat. Biotechnol. 33 (2): 139-142, the compositions and techniques of which can be used in and/or adapted for use with the present invention. Split CRISPR-Cas proteins are set forth herein and in documents incorporated herein by reference in further detail herein. In certain embodiments, each part of a split CRISPR protein are attached to a member of a specific binding pair, and when bound with each other, the members of the specific binding pair maintain the parts of the CRISPR protein in proximity. In certain embodiments, each part of a split CRISPR protein is associated with an inducible binding pair. An inducible binding pair is one which is capable of being switched "on" or "off" by a protein or small molecule that binds to both members of the inducible binding pair. In some embodiments, CRISPR proteins may preferably split between domains, leaving domains intact. In particular embodiments, said Cas split domains (e.g., RuvC and HNH domains in the case of Cas9) can be simultaneously or sequentially introduced into the cell such that said split Cas domain(s) process the target nucleic acid sequence in the algae cell. The reduced size of the split Cas compared to the wild type Cas allows other methods of delivery of the systems to the cells, such as the use of cell penetrating peptides as described herein.

DNA and RNA Base Editing

In some embodiments, a polynucleotide of the present invention described elsewhere herein (e.g., a MARC polynucleotide, such as a MARC1 or MARC2 gene or transcript) can be modified using a base editing system. In some embodiments, a Cas protein is connected or fused to a nucleotide deaminase. Thus, in some embodiments the Cas-based system can be a base editing system. As used herein "base editing" refers generally to the process of polynucleotide modification via a CRISPR-Cas-based or Cas-based system that does not include excising nucleotides to make the modification. Base editing can convert base pairs at precise locations without generating excess undesired editing byproducts that can be made using traditional CRISPR-Cas systems.

In certain example embodiments, the nucleotide deaminase may be a DNA base editor used in combination with a DNA binding Cas protein such as, but not limited to, Class 2 Type II and Type V systems. Two classes of DNA base editors are known: cytosine base editors (CBEs) and adenine base editors (ABEs). CBEs convert a C. G base pair into a T·A base pair (Komor et al. 2016. Nature. 533:420-424; Nishida et al. 2016. Science. 353; and Li et al. Nat. Biotech. 36:324-327) and ABEs convert an A. T base pair to a G. C base pair. Collectively, CBEs and ABEs can mediate all four possible transition mutations (C to T, A to G, T to C, and G to A). Rees and Liu. 2018. Nat. Rev. Genet. 19 (12): 770-788, particularly at FIGS. 1b, 2a-2c, 3a-3f, and Table 1. In some embodiments, the base editing system includes a CBE and/or an ABE. In some embodiments, a polynucleotide of the present invention described elsewhere herein (e.g., a MARC polynucleotide, such as a MARC1 or MARC2 gene or transcript) can be modified using a base editing system. Rees and Liu. 2018. Nat. Rev. Gent. 19 (12): 770-788. Base editors also generally do not need a DNA donor template and/or rely on homology-directed repair. Komor et al. 2016. Nature. 533:420-424; Nishida et al. 2016. Science. 353; and Gaudeli et al. 2017. Nature. 551:464-471. Upon binding to a target locus in the DNA, base pairing between the guide RNA of the system and the target DNA strand leads to displacement of a small segment of ssDNA in an "R-loop". Nishimasu et al. Cell. 156:935-949. DNA bases within the ssDNA bubble are modified by the enzyme component, such as a deaminase. In some systems, the catalytically disabled Cas protein can be a variant or modified Cas can have nickase functionality and can generate a nick in the non-edited DNA strand to induce cells to repair the non-edited strand using the edited strand as a template. Komor et al. 2016. Nature. 533:420-424; Nishida et al. 2016. Science. 353; and Gaudeli et al. 2017. Nature. 551:464-471.

Other Example Type V base editing systems are described in WO 2018/213708, WO 2018/213726, PCT/US2018/067207, PCT/US2018/067225, and PCT/US2018/067307 which are incorporated by referenced herein.

In certain example embodiments, the base editing system may be a RNA base editing system. As with DNA base editor a nucleotide deaminase capable of converting nucleotide bases may be fused to a Cas protein. However, in these embodiments, the Cas protein will need to be capable of binding RNA. Example RNA binding Cas proteins include, but are not limited to, RNA-binding Cas9s such as *Francisella novicida* Cas9 ("FnCas9"), and Class 2 Type VI Cas systems. The nucleotide deaminase may be a cytidine deaminase or an adenosine deaminase, or an adenosine deaminase engineered to have cytidine deaminase activity. In certain example embodiments, the RNA based editor may be used to delete or introduce a post-translation modification site in the expressed mRNA. In contrast to DNA base editors, whose edits are permanent in the modified cell, RNA base editors can provide edits where finer temporal control may be needed, for example in modulating a particular immune response. Example Type VI RNA-base editing systems are described in Cox et al. 2017. Science 358:1019-1027, WO 2019/005884, WO 2019/005886, WO 2019/071048, PCT/US20018/05179, PCT/US2018/067207, which are incorporated herein by reference. An example FnCas9 system that may be adapted for RNA base editing purposes is described in WO 2016/106236, which is incorporated herein by reference.

An example method for delivery of base-editing systems, including use of a split-intein approach to divide CBE and ABE into reconstitutable halves, is described in Levy et al. Nature Biomedical Engineering doi.org/10.1038/s41441-019-0505-5 (2019), which is incorporated herein by reference.

Prime Editors

In some embodiments, a polynucleotide of the present invention described elsewhere herein (e.g., a MARC polynucleotide, such as a MARC1 or MARC2 gene or transcript) can be modified using a prime editing system See e.g. Anzalone et al. 2019. Nature. 576:149-157. Like base editing systems, prime editing systems can be capable of targeted modification of a polynucleotide without generating double stranded breaks and does not require donor templates. Further prime editing systems can be capable of all 12 possible combination swaps. Prime editing can operate via a "search-and-replace" methodology and can mediate targeted insertions, deletions, all 12 possible base-to-base conversion, and combinations thereof. Generally, a prime editing system, as exemplified by PE1, PE2, and PE3 (Id.), can include a reverse transcriptase fused or otherwise coupled or associated with an RNA-programmable nickase, and a prime-editing extended guide RNA (pegRNA) to facility direct copying of genetic information from the extension on the pegRNA into the target polynucleotide. Embodiments that can be used with the present invention include these and variants thereof. Prime editing can have the advantage of lower off-target activity than traditional CRIPSR-Cas systems along with few byproducts and greater or similar efficiency as compared to traditional CRISPR-Cas systems.

In some embodiments, the prime editing guide molecule can specify both the target polynucleotide information (e.g. sequence) and contain new polynucleotide information that replaces target polynucleotides. Information transfer from the guide molecule to the target polynucleotide, the PE system can nick the target polynucleotide at a target side to expose a 3'hydroxyl group, which can prime reverse transcription of an edit-encoding extension region of the guide molecule (e.g. a prime editing guide molecule or peg guide molecule) directly into the target site in the target polynucleotide. See e.g. Anzalone et al. 2019. Nature. 576:149-157, particularly at Figures 1b, 1c, related discussion, and Supplementary discussion.

In some embodiments, a prime editing system can be composed of a Cas polypeptide having nickase activity, a reverse transcriptase, and a guide molecule. The Cas polypeptide can lack nuclease activity. The guide molecule can include a target binding sequence as well as a primer binding sequence and a template containing the edited polynucleotide sequence. The guide molecule, Cas polypeptide, and/or reverse transcriptase can be coupled together or otherwise associate with each other to form an effector complex and edit a target sequence. In some embodiments, the Cas polypeptide is a Class 2, Type V Cas polypeptide. In some embodiments, the Cas polypeptide is a Cas9 polypeptide (e.g. is a Cas9 nickase). In some embodiments, the Cas polypeptide is fused to the reverse transcriptase. In some embodiments, the Cas polypeptide is linked to the reverse transcriptase.

In some embodiments, the prime editing system can be a PE1 system or variant thereof, a PE2 system or variant thereof, or a PE3 (e.g. PE3, PE3b) system. See e.g., Anzalone et al. 2019. Nature. 576:149-157, particularly at pgs. 2-3, Fig. 2a, 3a-3f, 4a-4b, Extended data Figs. 3a-3b, 4.

The peg guide molecule can be about 10 to about 200 or more nucleotides in length, such as 10 to/or 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 or more nucleotides in length. Optimization of the peg guide molecule can be accomplished as described in Anzalone et al. 2019. Nature. 576:149-157, particularly at pg. 3, Fig. 2a-2b, and Extended Data Fig. 5a-c.

CRISPR Associated Transposase (CAST) Systems

In some embodiments, a polynucleotide of the present invention described elsewhere herein (e.g., a MARC polynucleotide, such as a MARC1 or MARC2 gene or transcript) can be modified using a CRISPR Associated Transposase ("CAST") system. CAST system can include a Cas protein that is catalytically inactive, or engineered to be catalytically active, and further comprises a transposase (or subunits thereof) that catalyze RNA-guided DNA transposition. Such systems are able to insert DNA sequences at a target site in a DNA molecule without relying on host cell repair machinery. CAST systems can be Class1 or Class 2 CAST systems. An example Class 1 system is described in Klompe et al. Nature, doi: 10.1038/s41586-019-1323, which is in incorporated herein by reference. Example Class 2 systems are described in Strecker et al. Science. 10/1126/science. aax9181 (2019), and PCT/US2019/066835 which are incorporated herein by reference.

Guide Molecules

The CRISPR-Cas or Cas-Based system described herein can, in some embodiments, include one or more guide molecules. The terms guide molecule, guide sequence and guide polynucleotide, refer to polynucleotides capable of guiding Cas to a target genomic locus and are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. The guide molecule can be a polynucleotide.

The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay (Qui et al. 2004. BioTechniques. 36 (4) 702-707). Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible and will occur to those skilled in the art.

In some embodiments, the guide molecule is an RNA. The guide molecule(s) (also referred to interchangeably herein as guide polynucleotide and guide sequence) that are included in the CRISPR-Cas or Cas based system can be any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, can be about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g., the Burrows Wheeler Aligner), Clustal W, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net).

A guide sequence, and hence a nucleic acid-targeting guide may be selected to target any target nucleic acid sequence. The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106 (1): 23-24; and P A Carr and G M Church, 2009, Nature Biotechnology 27 (12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27 to 30 nt, e.g., 27, 28, 29, or 30 nt, from 30 to 35 nt, e.g., 30, 31, 32, 33, 34, or 35 nt, or 35 nt or longer.

The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin.

In general, degree of complementarity is with reference to the optimal alignment of the sca sequence and tracr sequence, along the length of the shorter of the two sequences. Optimal alignment may be determined by any suitable alignment algorithm, and may further account for secondary structures, such as self-complementarity within either the sca sequence or tracr sequence. In some embodiments, the degree of complementarity between the tracr sequence and sca sequence along the length of the shorter of the two when optimally aligned is about or more than about 25%, 30%, 40%, 50%, 60%, 70%, 80%, 90%, 95%, 97.5%, 99%, or higher.

In some embodiments, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and tracr RNA can be 30 or 50 nucleotides in length. In some embodiments, the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In some embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e., an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence. Where the tracr RNA is on a different RNA than the RNA containing the guide and tracr sequence, the length of each RNA may be optimized to be shortened from their respective native lengths, and each may be independently chemically modified to protect from degradation by cellular RNase or otherwise increase stability.

Many modifications to guide sequences are known in the art and are further contemplated within the context of this invention. Various modifications may be used to increase the specificity of binding to the target sequence and/or increase the activity of the Cas protein and/or reduce off-target effects. Example guide sequence modifications are described in PCT US2019/045582, specifically paragraphs [0178]-[0333], which is incorporated herein by reference.

Target Sequences, PAMs, and PFSs

Target Sequences

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to an RNA polynucleotide being or comprising the target sequence. In other words, the target polynucleotide can be a polynucleotide or a part of a polynucleotide to which a part of the guide sequence is designed to have complementarity with and to which the effector function mediated by the complex comprising the CRISPR effector protein and a guide molecule is to be directed. In some embodiments, a target sequence is located in the nucleus or cytoplasm of a cell.

The guide sequence can specifically bind a target sequence in a target polynucleotide. The target polynucleotide may be DNA. The target polynucleotide may be RNA. The target polynucleotide can have one or more (e.g., 1, 2, 3, 4, 5, 6, 7, 8, 9, 10, etc. or more) target sequences. The target polynucleotide can be on a vector. The target polynucleotide can be genomic DNA. The target polynucleotide can be episomal. Other forms of the target polynucleotide are described elsewhere herein.

The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence (also referred to herein as a target polynucleotide) may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA.

In some more preferred embodiments, the target sequence may be a sequence within an mRNA molecule or a pre-mRNA molecule.

PAM and PFS Elements

PAM elements are sequences that can be recognized and bound by Cas proteins. Cas proteins/effector complexes can then unwind the dsDNA at a position adjacent to the PAM element. It will be appreciated that Cas proteins and systems that include them that target RNA do not require PAM sequences (Marraffini et al. 2010. Nature. 463:568-571). Instead, many rely on PFSs, which are discussed elsewhere herein. In certain embodiments, the target sequence should be associated with a PAM (protospacer adjacent motif) or PFS (protospacer flanking sequence or site), that is, a short sequence recognized by the CRISPR complex. Depending on the nature of the CRISPR-Cas protein, the target sequence should be selected, such that its complementary sequence in the DNA duplex (also referred to herein as the non-target sequence) is upstream or downstream of the PAM. In the embodiments, the complementary sequence of the target sequence is downstream or 3' of the PAM or upstream or 5' of the PAM. The precise sequence and length requirements for the PAM differ depending on the Cas protein used, but PAMs are typically 2-5 base pair sequences adjacent the protospacer (that is, the target sequence). Examples of the natural PAM sequences for different Cas proteins are provided herein below and the skilled person will be able to identify further PAM sequences for use with a given Cas protein.

The ability to recognize different PAM sequences depends on the Cas polypeptide(s) included in the system. See e.g., Gleditzsch et al. 2019. RNA Biology. 16 (4): 504-517. Table 3 below shows several Cas polypeptides and the PAM sequence they recognize.

TABLE 3

Example PAM Sequences

| Cas Protein | PAM Sequence |
|---|---|
| SpCas9 | NGG/NRG |
| SaCas9 | NGRRT or NGRRN |
| NmeCas9 | NNNNGATT |
| CjCas9 | NNNNRYAC |
| StCas9 | NNAGAAW |
| Cas12a (Cpf1) (including LbCpf1 and AsCpf1) | TTTV |
| Cas12b (C2c1) | TTT, TTA, and TTC |
| Cas12c (C2c3) | TA |
| Cas12d (CasY) | TA |
| Cas12e (CasX) | 5'-TTCN-3' |

In a preferred embodiment, the CRISPR effector protein may recognize a 3' PAM. In certain embodiments, the CRISPR effector protein may recognize a 3' PAM which is 5'H, wherein His A, C or U.

Further, engineering of the PAM Interacting (PI) domain on the Cas protein may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561): 481-5. doi: 10.1038/nature14592. As further detailed herein, the skilled person will understand that Cas13 proteins may be modified analogously. Gao et al, "Engineered Cpf1 Enzymes with Altered PAM Specificities," bioRxiv 091611; doi:dx.doi.org/10.1101/091611 (Dec. 4, 2016). Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

PAM sequences can be identified in a polynucleotide using an appropriate design tool, which are commercially available as well as online. Such freely available tools include, but are not limited to, CRISPRFinder and CRISPRTarget. Mojica et al. 2009. Microbiol. 155 (Pt. 3): 733-740; Atschul et al. 1990. J. Mol. Biol. 215:403-410; Biswass et al. 2013 RNA Biol. 10:817-827; and Grissa et al. 2007. Nucleic Acid Res. 35: W52-57. Experimental approaches to PAM identification can include, but are not limited to, plasmid depletion assays (Jiang et al. 2013. Nat. Biotechnol. 31:233-239; Esvelt et al. 2013. Nat. Methods. 10:1116-1121; Kleinstiver et al. 2015. Nature. 523:481-485), screened by a high-throughput in vivo model called PAM-SCNAR (Pattanayak et al. 2013. Nat. Biotechnol. 31:839-843 and Leenay et al. 2016. Mol. Cell. 16:253), and negative screening (Zetsche et al. 2015. Cell. 163:759-771).

As previously mentioned, CRISPR-Cas systems that target RNA do not typically rely on PAM sequences. Instead such systems typically recognize protospacer flanking sites (PFSs) instead of PAMs Thus, Type VI CRISPR-Cas systems typically recognize protospacer flanking sites (PFSs) instead of PAMs. PFSs represents an analogue to PAMs for RNA targets. Type VI CRISPR-Cas systems employ a Cas13. Some Cas13 proteins analyzed to date, such as Cas13a (C2c2) identified from Leptotrichia shahii (LShCAs13a) have a specific discrimination against G at the 3'end of the target RNA. The presence of a C at the corresponding crRNA repeat site can indicate that nucleotide pairing at this position is rejected. However, some Cas13 proteins (e.g., LwaCAs13a and PspCas13b) do not seem to have a PFS preference. See e.g., Gleditzsch et al. 2019. RNA Biology. 16 (4): 504-517.

Some Type VI proteins, such as subtype B, have 5'-recognition of D (G, T, A) and a 3'-motif requirement of NAN or NNA. One example is the Cas13b protein identified in Bergeyella zoohelcum (BzCas13b). See e.g., Gleditzsch et al. 2019. RNA Biology. 16 (4): 504-517.

Overall Type VI CRISPR-Cas systems appear to have less restrictive rules for substrate (e.g., target sequence) recognition than those that target DNA (e.g., Type V and type II).

Zinc Finger Nucleases

In some embodiments, the MARC polynucleotide is modified using a Zinc Finger nuclease or system thereof. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y.

et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

TALE Nucleases

In some embodiments, a TALE nuclease or TALE nuclease system can be used to modify a MARC polynucleotide. In some embodiments, the methods provided herein use isolated, non-naturally occurring, recombinant or engineered DNA binding proteins that comprise TALE monomers or TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable diresidues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$-$(X_{12}X_{13})$-$X_{14-33}$ or 34 or 35, where the subscript indicates the amino acid position and X represents any amino acid. $X_{12}X_{13}$ indicate the RVDs. In some polypeptide monomers, the variable amino acid at position 13 is missing or absent and in such monomers, the RVD consists of a single amino acid. In such cases the RVD may be alternatively represented as X*, where X represents $X_{12}$ and (*) indicates that $X_{13}$ is absent. The DNA binding domain comprises several repeats of TALE monomers and this may be represented as $(X_{1-11}$-$(X_{12}X_{13})$-$X_{14-33}$ or 34 or 35$)_z$, where in an advantageous embodiment, z is at least 5 to 40. In a further advantageous embodiment, z is at least 10 to 26.

The TALE monomers can have a nucleotide binding affinity that is determined by the identity of the amino acids in its RVD. For example, polypeptide monomers with an RVD of NI can preferentially bind to adenine (A), monomers with an RVD of NG can preferentially bind to thymine (T), monomers with an RVD of HD can preferentially bind to cytosine (C) and monomers with an RVD of NN can preferentially bind to both adenine (A) and guanine (G). In some embodiments, monomers with an RVD of IG can preferentially bind to T. Thus, the number and order of the polypeptide monomer repeats in the nucleic acid binding domain of a TALE determines its nucleic acid target specificity. In some embodiments, monomers with an RVD of NS can recognize all four base pairs and can bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011).

The polypeptides used in methods of the invention can be isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In some embodiments, polypeptide monomers having RVDs RN, NN, NK, SN, NH, KN, HN, NQ, HH, RG, KH, RH and SS can preferentially bind to guanine. In some embodiments, polypeptide monomers having RVDs RN, NK, NQ, HH, KH, RH, SS and SN can preferentially bind to guanine and can thus allow the generation of TALE polypeptides with high binding specificity for guanine containing target nucleic acid sequences. In some embodiments, polypeptide monomers having RVDs HH, KH, NH, NK, NQ, RH, RN and SS can preferentially bind to guanine and thereby allow the generation of TALE polypeptides with high binding specificity for guanine containing target nucleic acid sequences. In some embodiments, the RVDs that have high binding specificity for guanine are RN, NH RH and KH. Furthermore, polypeptide monomers having an RVD of NV can preferentially bind to adenine and guanine. In some embodiments, monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases, this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full-length TALE monomer and this half repeat may be referred to as a half-monomer. Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

MDPIRSRTPSPARELLSGPQPDGVQPTADRGVSP-PAGGP LDGLPARRTMSRTRLPSP-PAPSPAFSADSFSDLLRQFDPSLENTS LFD-SLPPFGAHHTEAATGEWDEVQSGLRAADAPPPTMR VAVTA ARPPRAKPAPRRRAAQPS-DASPAAQVDLRTLGYSQQQQEKIKP KVRSTVAQHHEALVGHGFTHAHIVALSQHPAAL-GTVAVKY QD MIAALPEATHEAIVGVGKQWSGA-RALEALLTVAGELRGPPLQL DTGQLLKI-AKRGGVTAVEAVHAWRNALTGAPLN (SEQ ID NO:46)

An exemplary amino acid sequence of a C-terminal capping region is:
RPALESIVAQLSRPDPALAALTNDHLVALACLGGR-PAL DAVKKGLPHAPALIKRTNRRIPERTSHR VAD-HAQVVRVLGFF Q CHSHPAQAFD-DAMTQFGMSRHGLLQLFRRVGVTELEARSGTLP PASQRWDRILQASGMKRAKPSPTSTQTPDQASLHA-FADSLERD LDAPSPMHEGDQTRAS (SEQ ID NO:47)

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full-length capping region, while fragments that include the C-terminal 20 amino acids retain greater than 50% of the efficacy of the full-length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies can be generated by any of a number of computer programs known in the art, which include but are not limited to BLAST or FASTA. Suitable computer programs for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In some embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an m Sin interaction domain (SID). SID4X domain or a Krüppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination of the activities described herein.

Meganucleases

In some embodiments, a meganuclease or system thereof can be used to modify a MARC polynucleotide. Meganucleases, which are endo deoxyribonucleases characterized by a large recognition site (double-stranded DNA sequences of 12 to 40 base pairs). Exemplary methods for using meganucleases can be found in U.S. Pat. Nos. 8,163,514, 8,133, 697, 8,021,867, 8,119,361, 8,119,381, 8,124,369, and 8,129, 134, which are specifically incorporated by reference.

RNA Modification

In some embodiments, RNA can be modified. In some embodiments, a CRISPR-Cas system can be used to modify the RNA, such as a polynucleotide modifying system that employs a Type VI Cas polypeptide. Such systems are described in greater detail elsewhere herein. In some embodiments, RNA can be modified using a base-editing system, such as a Cas13-based base-editing system. Such base-editing systems are described in greater detail elsewhere herein. In some embodiments, the base editing system does not employ a Cas molecule. Such systems include Antisense RNA-ADAR-based RNA modification systems, which are described in greater detail elsewhere herein.

Marc Modulators

In some embodiments, the expression and/or activity of MARC can be modulated by genetic and/or non-genetic modulators (i.e., modulating agents). In some embodiments, the modulator can modify (i.e. change) the sequence of a MARC polynucleotide. In some embodiments, the expression and/or activity of MARC can be reduced. In some embodiments, expression and/or activity of MARC can be reduced to a level that causes a physiological response in a cell and/or subject. In some embodiments, MARC expression and/or activity can be reduced to a level that provides a protective effect on the liver. In some embodiments, the MARC modulator can modulate MARC-related activity by modulating MARC expression and/or mARC protein activity or by modulating cellular components that regulate MARC expression and/or mARC activity. While the participation of mARC in liver disease is hereby established, mARC is an important drug metabolising enzyme which reduces N-hydroxylated compounds such as amidoximes to amidines and likely participates in other unknown processes. In some embodiments, MARC is partially suppressed while in other embodiments, MARC is completely inhibited. In some embodiments, MARC activity is inhibited or suppressed at a level effective for treatment or prophylaxis of a liver disease or disorder while maintaining an effective level of drug metabolising activity. In some embodiments, MARC activity is inhibited or suppressed with respect to treatment or prophylaxis of a liver disorder by selectively blocking interaction with another cellular component while drug metabolising activity or other activity is maintained. In some embodiments, MARC is inhibited or suppressed with respect to treatment or prophylaxis of a liver disorder in certain cell types but not others. For example, MacParland describes 20 discrete cell populations of hepatocytes, endothelial cells, cholangiocytes, hepatic stellate cells, B cells, conventional and non-conventional T cells, NK-like cells, and distinct intrahepatic monocyte/macrophage populations. (MacParland et al., "Single cell RNA sequencing of human liver reveals distinct intrahepatic macrophage populations," Nature Communications 9, Article number: 4383 (2018)).

Genetic Modifiers

In some embodiments, expression and/or activity of MARC can be modulated by modifying the MARC gene and/or transcript using a suitable polynucleotide modifying agent or system thereof. Such suitable polynucleotide modifying agent(s) or system(s) thereof are described in greater detail elsewhere herein and can include, without limitation, CRISPR-Cas based systems, Cas-based systems, meganucleases, TALENs, zinc fingers, and traditional modification systems that rely on homologous recombination. In some embodiments, a suitable polynucleotide modifying agent or system thereof can be used to modify a risk MARC variant allele or transcript into a protective MARC variant allele or transcript. In this way, expression and/or activity of the MARC can thus be modulated. Methods of delivering such polynucleotide modifying agent(s) and/or systems thereof are also described in greater detail elsewhere herein.

In some embodiments, gene and/or RNA modification can result in a reduction of MARC activity compared to an unmodified or native MARC. In some embodiments, MARC expression and/or activity can be reduced by 1 to/or about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%. In some embodiments, MARC expression and/or activity can be reduced to below detectable or measurable levels. In some embodiments, MARC expression and/or activity can be reduced to a level that is comparable or equivalent to the level of MARC expression and/or activity that is produced from a native, wild-type, or reference protective MARC allele. In some embodiments, the MARC expression and/or activity can be decreased to a level that causes a physiological response in a cell and/or subject. In some embodiments, MARC expression and/or activity can be reduced to a level that provides a protective effect on the liver.

Non-Genetic Modulators

In some embodiments, expression and/or activity of MARC can be modulated using a non-genome or non-transcript modification method. It will be appreciated that in this context "modification" is referring to permeant nucleotide change(s) to the genomic DNA or RNA that corresponds to a given gene or polynucleotide. As used herein with reference to the relationship between DNA, cDNA, CRNA, RNA, protein/peptides, and the like "corresponding to" or "encoding" (used interchangeably herein) refers to the underlying biological relationship between these different molecules. As such, one of skill in the art would understand that operatively "corresponding to" can direct them to determine the possible underlying and/or resulting sequences of other molecules given the sequence of any other molecule which has a similar biological relationship with these molecules. For example, from a DNA sequence an RNA sequence can be determined and from an RNA sequence a cDNA sequence can be determined.

Small Molecules

In some embodiments, expression and/or activity of a MARC can be modulated via a small molecule agent. In some embodiments, expression and/or activity of a MARC (e.g., MARC 1 and/or MARC2) can be modulated in a subject in need thereof by administering a suitable small molecule agent. In some embodiments, the subject in need thereof carries one or more MARC1 and/or MARC2 risk variant alleles. In some embodiments, the subject in need thereof carries one or more MARC1 and/or MARC2 protective variant alleles. In some embodiments, the small molecule agent can be a substrate of MARC1 and/or MARC2. In some embodiments, the small molecule agent is capable of modulating the molybdenum binding region of MARC1 and/or MARC2. In some embodiments, the small molecule agent is capable of modulating the accessibility/availability of molybdenum to MARC1 and/or MARC2. In some embodiments, the small molecule agent modulates cytochrome b5 amount, activity and/or its ability to interact with MARC1 and/or MARC2. In some embodiments, the small molecule agent modulates NADH-cytochrome b5 reductase amount, activity, and/or its ability to interact with MARC1 and/or MARC2. In some embodiments, the small molecule agent is an N-hydroxylated compound, a variant thereof, or an analogue thereof. In some embodiments, the small molecule agent compound is an amidoxime, a hydroxamic acid, an N-hydroxyguanidine, a sulfhydroxamic acid, a hydroxylamine, an N-oxide, or a variant of any of such agents, or an analogue of any such agents. In some embodiments, the small molecule agent is benzohydroxamic acid, suberanilohydroxamic acid, bufexamac, CP54439, or a variant of any such agents, or an analogue of any such agents.

In some embodiments, the liver disease or symptom thereof can be treated and/or prevented by administering a suitable small molecule agent to a subject in need thereof. In some embodiments, the subject in need thereof carries one or more MARC1 and/or MARC2 risk variant alleles. In some embodiments, the subject in need thereof carries one or more MARC1 and/or MARC2 protective variant alleles. In some embodiments, the small molecule agent can be a substrate of MARC1 and/or MARC2. In some embodiments, the small molecule agent is capable of modulating the molybdenum binding region of MARC1 and/or MARC2. In some embodiments, the small molecule agent is capable of modulating the accessibility/availability of molybdenum to MARC1 and/or MARC2. In some embodiments, the small molecule agent modulates cytochrome b5 amount, activity and/or its ability to interact with MARC1 and/or MARC2. In some embodiments, the small molecule agent modulates NADH-cytochrome b5 reductase amount, activity, and/or its ability to interact with MARC1 and/or MARC2. In some embodiments, the small molecule agent is an N-hydroxylated compound, a variant thereof, or an analogue thereof. In some embodiments, the small molecule agent compound is an amidoxime, a hydroxamic acid, an N-hydroxyguanidine, a sulfhydroxamic acid, a hydroxylamine, an N-oxide, or a variant of any such agents, or an analogue of any such agents. In some embodiments, the small molecule agent is benzohydroxamic acid, suberanilohydroxamic acid, bufexamac, CP54439, or a variant of any such agents, or an analogue of any such agents.

In some embodiments, elevated total cholesterol and/or elevated LDL cholesterol or symptom thereof can be treated and/or prevented by administering a small molecule agent to a subject in need thereof. In some embodiments, the subject in need thereof carries one or more MARC1 and/or MARC2 risk variant alleles. In some embodiments, the subject in need thereof carries one or more MARC1 and/or MARC2 protective variant alleles. In some embodiments, the small molecule agent can be a substrate of MARC1 and/or MARC2. In some embodiments, the small molecule agent is capable of modulating the molybdenum binding region of MARC1 and/or MARC2. In some embodiments, the small molecule agent is capable of modulating the accessibility/availability of molybdenum to MARC1 and/or MARC2. In some embodiments, the small molecule agent modulates cytochrome b5 amount, activity and/or its ability to interact with MARC1 and/or MARC2. In some embodiments, the small molecule agent modulates NADH-cytochrome b5 reductase amount, activity, and/or its ability to interact with MARC1 and/or MARC2. In some embodiments, the small molecule agent is an N-hydroxylated compound, a variant thereof, or an analogue thereof. In some embodiments, the small molecule agent compound is an amidoxime, a hydroxamic acid, an N-hydroxyguanidine, a sulfhydroxamic acid, a hydroxylamine, an N-oxide, or a variant of any of such agents, or an analogue of any such agents. In some embodiments, the small molecule agent is benzohydroxamic acid, suberanilohydroxamic acid, bufexamac, CP54439, or a variant of any such agents, or an analogue of any such agents.

In certain embodiments, mARC inhibition or suppression is accompanied by modulation of a second target, such as but not limited to liver disease targets linked to PNPLA3, TM6SF2, and rs72613567 in HSD17B13.

In some embodiments, a MARC modulator, such as a small molecule MARC modulator, can be identified using an electrochemical method, such as that described in Kalimuthu et al., "Human mitochondrial amidoxime reducing component (mARC): An electrochemical method for identifying new substrates and inhibitors," Electrochemistry Communications Vol. 84, pp. 90-93, 2017". Mediated electron transfer from the electrode via cytochrome $b_5$ to MARC results in a catalytic current in the presence of substrate. Other methods of screening and identifying suitable MARC modulating agents, are described in greater detail herein and/or will be appreciated by those of ordinary skill in the art in view of the description provided throughout the specification.

Other Non-Genetic Modulating Agents

Other non-small molecule modulating agents that do not modify the genome of a cell can also be used to modulate the expression of MARC. Such agents include, but are not limited to antibodies and RNAi or antisense RNA molecules.

Antibodies

In some embodiments, a MARC polypeptide or activity thereof can be modulated by an antibody or a fragment thereof that can specifically bind a MARC polypeptide. In this way, a MARC-specific antibody can be used as an inhibitor to a MARC polypeptide. In some embodiments, a MARC-specific antibody or a fragment thereof can be configured to bind an active site on the MARC protein and thus behave as a competitive inhibitor for a substrate and/or cofactor. In some embodiments, MARC activity can be reduced as a result of a MARC-specific antibody binding or otherwise interacting with the MARC protein. In some embodiments, the MARC-specific antibody can specifically bind a risk MARC variant. In some embodiments, the MARC-specific antibody can specifically bind a protective MARC variant.

In some embodiments, MARC activity can be reduced by 1 to/or about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%. In some embodiments, MARC activity can be reduced to below detectable or measurable levels. In some embodiments, MARC activity can be reduced to a level that is comparable or equivalent to the level of MARC expression and/or activity that is produced from the protective MARC allele. In some embodiments, the MARC activity can be decreased to a level that causes a physiological response in a cell and/or subject. In some embodiments, the MARC activity can be decreased to a level that creates a protective effect on the liver as is described elsewhere herein. In some embodiments, a subject who has a risk MARC variant can be treated using a MARC-targeting antibody and can, in some embodiments, appear from a physiological standpoint (e.g., as measured by extent of liver disease, biomarkers etc.) as if they had the protective MARC allele despite them having a risk variant without the need for genome modification.

As used herein, "antibody" can refer to a glycoprotein containing at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region and a light chain constant region. The VH and VL regions retain the binding specificity to the antigen and can be further subdivided into regions of hypervariability, termed complementarity determining regions (CDR). The CDRs are interspersed with regions that are more conserved, termed framework regions (FR). Each VH and VL is composed of three CDRs and four framework regions, arranged from amino-terminus to carboxy-terminus in the following order: FR1, CDR1, FR2, CDR2, FR3, CDR3, and FR4. The variable regions of the heavy and light chains contain a binding domain that interacts with an antigen. "Antibody" includes single valent, bivalent and multivalent antibodies.

RNAI and Antisense RNA

In some embodiments, expression of a MARC RNA molecule (e.g., a MARC mRNA) can be modulated using interfering RNA (RNAi) or other antisense-RNA method or technique. In short, RNAi and antisense RNA can result in degradation and/or inhibit translation of an RNA molecule, such as an mRNA, such that MARC transcript and/or protein expression is decreased. In some embodiments, the RNA and/or protein expression can be reduced below detectable or measurable levels. In some embodiments, the RNA and/or protein expression, such as of MARC, can be decreased to a level that causes a physiological response in a cell and/or subject. In some embodiments, MARC expression and/or activity can be reduced by 1 to/or about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%.

In some embodiments, the MARC that is reduced via RNAi or antisense RNA is the risk MARC allele. In some embodiments, MARC expression and/or activity is reduced to a level that is comparable or equivalent to the level of MARC expression and/or activity that is produced from the protective MARC allele. This can result in a protective effect on the liver as is described in greater detail elsewhere herein. In some embodiments, a subject who has a risk MARC variant can be treated using a MARC targeting RNAi or antisense composition and can, in some embodiments, appear from a physiological standpoint (e.g., as measured by extent of liver disease, biomarkers etc.) as if they had the protective MARC allele, despite them having a risk variant, without the need for genome modification. Any suitable RNAi or antisense RNA composition or technique can be used. Such compositions and techniques are described herein and others will be appreciated by those of ordinary skill in the art in view of the description herein. It will be appreciated that in the context of RNAi and related techniques herein, the target for the RNAi or antisense RNA effector molecules can be a MARC variant, such as a MARC risk variant polynucleotide. In some instances, it may be desirable to target the protective MARC variant. Thus, in some of these embodiments, the target for an RNAi or antisense RNA effector molecule can be the protective MARC variant.

Short Interfering Nucleic Acids

As used herein, the term "short interfering nucleic acid", "siNA", or "short interfering nucleic acid molecule" refers to any nucleic acid molecule capable of modulating gene expression or viral replication. Preferably siNA inhibits or down regulates gene expression or viral replication. siNA includes without limitation nucleic acid molecules that are capable of mediating sequence specific RNAi, for example, short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. As used herein, "short interfering nucleic acid", "siNA", or "short interfering nucleic acid molecule" has the meaning described in more detail elsewhere herein.

RNA interference refers to the process of sequence-specific post-transcriptional gene silencing in animals mediated by short interfering RNAs (siRNAs) (Zamore et al., 2000, Cell, 101, 25-33; Fire et al., 1998, Nature, 391, 806; Hamilton et al., 1999, Science, 286, 950-951; Lin et al., 1999, Nature, 402, 128-129; Sharp, 1999, Genes & Dev., 13:139-141; and Strauss, 1999, Science, 286, 886). The presence of dsRNA in cells triggers the RNAi response through a mechanism that has yet to be fully characterized.

Dicer is involved in the processing of the dsRNA into short pieces of dsRNA known as short interfering RNAs (siRNAs) (Zamore et al., 2000, Cell, 101, 25-33; Bass, 2000, Cell, 101, 235; Berstein et al., 2001, Nature, 409, 363). siRNAs derived from dicer activity can be about 21 to about 23 nucleotides in length and include about 19 base pair duplexes (Zamore et al., 2000, Cell, 101, 25-33; Elbashir et al., 2001, Genes Dev., 15, 188). Dicer has also been implicated in the excision of 21- and 22-nucleotide small temporal RNAs (stRNAs) from precursor RNA of conserved structure that are implicated in translational control (Hutvagner et al., 2001, Science, 293, 834). The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex (Elbashir et al., 2001, Genes Dev., 15, 188).

RNAi has been studied in a variety of systems. Fire et al., 1998, Nature, 391, 806, were the first to observe RNAi in *C. elegans*. Bahramian and Zarbl, 1999, Molecular and Cellular Biology, 19, 274-283 and Wianny and Goetz, 1999, Nature Cell Biol., 2, 70, describe RNAi mediated by dsRNA in mammalian systems. Elbashir et al., 2001, Nature, 411, 494 and Tuschl et al., WO0175164, describe RNAi induced by introduction of duplexes of synthetic 21-nucleotide RNAs in cultured mammalian cells including human embryonic kidney and HeLa cells. Recent work (Elbashir et al., 2001, EMBO J., 20, 6877 and Tuschl et al., WO0175164) has revealed certain requirements for siRNA length, structure, chemical composition, and sequence that are essential to mediate efficient RNAi activity.

Nucleic acid molecules (for example comprising structural features as disclosed herein) may inhibit or down regulate gene expression or viral replication by mediating RNA interference "RNAi" or gene silencing in a sequence-specific manner. (See, e.g., Zamore et al., 2000, Cell, 101, 25-33; Bass, 2001, Nature, 411, 428-429; Elbashir et al., 2001, Nature, 411, 494-498; and Kreutzer et al., WO0044895; Zernicka-Goetz et al., WO0136646; Fire, WO9932619; Plaetinck et al., WO0001846; Mello and Fire, WO0129058; Deschamps-Depaillette, WO9907409; and Li et al., WO0044914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831).

An siNA nucleic acid molecule can be assembled from two separate polynucleotide strands, where one strand is the sense strand and the other is the antisense strand in which the antisense and sense strands are self-complementary (i.e., each strand includes nucleotide sequence that is complementary to nucleotide sequence in the other strand), such as where the antisense strand and sense strand form a duplex or double-stranded structure having any length and structure as described herein for nucleic acid molecules as provided, for example wherein the double-stranded region (duplex region) is about 15 to about 49 base pairs (e.g., about 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 base pairs); the antisense strand includes nucleotide sequence that is complementary to nucleotide sequence in a target nucleic acid molecule (i.e., hsp47 mRNA) or a portion thereof, and the sense strand includes a nucleotide sequence corresponding to the target nucleic acid sequence or a portion thereof (e.g., about 17 to about 49 or more nucleotides of the nucleic acid molecules herein are complementary to the target nucleic acid or a portion thereof).

In certain aspects and embodiments, a nucleic acid molecule (e.g., a siNA molecule) provided herein may be a "RISC length" molecule or may be a Dicer substrate as described in more detail below.

Nucleic acid molecules (e.g., siNA molecules) provided herein may have a strand, preferably, the sense strand, that is nicked or gapped. As such, nucleic acid molecules may have three or more strand, for example, such as a meroduplex RNA (mdRNA) disclosed in PCT/US07/081836. Nucleic acid molecules with a nicked or gapped strand may be between about 1 to 49 nucleotides, or may be RISC length (e.g., about 15 to 25 nucleotides) or Dicer substrate length (e.g., about 25 to 30 nucleotides) such as disclosed herein.

Nucleic acid molecules with three or more strands include, for example, an 'A' (antisense) strand, 'S1' (second) strand, and S2' (third) strand in which the 'S1' and 'S2' strands are complementary to and form base pairs with non-overlapping regions of the 'A' strand (e.g., an mdRNA can have the form of A:S1S2). The S1, S2, or more strands together form what is substantially similar to a sense strand to the 'A' antisense strand. The double-stranded region formed by the annealing of the 'S1' and 'A' strands is distinct from and non-overlapping with the double-stranded region formed by the annealing of the 'S2' and 'A' strands. A nucleic acid molecule (e.g., an siNA molecule) may be a "gapped" molecule, meaning a "gap" ranging from 0 nucleotides up to about 10 nucleotides (e.g., 0, 1, 2, 3, 4, 5, 6, 7, 8, 9 or 10 nucleotides). Preferably, the sense strand is gapped. In some embodiments, the A:S1 duplex is separated from the A:S2 duplex by a gap resulting from at least one unpaired nucleotide (up to about 10 unpaired nucleotides) in the A' strand that is positioned between the A:S1 duplex and the A:S2 duplex and that is distinct from any one or more unpaired nucleotide at the 3'-end of one or more of the 'A', 'S1', or 'S2' strands. The A:S1 duplex may be separated from the A: B2 duplex by a gap of zero nucleotides (i.e., a nick in which only a phosphodiester bond between two nucleotides is broken or missing in the polynucleotide molecule) between the A:S1 duplex and the A:S2 duplex-which can also be referred to as nicked dsRNA (ndsRNA). For example, A:S1S2 may include a dsRNA having at least two double-stranded regions that combined total about 14 base pairs to about 40 base pairs and the double-stranded regions are separated by a gap of about 0 to about 10 nucleotides, optionally having blunt ends, or A:S1S2 may include a dsRNA having at least two double-stranded regions separated by a gap of up to ten nucleotides wherein at least one of the double-stranded regions includes between about five base pairs and thirteen base pairs.

In certain embodiments, the nucleic acid molecules (e.g., siNA molecules) provided herein may be a precursor "Dicer substrate" molecule, e.g., double-stranded nucleic acid, processed in vivo to produce an active nucleic acid molecules, for example, as described in Rossi, US Patent Publication 2005-0244858. In certain conditions and situations, it has been found that these relatively longer dsRNA siNA species, e.g., of from about 25 to about 30 nucleotides, can give unexpectedly effective results in terms of potency and duration of action. Without wishing to be bound by any particular theory, it is thought that the longer dsRNA species serve as a substrate for the enzyme Dicer in the cytoplasm of a cell. In addition to cleaving double-stranded nucleic acid into shorter segments, Dicer may facilitate the incorporation of a single-stranded cleavage product derived from the cleaved dsRNA into the RNA-induced silencing complex (RISC complex) that is responsible for the destruction of the cytoplasmic RNA derived from the target gene.

Dicer substrates may have certain properties which enhance its processing by Dicer. Dicer substrates are of a length sufficient such that it is processed by Dicer to produce an active nucleic acid molecule and may further include one or more of the following properties: (i) the dsRNA is asymmetric, e.g., has a 3'-overhang on the first strand (antisense strand); and (ii) the dsRNA has a modified 3'-end on the second strand (sense strand) to direct orientation of Dicer binding and processing of the dsRNA to an active siRNA. In certain embodiments, the longest strand in the Dicer substrate may be 24 to 30 nucleotides.

Dicer substrates may be symmetric or asymmetric. The Dicer substrate may have a sense strand includes 22 to 28 nucleotides and the antisense strand may include 24 to 30 nucleotides; thus, in some embodiments the resulting Dicer substrate may have an overhang on the 3' end of the antisense strand. Dicer substrate may have a sense strand 25 nucleotides in length, and the antisense strand having 27 nucleotides in length with a two base 3'-overhang. The overhang may be 1 to 3 nucleotides, for example 2 nucleotides. The sense strand may also have a 5'-phosphate.

An asymmetric Dicer substrate may further contain two deoxynucleotides at the 3'-end of the sense strand in place of two of the ribonucleotides. Some exemplary Dicer substrates lengths and structures are 21+0, 21+2, 21-2, 22+0, 22+1, 22-1, 23+0, 23+2, 23-2, 24+0, 24+2, 24-2, 25+0, 25+2, 25-2, 26+0, 26+2, 26-2, 27+0, 27+2, and 27-2.

The sense strand of a Dicer substrate may be between about 22 to about 30 (e.g., about 22, 23, 24, 25, 26, 27, 28, 29 or 30); about 22 to about 28; about 24 to about 30; about 25 to about 30; about 26 to about 30; about 26 to about 29; or about 27 to about 28 nucleotides in length. In certain preferred embodiments Dicer substrates contain sense and antisense strands that are at least about 25 nucleotides in length and no longer than about 30 nucleotides; between about 26 and 29 nucleotides; or 27 nucleotides in length. The sense and antisense strands may be the same length (blunt ended), different lengths (have overhangs), or a combination. The sense and antisense strands may exist on the same polynucleotide or on different polynucleotides. A Dicer substrate may have a duplex region of about 19, 20, 21, 22, 23, 24, 25 or 27 nucleotides.

Like other siNA molecules provided herein, the antisense strand of a Dicer substrate may have any sequence that anneals to the antisense strand under biological conditions, such as within the cytoplasm of a eukaryotic cell.

Dicer substrates may have any modifications to the nucleotide base, sugar or phosphate backbone as known in the art and/or as described herein for other nucleic acid molecules (such as siNA molecules). In certain embodiments, Dicer substrates may have a sense strand modified for Dicer processing by suitable modifiers located at the 3'-end of the sense strand, i.e., the dsRNA is designed to direct orientation of Dicer binding and processing. Suitable modifiers include nucleotides such as deoxyribonucleotides, dideoxyribonucleotides, acyclo-nucleotides and the like and sterically hindered molecules, such as fluorescent molecules and the like. Acyclo-nucleotides substitute a 2-hydroxyethoxymethyl group for-the 2'-deoxyribofuranosyl sugar normally present in dNMPs. Other nucleotides modifiers that could be used in Dicer substrate siNA molecules include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxynucleotides are used as the modifiers. When nucleotide modifiers are utilized, they may replace ribonucleotides (e.g., 1-3 nucleotide modifiers, or 2 nucleotide modifiers are substituted for the ribonucleotides on the 3'-end of the sense strand), such that the length of the Dicer substrate does not change. When sterically hindered molecules are utilized, they may be attached to the ribonucleotide at the 3'-end of the antisense strand. Thus, in certain embodiments, the length of the strand does not change with the incorporation of the modifiers. In certain embodiments, two DNA bases in the dsRNA are substituted to direct the orientation of Dicer processing of the antisense strand. In a further embodiment, two terminal DNA bases are substituted for two ribonucleotides on the 3'-end of the sense strand forming a blunt end of the duplex on the 3'-end of the sense strand and the 5'-end of the antisense strand, and a two-nucleotide RNA overhang is located on the 3'-end of the antisense strand. This is an asymmetric composition with DNA on the blunt end and RNA bases on the overhanging end.

In certain embodiments, modifications are included in the Dicer substrate such that the modification does not prevent the nucleic acid molecule from serving as a substrate for Dicer. In one embodiment, one or more modifications are made that enhance Dicer processing of the Dicer substrate. One or more modifications may be made that result in more effective RNAi generation. One or more modifications may be made that support a greater RNAi effect. One or more modifications are made that result in greater potency per each Dicer substrate to be delivered to the cell. Modifications may be incorporated in the 3'-terminal region, the 5'-terminal region, in both the 3'-terminal and 5'-terminal region or at various positions within the sequence. Any number and combination of modifications can be incorporated into the Dicer substrate so long as the modification does not prevent the nucleic acid molecule from serving as a substrate for Dicer. Where multiple modifications are present, they may be the same or different. Modifications to bases, sugar moieties, the phosphate backbone, and their combinations are contemplated. Either 5'-terminus can be phosphorylated.

Examples of Dicer substrate phosphate backbone modifications include phosphonates, including methylphosphonate, phosphorothioate, and phosphotriester modifications such as alkylphosphotriesters, and the like. Examples of Dicer substrate sugar moiety modifications include 2'-alkyl pyrimidine, such as 2'OMe, 2'-fluoro, amino, and deoxy modifications and the like (see, e.g., Amarzguioui et al., 2003). Examples of Dicer substrate base group modifications include abasic sugars, 2'-O-alkyl modified pyrimidines, 4-thiouracil, 5-bromouracil, 5-iodouracil, and 5-(3-aminoallyl)-uracil and the like. LNAs could also be incorporated.

The sense strand may be modified for Dicer processing by suitable modifiers located at the 3'-end of the sense strand, i.e., the Dicer substrate is designed to direct orientation of Dicer binding and processing. Suitable modifiers include nucleotides such as deoxyribonucleotides, dideoxyribonucleotides, acyclo-nucleotides and the like and sterically hindered molecules, such as fluorescent molecules and the like. Acyclo-nucleotides substitute a 2-hydroxyethoxymethyl group for-the 2'-deoxyribofuranosyl sugar normally present in dNMPs. Other nucleotides modifiers could include cordycepin, AZT, ddI, 3TC, d4T and the monophosphate nucleotides of AZT, 3TC and d4T. In one embodiment, deoxynucleotides are used as the modifiers. When nucleotide modifiers are utilized, 1-3 nucleotide modifiers, or 2 nucleotide modifiers are substituted for the ribonucleotides on the 3'-end of the sense strand. When sterically hindered molecules are utilized, they are attached to the ribonucleotide at the 3'-end of the antisense strand. Thus, the length of the strand does not change with the incorporation of the modifiers. In another embodiment, the description contemplates substituting two DNA bases in the Dicer substrate to direct the orientation of Dicer processing of the antisense strand. In a further embodiment of the present description, two terminal DNA bases are substituted for two ribonucleotides on the 3'-end of the sense strand forming a blunt end of the duplex on the 3'-end of the sense strand and the 5'-end of the antisense strand, and a two-nucleotide RNA overhang is located on the 3'-end of the antisense strand. This is an asymmetric composition with DNA on the blunt end and RNA bases on the overhanging end.

The antisense strand may be modified for Dicer processing by suitable modifiers located at the 3'-end of the antisense strand, i.e., the dsRNA is designed to direct orientation of Dicer binding and processing. Suitable modifiers include nucleotides such as deoxyribonucleotides, dideoxyribonucleotides, acyclo-nucleotides and the like and sterically hindered molecules, such as fluorescent molecules and the like. Acyclo-nucleotides substitute a 2-hydroxyethoxymethyl group for the 2'-deoxyribofuranosyl sugar normally present in dNMPs. Other nucleotides modifiers could include cordycepin, AZT, ddI, 3TC, d4T and the monophosphate nucleotides of AZT, 3TC and d4T. In one embodiment, deoxynucleotides are used as the modifiers. When nucleotide modifiers are utilized, 1-3 nucleotide modifiers, or 2 nucleotide modifiers are substituted for the ribonucleotides on the 3'-end of the antisense strand. When sterically hindered molecules are utilized, they are attached to the ribonucleotide at the 3'-end of the antisense strand. Thus, the length of the strand does not change with the incorporation of the modifiers. In another embodiment, the description contemplates substituting two DNA bases in the dsRNA to direct the orientation of Dicer processing. In a further description, two terminal DNA bases are located on the 3'-end of the antisense strand in place of two ribonucleotides forming a blunt end of the duplex on the 5'-end of the sense strand and the 3'-end of the antisense strand, and a two-nucleotide RNA overhang is located on the 3'-end of the sense strand. This is an asymmetric composition with DNA on the blunt end and RNA bases on the overhanging end.

Dicer substrates with a sense and an antisense strand can be linked by a third structure. The third structure will not block Dicer activity on the Dicer substrate and will not interfere with the directed destruction of the RNA transcribed from the target gene. The third structure may be a chemical linking group. Suitable chemical linking groups are known in the art and can be used. Alternatively, the third structure may be an oligonucleotide that links the two oligonucleotides of the dsRNA is a manner such that a hairpin structure is produced upon annealing of the two oligonucleotides making up the Dicer substrate. The hairpin structure preferably does not block Dicer activity on the Dicer substrate or interfere with the directed destruction of the RNA transcribed from the target gene.

The sense and antisense strands of the Dicer substrate are not required to be completely complementary. They only need to be substantially complementary to anneal under biological conditions and to provide a substrate for Dicer that produces a siRNA sufficiently complementary to the target sequence.

Dicer substrate can have certain properties that enhance its processing by Dicer. The Dicer substrate can have a length sufficient such that it is processed by Dicer to produce an active nucleic acid molecules (e.g., siRNA) and may have one or more of the following properties: the Dicer substrate is asymmetric, e.g., has a 3'-overhang on the first strand (antisense strand) and/or the Dicer substrate has a modified 3' end on the second strand (sense strand) to direct orientation of Dicer binding and processing of the Dicer substrate to an active siRNA. The Dicer substrate can be asymmetric such that the sense strand includes 22 to 28 nucleotides and the antisense strand includes 24 to 30 nucleotides. Thus, the resulting Dicer substrate has an overhang on the 3' end of the antisense strand. The overhang is Ito 3 nucleotides, for example two nucleotides. The sense strand may also have a 5' phosphate.

A Dicer substrate may have an overhang on the 3'-end of the antisense strand, and the sense strand is modified for Dicer processing. The 5'-end of the sense strand may have a phosphate. The sense and antisense strands may anneal under biological conditions, such as the conditions found in the cytoplasm of a cell. A region of one of the strands, particularly the antisense strand, of the Dicer substrate may have a sequence length of at least 19 nucleotides, wherein these nucleotides are in the 21-nucleotide region adjacent to the 3'-end of the antisense strand and are sufficiently complementary to a nucleotide sequence of the RNA produced from the target gene. A Dicer substrate may also have one or more of the following additional properties: the antisense strand has a right shift from a corresponding 21-mer (i.e., the antisense strand includes nucleotides on the right side of the molecule when compared to the corresponding 21-mer); and, the strands may not be completely complementary, i.e., the strands may contain simple mismatch pairings and base modifications such as LNA may be included in the 5'-end of the sense strand.

An antisense strand of a Dicer substrate nucleic acid molecule may be modified to include 1-9 ribonucleotides on the 5'-end to give a length of 22 to 28 nucleotides. When the antisense strand has a length of 21 nucleotides, then 1 to 7 ribonucleotides, or 2-5 ribonucleotides and/or 4 ribonucleotides may be added on the 3'-end. The added ribonucleotides may have any sequence. Although the added ribonucleotides may be complementary to the target gene sequence, full complementarity between the target sequence and the antisense strands is not required. That is, the resultant antisense strand is sufficiently complementary with the target sequence. A sense strand may then have 24 to 30 nucleotides. The sense strand may be substantially complementary with the antisense strand to anneal to the antisense strand under biological conditions. In one embodiment, the antisense strand may be synthesized to contain a modified 3'-end to direct Dicer processing. The sense strand may have a 3' overhang. The antisense strand may be synthesized to contain a modified 3'-end for Dicer binding and processing and the sense strand has a 3' overhang.

An siRNA nucleic acid molecule may include separate sense and antisense sequences or regions, where the sense and antisense regions are covalently linked by nucleotide or non-nucleotide linkers molecules as is known in the art, or are alternately non-covalently linked by ionic interactions, hydrogen bonding, van der Waals interactions, hydrophobic interactions, and/or stacking interactions. Nucleic acid molecules may include a nucleotide sequence that is complementary to nucleotide sequence of a target gene. Nucleic acid molecules may interact with nucleotide sequence of a target gene in a manner that causes inhibition of expression of the target gene.

Alternatively, an siRNA nucleic acid molecule is assembled from a single polynucleotide, where the self-complementary sense and antisense regions of the nucleic acid molecules are linked by means of a nucleic acid based or non-nucleic acid-based linker(s), i.e., the antisense strand and the sense strand are part of one single polynucleotide that having an antisense region and sense region that fold to form a duplex region (for example, to form a "hairpin" structure as is well known in the art). Such siNA nucleic acid molecules can be a polynucleotide with a duplex, asymmetric duplex, hairpin or asymmetric hairpin secondary structure, having self-complementary sense and antisense regions, wherein the antisense region includes a nucleotide sequence that is complementary to a nucleotide sequence in a separate target nucleic acid molecule or a portion thereof and the sense region having a nucleotide sequence corresponding to the target nucleic acid sequence (e.g., a sequence of hsp47 mRNA). Such siNA nucleic acid molecules can be a circular single-stranded polynucleotide having two or more loop structures and a stem comprising self-complementary sense and antisense regions, wherein the antisense region includes a nucleotide sequence that is complementary to a nucleotide sequence in a target nucleic acid molecule or a portion thereof, and the sense region having a nucleotide sequence corresponding to the target nucleic acid sequence or a portion thereof, and wherein the circular polynucleotide can be processed either in vivo or in vitro to generate an active nucleic acid molecule capable of mediating RNAi.

The following nomenclature is often used in the art to describe lengths and overhangs of siRNA molecules and may be used throughout the specification and Examples. In all descriptions of oligonucleotides herein, the identification of nucleotides in a sequence is given in the 5' to 3' direction for both sense and antisense strands. Names given to duplexes indicate the length of the oligomers and the presence or absence of overhangs. For example, a "21+2" duplex contains two nucleic acid strands both of which are 21 nucleotides in length, also termed a 21-mer siRNA duplex or a 21-mer nucleic acid and having a 2 nucleotides 3'-overhang. A "21-2" design refers to a 21-mer nucleic acid duplex with a 2 nucleotides 5'-overhang. A 21-0 design is a 21-mer nucleic acid duplex with no overhangs (blunt). A "21+2UU" is a 21-mer duplex with 2-nucleotides 3'-overhang, and the terminal 2 nucleotides at the 3'-ends are both U residues (which may result in mismatch with target sequence). The aforementioned nomenclature can be applied to siNA molecules of various lengths of strands, duplexes and overhangs (such as 19-0, 21+2, 27+2, and the like). In an alternative but similar nomenclature, a "25/27" is an asymmetric duplex having a 25 base sense strand and a 27 base antisense strand with a 2-nucleotides 3'-overhang. A "27/25" is an asymmetric duplex having a 27 base sense strand and a 25 base antisense strand.

In certain aspects and embodiments, nucleic acid molecules (e.g., siNA molecules) as provided herein include one or more modifications (or chemical modifications). In certain embodiments, such modifications include any changes to a nucleic acid molecule or polynucleotide that would make the molecule different than a standard ribonucleotide or RNA molecule (i.e., that includes standard adenosine, cytosine, uracil, or guanosine moieties), which may be referred to as an "unmodified" ribonucleotide or unmodified ribonucleic acid. Traditional DNA bases and polynucleotides having a 2'-deoxy sugar represented by adenosine, cytosine, thymine, or guanosine moieties may be referred to as an "unmodified deoxyribonucleotide" or "unmodified deoxyribonucleic acid"; accordingly, the term "unmodified nucleotide" or "unmodified nucleic acid" as used herein refers to an "unmodified ribonucleotide" or "unmodified ribonucleic acid" unless there is a clear indication to the contrary. Such modifications can be in the nucleotide sugar, nucleotide base, nucleotide phosphate group and/or the phosphate backbone of a polynucleotide.

In certain embodiments, modifications as disclosed herein may be used to increase RNAi activity of a molecule and/or to increase the in vivo stability of the molecules, particularly the stability in serum, and/or to increase bioavailability of the molecules. Non-limiting examples of modifications include internucleotide or internucleoside linkages; deoxynucleotides or dideoxyribonucleotides at any position and strand of the nucleic acid molecule; nucleic acid (e.g., ribonucleic acid) with a modification at the 2'-position preferably selected from an amino, fluoro, methoxy, alkoxy and alkyl; 2'-deoxyribonucleotides, 2'OMe ribonucleotides, 2'-deoxy-2'-fluoro ribonucleotides, "universal base" nucleotides, "acyclic" nucleotides, 5-C-methyl nucleotides, biotin group, and terminal glyceryl and/or inverted deoxy abasic residue incorporation, sterically hindered molecules, such as fluorescent molecules and the like. Other nucleotides modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). Further details on various modifications are described in more detail below.

Modified nucleotides include those having a Northern conformation (e.g., Northern pseudorotation cycle, See for example Sanger, Principles of Nucleic Acid Structure, Springer-Verlag ed., 1984). Non-limiting examples of nucleotides having a northern configuration include LNA nucleotides (e.g., 2'-O, 4'-C-methylene-(D-ribofuranosyl) nucleotides); 2'-methoxyethoxy (MOE) nucleotides; 2'-methyl-thio-ethyl, 2'-deoxy-2'-fluoro nucleotides, 2'-deoxy-2'-chloro nucleotides, 2'-azido nucleotides, and 2'OMe nucleotides. LNAs are described, for example, in Elman et al., 2005; Kurreck et al., 2002; Crinelli et al., 2002; Braasch and Corey, 2001; Bondensgaard et al., 2000; Wahlestedt et al., 2000; and WO0047599, WO9914226, WO9839352, and WO04083430. In one embodiment, an LNA is incorporated at the 5'-terminus of the sense strand.

Chemical modifications also include UNAs, which are non-nucleotide, acyclic analogues, in which the C2'-C3' bond is not present (although UNAs are not truly nucleotides, they are expressly included in the scope of "modified" nucleotides or modified nucleic acids as contemplated herein). In particular embodiments, nucleic acid molecules with an overhang may be modified to have UNAs at the overhang positions (i.e., 2 nucleotide overhang). In other embodiments, UNAs are included at the 3'- or 5'-ends. A UNA may be located anywhere along a nucleic acid strand, i.e., in position 7. Nucleic acid molecules may contain one or more UNA. Exemplary UNAs are disclosed in Nucleic Acids Symposium Series No. 52 p. 133-134 (2008). In certain embodiments, nucleic acid molecules (e.g., siNA molecules) as described herein, include one or more UNAs; or one UNA. In some embodiments, a nucleic acid molecule (e.g., a siNA molecule) as described herein that has a 3'-overhang include one or two UNAs in the 3' overhang. In some embodiments, a nucleic acid molecule (e.g., a siNA molecule) as described herein includes a UNA (for example, one UNA) in the antisense strand, for example in position 6 or position 7 of the antisense strand. Chemical modifications also include non-pairing nucleotide analogs, for example as disclosed herein. Chemical modifications further include unconventional moieties as disclosed herein.

Chemical modifications also include terminal modifications on the 5' and/or 3' part of the oligonucleotides and are also known as capping moieties. Such terminal modifications are selected from a nucleotide, a modified nucleotide, a lipid, a peptide, and a sugar.

Chemical modifications also include "six membered ring nucleotide analogs." Examples of six-membered ring nucleotide analogs are disclosed in Allart, et al (Nucleosides & Nucleotides, 1998, 17:1523-1526; and Perez-Perez, et al., 1996, Bioorg. and Medicinal Chem Letters 6:1457-1460). Oligonucleotides including 6-membered ring nucleotide analogs including hexitol and altritol nucleotide monomers are disclosed in WO2006047842.

Chemical modifications also include "mirror" nucleotides which have a reversed chirality as compared to normal naturally occurring nucleotide; that is, a mirror nucleotide may be an "L-nucleotide" analogue of naturally occurring D-nucleotide (see U.S. Pat. No. 6,602,858). Mirror nucleotides may further include at least one sugar or base modification and/or a backbone modification, for example, as described herein, such as a phosphorothioate or phosphonate moiety. U.S. Pat. No. 6,602,858 discloses nucleic acid catalysts including at least one L-nucleotide substitution. Mirror nucleotides include, for example, L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror image dT)) and L-RNA (L-riboadenosine-3'-phosphate (mirror rA); L-ribocytidine-3'-phosphate (mirror rC); and L-riboguanosine-3'-phosphate (mirror rG); L-ribouracil-3'-phosphate (mirror dU).

In embodiments, some modified ribonucleotides include modified deoxyribonucleotides, for example, 5'OMe DNA (5-methyl-deoxyriboguanosine-3'-phosphate) which may be useful as a nucleotide in the 5' terminal position (position number 1); PACE (deoxyriboadenosine 3' phosphonoacetate, deoxyribocytidine 3' phosphonoacetate, deoxyriboguanosine 3' phosphonoacetate, deoxyribothymidine 3' phosphonoacetate).

Modifications may be present in one or more strands of a nucleic acid molecule disclosed herein, e.g., in the sense strand, the antisense strand, or both strands. In certain embodiments, the antisense strand may include modifications and the sense strand my only include unmodified RNA.

The present invention also includes methods set forth in U.S. Pat. No. 8,097,710, which relates to post-transcriptional gene silencing with short RNA molecules (SRMs). SRMs are short sense RNA molecules (SSRMs) and short antisense RNA molecules (SARMs). SARMs are complementary to a region of a target RNA transcribed from a gene to be silenced, and SSRMs correspond to the sequence of the target RNA.

"Silencing" in this context is a term generally used to refer to suppression of expression of a gene. The degree of reduction may be so as to totally abolish production of the encoded gene product, but more usually the abolition of expression is partial, with some degree of expression remaining. The term should not therefore be taken to require complete "silencing" of expression. It is used herein where convenient because those skilled in the art well understand this.

In one embodiment, the method comprises introducing anti-sense molecules [SARMs] appropriate for the target gene into the organism in order to induce silencing. This could be done, for instance, by use of transcribable constructs encoding the SARMs.

In a related embodiment, the silencing may be achieved using constructs targeting those regions identified by the SRMs-based method disclosed above. Such constructs may for example, encode anti-sense oligonucleotides which target all are part of the identified region, or a region within 1, 2, 3, 4, 5, 10, 15 or 20 nucleotides of the identified region.

Specifically regarding higher animals (e.g., mammals, fish, birds, reptiles etc.) methods of the present invention include, inter alia, (i) methods for detecting or diagnosing gene silencing, or silencing of particular genes, in the animal by using SRMs as described above; (ii) methods for identifying silenced genes in the animal by using SRMs as described above; (iii) methods for selecting target sites on genes to be silenced using SRMs as described above; and (iv) methods for silencing a target gene in the animal, either directly, or through an animal-derived transgene in a second organism (e.g., a plant) as described above.

In one embodiment, an RNAi agent of the invention includes a single stranded RNA that interacts with a target RNA sequence to direct the cleavage of the target RNA. Without wishing to be bound by theory, it is believed that long double stranded RNA introduced into cells is broken down into double stranded short interfering RNAs (siRNAs) comprising a sense strand and an antisense strand by a Type III endonuclease known as Dicer (Sharp, et al. (2001) Genes Dev. 15:485). Dicer, a ribonuclease-III-like enzyme, processes these dsRNA into 19-23 base pair short interfering RNAs with characteristic two base 3' overhangs (Bernstein, et al., (2001) Nature 409:363). These siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleave the target to induce silencing (Elbashir, et al., (2001) Genes Dev. 15:188). Thus, in one aspect the invention relates to a single-stranded siRNA (ssRNA) (the antisense strand of an siRNA duplex) generated within a cell and which promotes the formation of a RISC complex to effect silencing of the target gene, i.e., a TTR gene. Accordingly, the term "siRNA" is also used herein to refer to an RNAi as described above.

In another embodiment, the RNAi agent may be a single-stranded RNA that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded siRNAs are described in U.S. Pat. No. 8,101,348 and in Lima et al., (2012) Cell 150:883-894, the entire contents of each of which are hereby incorporated herein by reference. Any of the antisense nucleotide sequences described herein may be used as a single-stranded RNA as described herein or as chemically modified by the methods described in Lima et al., (2012) Cell 150:883-894.

In another embodiment, an "iRNA" for use in the compositions, uses, and methods of the invention is a double stranded RNA and is referred to herein as a "double stranded RNAi agent," "double stranded RNA (dsRNA) molecule," "dsRNA agent," or "dsRNA". The term "dsRNA" refers to a complex of ribonucleic acid molecules, having a duplex structure comprising two anti-parallel and substantially complementary nucleic acid strands, referred to as having "sense" and "antisense" orientations with respect to a target RNA, i.e., a TTR gene. In some embodiments of the invention, a double stranded RNA (dsRNA) triggers the degradation of a target RNA, e.g., an mRNA, through a post-transcriptional gene-silencing mechanism referred to herein as RNA interference or RNAi.

While a target sequence is generally about 15 to 30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally, can identify those RNA sequences that, when targeted with an iRNA agent, mediate the best inhibition of target gene expression.

The RNA of an iRNA can also be modified to include one or more bicyclic sugar moieties. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an agent of the invention may include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-CH2-O-2' bridge. This structure effectively "locks" the ribose in the 3'-endo structural conformation. The addition of locked nucleic acids to siRNAs has been shown to increase siRNA stability in serum and to reduce off-target effects (Elmen, J. et al., (2005) Nucleic Acids Research 33 (1): 439-447; Mook, O R. et al., (2007) Mol Canc Ther 6 (3): 833-843; Grunweller, A. et al., (2003) Nucleic Acids Research 31 (12): 3185-3193). Examples of bicyclic nucleosides for use in the polynucleotides of the invention include, without limitation, nucleosides comprising a bridge between the 4' and the 2' ribosyl ring atoms. In certain embodiments, the antisense polynucleotide agents of the invention include one or more bicyclic nucleosides comprising a 4' to 2' bridge. Examples of such 4' to 2' bridged bicyclic nucleosides, include but are not limited to 4'-(CH2)-O-2' (LNA); 4'-(CH2)-S-2'; 4'-(CH2) 2-O-2' (ENA); 4'-CH (CH3)-O-2' (also referred to as "constrained ethyl" or "cEt") and 4'-CH (CH2OCH3)-O-2' (and analogs thereof; see, e.g., U.S. Pat. No. 7,399,845); 4'-C(CH3) (CH3)-O-2' (and analogs thereof; see e.g., U.S. Pat. No. 8,278,283); 4'-CH2-N (OCH3)-2' (and analogs thereof; see e.g., U.S. Pat. No. 8,278,425); 4'-CH2-O—N(CH3)-2' (see, e.g., U.S. Patent Publication No. 2004/0171570); 4'-CH2-N(R)—O-2', wherein R is H, C1-C12 alkyl, or a protecting group (see, e.g., U.S. Pat. No. 7,427,672); 4'-CH2-C(H) (CH3)-2' (see, e.g., Chattopadhyaya et al., J. Org. Chem., 2009, 74, 118-134); and 4'-CH2-C(·dbd·CH2)-2' (and analogs thereof; see, e.g., U.S. Pat. No. 8,278,426). The entire contents of each of the foregoing are hereby incorporated herein by reference.

Additional representative U.S. Patents and US Patent Publications that teach the preparation of locked nucleic acid nucleotides include, but are not limited to, the following: U.S. Pat. Nos. 6,268,490, 6,525,191, 6,670,461, 6,770,74, 6,794,499, 6,998,484, 7,053,207, 7,034, 133, 7,084,125, 7,399,845, 7,427,67, 7,569,686, 7,741,457, 8,022,193, 8,030,467, 8,278,425, 8,278,426, and 8,278,283, and U.S. Patent Publication Nos. US 2008-0039618 and US 2009-0012281, the entire contents of each of which are hereby incorporated herein by reference.

Any of the foregoing bicyclic nucleosides can be prepared having one or more stereochemical sugar configurations including, for example, .alpha.-L-ribofuranose and (3-D-ribofuranose (see WO 99/14226).

The RNA of an iRNA can also be modified to include one or more constrained ethyl nucleotides. As used herein, a "constrained ethyl nucleotide" or "cEt" is a locked nucleic acid comprising a bicyclic sugar moiety comprising a 4'-CH (CH3)-O-2' bridge. In one embodiment, a constrained ethyl nucleotide is in the S conformation referred to herein as "S-cEt."

An iRNA of the invention may also include one or more "conformationally restricted nucleotides" ("CRN"). CRN are nucleotide analogs with a linker connecting the C2' and C4' carbons of ribose or the C3 and —C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, US Patent Publication No. 2013-0190383; and PCT Patent Publiction WO 2013/036868, the entire contents of each of which are hereby incorporated herein by reference.

One or more of the nucleotides of an iRNA of the invention may also include a hydroxymethyl substituted nucleotide. A "hydroxymethyl substituted nucleotide" is an acyclic 2'-3'-seco-nucleotide, also referred to as an "unlocked nucleic acid" ("UNA") modification.

Representative U.S. publications that teach the preparation of UNA include, but are not limited to, U.S. Pat. No. 8,314,227; and US Patent Publication Nos. 2013-0096289, 2013-0011922, and 2011-0313020, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT (idT) and others. Disclosure of this modification can be found in PCT Patent Publication No. WO 2011/005861.

Other modifications of the nucleotides of an iRNA of the invention include a 5' phosphate or 5' phosphate mimic, e.g., a 5'-terminal phosphate or phosphate mimic on the antisense strand of an RNAi agent. Suitable phosphate mimics are disclosed in, for example US Patent Publication No. 2012/0157511.

Methods of Identifying MARC Modulators

In certain embodiments, the compositions, methods, and/or cells as described herein can be used in screening methods for therapeutic agents capable of modulating MARC. As used herein, "agent" refers to any substance, compound, molecule, and the like, which can be biologically active or otherwise can induce a biological and/or physiological effect on a subject to which it is administered to. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

Candidate therapeutic agents may have a different effect of temporal expression profiles, which may be read out according to the methods as described herein. Kalimuthu describes an electrochemical method for identifying substrates and modulators of MARC, which utilizes the natural electron partner of mARC, cytochrome b5, coupled to an electrochemical electrode. (Kalimuthu et al., "Human mitochondrial amidoxime reducing component (mARC): An electrochemical method for identifying new substrates and inhibitors," Electrochemistry Communications Vol. 84, pp. 90-93, 2017) Mediated electron transfer from the electrode via cytochrome $b_5$ to mARC results in a catalytic current in the presence of substrate. These methods can be adapted for and/or used to identify agents that can be effective to modulate MARC.

Vectors

Also provided herein are vectors that can contain one or more of the MARC modulating and/or modifying agents described elsewhere herein. In aspects, the vector can contain one or more polynucleotides encoding one or more elements of one or more MARC modulating and/or modifying agents described herein. The vectors can be useful in producing bacterial, fungal, yeast, plant cells, animal cells, and transgenic animals that can express one or more MARC modulating and/or modifying agents described herein. Within the scope of this disclosure are vectors containing one or more of the polynucleotide sequences described herein. One or more of the polynucleotides that are part of the MARC modulating and/or modifying agents described herein can be included in a vector or vector system. The vectors and/or vector systems can be used, for example, to express one or more of the polynucleotides in a cell, such as a producer cell, to produce virus particles containing one or more of the MARC modulating and/or modifying agents described elsewhere herein. Other uses for the vectors and vector systems described herein are also within the scope of this disclosure. In general, and throughout this specification, the term "vector" refers to a tool that allows or facilitates the transfer of an entity from one environment to another. In some contexts which will be appreciated by those of ordinary skill in the art, "vector" can be a term of art to refer to a nucleic acid molecule capable of transporting another nucleic acid to which it has been linked. A vector can be a replicon, such as a plasmid, phage, or cosmid, into which another DNA segment may be inserted so as to bring about the replication of the inserted segment. Generally, a vector is capable of replication when associated with the proper control elements.

Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can be composed of a nucleic acid (e.g., a polynucleotide) of the invention in a form suitable for expression of the nucleic acid in a host cell, which means that the recombinant expression vectors include one or more regulatory elements, which can be selected on the basis of the host cells to be used for expression, that is operatively-linked to the nucleic acid sequence to be expressed. Within a recombinant expression vector, "operably linked" and "operatively-linked" are used interchangeably herein and further defined elsewhere herein.

In the context of a vector, the term "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). Advantageous vectors include lentiviruses and adeno-associated viruses, and types of such vectors can also be selected for targeting particular types of cells. These and other aspects of the vectors and vector systems are described elsewhere herein.

In some aspects, the vector can be a bicistronic vector. In some aspects, a bicistronic vector can be used for one or more elements of a MARC modulating and/or modifying agents described herein. In some aspects, expression of elements of the MARC modulating and/or modifying agents described herein described herein can be driven by a suitable promoter, including but not limited to, the CBh promoter. Where the element of the MARC modulating and/or modifying agents described herein is an RNA, its expression can be driven by a Pol III promoter, such as a U6 promoter. In some aspects, the two are combined.

Cell-Based Vector Amplification and Expression

Vectors can be designed for expression of one or more MARC modulating and/or modifying agents described herein (e.g., polynucleotides, proteins, enzymes, and combinations thereof) in a suitable host cell. In some aspects, the suitable host cell is a prokaryotic cell. Suitable host cells include, but are not limited to, bacterial cells, yeast cells, insect cells, and mammalian cells. The vectors can be viral-based or non-viral based. In some aspects, the suitable host cell is a eukaryotic cell. In some aspects, the suitable host cell is a suitable bacterial cell. Suitable bacterial cells include, but are not limited to bacterial cells from the bacteria of the species *Escherichia coli*. Many suitable strains of *E. coli* are known in the art for expression of vectors. These include, but are not limited to Pirl, Stb12, Stb13, Stb14, TOP10, XL1 Blue, and XL10 Gold. In some aspects, the host cell is a suitable insect cell. Suitable insect cells include those from *Spodoptera frugiperda*. Suitable strains of *S. frugiperda* cells include, but are not limited to Sf9 and Sf21. In some aspects, the host cell is a suitable yeast cell. In some aspects, the yeast cell can be from *Saccharomyces cerevisiae*. In some aspects, the host cell is a suitable mammalian cell. Many types of mammalian cells have been developed to express vectors. Suitable mammalian cells include, but are not limited to, HEK293, Chinese Hamster Ovary Cells (CHOs), mouse myeloma cells, HeLa, U2OS, A549, HT1080, CAD, P19, NIH 3T3, L929, N2a, MCF-7, Y79, SO-Rb50, HepG G2, DIKX-X11, J558L, Baby hamster kidney cells (BHK), and chicken embryo fibroblasts (CEFs). Suitable host cells are discussed further in Goeddel, GENE EXPRESSION TECHNOLOGY: METHODS IN ENZYMOLOGY 185, Academic Press, San Diego, Calif. (1990). Additional cell lines for tissue culture are known in the art, including but not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, CIR, Rat6, CVI, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr−/−, COR-L23, COR-L23/CPR, COR-L23/5010, COR-L23/R23, COS-7, COV-434, CML TI, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THPI cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, cells transiently or non-transiently transfected with one or more vectors described herein, or cell lines derived from such cells are used in assessing one or more test compounds.

In some aspects, the vector can be a yeast expression vector. Examples of vectors for expression in yeast *Saccharomyces cerevisiae* include pYepSec1 (Baldari, et al., 1987. EMBO J. 6:229-234), pMFa (Kuijan and Herskowitz, 1982. Cell 30:933-943), pJRY88 (Schultz et al., 1987. Gene 54:113-123), pYES2 (Invitrogen Corporation, San Diego, Calif.), and picZ (In Vitrogen Corp, San Diego, Calif.). As used herein, a "yeast expression vector" refers to a nucleic acid that contains one or more sequences encoding an RNA and/or polypeptide and may further contain any desired elements that control the expression of the nucleic acid(s), as well as any elements that enable the replication and maintenance of the expression vector inside the yeast cell. Many suitable yeast expression vectors and features thereof are known in the art; for example, various vectors and techniques are illustrated in in Yeast Protocols, 2nd edition, Xiao, W., ed. (Humana Press, New York, 2007) and Buckholz, R. G. and Gleeson, M. A. (1991) Biotechnology (NY) 9 (11): 1067-72. Yeast vectors can contain, without limitation, a centromeric (CEN) sequence, an autonomous replication sequence (ARS), a promoter, such as an RNA Polymerase III promoter, operably linked to a sequence or gene of interest, a terminator such as an RNA polymerase III terminator, an origin of replication, and a marker gene (e.g., auxotrophic, antibiotic, or other selectable markers). Examples of expression vectors for use in yeast may include plasmids, yeast artificial chromosomes, 2μ plasmids, yeast integrative plasmids, yeast replicative plasmids, shuttle vectors, and episomal plasmids.

In some aspects, the vector is a baculovirus vector or expression vector and can be suitable for expression of polynucleotides and/or proteins in insect cells. Baculovirus vectors available for expression of proteins in cultured insect cells (e.g., SF9 cells) include the pAc series (Smith, et al., 1983. Mol. Cell. Biol. 3:2156-2165) and the pVL series (Lucknow and Summers, 1989. Virology 170:31-39). rAAV (recombinant Adeno-associated viral) vectors are preferably produced in insect cells, e.g., *Spodoptera frugiperda* Sf9 insect cells, grown in serum-free suspension culture. Serum-free insect cells can be purchased from commercial vendors, e.g., Sigma Aldrich (EX-CELL 405).

In some embodiments, the vector is a mammalian expression vector. In some aspects, the mammalian expression vector is capable of expressing one or more polynucleotides and/or polypeptides in a mammalian cell. Examples of mammalian expression vectors include, but are not limited to, pCDM8 (Seed, 1987. Nature 329:840) and pMT2PC (Kaufman, et al., 1987. EMBO J. 6:187-195). The mammalian expression vector can include one or more suitable regulatory elements capable of controlling expression of the one or more polynucleotides and/or proteins in the mammalian cell. For example, commonly used promoters are derived from polyoma, adenovirus 2, cytomegalovirus, simian virus 40, and others disclosed herein and known in the art. More detail on suitable regulatory elements are described elsewhere herein.

For other suitable expression vectors and vector systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1:268-277), lymphoid-specific promoters (Calame and Eaton, 1988. Adv. Immunol. 43:235-275), in particular promoters of T cell receptors (Winoto and Baltimore, 1989. EMBO J. 8:729-733) and immunoglobulins (Baneiji, et al., 1983. Cell 33:729-740; Queen and Baltimore, 1983. Cell 33:741-748), neuron-specific promoters (e.g., the neurofilament promoter; Byrne and Ruddle, 1989. Proc. Natl. Acad. Sci. USA 86:5473-5477), pancreas-specific promoters (Edlund, et al., 1985. Science 230:912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249:374-379) and the α-fetoprotein promoter (Campes and Tilghman, 1989. Genes Dev. 3:537-546). With regards to these prokaryotic and eukaryotic vectors, mention is made of U.S. Pat. No. 6,750,059, the contents of which are incorporated by reference herein in their entirety. Other aspects can utilize viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element can be operably linked to one or more MARC modulating and/or modifying agents described herein so as to drive expression of the one or more MARC modulating and/or modifying agents described herein described herein.

Vectors may be introduced and propagated in a prokaryote or prokaryotic cell. In some aspects, a prokaryote is used to amplify copies of a vector to be introduced into a eukaryotic cell or as an intermediate vector in the production of a vector to be introduced into a eukaryotic cell (e.g., amplifying a plasmid as part of a viral vector packaging system). In some aspects, a prokaryote is used to amplify copies of a vector and express one or more nucleic acids, such as to provide a source of one or more proteins for delivery to a host cell or host organism.

In some aspects, the vector can be a fusion vector or fusion expression vector. In some aspects, fusion vectors add a number of amino acids to a protein encoded therein, such as to the amino terminus, carboxy terminus, or both of a recombinant protein. Such fusion vectors can serve one or more purposes, such as (i) to increase expression of recombinant protein; (ii) to increase the solubility of the recombinant protein; and (iii) to aid in the purification of the recombinant protein by acting as a ligand in affinity purification. In some aspects, expression of polynucleotides (such as non-coding polynucleotides) and proteins in prokaryotes can be carried out in *Escherichia coli* with vectors containing constitutive or inducible promoters directing the expression of either fusion or non-fusion polynucleotides and/or proteins. In some aspects, the fusion expression vector can include a proteolytic cleavage site, which can be introduced at the junction of the fusion vector backbone or other fusion moiety and the recombinant polynucleotide or protein to enable separation of the recombinant polynucleotide or protein from the fusion vector backbone or other fusion moiety subsequent to purification of the fusion polynucleotide or protein. Such enzymes, and their cognate recognition sequences, include Factor Xa, thrombin and enterokinase. Example fusion expression vectors include pGEX (Pharmacia Biotech Inc; Smith and Johnson, 1988. Gene 67:31-40), pMAL (New England Biolabs, Beverly, Mass.) and pRIT5 (Pharmacia, Piscataway, N. J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

In some embodiments, one or more vectors driving expression of one or more MARC modulating and/or modifying agents described herein are introduced into a host cell such that expression of one or more elements of a MARC modulating and/or modifying agents described herein direct formation of the MARC modulating and/or modifying agent (s) described herein. For example, different elements of a MARC modulating and/or modifying agents described herein can each be operably linked to separate regulatory elements on separate vectors. RNA(s) of different elements of the engineered delivery system described herein can be delivered to an animal or mammal or cell thereof to produce an animal or mammal or cell thereof that constitutively or inducibly or conditionally expresses different MARC modulating and/or modifying agents described herein that can incorporates one or more elements of the MARC modulating and/or modifying agents described herein, or contains one or more cells that incorporates and/or expresses one or more elements of the MARC modulating and/or modifying agents described herein.

In some aspects, two or more of the elements expressed from the same or different regulatory element(s), can be combined in a single vector, with one or more additional vectors providing any components of the system not included in the first vector. MARC modulating and/or modifying agent polynucleotides that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding one or more xb proteins, embedded within one or more intron sequences (e.g., each in a different intron, two or more in at least one intron, or all in a single intron). In some embodiments, the MARC modulating and/or modifying agents described herein can be operably linked to and expressed from the same promoter.

Vector Features

The vectors can include additional features that can confer one or more functionalities to the vector, the polynucleotide to be delivered, a virus particle produced therefrom, or polypeptide expressed thereof. Such features include, but are not limited to, regulatory elements, selectable markers, molecular identifiers (e.g., molecular barcodes), stabilizing elements, and the like. It will be appreciated by those skilled in the art that the design of the expression vector and additional features included can depend on such factors as the choice of the host cell to be transformed, the level of expression desired, etc.

Regulatory Elements

In aspects, the polynucleotides and/or vectors thereof described herein (such as the MARC modulating and/or modifying agent polynucleotides of the present invention) can include one or more regulatory elements that can be operatively linked to the polynucleotide. The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter can direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) (see, e.g., Boshart et al, Cell, 41:521-530 (1985)), the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8 (1), p. 466-472, 1988); SV40 enhancer; and the intron sequence between exons 2 and 3 of rabbit β-globin (Proc. Natl. Acad. Sci. USA., Vol. 78 (3), p. 1527-31, 1981).

In some aspects, the regulatory sequence can be a regulatory sequence described in U.S. Pat. No. 7,776,321, U.S. Patent Publication No. 2011-0027239, and PCT Publication WO 2011/028929, the contents of which are incorporated by reference herein in their entirety. In some aspects, the vector can contain a minimal promoter. In some aspects, the minimal promoter is the Mecp2 promoter, tRNA promoter, or U6. In a further embodiment, the minimal promoter is tissue specific. In some aspects, the length of the vector polynucleotide the minimal promoters and polynucleotide sequences is less than 4.4 Kb.

To express a polynucleotide, the vector can include one or more transcriptional and/or translational initiation regulatory sequences, e.g., promoters, that direct the transcription of the gene and/or translation of the encoded protein in a cell. In some aspects a constitutive promoter may be employed. Suitable constitutive promoters for mammalian cells are generally known in the art and include, but are not limited to SV40, CAG, CMV, EF-1α, β-actin, RSV, and PGK. Suitable constitutive promoters for bacterial cells, yeast cells, and fungal cells are generally known in the art, such as a T-7 promoter for bacterial expression and an alcohol dehydrogenase promoter for expression in yeast.

In some aspects, the regulatory element can be a regulated promoter. "Regulated promoter" refers to promoters that direct gene expression not constitutively, but in a temporally- and/or spatially-regulated manner, and includes tissue-specific, tissue-preferred and inducible promoters. Regulated promoters include conditional promoters and inducible promoters. In some aspects, conditional promoters can be employed to direct expression of a polynucleotide in a specific cell type, under certain environmental conditions, and/or during a specific state of development. Suitable tissue specific promoters can include, but are not limited to, liver specific promoters (e.g., APOA2, SERPIN A1 (hAAT), CYP3A4, and MIR122), pancreatic cell promoters (e.g., INS, IRS2, Pdx1, Alx3, Ppy), cardiac specific promoters (e.g., Myh6 (alpha MHC), MYL2 (MLC-2v), TNI3 (cTn1), NPPA (ANF), Slc8a1 (Ncx1)), central nervous system cell promoters (SYN1, GFAP, INA, NES, MOBP, MBP, TH, FOXA2 (HNF3 beta)), skin cell specific promoters (e.g., FLG, K14, TGM3), immune cell specific promoters, (e.g., ITGAM, CD43 promoter, CD14 promoter, CD45 promoter, CD68 promoter), urogenital cell specific promoters (e.g., Pbsn, Upk2, Sbp, Ferl14), endothelial cell specific promoters (e.g., ENG), pluripotent and embryonic germ layer cell specific promoters (e.g., Oct4, NANOG, Synthetic Oct4, T brachyury, NES, SOX17, FOXA2, MIR122), and muscle cell specific promoter (e.g., Desmin). Other tissue and/or cell specific promoters are generally known in the art and are within the scope of this disclosure.

Inducible/conditional promoters can be positively inducible/conditional promoters (e.g., a promoter that activates transcription of the polynucleotide upon appropriate interaction with an activated activator, or an inducer (compound, environmental condition, or other stimulus) or a negative/conditional inducible promoter (e.g., a promoter that is repressed (e.g., bound by a repressor) until the repressor condition of the promotor is removed (e.g., inducer binds a repressor bound to the promoter stimulating release of the promoter by the repressor or removal of a chemical repressor from the promoter environment). The inducer can be a compound, environmental condition, or other stimulus. Thus, inducible/conditional promoters can be responsive to any suitable stimuli such as chemical, biological, or other molecular agents, temperature, light, and/or pH. Suitable inducible/conditional promoters include, but are not limited to, Tet-On, Tet-Off, Lac promoter, pBad, AlcA, LexA, Hsp70 promoter, Hsp90 promoter, pDawn, XVE/OlexA, GVG, and pOp/LhGR.

Where expression in a plant cell is desired, the MARC modulating and/or modifying agent polynucleotides described herein are typically placed under control of a plant promoter, i.e. a promoter operable in plant cells. One or more different types of promoters can be used.

A constitutive plant promoter is a promoter that is able to express the open reading frame (ORF) that it controls in all or nearly all of the plant tissues during all or nearly all developmental stages of the plant (referred to as "constitutive expression"). One non-limiting example of a constitutive promoter is the cauliflower mosaic virus 35S promoter. Different promoters may direct the expression of a gene in different tissues or cell types, or at different stages of development, or in response to different environmental conditions. In particular embodiments, one or more of the MARC modulating and/or modifying agent polynucleotides described herein are expressed under the control of a constitutive promoter, such as the cauliflower mosaic virus 35S promoter issue-preferred promoters can be utilized to target enhanced expression in certain cell types within a particular plant tissue, for instance vascular cells in leaves or roots or in specific cells of the seed. Examples of particular promoters that can be used for plant expression can be found in Kawamata et al., (1997) Plant Cell Physiol 38:792-803; Yamamoto et al., (1997) Plant J 12:255-65; Hire et al, (1992) Plant Mol Biol 20:207-18, Kuster et al, (1995) Plant Mol Biol 29:759-72, and Capana et al., (1994) Plant Mol Biol 25:681-91.

In some embodiments, promoters that are inducible and that can allow for spatiotemporal control of gene editing or gene expression can optionally use and/or be responsive to a form of energy. The form of energy may include, but is not limited to, sound energy, electromagnetic radiation, chemical energy and/or thermal energy. Examples of inducible systems include tetracycline inducible promoters (Tet-On or Tet-Off), small molecule two-hybrid transcription activations systems (FKBP, ABA, etc), or light inducible systems (Phytochrome, LOV domains, or cryptochrome), such as a Light Inducible Transcriptional Effector (LITE) that direct changes in transcriptional activity in a sequence-specific manner. The components of a light inducible system may include one or more e MARC modulating and/or modifying agent polynucleotides described herein, a light-responsive cytochrome heterodimer (e.g., from *Arabidopsis thaliana*), and a transcriptional activation/repression domain. In some aspects, the vector can include one or more of the inducible DNA binding proteins provided in PCT publication WO 2014/018423 and US Patent Publication Nos. 2015-0291966, 2017-0166903, 2019-0203212, which describe, for example, aspects of inducible DNA binding proteins and methods of use and can be adapted for use with the present invention.

In some aspects, transient or inducible expression can be achieved by including, for example, chemical-regulated promotors, i.e., whereby the application of an exogenous chemical induces gene expression. Modulation of gene expression can also be obtained by including a chemical-repressible promoter, where application of the chemical represses gene expression. Chemical-inducible promoters include, but are not limited to, the maize In2-2 promoter, activated by benzene sulfonamide herbicide safeners (De Veylder et al., (1997) Plant Cell Physiol 38:568-77), the maize GST promoter (GST-11-27, WO93/01294), activated by hydrophobic electrophilic compounds used as pre-emergent herbicides, and the tobacco PR-1 a promoter (Ono et al., (2004) Biosci Biotechnol Biochem 68:803-7) activated by salicylic acid. Promoters which are regulated by antibiotics, such as tetracycline-inducible and tetracycline-repressible promoters (Gatz et al., (1991) Mol Gen Genet 227: 229-37; U.S. Pat. Nos. 5,814,618 and 5,789,156) can also be used herein.

In some aspects, the vector or system thereof can include one or more elements capable of translocating and/or expressing a MARC modulating and/or modifying agent polynucleotide described herein to/in a specific cell component or organelle. Such organelles can include, but are not limited to, nucleus, ribosome, endoplasmic reticulum, golgi apparatus, chloroplast, mitochondria, vacuole, lysosome, cytoskeleton, plasma membrane, cell wall, peroxisome, centrioles, etc.

Selectable Markers and Tags

One or more of the MARC modulating and/or modifying agent polynucleotides described herein can be can be operably linked, fused to, or otherwise modified to include a polynucleotide that encodes or is a selectable marker or tag, which can be a polynucleotide or polypeptide. In some aspects, the polypeptide encoding a polypeptide selectable marker can be incorporated in the MARC modulating and/or modifying agent polynucleotide such that the selectable marker polypeptide, when translated, is inserted between two amino acids between the N- and C-terminus of the MARC modulating and/or modifying agent polypeptide or at the N- and/or C-terminus of the MARC modulating and/or modifying agent polypeptide. In some aspects, the selectable marker or tag is a polynucleotide barcode or unique molecular identifier (UMI).

It will be appreciated that the polynucleotide encoding such selectable markers or tags can be incorporated into a polynucleotide encoding one or more MARC modulating and/or modifying agent polynucleotides described herein or elements thereof in an appropriate manner to allow expression of the selectable marker or tag. Such techniques and methods are described elsewhere herein and will be instantly appreciated by one of ordinary skill in the art in view of this disclosure. Many such selectable markers and tags are generally known in the art and are intended to be within the scope of this disclosure.

Suitable selectable markers and tags include, but are not limited to, affinity tags, such as chitin binding protein (CBP), maltose binding protein (MBP), glutathione-S-transferase (GST), poly (His) tag; solubilization tags such as thioredoxin (TRX) and poly (NANP), MBP, and GST; chromatography tags such as those consisting of polyanionic amino acids, such as FLAG-tag; epitope tags such as V5-tag, Myc-tag, HA-tag and NE-tag; protein tags that can allow specific enzymatic modification (such as biotinylation by biotin ligase) or chemical modification (such as reaction with FLASH-EDT2 for fluorescence imaging), DNA and/or RNA segments that contain restriction enzyme or other enzyme cleavage sites; DNA segments that encode products that provide resistance against otherwise toxic compounds including antibiotics, such as, spectinomycin, ampicillin, kanamycin, tetracycline, Basta, neomycin phosphotransferase II (NEO), hygromycin phosphotransferase (HPT)) and the like; DNA and/or RNA segments that encode products that are otherwise lacking in the recipient cell (e.g., tRNA genes, auxotrophic markers); DNA and/or RNA segments that encode products which can be readily identified (e.g., phenotypic markers such as β-galactosidase, GUS; fluorescent proteins such as green fluorescent protein (GFP), cyan (CFP), yellow (YFP), red (RFP), luciferase, and cell surface proteins); polynucleotides that can generate one or more new primer sites for PCR (e.g., the juxtaposition of two DNA sequences not previously juxtaposed); DNA sequences not acted upon or acted upon by a restriction endonuclease or other DNA modifying enzyme, chemical, etc.; epitope tags (e.g., GFP, FLAG- and His-tags); and DNA sequences that make a molecular barcode or unique molecular identifier (UMI), DNA sequences required for a specific modification (e.g., methylation) that allows its identification. Other suitable markers will be appreciated by those of skill in the art.

Selectable markers and tags can be operably linked to one or more MARC modulating and/or modifying agents or elements thereof described herein via suitable linker, such as a glycine or glycine serine linkers as short as GS or GG up to (GGGGS); (SEQ ID NO: 48) or (GGGGS) 6 (SEQ ID NO: 49) or (GGGGS) 9 (SEQ ID NO: 50). Other suitable linkers are described elsewhere herein.

The vector or vector system can include one or more polynucleotides encoding one or more targeting moieties. In some aspects, the targeting moiety encoding polynucleotides can be included in the vector or vector system, such as a viral vector system, such that they are expressed within and/or on the virus particle(s) produced such that the virus particles can be targeted to specific cells, tissues, organs, etc. In some aspects, the targeting moiety encoding polynucleotides can be included in the vector or vector system such that the MARC modulating and/or modifying agent polynucleotide(s) and/or products expressed therefrom include the targeting moiety and can be targeted to specific cells, tissues, organs, etc. In some aspects, such as non-viral carriers, the targeting moiety can be attached to the carrier (e.g., polymer, lipid, inorganic molecule etc.) and can be capable of targeting the carrier and any attached or associated MARC modulating and/or modifying agent polynucleotide(s) to specific cells, tissues, organs, etc.

Cell-Free Vector and Polynucleotide Expression

In some aspects, the polynucleotide encoding one or more MARC modulating and/or modifying agents or elements thereof can be expressed from a vector or suitable polynucleotide in a cell-free in vitro system. In other words, the polynucleotide can be transcribed and optionally translated in vitro. In vitro transcription/translation systems and appropriate vectors are generally known in the art and commercially available. Generally, in vitro transcription and in vitro translation systems replicate the processes of RNA and protein synthesis, respectively, outside of the cellular environment. Vectors and suitable polynucleotides for in vitro transcription can include T7, SP6, T3, promoter regulatory sequences that can be recognized and acted upon by an appropriate polymerase to transcribe the polynucleotide or vector.

In vitro translation can be stand-alone (e.g., translation of a purified polyribonucleotide) or linked/coupled to transcription. In some aspects, the cell-free (or in vitro) translation system can include extracts from rabbit reticulocytes, wheat germ, and/or E. coli. The extracts can include various macromolecular components that are needed for translation of exogenous RNA (e.g., 70S or 80S ribosomes, tRNAs, aminoacyl-tRNA, synthetases, initiation, elongation factors, termination factors, etc.). Other components can be included or added during the translation reaction, including but not limited to, amino acids, energy sources (ATP, GTP), energy regenerating systems (creatine phosphate and creatine phosphokinase (eukaryotic systems)) (phosphoenol pyruvate and pyruvate kinase for bacterial systems), and other co-factors (Mg2+, K+, etc.). As previously mentioned, in vitro translation can be based on RNA or DNA starting material. Some translation systems can utilize an RNA template as starting material (e.g., reticulocyte lysates and wheat germ extracts). Some translation systems can utilize a DNA template as a starting material (e.g., *E. coli*-based systems). In these systems transcription and translation are coupled and DNA is first transcribed into RNA, which is subsequently translated. Suitable standard and coupled cell-free translation systems are generally known in the art and are commercially available.

Codon Optimization of Vector Polynucleotides

As described elsewhere herein, the polynucleotide encoding one or more MARC modulating and/or modifying agents or elements thereof described herein can be codon optimized. In some aspects, one or more polynucleotides contained in a vector ("vector polynucleotides") described herein that are in addition to an optionally codon optimized polynucleotide encoding one or more MARC modulating and/or modifying agents or elements thereof described herein can be codon optimized. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/, and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g., 1, 2, 3, 4, 5, 10, 15, 20, 25, 50, or more, or all codons) in a sequence encoding a DNA/RNA-targeting Cas protein corresponds to the most frequently used codon for a particular amino acid. As to codon usage in yeast, reference is made to the online Yeast Genome database available at www.yeastgenome.org/community/codon_usage.shtml, or *Codon selection in yeast*, Bennetzen and Hall, J Biol Chem. 1982 Mar. 25; 257 (6): 3026-31. As to codon usage in plants including algae, reference is made to *Codon usage in higher plants, green algae, and cyanobacteria*, Campbell and Gowri, Plant Physiol. 1990 January; 92 (1): 1-11; as well as *Codon usage in plant genes*, Murray et al, Nucleic Acids Res. 1989 Jan. 25; 17 (2): 477-98; or *Selection on the codon bias of chloroplast and cyanelle genes in different plant and algal lineages*, Morton BR, J Mol Evol. 1998 April; 46 (4):449-59.

The vector polynucleotide can be codon optimized for expression in a specific cell-type, tissue type, organ type, and/or subject type. In some aspects, a codon optimized sequence is a sequence optimized for expression in a eukaryote, e.g., humans (i.e., being optimized for expression in a human or human cell), or for another eukaryote, such as another animal (e.g., a mammal or avian) as is described elsewhere herein. Such codon optimized sequences are within the ambit of the ordinary skilled artisan in view of the description herein. In some aspects, the polynucleotide is codon optimized for a specific cell type. Such cell types can include, but are not limited to, epithelial cells (including skin cells, cells lining the gastrointestinal tract, cells lining other hollow organs), nerve cells (nerves, brain cells, spinal column cells, nerve support cells (e.g., astrocytes, glial cells, Schwann cells etc.), muscle cells (e.g., cardiac muscle, smooth muscle cells, and skeletal muscle cells), connective tissue cells (fat and other soft tissue padding cells, bone cells, tendon cells, cartilage cells), blood cells, stem cells and other progenitor cells, immune system cells, germ cells, and combinations thereof. Such codon optimized sequences are within the ambit of the ordinary skilled artisan in view of the description herein. In some aspects, the polynucleotide is codon optimized for a specific tissue type. Such tissue types can include, but are not limited to, muscle tissue, connective tissue, connective tissue, nervous tissue, and epithelial tissue. Such codon optimized sequences are within the ambit of the ordinary skilled artisan in view of the description herein. In some aspects, the polynucleotide is codon optimized for a specific organ. Such organs include, but are not limited to, muscles, skin, intestines, liver, spleen, brain, lungs, stomach, heart, kidneys, gallbladder, pancreas, bladder, thyroid, bone, blood vessels, blood, and combinations thereof. Such codon optimized sequences are within the ambit of the ordinary skilled artisan in view of the description herein.

In some embodiments, a vector polynucleotide is codon optimized for expression in particular cells, such as prokaryotic or eukaryotic cells. The eukaryotic cells may be those of or derived from a particular organism, such as a plant or a mammal, including but not limited to human, or non-human eukaryote or animal or mammal as discussed herein, e.g., mouse, rat, rabbit, dog, livestock, or non-human mammal or primate.

Non-Viral Vectors and Carriers

In some aspects, the vector is a non-viral vector or carrier. In some aspects, non-viral vectors can have the advantage(s) of reduced toxicity and/or immunogenicity and/or increased biosafety as compared to viral vectors The terms of art "Non-viral vectors and carriers" and as used herein in this context refers to molecules and/or compositions that are not based on one or more component of a virus or virus genome (excluding any nucleotide to be delivered and/or expressed by the non-viral vector) that can be capable of attaching to, incorporating, coupling, and/or otherwise interacting with an MARC modulating and/or modifying agents or elements thereof and/or polynucleotides of the present invention and can be capable of ferrying the polynucleotide to a cell and/or expressing the polynucleotide. It will be appreciated that this does not exclude the inclusion of a virus-based polynucleotide that is to be delivered. For example, if a gRNA to be delivered is directed against a virus component, and it is inserted or otherwise coupled to an otherwise non-viral vector or carrier, this would not make said vector a "viral vector". Non-viral vectors and carriers include naked polynucleotides, chemical-based carriers, polynucleotide (non-viral) based vectors, and particle-based carriers. It will be appreciated that the term "vector" as used in the context of non-viral vectors and carriers refers to polynucleotide vectors and "carriers" used in this context refers to a non-nucleic acid or polynucleotide molecule or composition that be attached to or otherwise interact with a polynucleotide to be delivered, such as a MARC modulating and/or modifying agent polynucleotide of the present invention.

Naked Polynucleotides

In some aspects one or more MARC modulating and/or modifying agent polynucleotides described elsewhere herein can be included in a naked polynucleotide. The term of art "naked polynucleotide" as used herein refers to polynucleotides that are not associated with another molecule (e.g., proteins, lipids, and/or other molecules) that can often help protect it from environmental factors and/or degradation. As used herein, associated with includes, but is not limited to, linked to, adhered to, adsorbed to, enclosed in, enclosed in or within, mixed with, and the like. Naked polynucleotides that include one or more of the MARC modulating and/or modifying agent polynucleotides described herein can be delivered directly to a host cell and optionally expressed therein. The naked polynucleotides can have any suitable two- and three-dimensional configurations. By way of non-limiting examples, naked polynucleotides can be single-stranded molecules, double stranded molecules, circular molecules (e.g., plasmids and artificial chromosomes), molecules that contain portions that are single stranded and portions that are double stranded (e.g., ribozymes), and the like. In some aspects, the naked polynucleotide contains only the MARC modulating and/or modifying agent polynucleotide(s) of the present invention. In some aspects, the naked polynucleotide can contain other nucleic acids and/or polynucleotides in addition to the MARC modulating and/or modifying agent polynucleotide(s) of the present invention. The naked polynucleotides can include one or more elements of a transposon system. Transposons and system thereof are described in greater detail elsewhere herein.

Non-Viral Polynucleotide Vectors

In some aspects, one or more of the MARC modulating and/or modifying agent polynucleotides can be included in a non-viral polynucleotide vector. Suitable non-viral polynucleotide vectors include, but are not limited to, transposon vectors and vector systems, plasmids, bacterial artificial chromosomes, yeast artificial chromosomes, AR (antibiotic resistance)-free plasmids and miniplasmids, circular covalently closed vectors (e.g., minicircles, minivectors, miniknots), linear covalently closed vectors ("dumbbell shaped"), MIDGE (minimalistic immunologically defined gene expression) vectors, MiLV (micro-linear vector) vectors, Ministrings, mini-intronic plasmids, PSK systems (post-segregationally killing systems), ORT (operator repressor titration) plasmids, and the like. See e.g., Hardee et al. 2017. Genes. 8 (2): 65.

In some aspects, the non-viral polynucleotide vector can have a conditional origin of replication. In some aspects, the non-viral polynucleotide vector can be an ORT plasmid. In some aspects, the non-viral polynucleotide vector can have a minimalistic immunologically defined gene expression. In some aspects, the non-viral polynucleotide vector can have one or more post-segregationally killing system genes. In some aspects, the non-viral polynucleotide vector is AR-free. In some aspects, the non-viral polynucleotide vector is a minivector. In some aspects, the non-viral polynucleotide vector includes a nuclear localization signal. In some aspects, the non-viral polynucleotide vector can include one or more CpG motifs. In some aspects, the non-viral polynucleotide vectors can include one or more scaffold/matrix attachment regions (S/MARs). See e.g., Mirkovitch et al. 1984. Cell. 39:223-232, Wong et al. 2015. Adv. Genet. 89:113-152, whose techniques and vectors can be adapted for use in the present invention. S/MARs are AT-rich sequences that play a role in the spatial organization of chromosomes through DNA loop base attachment to the nuclear matrix. S/MARs are often found close to regulatory elements such as promoters, enhancers, and origins of DNA replication. Inclusion of one or S/MARs can facilitate a once-per-cell-cycle replication to maintain the non-viral polynucleotide vector as an episome in daughter cells. In aspects, the S/MAR sequence is located downstream of an actively transcribed polynucleotide (e.g., one or more MARC modulating and/or modifying agents or polynucleotides of the present invention) included in the non-viral polynucleotide vector. In some aspects, the S/MAR can be a S/MAR from the beta-interferon gene cluster. See e.g., Verghese et al. 2014. Nucleic Acid Res. 42: e53; Xu et al. 2016. Sci. China Life Sci. 59:1024-1033; Jin et al. 2016. 8:702-711; Koirala et al. 2014. Adv. Exp. Med. Biol. 801: 703-709; and Nehlsen et al. 2006. Gene Ther. Mol. Biol. 10:233-244, whose techniques and vectors can be adapted for use in the present invention.

In some aspects, the non-viral vector is a transposon vector or system thereof. As used herein, "transposon" (also referred to as transposable element) refers to a polynucleotide sequence that is capable of moving form location in a genome to another. There are several classes of transposons. Transposons include retrotransposons and DNA transposons. Retrotransposons require the transcription of the polynucleotide that is moved (or transposed) in order to transpose the polynucleotide to a new genome or polynucleotide. DNA transposons are those that do not require reverse transcription of the polynucleotide that is moved (or transposed) in order to transpose the polynucleotide to a new genome or polynucleotide. In some aspects, the non-viral polynucleotide vector can be a retrotransposon vector. In some aspects, the retrotransposon vector includes long terminal repeats. In some aspects, the retrotransposon vector does not include long terminal repeats. In some aspects, the non-viral polynucleotide vector can be a DNA transposon vector. DNA transposon vectors can include a polynucleotide sequence encoding a transposase. In some aspects, the transposon vector is configured as a non-autonomous transposon vector, meaning that the transposition does not occur spontaneously on its own. In some of these aspects, the transposon vector lacks one or more polynucleotide sequences encoding proteins required for transposition. In some aspects, the non-autonomous transposon vectors lack one or more Ac elements.

In some aspects a non-viral polynucleotide transposon vector system can include a first polynucleotide vector that contains the MARC modulating and/or modifying agent polynucleotide(s) of the present invention flanked on the 5' and 3' ends by transposon terminal inverted repeats (TIRs) and a second polynucleotide vector that includes a polynucleotide capable of encoding a transposase coupled to a promoter to drive expression of the transposase. When both are expressed in the same cell the transposase can be expressed from the second vector and can transpose the material between the TIRs on the first vector (e.g., the MARC modulating and/or modifying agents or elements thereof polynucleotide(s) of the present invention) and integrate it into one or more positions in the host cell's genome. In some aspects the transposon vector or system thereof can be configured as a gene trap. In some aspects, the TIRs can be configured to flank a strong splice acceptor site followed by a reporter and/or other gene (e.g., one or more of the MARC modulating and/or modifying agent polynucleotide(s) of the present invention) and a strong poly A tail.

When transposition occurs while using this vector or system thereof, the transposon can insert into an intron of a gene and the inserted reporter or other gene can provoke a mis-splicing process and as a result it in activates the trapped gene.

Any suitable transposon system can be used. Suitable transposon and systems thereof can include, Sleeping Beauty transposon system (Tc1/mariner superfamily) (see e.g., Ivics et al. 1997. Cell. 91 (4): 501-510), piggyBac (piggyBac superfamily) (see e.g., Li et al. 2013 110 (25): E2279-E2287 and Yusa et al. 2011. PNAS. 108 (4): 1531-1536), Tol2 (superfamily hAT), Frog Prince (Tc1/mariner superfamily) (see e.g., Miskey et al. 2003 Nucleic Acid Res. 31 (23): 6873-6881) and variants thereof.

Chemical Carriers

In some aspects the MARC modulating and/or modifying agent polynucleotide(s) can be coupled to a chemical carrier. Chemical carriers that can be suitable for delivery of polynucleotides can be broadly classified into the following classes: (i) inorganic particles; (ii) lipid-based; (iii) polymer-based; and (iv) peptide based. They can be categorized as (1) those that can form condensed complexes with a polynucleotide (such as the MARC modulating and/or modifying agent polynucleotide(s) of the present invention); (2) those capable of targeting specific cells; (3) those capable of increasing delivery of the polynucleotide (such as the MARC modulating and/or modifying agent polynucleotide(s) of the present invention) to the nucleus or cytosol of a host cell; (4) those capable of disintegrating from DNA/RNA in the cytosol of a host cell; and (5) those capable of sustained or controlled release. It will be appreciated that any one given chemical carrier can include features from multiple categories. The term "particle" as used herein, refers to any suitable sized particles for delivery of the MARC modulating and/or modifying agent or elements thereof described herein. Suitable sizes include macro-, micro-, and nano-sized particles.

In some aspects, the non-viral carrier can be an inorganic particle. In some aspects, the inorganic particle, can be a nanoparticle. The inorganic particles can be configured and optimized by varying size, shape, and/or porosity. In some aspects, the inorganic particles are optimized to escape from the reticulo endothelial system. In some aspects, the inorganic particles can be optimized to protect an entrapped molecule from degradation, the Suitable inorganic particles that can be used as non-viral carriers in this context can include, but are not limited to, calcium phosphate, silica, metals (e.g., gold, platinum, silver, palladium, rhodium, osmium, iridium, ruthenium, mercury, copper, rhenium, titanium, niobium, tantalum, and combinations thereof), magnetic compounds, particles, and materials, (e.g., supermagnetic iron oxide and magnetite), quantum dots, fullerenes (e.g., carbon nanoparticles, nanotubes, nanostrings, and the like), and combinations thereof. Other suitable inorganic non-viral carriers are discussed elsewhere herein.

In some aspects, the non-viral carrier can be lipid-based. Suitable lipid-based carriers are also described in greater detail herein. In some aspects, the lipid-based carrier includes a cationic lipid or an amphiphilic lipid that is capable of binding or otherwise interacting with a negative charge on the polynucleotide to be delivered (e.g., such as a MARC modulating and/or modifying agent polynucleotide(s) of the present invention). In some aspects, chemical non-viral carrier systems can include a polynucleotide such as the MARC modulating and/or modifying agent polynucleotide(s) of the present invention) and a lipid (such as a cationic lipid). These are also referred to in the art as lipoplexes. Other aspects of lipoplexes are described elsewhere herein. In some aspects, the non-viral lipid-based carrier can be a lipid nano emulsion. Lipid nano emulsions can be formed by the dispersion of an immiscible liquid in another stabilized emulsifying agent and can have particles of about 200 nm that are composed of the lipid, water, and surfactant that can contain the polynucleotide to be delivered (e.g., the MARC modulating and/or modifying agent polynucleotide(s) of the present invention). In some aspects, the lipid-based non-viral carrier can be a solid lipid particle or nanoparticle.

In some aspects, the non-viral carrier can be peptide-based. In some aspects, the peptide-based non-viral carrier can include one or more cationic amino acids. In some aspects, 35 to 40, 45, 50, 55, 60, 65, 70, 75, 80, 85, 90, 95, 99 or 100% of the amino acids are cationic. In some aspects, peptide carriers can be used in conjunction with other types of carriers (e.g., polymer-based carriers and lipid-based carriers to functionalize these carriers). In some aspects, the functionalization is targeting a host cell. Suitable polymers that can be included in the polymer-based non-viral carrier can include, but are not limited to, polyethylenimine (PEI), chitosan, poly (DL-lactide) (PLA), poly (DL-Lactide-co-glycoside) (PLGA), dendrimers (see e.g., US Patent Publication No. 2017-0079916 whose techniques and compositions can be adapted for use with the MARC modulating and/or modifying agent polynucleotides of the present invention), polymethacrylate, and combinations thereof.

In some aspects, the non-viral carrier can be configured to release an engineered delivery system polynucleotide that is associated with or attached to the non-viral carrier in response to an external stimulus, such as pH, temperature, osmolarity, concentration of a specific molecule or composition (e.g., calcium, NaCl, and the like), pressure and the like. In some aspects, the non-viral carrier can be a particle that is configured includes one or more of the MARC modulating and/or modifying agent polynucleotide(s) described herein and an environmental triggering agent response element, and optionally a triggering agent. In some aspects, the particle can include a polymer that can be selected from the group of polymethacrylates and polyacrylates. In some aspects, the non-viral particle can include one or more aspects of the compositions microparticles described in US Patent Publication Nos. 2015-0232883 and 2005-0123596, whose techniques and compositions can be adapted for use in the present invention.

In some aspects, the non-viral carrier can be a polymer-based carrier. In some aspects, the polymer is cationic or is predominantly cationic such that it can interact in a charge-dependent manner with the negatively charged polynucleotide to be delivered (such as MARC modulating and/or modifying agent polynucleotide(s) of the present invention). Polymer-based systems are described in greater detail elsewhere herein.

Viral Vectors

In some aspects, the vector is a viral vector. The term of art "viral vector" and as used herein in this context refers to polynucleotide based vectors that contain one or more elements from or based upon one or more elements of a virus that can be capable of expressing and packaging a polynucleotide, such as an MARC modulating and/or modifying agent polynucleotide(s) of the present invention, into a virus particle and producing said virus particle when used alone or with one or more other viral vectors (such as in a viral vector system). Viral vectors and systems thereof can be used for producing viral particles for delivery of and/or expression of one or more components of the MARC modulating and/or modifying agents described herein. The viral vector can be part of a viral vector system involving multiple vectors. In some aspects, systems incorporating multiple viral vectors can increase the safety of these systems. Suitable viral vectors can include retroviral-based vectors, lentiviral-based vectors, adenoviral-based vectors, adeno associated vectors, helper-dependent adenoviral (HdAd) vectors, hybrid adenoviral vectors, herpes simplex virus-based vectors, poxvirus-based vectors, and Epstein-Barr virus-based vectors. Other aspects of viral vectors and viral particles produce therefrom are described elsewhere herein. In some aspects, the viral vectors are configured to produce replication incompetent viral particles for improved safety of these systems.

Retroviral and Lentiviral Vectors

Retroviral vectors can be composed of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Suitable retroviral vectors for the MARC modulating and/or modifying agents can include those based upon murine leukemia virus (MuLV), gibbon ape leukemia virus (GaLV), Simian immunodeficiency virus (SIV), human immunodeficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700). Selection of a retroviral gene transfer system may therefore depend on the target tissue.

The tropism of a retrovirus can be altered by incorporating foreign envelope proteins, expanding the potential target population of target cells. Lentiviral vectors are retroviral vectors that are able to transduce or infect non-dividing cells and are described in greater detail elsewhere herein. A retrovirus can also be engineered to allow for conditional expression of the inserted transgene, such that only certain cell types are infected by the lentivirus.

Lentiviruses are complex retroviruses that have the ability to infect and express their genes in both mitotic and postmitotic cells. Advantages of using a lentiviral approach can include the ability to transduce or infect non-dividing cells and their ability to typically produce high viral titers, which can increase efficiency or efficacy of production and delivery. Suitable lentiviral vectors include, but are not limited to, human immunodeficiency virus (HIV)-based lentiviral vectors, feline immunodeficiency virus (FIV)-based lentiviral vectors, simian immunodeficiency virus (SIV)-based lentiviral vectors, Moloney Murine Leukaemia Virus (Mo-MLV), Visna.maedi virus (VMV)-based lentiviral vector, carpine arthritis-encephalitis virus (CAEV)-based lentiviral vector, bovine immune deficiency virus (BIV)-based lentiviral vector, and Equine infectious anemia (EIAV)-based lentiviral vector. In some embodiments, an HIV-based lentiviral vector system can be used. In some embodiments, a FIV-based lentiviral vector system can be used.

In some aspects, the lentiviral vector is an EIAV-based lentiviral vector or vector system. EIAV vectors have been used to mediate expression, packaging, and/or delivery in other contexts, such as for ocular gene therapy (see, e.g., Balagaan, J Gene Med 2006; 8:275-285). In another embodiment, RetinoStat®, (see, e.g., Binley et al., HUMAN GENE THERAPY 23:980-991 (September 2012)), which describes RetinoStat®, an equine infectious anemia virus-based lentiviral gene therapy vector that expresses angiostatic proteins endostatin and angiostatin that is delivered via a subretinal injection for the treatment of the wet form of age-related macular degeneration. Any of these vectors described in these publications can be modified for the elements of the MARC modulating and/or modifying agents described herein.

In some aspects, the lentiviral vector or vector system thereof can be a first-generation lentiviral vector or vector system thereof. First-generation lentiviral vectors can contain a large portion of the lentivirus genome, including the gag and pol genes, other additional viral proteins (e.g., VSV-G) and other accessory genes (e.g., vif, vprm vpu, nef, and combinations thereof), regulatory genes (e.g., tat and/or rev) as well as the gene of interest between the LTRs. First generation lentiviral vectors can result in the production of virus particles that can be capable of replication in vivo, which may not be appropriate for some instances or applications.

In some aspects, the lentiviral vector or vector system thereof can be a second-generation lentiviral vector or vector system thereof. Second-generation lentiviral vectors do not contain one or more accessory virulence factors and do not contain all components necessary for virus particle production on the same lentiviral vector. This can result in the production of a replication-incompetent virus particle and thus increase the safety of these systems over first-generation lentiviral vectors. In some aspects, the second-generation vector lacks one or more accessory virulence factors (e.g., vif, vprm, vpu, nef, and combinations thereof). Unlike the first-generation lentiviral vectors, no single second generation lentiviral vector includes all features necessary to express and package a polynucleotide into a virus particle. In some aspects, the envelope and packaging components are split between two different vectors with the gag, pol, rev, and tat genes being contained on one vector and the envelope protein (e.g., VSV-G) are contained on a second vector. The gene of interest, its promoter, and LTRs can be included on a third vector that can be used in conjunction with the other two vectors (packaging and envelope vectors) to generate a replication-incompetent virus particle.

In some aspects, the lentiviral vector or vector system thereof can be a third-generation lentiviral vector or vector system thereof. Third-generation lentiviral vectors and vector systems thereof have increased safety over first- and second-generation lentiviral vectors and systems thereof because, for example, the various components of the viral genome are split between two or more different vectors but used together in vitro to make virus particles, they can lack the tat gene (when a constitutively active promoter is included up-stream of the LTRs), and they can include one or more deletions in the 3'LTR to create self-inactivating (SIN) vectors having disrupted promoter/enhancer activity of the LTR. In some aspects, a third-generation lentiviral vector system can include (i) a vector plasmid that contains the polynucleotide of interest and upstream promoter that are flanked by the 5' and 3' LTRs, which can optionally include one or more deletions present in one or both of the LTRs to render the vector self-inactivating; (ii) a "packaging vector(s)" that can contain one or more genes involved in packaging a polynucleotide into a virus particle that is produced by the system (e.g., gag, pol, and rev) and upstream regulatory sequences (e.g., promoter(s)) to drive expression of the features present on the packaging vector, and (iii) an "envelope vector" that contains one or more envelope protein genes and upstream promoters. In aspects, the third-generation lentiviral vector system can include at least two packaging vectors, with the gag-pol being present on a different vector than the rev gene.

In some aspects, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2: 36ra43) can be used/and or adapted to the MARC modulating and/or modifying agents of the present invention.

In some aspects, the pseudotype and infectivity or tropism of a lentivirus particle can be tuned by altering the type of envelope protein(s) included in the lentiviral vector or system thereof. As used herein, an "envelope protein" or "outer protein" means a protein exposed at the surface of a viral particle that is not a capsid protein. For example, envelope or outer proteins typically comprise proteins embedded in the envelope of the virus. In some aspects, a lentiviral vector or vector system thereof can include a VSV-G envelope protein. VSV-G mediates viral attachment to an LDL receptor (LDLR) or an LDLR family member present on a host cell, which triggers endocytosis of the viral particle by the host cell. Because LDLR is expressed by a wide variety of cells, viral particles expressing the VSV-G envelope protein can infect or transduce a wide variety of cell types. Other suitable envelope proteins can be incorporated based on the host cell that a user desires to be infected by a virus particle produced from a lentiviral vector or system thereof described herein and can include, but are not limited to, feline endogenous virus envelope protein (RD114) (see e.g., Hanawa et al. Molec. Ther. 2002 5(3) 242-251), modified Sindbis virus envelope proteins (see e.g., Morizono et al. 2010. J. Virol. 84 (14) 6923-6934; Morizono et al. 2001. J. Virol. 75:8016-8020; Morizono et al. 2009. J. Gene Med. 11:549-558; Morizono et al. 2006 Virology 355:71-81; Morizono et al J. Gene Med. 11:655-663, Morizono et al. 2005 Nat. Med. 11:346-352), baboon retroviral envelope protein (see e.g., Girard-Gagnepain et al. 2014. Blood. 124:1221-1231); Tupaia paramyxovirus glycoproteins (see e.g., Enkirch T. et al., 2013. Gene Ther. 20:16-23); measles virus glycoproteins (see e.g., Funke et al. 2008. Molec. Ther. 16 (8): 1427-1436), rabies virus envelope proteins, MLV envelope proteins, Ebola envelope proteins, baculovirus envelope proteins, filovirus envelope proteins, hepatitis E1 and E2 envelope proteins, gp41 and gp120 of HIV, hemagglutinin, neuraminidase, M2 proteins of influenza virus, and combinations thereof.

In some aspects, the tropism of the resulting lentiviral particle can be tuned by incorporating cell targeting peptides into a lentiviral vector such that the cell targeting peptides are expressed on the surface of the resulting lentiviral particle. In some aspects, a lentiviral vector can contain an envelope protein that is fused to a cell targeting protein (see e.g., Buchholz et al. 2015. Trends Biotechnol. 33:777-790; Bender et al. 2016. PLOS Pathog. 12 (e1005461); and Friedrich et al. 2013. Mol. Ther. 2013. 21:849-859.

In some aspects, a split-intein-mediated approach to target lentiviral particles to a specific cell type can be used (see e.g., Chamoun-Emaneulli et al. 2015. Biotechnol. Bioeng. 112:2611-2617, Ramirez et al. 2013. Protein. Eng. Des. Sel. 26:215-233. In these aspects, a lentiviral vector can contain one half of a splicing-deficient variant of the naturally split intein from *Nostoc punctiforme* fused to a cell targeting peptide and the same or different lentiviral vector can contain the other half of the split intein fused to an envelope protein, such as a binding-deficient, fusion-competent virus envelope protein. This can result in production of a virus particle from the lentiviral vector or vector system that includes a split intein that can function as a molecular Velcro linker to link the cell-binding protein to the pseudotyped lentivirus particle. This approach can be advantageous for use where surface-incompatibilities can restrict the use of, e.g., cell targeting peptides.

In some aspects, a covalent-bond-forming protein-peptide pair can be incorporated into one or more of the lentiviral vectors described herein to conjugate a cell targeting peptide to the virus particle (see e.g., Kasaraneni et al. 2018. Sci. Reports (8) No. 10990). In some aspects, a lentiviral vector can include an N-termial PDZ domain of InaD protein (PDZ1) and its pentapeptide ligand (TEFCA) from NorpA, which can conjugate the cell targeting peptide to the virus particle via a covalent bond (e.g., a disulfide bond). In some aspects, the PDZI protein can be fused to an envelope protein, which can optionally be binding deficient and/or fusion competent virus envelope protein and included in a lentiviral vector. In some aspects, the TEFCA can be fused to a cell targeting peptide and the TEFCA-CPT fusion construct can be incorporated into the same or a different lentiviral vector as the PDZ1-envenlope protein construct. During virus production, specific interaction between the PDZI and TEFCA facilitates producing virus particles covalently functionalized with the cell targeting peptide and thus capable of targeting a specific cell-type based upon a specific interaction between the cell targeting peptide and cells expressing its binding partner. This approach can be advantageous for use where surface-incompatibilities can restrict the use of, e.g., cell targeting peptides.

Lentiviral vectors have been disclosed as in the treatment for Parkinson's Disease (see, e.g., US Patent Publication No. US 2012-0295960 and U.S. Pat. Nos. 7,303,910 and 7,351,585. Lentiviral vectors have also been disclosed for the treatment of ocular diseases, see e.g., US Patent Publication Nos. US 2006-0281180, US 2009-0007284, US2011-0117189, US 2009-0017543; US 2007-0054961, and US 2010-0317109. Lentiviral vectors have also been disclosed for delivery to the brain (see, e.g., US Patent Publication Nos. US 2011-029357, US 2011-0293571, US 2004-0013648, US 2007-0025970, US 2009-0111106 and U.S. Pat. No. 7,259,015. Any of these systems or a variant thereof can be used to deliver a MARC modulating and/or modifying agent polynucleotide described herein to a cell.

In some aspects, a lentiviral vector system can include one or more transfer plasmids. Transfer plasmids can be generated from various other vector backbones and can include one or more features that can work with other retroviral and/or lentiviral vectors in the system that can, for example, improve safety of the vector and/or vector system, increase virial titers, and/or increase or otherwise enhance expression of the desired insert to be expressed and/or packaged into the viral particle. Suitable features that can be included in a transfer plasmid can include, but are not limited to, 5'LTR, 3'LTR, SIN/LTR, origin of replication (Ori), selectable marker genes (e.g., antibiotic resistance genes), Psi (4'), RRE (rev response element), cPPT (central polypurine tract), promoters, WPRE (woodchuck hepatitis post-transcriptional regulatory element), SV40 polyadenylation signal, pUC origin, SV40 origin, F1 origin, and combinations thereof.

Adenoviral Vectors, Helper-Dependent Adenoviral Vectors, and Hybrid Adenoviral Vectors In some aspects, the vector can be an adenoviral vector. In some aspects, the adenoviral vector can include elements such that the virus particle produced using the vector or system thereof can be serotype 2 or serotype 5. In some aspects, the polynucleotide to be delivered via the adenoviral particle can be up to about 8 kb. Thus, in some aspects, an adenoviral vector can include a DNA polynucleotide to be delivered that can range in size from about 0.001 kb to about 8 kb. Adenoviral vectors have been used successfully in several contexts (see e.g., Teramato et al. 2000. Lancet. 355:1911-1912; Lai et al. 2002. DNA Cell. Biol. 21:895-913; Flotte et al., 1996. Hum. Gene. Ther. 7:1145-1159; and Kay et al. 2000. Nat. Genet. 24:257-261).

In some aspects the vector can be a helper-dependent adenoviral vector or system thereof. These are also referred to in the art as "gutless" or "gutted" vectors and are a modified generation of adenoviral vectors (see e.g., Thrasher et al. 2006. Nature. 443: E5-7). In aspects of the helper-dependent adenoviral vector system, one vector (the helper) can contain all the viral genes required for replication but contains a conditional gene defect in the packaging domain. The second vector of the system can contain only the ends of the viral genome, one or more MARC modulating and/or modifying agent polynucleotides, and the native packaging recognition signal, which can allow selective packaged release from the cells (see e.g., Cideciyan et al. 2009. N Engl J Med. 361:725-727). Helper-dependent adenoviral vector systems have been successful for gene delivery in several contexts (see e.g., Simonelli et al. 2010. J Am Soc Gene Ther. 18:643-650; Cideciyan et al. 2009. N Engl J Med. 361:725-727; Crane et al. 2012. Gene Ther. 19 (4): 443-452; Alba et al. 2005. Gene Ther. 12:18-S27; Croyle et al. 2005. Gene Ther. 12:579-587; Amalfitano et al. 1998. J. Virol. 72:926-933; and Morral et al. 1999. PNAS. 96:12816-12821). The techniques and vectors described in these publications can be adapted for inclusion and delivery of the MARC modulating and/or modifying agent polynucleotides described herein. In some aspects, the polynucleotide to be delivered via the viral particle produced from a helper-dependent adenoviral vector or system thereof can be up to about 37 kb. Thus, in some aspects, an adenoviral vector can include a DNA polynucleotide to be delivered that can range in size from about 0.001 kb to about 37 kb (see e.g., Rosewell et al. 2011. J. Genet. Syndr. Gene Ther. Suppl. 5:001).

In some aspects, the vector is a hybrid-adenoviral vector or system thereof. Hybrid adenoviral vectors are composed of the high transduction efficiency of a gene-deleted adenoviral vector and the long-term genome-integrating potential of adeno-associated, retroviruses, lentivirus, and transposon based-gene transfer. In some aspects, such hybrid vector systems can result in stable transduction and limited integration site. (See e.g., Balague et al. 2000. Blood. 95:820-828; Morral et al. 1998. Hum. Gene Ther. 9:2709-2716; Kubo and Mitani. 2003. J. Virol. 77 (5): 2964-2971; Zhang et al. 2013. PloS One. 8 (10) e76771; and Cooney et al. 2015. Mol. Ther. 23 (4): 667-674), whose techniques and vectors described therein can be modified and adapted for use in the MARC modulating and/or modifying agents of the present invention. In some aspects, a hybrid-adenoviral vector can include one or more features of a retrovirus and/or an adeno-associated virus. In some aspects the hybrid-adenoviral vector can include one or more features of a spuma retrovirus or foamy virus (FV). See e.g., Ehrhardt et al. 2007. Mol. Ther. 15:146-156 and Liu et al. 2007. Mol. Ther. 15:1834-1841, whose techniques and vectors described therein can be modified and adapted for use in the MARC modulating and/or modifying agents of the present invention. Advantages of using one or more features from the FVs in the hybrid-adenoviral vector or system thereof can include the ability of the viral particles produced therefrom to infect a broad range of cells, a large packaging capacity as compared to other retroviruses, and the ability to persist in quiescent (non-dividing) cells. See also e.g., Ehrhardt et al. 2007. Mol. Ther. 156:146-156 and Shuji et al. 2011. Mol. Ther. 19:76-82, whose techniques and vectors described therein can be modified and adapted for use in the MARC modulating and/or modifying agents of the present invention.

Adeno Associated Viral (AAV) Vectors

In an embodiment, the vector can be an adeno-associated virus (AAV) vector. See, e.g., West et al., Virology 160:38-47 (1987); U.S. Pat. No. 4,797,368; WO 93/24641; Kotin, Human Gene Therapy 5:793-801 (1994); and Muzyczka, J. Clin. Invest. 94:1351 (1994). Although similar to adenoviral vectors in some of their features, AAVs have some deficiency in their replication and/or pathogenicity and thus can be safer that adenoviral vectors. In some aspects the AAV can integrate into a specific site on chromosome 19 of a human cell with no observable side effects. In some aspects, the capacity of the AAV vector, system thereof, and/or AAV particles can be up to about 4.7 kb.

The AAV vector or system thereof can include one or more regulatory molecules. In some aspects the regulatory molecules can be promoters, enhancers, repressors and the like, which are described in greater detail elsewhere herein. In some aspects, the AAV vector or system thereof can include one or more polynucleotides that can encode one or more regulatory proteins. In some aspects, the one or more regulatory proteins can be selected from Rep78, Rep68, Rep52, Rep40, variants thereof, and combinations thereof.

The AAV vector or system thereof can include one or more polynucleotides that can encode one or more capsid proteins. The capsid proteins can be selected from VP1, VP2, VP3, and combinations thereof. The capsid proteins can be capable of assembling into a protein shell of the AAV virus particle. In some aspects, the AAV capsid can contain 60 capsid proteins. In some aspects, the ratio of VP1: VP2: VP3 in a capsid can be about 1:1:10.

In some aspects, the AAV vector or system thereof can include one or more adenovirus helper factors or polynucleotides that can encode one or more adenovirus helper factors. Such adenovirus helper factors can include, but are not limited, E1A, E1B, E2A, E4ORF6, and VA RNAs. In some aspects, a producing host cell line expresses one or more of the adenovirus helper factors.

The AAV vector or system thereof can be configured to produce AAV particles having a specific serotype. In some aspects, the serotype can be AAV-1, AAV-2, AAV-3, AAV-4, AAV-5, AAV-6, AAV-8, AAV-9 or any combinations thereof. In some aspects, the AAV can be AAVI, AAV-2, AAV-5 or any combination thereof. One can select the AAV of the AAV with regard to the cells to be targeted; for example, one can select AAV serotypes 1, 2, 5 or a hybrid capsid AAV-1, AAV-2, AAV-5 or any combination thereof for targeting brain and/or neuronal cells; one can select AAV-4 for targeting cardiac tissue; and one can select AAV8 for delivery to the liver. Thus, in some aspects, an AAV vector or system thereof capable of producing AAV particles capable of targeting the brain and/or neuronal cells can be configured to generate AAV particles having serotypes 1, 2, 5 or a hybrid capsid AAV-1, AAV-2, AAV-5 or any combination thereof. In some aspects, an AAV vector or system thereof capable of producing AAV particles capable of targeting cardiac tissue can be configured to generate an AAV particle having an AAV-4 serotype. In some aspects, an AAV vector or system thereof capable of producing AAV particles capable of targeting the liver can be configured to generate an AAV having an AAV-8 serotype. In some aspects, the AAV vector is a hybrid AAV vector or system thereof. Hybrid AAVs are AAVs that include genomes with elements from one serotype that are packaged into a capsid derived from at least one different serotype. For example, if it is the rAAV2/5 that is to be produced, and if the production method is based on the helper-free, transient transfection method discussed above, the 1st plasmid and the 3rd plasmid (the adeno helper plasmid) will be the same as discussed for rAAV2 production. However, the 2nd plasmid, the pRepCap will be different. In this plasmid, called pRep2/Cap5, the Rep gene is still derived from AAV2, while the Cap gene is derived from AAV5. The production scheme is the same as the above-mentioned approach for AAV2 production. The resulting rAAV is called rAAV2/5, in which the genome is based on recombinant AAV2, while the capsid is based on AAV5. It is assumed the cell or tissue-tropism displayed by this AAV2/5 hybrid virus should be the same as that of AAV5.

A tabulation of certain AAV serotypes as to these cells can be found in Grimm, D. et al, J. Virol. 82:5887-5911 (2008), which is recapitulated below in Table 4.

TABLE 4

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

In some aspects, the AAV vector or system thereof is configured as a "gutless" vector, similar to that described in connection with a retroviral vector. In some aspects, the "gutless" AAV vector or system thereof can have the cis-acting viral DNA elements involved in genome amplification and packaging in linkage with the heterologous sequences of interest (e.g., the MARC modulating and/or modifying agent polynucleotide(s)).

Herpes Simplex Viral Vectors

In some aspects, the vector can be a Herpes Simplex Viral (HSV)-based vector or system thereof. HSV systems can include the disabled infections single copy (DISC) viruses, which are composed of a glycoprotein H defective mutant HSV genome. When the defective HSV is propagated in complementing cells, virus particles can be generated that are capable of infecting subsequent cells permanently replicating their own genome but are not capable of producing more infectious particles. See e.g., 2009. Trobridge. Exp. Opin. Biol. Ther. 9:1427-1436, whose techniques and vectors described therein can be modified and adapted for use in the MARC modulating and/or modifying agent of the present invention. In some aspects where an HSV vector or system thereof is utilized, the host cell can be a complementing cell. In some aspects, HSV vector or system thereof can be capable of producing virus particles capable of delivering a polynucleotide cargo of up to 150 kb. Thus, in some aspect the MARC modulating and/or modifying agent polynucleotide(s) included in the HSV-based viral vector or system thereof can sum from about 0.001 to about 150 kb.

HSV-based vectors and systems thereof have been successfully used in several contexts including various models of neurologic disorders. See e.g., Cockrell et al. 2007. Mol. Biotechnol. 36:184-204; Kafri T. 2004. Mol. Biol. 246:367-390; Balaggan and Ali. 2012. Gene Ther. 19:145-153; Wong et al. 2006. Hum. Gen. Ther. 2002. 17:1-9; Azzouz et al. J. Neruosci. 22L10302-10312; and Betchen and Kaplitt. 2003. Curr. Opin. Neurol. 16:487-493, whose techniques and vectors described therein can be modified and adapted for use in the MARC modulating and/or modifying agents of the present invention.

Poxvirus Vectors

In some aspects, the vector can be a poxvirus vector or system thereof. In some aspects, the poxvirus vector can result in cytoplasmic expression of one or more MARC modulating and/or modifying agent polynucleotides of the present invention. In some aspects the capacity of a poxvirus vector or system thereof can be about 25 kb or more. In some aspects, a poxivirus vector or system thereof can include a Vector Construction The vectors described herein can be constructed using any suitable process or technique. In some aspects, one or more suitable recombination and/or cloning methods or techniques can be used to the vector(s) described herein. Suitable recombination and/or cloning techniques and/or methods can include, but not limited to, those described in U.S. Patent Publication No. US 2004-0171156 A1. Other suitable methods and techniques are described elsewhere herein.

Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989). Any of the techniques and/or methods can be used and/or adapted for constructing an AAV or other vector described herein. nAAV vectors are discussed elsewhere herein.

In some embodiments, the vector can have one or more insertion sites, such as a restriction endonuclease recognition sequence (also referred to as a "cloning site"). In some embodiments, one or more insertion sites (e.g., about or more than about 1, 2, 3, 4, 5, 6, 7, 8, 9, 10, or more insertion sites) are located upstream and/or downstream of one or more sequence elements of one or more vectors.

Delivery vehicles, vectors, particles, nanoparticles, formulations and components thereof for expression of one or more elements of a MARC modulating and/or modifying agent described herein are as used in the foregoing documents, such as PCT Patent Publication WO 2014/093622 (PCT/US2013/074667) and are discussed in greater detail herein.

Virus Particle Production from Viral Vectors

Retroviral Production

In some aspects, one or more viral vectors and/or system thereof can be delivered to a suitable cell line for production of virus particles containing the polynucleotide or other payload to be delivered to a host cell. Suitable host cells for virus production from viral vectors and systems thereof described herein are known in the art and are commercially available. For example, suitable host cells include HEK 293 cells and its variants (HEK 293T and HEK 293TN cells). In some aspects, the suitable host cell for virus production from viral vectors and systems thereof described herein can stably express one or more genes involved in packaging (e.g., pol, gag, and/or VSV-G) and/or other supporting genes.

In some aspects, after delivery of one or more viral vectors to the suitable host cells for or virus production from viral vectors and systems thereof, the cells are incubated for an appropriate length of time to allow for viral gene expression from the vectors, packaging of the polynucleotide to be delivered (e.g., an MARC modulating and/or modifying agent polynucleotide), and virus particle assembly, and secretion of mature virus particles into the culture media. Various other methods and techniques are generally known to those of ordinary skill in the art.

Mature virus particles can be collected from the culture media by a suitable method. In some aspects, this can involve centrifugation to concentrate the virus. The titer of the composition containing the collected virus particles can be obtained using a suitable method. Such methods can include transducing a suitable cell line (e.g., NIH 3T3 cells) and determining transduction efficiency, infectivity in that cell line by a suitable method. Suitable methods include PCR-based methods, flow cytometry, and antibiotic selection-based methods. Various other methods and techniques are generally known to those of ordinary skill in the art. The concentration of virus particle can be adjusted as needed. In some aspects, the resulting composition containing virus particles can contain $1\times10^1$-$1\times10^{20}$ particles/mL.

AAV Particle Production

There are two main strategies for producing AAV particles from AAV vectors and systems thereof, such as those described herein, which depend on how the adenovirus helper factors are provided (helper v. helper free). In some aspects, a method of producing AAV particles from AAV vectors and systems thereof can include adenovirus infection into cell lines that stably harbor AAV replication and capsid encoding polynucleotides along with AAV vector containing the polynucleotide to be packaged and delivered by the resulting AAV particle (e.g., the MARC modulating and/or modifying agent polynucleotide(s)). In some aspects, a method of producing AAV particles from AAV vectors and systems thereof can be a "helper free" method, which includes co-transfection of an appropriate producing cell line with three vectors (e.g., plasmid vectors): (1) an AAV vector that contains a polynucleotide of interest (e.g., the MARC modulating and/or modifying agent polynucleotide(s)) between 2 ITRs; (2) a vector that carries the AAV Rep-Cap encoding polynucleotides; and (3) helper polynucleotides. One of skill in the art will appreciate various methods and variations thereof that are both helper and -helper free and as well as the different advantages of each system.

Vector and Virus Particle Delivery

A vector (including non-viral carriers) described herein can be introduced into host cells to thereby produce transcripts, proteins, or peptides, including fusion proteins or peptides encoded by nucleic acids as described herein (e.g., MARC modulating and/or modifying agent transcripts, proteins, enzymes, mutant forms thereof, fusion proteins thereof, etc.), and virus particles (such as from viral vectors and systems thereof).

One or more MARC modulating and/or modifying agent polynucleotides can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as described in U.S. Pat. No. 8,454,972 and as in clinical trials involving AAV. For Adenovirus, the route of administration, formulation and dose can be as in U.S. Pat. No. 8,404,658 and as in clinical trials involving adenovirus.

For plasmid delivery, the route of administration, formulation and dose can be as described in U.S. Pat. No. 5,846,946 and as in clinical studies involving plasmids. In some aspects, doses can be based on or extrapolated to an average 70 kg individual (e.g., a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into or otherwise delivered to the tissue or cell of interest.

In terms of in vivo delivery, AAV is advantageous over other viral vectors based on factors such as low toxicity (this may be due to the purification method not requiring ultracentrifugation of cell particles that can activate the immune response) and a low probability of causing insertional mutagenesis because it doesn't integrate into the host genome.

The vector(s) and virus particles described herein can be delivered in to a host cell in vitro, in vivo, and/or ex vivo. Delivery can occur by any suitable method including, but not limited to, physical methods, chemical methods, and biological methods. Physical delivery methods are those methods that employ physical force to counteract the membrane barrier of the cells to facilitate intracellular delivery of the vector. Suitable physical methods include, but are not limited to, needles (e.g., injections), ballistic polynucleotides (e.g., particle bombardment, micro projectile gene transfer, and gene gun), electroporation, sonoporation, photoporation, magnetofection, hydroporation, and mechanical massage. Chemical methods are those methods that employ a chemical to elicit a change in the cells membrane permeability or other characteristic(s) to facilitate entry of the vector into the cell. For example, the environmental pH can be altered which can elicit a change in the permeability of the cell membrane. Biological methods are those that rely and capitalize on the host cell's biological processes or biological characteristics to facilitate transport of the vector (with or without a carrier) into a cell. For example, the vector and/or its carrier can stimulate an endocytosis or similar process in the cell to facilitate uptake of the vector into the cell.

Delivery of MARC modulating and/or modifying agents and elements thereof (e.g., polynucleotides encoding MARC modulating and/or modifying agent polypeptides) to cells via particles. The term "particle" as used herein, refers to any suitable sized particles for delivery of the MARC modulating and/or modifying agents and elements thereof described herein. Suitable sizes include macro-, micro-, and nano-sized particles. In some aspects, any of the MARC modulating and/or modifying agent components (e.g., polypeptides, polynucleotides, vectors and combinations thereof described herein) can be attached to, coupled to, integrated with, otherwise associated with one or more particles or component thereof as described herein. The particles described herein can then be administered to a cell or organism by an appropriate route and/or technique. In some aspects, particle delivery can be selected and be advantageous for delivery of the polynucleotide or vector components. It will be appreciated that in aspects, particle delivery can also be advantageous for other MARC modulating and/or modifying agent molecules and formulations described elsewhere herein.

Modified Cells and Organisms

Described herein are modified cells, cell populations, and organisms that can be modified by any suitable polynucleotide and/or genome modifying agent(s) and/or systems described herein or that are generally known to one of ordinary skill in the art. The modified cells, cell populations, and organisms can have an insertion of one or more polynucleotides, deletion of one or more polynucleotides, mutation of one or more polynucleotides, or a combination thereof. The modification can result in activation of one or more genes, inactivation of one or more genes, modulation of one or more genes, or a combination thereof. Cells, including cells in an organism, can be modified in vitro, in situ, ex vivo, or in vivo. In some embodiments, the modification is insertion or deletion of a polynucleotide, gene, or allele of interest. In some embodiments, the polynucleotide, gene, or allele of interest is a MARC polynucleotide, such as any of those in Tables 1 or 2, or a variant thereof. In some embodiments, the MARC polynucleotide corresponds to the risk MARC variant. In some embodiments, the MARC polynucleotide corresponds to the protective MARC variant. MARC variants and polynucleotides are described in greater detail elsewhere herein.

Modified Cells

Also described herein are modified cells and cell populations that can be modified by an embodiment of a polynucleotide modifying agent or system described in greater detail elsewhere herein. In some embodiments, a cell is modified by a programmable nuclease-based system such as a TALEN, Zinc-finger nuclease, or a CRISPR-Cas or Cas-based system. In some embodiments, the cell is a eukaryotic cell. In some embodiments, the eukaryotic cell is a mammalian cell. In some embodiments, the eukaryotic cell is a non-human mammalian cell. In some embodiments, the cell is a human cell. In some embodiments, the cell is a plant cell. In some embodiments, the cell is a fungal cell. In some embodiments, the cell is a prokaryotic cell. The cells can be modified in vitro, ex vivo, or in vivo. The cells can be modified by delivering a polynucleotide modifying agent or system described in greater detail elsewhere herein or a component thereof into a cell by a suitable delivery mechanism. Suitable delivery methods and techniques include but are not limited to, transfection via a vector, transduction with viral particles, electroporation, endocytic methods, and others, which are described elsewhere herein and will be appreciated by those of ordinary skill in the art in view of this disclosure.

The modified cells can be further optionally cultured and/or expanded in vitro or ex vivo using any suitable cell culture techniques or conditions, which unless specified otherwise herein, will be appreciated by one of ordinary skill in the art in view of this disclosure. In some embodiments, the cells can be modified, optionally cultured and/or expanded, and administered to a subject in need thereof. In some embodiments, cells can be isolated from a subject, subsequently modified and optionally cultured and/or expanded, and administered back to the subject. Such administration can be referred to as autologous administration. In some embodiments, cells can be isolated from a first subject, subsequently modified, optionally cultured and/or expanded, and administered to a second subject, where the first subject and the second subject are different. Such administration can be referred to as non-autologous administration.

Organisms

Also described herein are modified organisms. In some embodiments, the modified organisms can include one or more modified cells as are described elsewhere herein. In some embodiments, the modified organism is a non-human mammal. In some embodiments, the modified organism is a modified plant. In some embodiments, the modified organism is an insect. In some embodiments, the modified organism is a fungus. The modified organisms can be generated using a that can be modified by an embodiment of the engineered or non-natural guided excision-transposition system described herein. Methods of making modified organisms are described in greater detail elsewhere herein.

The systems and methods described herein can be used in non-animal organisms, e.g., plants, fungi to generated modified non-animal organisms. The system and methods described can be used to generate non-human animal organisms. The system and methods described herein can be used to modify non-germline cells in a human. In some embodiments, the modification is expression of a polynucleotide of interest, gene of interest, and/or allele of interest. In some embodiments, the polynucleotide of interest is a MARC polynucleotide, such as any of those in Tables 1 or 2, or a variant thereof. In some embodiments, the MARC polynucleotide corresponds to the risk MARC variant. In some embodiments, the MARC polynucleotide corresponds to the protective MARC variant. MARC variants and polynucleotides are described in greater detail elsewhere herein.

Non-Animal Organisms

The polynucleotide modifying agents and systems described herein can be used to modify non-animal organisms such as plants, yeast, etc. In general, the term "plant" relates to any various photosynthetic, eukaryotic, unicellular or multicellular organism of the kingdom Plantae characteristically growing by cell division, containing chloroplasts, and having cell walls comprised of cellulose. The term plant encompasses monocotyledonous and dicotyledonous plants. Specifically, the plants are intended to comprise without limitation angiosperm and gymnosperm plants such as acacia, alfalfa, amaranth, apple, apricot, artichoke, ash tree, asparagus, avocado, banana, barley, beans, beet, birch, beech, blackberry, blueberry, broccoli, Brussel's sprouts, cabbage, canola, cantaloupe, carrot, cassava, cauliflower, cedar, a cereal, celery, chestnut, cherry, Chinese cabbage, citrus, clementine, clover, coffee, corn, cotton, cowpea, cucumber, cypress, eggplant, elm, endive, *eucalyptus*, fennel, figs, fir, geranium, grape, grapefruit, groundnuts, ground cherry, gum hemlock, hickory, kale, kiwifruit, kohlrabi, larch, lettuce, leek, lemon, lime, locust, pine, maidenhair, maize, mango, maple, melon, millet, mushroom, mustard, nuts, oak, oats, oil palm, okra, onion, orange, an ornamental plant or flower or tree, *papaya*, palm, parsley, parsnip, pea, peach, peanut, pear, peat, pepper, persimmon, pigeon pea, pine, pineapple, plantain, plum, pomegranate, potato, pumpkin, radicchio, radish, rapeseed, raspberry, rice, rye, sorghum, safflower, sallow, soybean, spinach, spruce, squash, strawberry, sugar beet, sugarcane, sunflower, sweet potato, sweet corn, tangerine, tea, tobacco, tomato, trees, triticale, turf grasses, turnips, vine, walnut, watercress, watermelon, wheat, yams, yew, and zucchini. The term plant also encompasses Algae, which are mainly photoautotrophs unified primarily by their lack of roots, leaves and other organs that characterize higher plants.

The methods polynucleotide modification and the polynucleotide modifying agents and systems as described herein can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., *petunia*, rose, *chrysanthemum*), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Plant cells and tissues for engineering include, without limitation, roots, stems, leaves, flowers, and reproductive structures, undifferentiated meristematic cells, parenchyma, collenchyma, sclerenchyma, xylem, phloem, epidermis, and germplasm. Thus, the methods and modifying agents and systems described herein can be used over a broad range of plants, such as, for example, with dicotyledonous plants belonging to the orders Magnoliales, Illiciales, Laurales, Piperales, Aristolochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, San tales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. The methods and CRISPR-Cas systems can be used with monocotyledonous plants such as those belonging to the orders Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchid ales, or with plants belonging to Gymnospermae, e.g those belonging to the orders Pinales, Ginkgoales, Cycadales, Araucariales, Cupressales and Gnetales.

The polynucleotide modifying systems and methods of use described herein can be used over a broad range of plant species, included in the non-limitative list of dicot, monocot or gymnosperm genera hereunder: *Atropa, Alseodaphne, Anacardium, Arachis, Beilschmiedia, Brassica, Carthamus, Cocculus, Croton, Cucumis, Citrus, Citrullus, Capsicum, Catharanthus, Cocos, Coffea, Cucurbita, Daucus, Duguetia, Eschscholzia, Ficus, Fragaria, Glaucium, Glycine, Gossypium, Helianthus, Hevea, Hyoscyamus, Lactuca, Landolphia, Linum, Litsea, Lycopersicon, Lupinus, Manihot, Majorana, Malus, Medicago, Nicotiana, Olea, Parthenium, Papaver, Persea, Phaseolus, Pistacia, Pisum, Pyrus, Prunus, Raphanus, Ricinus, Senecio, Sinomenium, Stephania, Sinapis, Solanum, Theobroma, Trifolium, Trigonella, Vicia, Vinca, Vilis*, and *Vigna*; and the genera *Allium, Andropogon, Eragrostis, Asparagus, Avena, Cynodon, Elaeis, Festuca, Festulolium, Hemerocallis, Hordeum, Lemna, Lolium, Musa, Oryza, Panicum, Pennisetum, Phleum, Poa, Secale, Sorghum, Triticum, Zea, Abies, Cunninghamia, Ephedra, Picea, Pinus*, and *Pseudotsuga*.

The polynucleotide modification systems and methods of modifying described herein can also be used over a broad range of "algae" or "algae cells"; including for example algae selected from several eukaryotic phyla, including the Rhodophyta (red algae), Chlorophyta (green algae), Phaeophyta (brown algae), Bacillariophyta (diatoms), Eustigmatophyta and dinoflagellates as well as the prokaryotic phylum Cyanobacteria (blue-green algae). The term "algae" includes for example algae selected from: *Amphora, Anabaena, Ankistrodesmus, Botryococcus, Chaetoceros, Chlamydomonas, Chlorella, Chlorococcum, Cyclotella, Cylindrotheca, Dunaliella, Emiliana, Euglena, Haematococcus, Isochrysis, Monochrysis, Monoraphidium, Nannochloris, Nannochloropsis, Navicula, Nephrochloris, Nephroselmis, Nitzschia, Nodularia, Nostoc, Ochromonas, Oocystis, Oscillatoria, Pavlova, Phaeodactylum, Platymonas, Pleurochrysis, Porphyra, Pseudoanabaena, Pyramimonas, Stichococcus, Synechococcus, Synechocystis, Tetraselmis, Thalassiosira*, and *Trichodesmium*.

A part of a plant, e.g., a "plant tissue" may be treated according to the methods of the present invention to produce an improved plant. Plant tissue also encompasses plant cells. The term "plant cell" as used herein refers to individual units of a living plant, either in an intact whole plant or in an isolated form grown in in vitro tissue cultures, on media or agar, in suspension in a growth media or buffer or as a part of higher organized unites, such as, for example, plant tissue, a plant organ, or a whole plant.

A "protoplast" refers to a plant cell that has had its protective cell wall completely or partially removed using, for example, mechanical or enzymatic means resulting in an intact biochemical competent unit of living plant that can reform their cell wall, proliferate and regenerate grow into a whole plant under proper growing conditions.

The term "transformation" broadly refers to the process by which a plant host is genetically modified by the introduction of DNA by means of Agrobacteria or one of a variety of chemical or physical methods. As used herein, the term "plant host" refers to plants, including any cells, tissues, organs, or progeny of the plants. Many suitable plant tissues or plant cells can be transformed and include, but are not limited to, protoplasts, somatic embryos, pollen, leaves, seedlings, stems, calli, stolons, microtubers, and shoots. A plant tissue also refers to any clone of such a plant, seed, progeny, propagule whether generated sexually or asexually, and descendants of any of these, such as cuttings or seed.

The term "transformed" as used herein, refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is transmitted to the subsequent progeny. In these embodiments, the "transformed" or "transgenic" cell or plant may also include progeny of the cell or plant and progeny produced from a breeding program employing such a transformed plant as a parent in a cross and exhibiting an altered phenotype resulting from the presence of the introduced DNA molecule. Preferably, the transgenic plant is fertile and capable of transmitting the introduced DNA to progeny through sexual reproduction.

The term "progeny", such as the progeny of a transgenic plant, is one that is born of, begotten by, or derived from a plant or the transgenic plant. The introduced DNA molecule may also be transiently introduced into the recipient cell such that the introduced DNA molecule is not inherited by subsequent progeny and thus not considered "transgenic". Accordingly, as used herein, a "non-transgenic" plant or plant cell is a plant which does not contain a foreign DNA stably integrated into its genome.

The term "plant promoter" as used herein is a promoter capable of initiating transcription in plant cells, whether or not its origin is a plant cell. Exemplary suitable plant promoters include, but are not limited to, those that are obtained from plants, plant viruses, and bacteria such as *Agrobacterium* or *Rhizobium* which comprise genes expressed in plant cells.

As used herein, a "fungal cell" refers to any type of eukaryotic cell within the kingdom of fungi. Phyla within the kingdom of fungi include Ascomycota, Basidiomycota, Blastocladiomycota, Chytridiomycota, Glomeromycota, Microsporidia, and Neocallimastigomycota. Fungal cells may include yeasts, molds, and filamentous fungi. In some embodiments, the fungal cell is a yeast cell.

As used herein, the term "yeast cell" refers to any fungal cell within the phyla Ascomycota and Basidiomycota. Yeast cells may include budding yeast cells, fission yeast cells, and mold cells. Without being limited to these organisms, many types of yeast used in laboratory and industrial settings are part of the phylum Ascomycota. In some embodiments, the yeast cell is an *S. cerevisiae, Kluyveromyces marxianus*, or *Issatchenkia orientalis* cell. Other yeast cells may include without limitation *Candida* spp. (e.g., *Candida albicans*), *Yarrowia* spp. (e.g., *Yarrowia lipolytica*), *Pichia* spp. (e.g., *Pichia pastoris*), *Kluyveromyces* spp. (e.g., *Kluyveromyces lactis* and *Kluyveromyces marxianus*), *Neurospora* spp. (e.g., *Neurospora crassa*), *Fusarium* spp. (e.g., *Fusarium oxysporum*), and *Issatchenkia* spp. (e.g., *Issatchenkia orientalis*, a.k.a. *Pichia kudriavzevii* and *Candida acidothermophilum*). In some embodiments, the fungal cell is a filamentous fungal cell. As used herein, the term "filamentous fungal cell" refers to any type of fungal cell that grows in filaments, i.e., hyphae or mycelia. Examples of filamentous fungal cells may include without limitation *Aspergillus* spp. (e.g., *Aspergillus niger*), *Trichoderma* spp. (e.g., *Trichoderma reesei*), *Rhizopus* spp. (e.g., *Rhizopus oryzae*), and *Mortierella* spp. (e.g., *Mortierella isabellina*).

In some embodiments, the fungal cell is an industrial strain. As used herein, "industrial strain" refers to any strain of fungal cell used in or isolated from an industrial process, e.g., production of a product on a commercial or industrial scale. Industrial strain may refer to a fungal species that is typically used in an industrial process, or it may refer to an isolate of a fungal species that may be also used for non-industrial purposes (e.g., laboratory research). Examples of industrial processes may include fermentation (e.g., in production of food or beverage products), distillation, biofuel production, production of a compound, and production of a polypeptide. Examples of industrial strains may include, without limitation, JAY270 and ATCC4124.

In some embodiments, the fungal cell is a polyploid cell. As used herein, a "polyploid" cell may refer to any cell whose genome is present in more than one copy. A polyploid cell may refer to a type of cell that is naturally found in a polyploid state, or it may refer to a cell that has been induced to exist in a polyploid state (e.g., through specific regulation, alteration, inactivation, activation, or modification of meiosis, cytokinesis, or DNA replication). A polyploid cell may refer to a cell whose entire genome is polyploid, or it may refer to a cell that is polyploid in a particular genomic locus of interest. Without wishing to be bound to theory, it is thought that the abundance of guide RNA may more often be a rate-limiting component in genome engineering of polyploidy cells than in haploid cells, and thus the methods using the systems described herein may take advantage of using a certain fungal cell type.

In some embodiments, the fungal cell is a diploid cell. As used herein, a "diploid" cell may refer to any cell whose genome is present in two copies. A diploid cell may refer to a type of cell that is naturally found in a diploid state, or it may refer to a cell that has been induced to exist in a diploid state (e.g., through specific regulation, alteration, inactivation, activation, or modification of meiosis, cytokinesis, or DNA replication). For example, the *S. cerevisiae* strain S228C may be maintained in a haploid or diploid state. A diploid cell may refer to a cell whose entire genome is diploid, or it may refer to a cell that is diploid in a particular genomic locus of interest. In some embodiments, the fungal cell is a haploid cell. As used herein, a "haploid" cell may refer to any cell whose genome is present in one copy. A haploid cell may refer to a type of cell that is naturally found in a haploid state, or it may refer to a cell that has been induced to exist in a haploid state (e.g., through specific regulation, alteration, inactivation, activation, or modification of meiosis, cytokinesis, or DNA replication). For example, the *S. cerevisiae* strain S228C may be maintained in a haploid or diploid state. A haploid cell may refer to a cell whose entire genome is haploid, or it may refer to a cell that is haploid in a particular genomic locus of interest.

As used herein, a "yeast expression vector" refers to a nucleic acid that contains one or more sequences encoding an RNA and/or polypeptide and may further contain any desired elements that control the expression of the nucleic acid(s), as well as any elements that enable the replication and maintenance of the expression vector inside the yeast cell. Many suitable yeast expression vectors and features thereof are known in the art; for example, various vectors and techniques are illustrated in in Yeast Protocols, 2nd edition, Xiao, W., ed. (Humana Press, New York, 2007) and Buckholz, R. G. and Gleeson, M. A. (1991) Biotechnology (NY) 9 (11): 1067-72. Yeast vectors may contain, without limitation, a centromeric (CEN) sequence, an autonomous replication sequence (ARS), a promoter, such as an RNA Polymerase III promoter, operably linked to a sequence or gene of interest, a terminator such as an RNA polymerase III terminator, an origin of replication, and a marker gene (e.g., auxotrophic, antibiotic, or other selectable markers). Examples of expression vectors for use in yeast may include plasmids, yeast artificial chromosomes, 2µ plasmids, yeast integrative plasmids, yeast replicative plasmids, shuttle vectors, and episomal plasmids.

Described herein are plants and/or plant cells that can be produced by one or more of the methods described herein, or a progeny thereof. The progeny may be a clone of the produced plant or animal, or may result from sexual reproduction by crossing with other individuals of the same species to introgress further desirable traits into their offspring. The cell may be in vivo or ex vivo in the cases of multicellular organisms, particularly plant. This is described in greater detail herein.

Also described herein are gametes, seeds, germplasm, embryos, either zygotic or somatic, progeny or hybrids of plants comprising the genetic modification, which are produced by traditional breeding methods, are also included within the scope of the present invention. Such plants may contain a heterologous or foreign DNA sequence inserted at or instead of a target sequence. Alternatively, such plants may contain only an alteration (mutation, deletion, insertion, substitution) in one or more nucleotides. As such, such plants will only be different from their progenitor plants by the presence of the particular modification.

The polynucleotide modifying agent(s) and/or systems described herein can be used to confer desired traits on essentially any plant, algae, fungus, yeast, etc. A wide variety of plants, algae, fungus, yeast, etc. and plant algae, fungus, yeast cell or tissue systems may be engineered for the desired physiological and agronomic characteristics described herein using the nucleic acid constructs of the present disclosure and the various transformation methods mentioned above.

In particular embodiments, the methods described herein are used to modify endogenous genes or to modify their expression without the permanent introduction into the genome of the plant, algae, fungus, yeast, etc. of any foreign gene, including those encoding CRISPR components, so as to avoid the presence of foreign DNA in the genome of the plant. This can be of interest as the regulatory requirements for non-transgenic plants are less rigorous.

Also described herein are modified non-animal organisms (plants, yeast, algae, and other microorganisms) that can express one or more polynucleotides, genes or alleles of interest. In some embodiments, the polynucleotide of interest is a MARC polynucleotide, such as any of those in Tables 1 or 2, or a variant thereof. In some embodiments, the MARC polynucleotide corresponds to the risk MARC variant. In some embodiments, the MARC polynucleotide corresponds to the protective MARC variant. MARC variants and polynucleotides are described in greater detail elsewhere herein.

Stable Integration in the Genome of Plants and Plant Cells

In particular embodiments, the polynucleotides encoding the polynucleotide modifying agents or systems thereof are introduced for stable integration into the genome of a plant cell. In these embodiments, the design of the transformation vector or the expression system can be adjusted depending on for when, where and under what conditions the polynucleotide modifying agents or systems thereof are expressed. Suitable vectors and delivery are described in greater detail elsewhere herein.

In particular embodiments, the polynucleotide modifying agents or systems thereof are stably introduced into the genomic DNA of a plant cell. In particular embodiments, the polynucleotide modifying agents or systems thereof are introduced for stable integration into the DNA of a plant organelle such as, but not limited to a plastid, e mitochondrion or a chloroplast. In some embodiments, the expression system for stable integration into the genome of a plant cell can contain one or more of the following elements: a promoter element that can be used to express a polynucleotide modifying agent(s) or a system thereof in a plant cell; a 5' untranslated region to enhance expression; an intron element to further enhance expression in certain cells, such as monocot cells; a multiple-cloning site to provide convenient restriction sites for inserting the polynucleotide modifying agent(s) or a system thereof and other desired elements; and a 3' untranslated region to provide for efficient termination of the expressed transcript. The elements of the expression system may be on one or more expression constructs which are either circular such as a plasmid or transformation vector, or non-circular such as linear double stranded DNA.

DNA construct(s) containing the components of the systems, and, where applicable, template sequence may be introduced into the genome of a plant, plant part, or plant cell by a variety of conventional techniques. The process generally comprises the steps of selecting a suitable host cell or host tissue, introducing the construct(s) into the host cell or host tissue.

In particular embodiments, the DNA construct may be introduced into the plant cell using techniques such as but not limited to electroporation, microinjection, aerosol beam injection of plant cell protoplasts, or the DNA constructs can be introduced directly to plant tissue using biolistic methods, such as DNA particle bombardment (see also Fu et al., Transgenic Res. 2000 February; 9 (1): 11-9). The basis of particle bombardment is the acceleration of particles coated with gene/s of interest toward cells, resulting in the penetration of the protoplasm by the particles and typically stable integration into the genome. (see e.g., Klein et al, Nature (1987), Klein et ah, Bio/Technology (1992), Casas et ah, Proc. Natl. Acad. Sci. USA (1993).).

In particular embodiments, the DNA constructs containing components of the systems may be introduced into the plant by *Agrobacterium*-mediated transformation. The DNA constructs may be combined with suitable T-DNA flanking regions and introduced into a conventional *Agrobacterium tumefaciens* host vector. The foreign DNA can be incorporated into the genome of plants by infecting the plants or by incubating plant protoplasts with *Agrobacterium* bacteria, containing one or more Ti (tumor-inducing) plasmids. (see e.g., Fraley et al., (1985), Rogers et al., (1987) and U.S. Pat. No. 5,563,055).

Transient Expression of in Plants and Plant Cells

In some embodiments, the polynucleotide modifying agent(s) and/or systems can be transiently expressed in the plant cell. In these embodiments, the system can ensure modification of a target gene only when all the required components of the system (e.g., in the context of a typical CRISPR-Cas system, the Cas enzyme(s) and guide RNA(s)) are present in a cell, such that polynucleotide modification can further be controlled. As the expression of the necessary components of the modification agent and/or system is transient, plants regenerated from such plant cells typically contain no foreign DNA. It will be appreciated that not all components must be expressed transiently for modification to be controlled by transient expression. In some embodiments where multiple components are necessary for modification to occur, one or more components of the modification system are expressed transiently and one or more components of the system are stably expressed. In some embodiments where a CRISPR-Cas system is employed, the Cas enzyme is stably expressed by the plant cell and the guide sequence is transiently expressed. In some embodiments where a CRISPR-Cas system is employed, the Cas enzyme is transiently expressed by the plant cell and the guide sequence is stably expressed.

In particular embodiments, the polynucleotide modifying agent(s) and/or system components can be transiently introduced in the plant cells using a plant viral vector (Scholthof et al. 1996, Annu Rev Phytopathol. 1996; 34:299-323). In further particular embodiments, said viral vector is a vector from a DNA virus. For example, geminivirus (e.g., cabbage leaf curl virus, bean yellow dwarf virus, wheat dwarf virus, tomato leaf curl virus, maize streak virus, tobacco leaf curl virus, or tomato golden mosaic virus) or nanovirus (e.g., *Faba* bean necrotic yellow virus). In other particular embodiments, said viral vector is a vector from an RNA virus. For example, tobravirus (e.g., tobacco rattle virus, tobacco mosaic virus), potexvirus (e.g., potato virus X), or hordeivirus (e.g., barley stripe mosaic virus). The replicating genomes of plant viruses are non-integrative vectors.

In particular embodiments, the vector used for transient expression of constructs is for instance a pEAQ vector, which is tailored for *Agrobacterium*-mediated transient expression (Sainsbury F. et al., Plant Biotechnol J. 2009 September; 7 (7): 682-93) in the protoplast. Precise targeting of genomic locations was demonstrated using a modified Cabbage Leaf Curl virus (CaLCuV) vector to express gRNAs in stable transgenic plants expressing a CRISPR enzyme (Scientific Reports 5, Article number: 14926 (2015), doi: 10.1038/srep14926).

In particular embodiments, double-stranded DNA fragments encoding the polynucleotide modifying agent(s) and/or system component(s) (e.g., where a CRISPR-Cas system is employed, a guide RNA and/or the Cas gene) can be transiently introduced into the plant cell. In such embodiments, the introduced double-stranded DNA fragments are provided in sufficient quantity to modify the cell but do not persist after a contemplated period of time has passed or after one or more cell divisions. Methods for direct DNA transfer in plants are known by the skilled artisan (see for instance Davey et al. Plant Mol Biol. 1989 September; 13 (3): 273-85.)

In other embodiments, an RNA polynucleotide encoding the protein polynucleotide modifying agent or system component (e.g., where a CRISPR-Cas system is employed, a Cas protein) is introduced into the plant cell, which is then translated and processed by the host cell generating the protein in sufficient quantity to modify the cell (in the presence of at least one guide RNA) but which does not persist after a contemplated period of time has passed or after one or more cell divisions. Methods for introducing mRNA to plant protoplasts for transient expression are known by the skilled artisan (see for instance in Gallie, Plant Cell Reports (1993), 13; 119-122).

In some embodiments, a combination of the different methods described above can be used.

Plant Promoters

In some embodiments, the polynucleotide modifying agent(s) or systems thereof described elsewhere herein can be placed under control of a suitable plant promoter, i.e. a promoter operable in plant cells. The use of different types of promoters is envisaged. Plant promoters can be constitutive, inducible, and/or tissue specific.

A constitutive plant promoter is a promoter that is able to express the open reading frame (ORF) that it controls in all or nearly all of the plant tissues during all or nearly all developmental stages of the plant (referred to as "constitutive expression"). One non-limiting example of a constitutive promoter is the cauliflower mosaic virus 35S promoter. "Regulated promoter" refers to promoters that direct gene expression not constitutively, but in a temporally- and/or spatially-regulated manner, and includes tissue-specific, tissue-preferred and inducible promoters. Different promoters may direct the expression of a gene in different tissues or cell types, or at different stages of development, or in response to different environmental conditions. In particular embodiments, one or more of the gene modifying agents are expressed under the control of a constitutive promoter, such as the cauliflower mosaic virus 35S promoter issue-preferred promoters can be utilized to target enhanced expression in certain cell types within a particular plant tissue, for instance vascular cells in leaves or roots or in specific cells of the seed. Examples of particular promoters for use in the system are found in Kawamata et al., (1997) Plant Cell Physiol 38:792-803; Yamamoto et al., (1997) Plant J 12:255-65; Hire et al, (1992) Plant Mol Biol 20:207-18, Kuster et al, (1995) Plant Mol Biol 29:759-72, and Capana et al., (1994) Plant Mol Biol 25:681-91.

Examples of promoters that are inducible and that allow for spatiotemporal control of gene editing or gene expression may use a form of energy. The form of energy may include but is not limited to sound energy, electromagnetic radiation, chemical energy and/or thermal energy. Examples of inducible systems include tetracycline inducible promoters (Tet-On or Tet-Off), small molecule two-hybrid transcription activations systems (FKBP, ABA, etc), or light inducible systems (Phytochrome, LOV domains, or cryptochrome), such as a Light Inducible Transcriptional Effector (LITE) that direct changes in transcriptional activity in a sequence-specific manner. The components of a light inducible system may include one or more gene modifying agents, a light-responsive cytochrome heterodimer (e.g., from *Arabidopsis thaliana*), and a transcriptional activation/repression domain. Further examples of inducible DNA binding proteins and methods for their use are provided in U.S. 61/736,465 and U.S. 61/721,283, which is hereby incorporated by reference in its entirety.

In particular embodiments, transient or inducible expression can be achieved by using, for example, chemical-regulated promotors, i.e. whereby the application of an exogenous chemical induces gene expression. Modulating of gene expression can also be obtained by a chemical-repressible promoter, where application of the chemical represses gene expression. Chemical-inducible promoters include, but are not limited to, the maize In2-2 promoter, activated by benzene sulfonamide herbicide safeners (De Veylder et al., (1997) Plant Cell Physiol 38:568-77), the maize GST promoter (GST-11-27, WO93/01294), activated by hydrophobic electrophilic compounds used as pre-emergent herbicides, and the tobacco PR-1 a promoter (Ono et al., (2004) Biosci Biotechnol Biochem 68:803-7) activated by salicylic acid. Promoters which are regulated by antibiotics, such as tetracycline-inducible and tetracycline-repressible promoters (Gatz et al., (1991) Mol Gen Genet 227: 229-37; U.S. Pat. Nos. 5,814,618 and 5,789,156) can also be used herein.

Translocation to and or Expression in Specific Plant Organelles

The system may comprise elements for translocation to and/or expression in a specific plant organelle. In some embodiments, a tissue specific promoter can be included in the expression construct. In some embodiments, a tissue localization or organelle localization sequence or signal can be incorporated into the expression constructs. Such promoters and localization signals are described in greater detail elsewhere herein and/or will be appreciated by one of ordinary skill in the art.

Chloroplast Targeting

In some embodiments, the polynucleotide modifying system can specifically modify chloroplast genes or to ensure expression in the chloroplast. In some embodiments, chloroplast transformation methods or compartmentalization of the system components to the chloroplast. For instance, the introduction of genetic modifications in the plastid genome can reduce biosafety issues such as gene flow through pollen.

Methods of chloroplast transformation are known in the art and include Particle bombardment, PEG treatment, and microinjection. Additionally, methods involving the translocation of transformation cassettes from the nuclear genome to the plastid can be used as described in WO2010061186.

In some embodiments, one or more of the polynucleotide modifying system components can be targeted to the plant chloroplast. This can be achieved by incorporating in the expression construct a sequence encoding a chloroplast transit peptide (CTP) or plastid transit peptide, operably linked to the 5' region of the sequence encoding the Cas protein. The CTP is removed in a processing step during translocation into the chloroplast. Chloroplast targeting of expressed proteins is well known to the skilled artisan (see for instance Protein Transport into Chloroplasts, 2010, Annual Review of Plant Biology, Vol. 61:157-180). In such embodiments, it is also can be desirable to target the guide RNA to the plant chloroplast. Methods and constructs which can be used for translocating guide RNA into the chloroplast by means of a chloroplast localization sequence are described, for instance, in US Patent Publication No. 2004-0142476, incorporated herein by reference. Such variations of constructs can be incorporated into the expression systems of the invention to efficiently translocate the Cas-guide RNA.

Introduction of Polynucleotides in Algal Cells.

In some embodiments, the modified organism is algae. Modified algae (or other plants such as rape) can be useful in a variety of situations, such as in the production of vegetable oils or biofuels such as alcohols (especially methanol and ethanol) or other products. In some embodiments, such organisms can be engineered to express or overexpress high levels of a useful product. For example, they can be modified to produce oil and/or alcohols for use in the oil or biofuel industries.

Algae modification using polynucleotide modifying agents has been described in, for example U.S. Pat. No. 8,945,839 and PCT Patent Publication WO 2015-086795, which can be adapted to modifying algae and similar organisms with the polynucleotide modifying agents and systems described herein. In some embodiments, the polynucleotide modifying agent(s) or system thereof can be introduced to the algae using a vector that expresses the polynucleotide modifying agent(s) or system thereof under the control of a constitutive promoter such as Hsp70A-Rbc S2 or Beta2-tubulin. Some components of the polynucleotide modifying system (such as a guide RNA or other RNAs) can be optionally delivered using a vector containing T7 promoter. In some embodiments, a polynucleotide modifying agent and/or other components of the polynucleotide modifying system mRNA can be expressed and in vitro transcribed guide RNA can be delivered to algal cells. In some embodiments, delivery can be via electroporation. Electroporation protocols are available to the skilled person such as the standard recommended protocol from the GeneArt *Chlamydomonas* Engineering kit.

In particular embodiments, the endonuclease used herein is a split Cas enzyme or in other words can be a split CRISPR-Cas system. Split Cas enzymes used in Algae for targeted genome modification as has been described for Cas9 in PCT Patent Publication WO 2015-086795. Use of the Cas split system is suitable for an inducible method of genome targeting and can avoid or mitigate the potential toxic effect of the Cas overexpression within the algae cell.

Introduction of Polynucleotides in Yeast Cells

In some embodiments, a yeast cell can be modified using the polynucleotide modifying agents and/or systems described herein. Methods for transforming yeast cells which can be used to introduce polynucleotides encoding the systems components are well known to the artisan and are reviewed by Kawai et al., 2010, Bioeng Bugs. 2010 November-December; 1 (6): 395-403). Non-limiting examples include transformation of yeast cells by lithium acetate treatment (which may further include carrier DNA and PEG treatment), bombardment or by electroporation.

Delivery to the Plant Cell

In particular embodiments, it is of interest to deliver one or more polynucleotide modifying agent(s) or components of the system directly to the plant cell. In particular embodiments, one or more of the polynucleotide modifying agent(s) or components of the system can be prepared outside the plant or plant cell and delivered to the cell. In some embodiments, the protein polynucleotide modifying agent (e.g., where a CRISPR-Cas system is used, a Cas protein) or system component is prepared in vitro prior to introduction to the plant cell. Proteins can be prepared by various methods known by one of skill in the art and include recombinant production and de novo synthesis. After expression, the protein can be isolated, refolded if needed, purified and optionally treated to remove any purification tags, such as a His-tag. Once crude, partially purified, or more completely purified protein is obtained, the protein may be introduced to the plant cell.

In some embodiments where a CRISPR-Cas or RNA guided system is employed, the Cas or other protein(s) can be mixed with guide RNA(s) targeting the gene(s) of interest to form a pre-assembled ribonucleoprotein.

The individual components or pre-assembled ribonucleoprotein can be introduced into the plant cell via electroporation, by bombardment with Cas-associated gene product coated particles, by chemical transfection or by some other means of transport across a cell membrane. For instance, transfection of a plant protoplast with a pre-assembled CRISPR ribonucleoprotein has been demonstrated to ensure targeted modification of the plant genome (as described by Woo et al. Nature Biotechnology, 2015; DOI: 10.1038/nbt.3389), which can be adapted for use with the present invention.

In particular embodiments, the system components are introduced into the plant cells using nanoparticles. The components, either as protein or nucleic acid or in a combination thereof, can be uploaded onto or packaged in nanoparticles and applied to the plants (such as for instance described in PCT Patent Publication WO 2008-042156 and US Patent Publication No. 2013-0185823). In particular, embodiments of the invention comprise nanoparticles uploaded with or packed with DNA molecule(s) encoding the Cas protein, DNA molecules encoding the guide RNA and/or isolated guide RNA as described in WO2015089419.

In some embodiments, the polynucleotide modifying agent(s) or one or more components of the system to the plant cell is by using cell penetrating peptides (CPP). In some embodiments, the cell penetrating peptide can be linked to the protein polynucleotide modifying agent or other component of a polynucleotide modifying agent or system thereof.

In some embodiments where a CRISPR-Cas system is employed, the Cas protein and/or guide RNA is coupled to one or more CPPs to effectively transport them inside plant protoplasts. See also Ramakrishna (20140Genome Res. 2014 June; 24 (6): 1020-7 for Cas9 in human cells). In other embodiments, the Cas gene and/or guide RNA are encoded by one or more circular or non-circular DNA molecule(s) which are coupled to one or more CPPs for plant protoplast delivery. The plant protoplasts can then regenerated to plant cells and further to plants.

CPPs are generally described as short peptides of fewer than 35 amino acids either derived from proteins or from chimeric sequences which are capable of transporting biomolecules across cell membranes in a receptor independent manner. CPP can be cationic peptides, peptides having hydrophobic sequences, amphipathic peptides, peptides having proline-rich and anti-microbial sequence, and chimeric or bipartite peptides (Pooga and Langel 2005). CPPs are able to penetrate biological membranes and as such, trigger the movement of various biomolecules across cell membranes into the cytoplasm and to improve their intracellular routing, and hence facilitate interaction of the biomolecule with the target. Examples of CPP include, amongst others, Tat, a nuclear transcriptional activator protein required for viral replication by HIV typel, penetratin, Kaposi fibroblast growth factor (FGF) signal peptide sequence, integrin β3 signal peptide sequence, polyarginine peptide Args sequence, Guanine rich-molecular transporters, sweet arrow peptide, etc.

Making Genetically Modified Non-Transgenic Plants

In particular embodiments, the systems and methods described herein are used to modify endogenous genes or to modify their expression without the permanent introduction into the genome of the plant of any foreign gene, including those encoding polynucleotide modifying agent(s) or components of a polynucleotide modifying system, so as to avoid the presence of foreign DNA in the genome of the plant. This can be of interest as the regulatory requirements for non-transgenic plants are less rigorous.

In particular embodiments, this can be achieved by transient expression of the system components. In particular embodiments, one or more of the systems components are expressed on one or more viral vectors which produce sufficient components of the systems to consistently steadily ensure modification of a gene of interest according to a method described herein. In particular embodiments, transient expression of constructs is ensured in plant protoplasts and thus not integrated into the genome. The limited window of expression can be sufficient to allow the system to ensure modification of the target gene(s) as described herein.

In particular embodiments, different components of the system are introduced in the plant cell, protoplast or plant tissue either separately or in mixture, with the aid of particulate delivering molecules such as nanoparticles or CPP molecules as described herein above.

The expression of the components of the systems herein can induce targeted modification of the genome, either by direct activity of the polynucleotide modifying agent (e.g., when a CRISPR-Cas system is employed, a Cas protein) and optionally introduction of template DNA or by modification of genes targeted using the system as described herein. The different strategies described herein above can allow targeted genome editing without requiring the introduction of the components into the plant genome. Components which are transiently introduced into the plant cell can be, in some embodiments, removed upon crossing.

Protocols for targeted plant genome editing via CRISPR-Cas are also available based on those disclosed for the CRISPR-Cas9 system in volume 1284 of the series Methods in Molecular Biology pp 239-255 10 Feb. 2015. A detailed procedure to design, construct, and evaluate dual gRNAs for plant codon optimized Cas9 (pcoCas9) mediated genome editing using *Arabidopsis thaliana* and *Nicotiana benthamiana* protoplasts s model cellular systems are described. Strategies to apply the CRISPR-Cas9 system to generating targeted genome modifications in whole plants are also discussed. The protocols described in the chapter can be applied to the polynucleotide modifying agent(s) and systems described herein.

Sugano et al. (Plant Cell Physiol. 2014 March; 55 (3): 475-81. doi: 10.1093/pcp/pcu014. Epub 2014 Jan. 18) reports the application of CRISPR-Cas9 to targeted mutagenesis in the liverwort Marchantia *polymorpha* L., which has emerged as a model species for studying land plant evolution. The U6 promoter of *M. polymorpha* was identified and cloned to express the gRNA. The target sequence of the gRNA was designed to disrupt the gene encoding auxin response factor 1 (ARF1) in *M. polymorpha*. Using *Agrobacterium*-mediated transformation, Sugano et al. isolated stable mutants in the gametophyte generation of *M. polymorpha*. CRISPR-Cas9-based site-directed mutagenesis in vivo was achieved using either the Cauliflower mosaic virus 35S or *M. polymorpha* EFla promoter to express Cas9. Isolated mutant individuals showing an auxin-resistant phenotype were not chimeric. Moreover, stable mutants were produced by asexual reproduction of T1 plants. Multiple arfl alleles were easily established using CRIPSR-Cas9-based targeted mutagenesis. The methods of Sugano et al. can be applied to the polynucleotide modifying agent(s) and systems described herein.

Lowder et al. (Plant Physiol. 2015 Aug. 21. pii: pp. 00636.2015) also developed a CRISPR-Cas9 toolbox enables multiplex genome editing and transcriptional regulation of expressed, silenced or non-coding genes in plants. This toolbox provides researchers with a protocol and reagents to quickly and efficiently assemble functional CRISPR-Cas9 T-DNA constructs for monocots and dicots using Golden Gate and Gateway cloning methods. It comes with a full suite of capabilities, including multiplexed gene editing and transcriptional activation or repression of plant endogenous genes. T-DNA based transformation technology is fundamental to modern plant biotechnology, genetics, molecular biology and physiology. As such, Applicants developed a method for the assembly of Cas (WT, nickase or dCas) and gRNA(s) into a T-DNA destination-vector of interest. The assembly method is based on both Golden Gate assembly and MultiSite Gateway recombination. Three modules are required for assembly. The first module is a Cas entry vector, which contains promoterless Cas or its derivative genes flanked by attL 1 and attR5 sites. The second module is a gRNA entry vector which contains entry gRNA expression cassettes flanked by attL5 and attL2 sites. The third module includes attR1-attR2-containing destination T-DNA vectors that provide promoters of choice for Cas expression. The toolbox of Lowder et al. can be applied to the polynucleotide modifying agent(s) and systems described herein.

Wang et al. (bioRxiv 051342; doi: doi.org/10.1101/051342; Epub. May 12, 2016) demonstrate editing of homoeologous copies of four genes affecting important agronomic traits in hexaploid wheat using a multiplexed gene editing construct with several gRNA-tRNA units under the control of a single promoter. The methods of Wang et al. can be applied to the polynucleotide modifying agent(s) and systems described herein.

In an advantageous embodiment, the plant may be a tree. The present invention may also utilize the herein disclosed systems for herbaceous systems (see, e.g., Belhaj et al., Plant Methods 9:39 and Harrison et al., Genes & Development 28:1859-1872). In a particularly advantageous embodiment, the polynucleotide modifying agent(s) and systems thereof can target single nucleotide polymorphisms (SNPs) in trees (see, e.g., Zhou et al., New Phytologist, Volume 208, Issue 2, pages 298-301, October 2015). In the Zhou et al. study, the authors applied a systems in the woody perennial *Populus* using the 4-coumarate: CoA ligase (4CL) gene family as a case study and achieved 100% mutational efficiency for two 4CL genes targeted, with every transformant examined carrying biallelic modifications. In the Zhou et al., study, the CRISPR-Cas9 system was highly sensitive to single nucleotide polymorphisms (SNPs), as cleavage for a third 4CL gene was abolished due to SNPs in the target sequence. These methods Wang et al. (bioRxiv 051342; doi: doi.org/10.1101/051342; Epub. May 12, 2016) demonstrate editing of homoeologous copies of four genes affecting important agronomic traits in hexaploid wheat using a multiplexed gene editing construct with several gRNA-tRNA units under the control of a single promoter. These techniques and methods can be applied to the polynucleotide modifying agent(s) and systems described herein.

In particular embodiments, the polynucleotide modification systems described herein, can be used for self-cleavage. In these embodiments, the promotor of the Cas enzyme and gRNA can be a constitutive promotor and a second gRNA is introduced in the same transformation cassette, but controlled by an inducible promoter. This second gRNA can be designated to induce site-specific cleavage in the Cas gene in order to create a non-functional Cas. In a further particular embodiment, the second gRNA induces cleavage on both ends of the transformation cassette, resulting in the removal of the cassette from the host genome. This system offers a controlled duration of cellular exposure to the Cas enzyme and further minimizes off-target editing. Furthermore, cleavage of both ends of a CRISPR/Cas cassette can be used to generate transgene-free TO plants with bi-allelic mutations (as described for Cas9 e.g., Moore et al., Nucleic Acids Research, 2014; Schaeffer et al., Plant Science, 2015). The methods of Moore et al. can be applied to the polynucleotide modifying agent(s) and systems described herein.

Kabadi et al. (Nucleic Acids Res. 2014 Oct. 29; 42 (19): e147. doi: 10.1093/nar/gku749. Epub 2014 Aug. 13) developed a single lentiviral system to express a Cas9 variant, a reporter gene, and up to four sgRNAs from independent RNA polymerase III promoters that are incorporated into the vector by a convenient Golden Gate cloning method. Each sgRNA was efficiently expressed and can mediate multiplex gene editing and sustained transcriptional activation in immortalized and primary human cells. The methods of Kabadi et al. may be applied to the Cas effector protein system of the present invention.

Ling et al. (BMC Plant Biology 2014, 14:327) developed a CRISPR-Cas9 binary vector set based on the pGreen or pCAMBIA backbone, as well as a gRNA This toolkit requires no restriction enzymes besides BsaI to generate final constructs harboring maize-codon optimized Cas9 and one or more gRNAs with high efficiency in as little as one cloning step. The toolkit was validated using maize protoplasts, transgenic maize lines, and transgenic *Arabidopsis* lines and was shown to exhibit high efficiency and specificity. More importantly, using this toolkit, targeted mutations of three *Arabidopsis* genes were detected in transgenic seedlings of the T1 generation. Moreover, the multiple-gene mutations could be inherited by the next generation. The toolbox of Lin et al. can be applied to the polynucleotide modifying agent(s) and systems described herein.

The methods of Zhou et al. (New Phytologist, Volume 208, Issue 2, pages 298-301, October 2015) may be applied to the present invention as follows. Two 4CL genes, 4CL1 and 4CL2, associated with lignin and flavonoid biosynthesis, respectively are targeted for CRISPR-Cas9 editing. The *Populus tremula*×alba clone 717-1B4 routinely used for transformation is divergent from the genome-sequenced *Populus trichocarpa*. Therefore, the 4CL1 and 4CL2 gRNAs designed from the reference genome are interrogated with in-house 717 RNA-Seq data to ensure the absence of SNPs which could limit Cas efficiency. A third gRNA designed for 4CL5, a genome duplicate of 4CL1, is also included. The corresponding 717 sequence harbors one SNP in each allele near/within the PAM, both of which are expected to abolish targeting by the 4CL5-gRNA. All three gRNA target sites are located within the first exon. For 717 transformation, the gRNA is expressed from the *Medicago* U6.6 promoter, along with a human codon-optimized Cas under control of the CaMV 35S promoter in a binary vector. Transformation with the Cas-only vector can serve as a control. Randomly selected 4CL1 and 4CL2 lines are subjected to amplicon-sequencing. The data is then processed and biallelic mutations are confirmed in all cases. These methods can be applied to the polynucleotide modifying agent(s) and systems described herein.

The following table (Table 5) provides additional references and related fields for which the systems, complexes, modified effector proteins, systems, and methods of optimization may be used to generate modified non-animal organisms.

TABLE 5

| | | |
|---|---|---|
| Feb. 17, 2014 | PCT/US2015/63434 (WO2016/099887) | Compositions and methods for efficient gene editing in *E. coli* using guide RNA/Cas endonuclease systems in combination with circular polynucleotide modification templates. |
| Aug. 13, 2014 | PCT/US2015/41256 (WO2016/025131) | Genetic targeting in non-conventional yeast using an RNA-guided endonuclease. |
| Nov. 6, 2014 | PCT/US2015/58760 (WO2016/073433) | Peptide-mediated delivery of RNA-guided endonuclease into cells. |
| Oct. 12, 2015 | PCT/US2016/56404 (WO2017/066175) | Protected DNA templates for gene modification and increased homologous recombination in cells and methods of use. |
| Dec. 11, 2015 | PCT/US2016/65070 (WO2017/100158) | Methods and compositions for enhanced nuclease-mediated genome modification and reduced off-target site effects. |
| Dec. 18, 2015 | PCT/US2016/65537 (WO 2017/105991) | Methods and compositions for T-RNA based guide RNA expression. |

TABLE 5-continued

| Dec. 18, 2015 | PCT/US2016/66772 (WO2017/106414) | Methods and compositions for polymerase II (Pol-II) based guide RNA expression. |
| Dec. 16, 2014 | PCT/US2015/65693 (WO2016/100272) | Fungal genome modification systems and methods of use. |
| Dec. 16, 2014 | PCT/US2015/66195 (WO2016/100571) | Fungal genome modification systems and methods of use |
| Dec. 16, 2014 | PCT/US2015/66192 (WO 2016/100568) | Fungal genome modification systems and methods of use. |
| Dec. 16, 2014 | PCT/US2015/66178 (WO 2016/100562) | Use of a helper strain with silenced NHEJ to improve homologous integration of targeted DNA cassettes in Trichoderma reesei. |
| Jul. 28, 2015 | PCT/US2016/44489 (WO 2017/019867) | Genome editing systems and methods of use. |

Detecting Modifications in the Plant Genome-Selectable Markers

In particular embodiments, a selectable marker can be included or introduced to allow for identification of modified cells. Selectable markers can be advantageous for many situations, such as when the modification is made to an endogenous target gene of the plant genome. Any suitable method can be used to determine, after the plant, plant part, or plant cell is infected or transfected with the system, whether gene targeting or targeted mutagenesis has occurred at the target site.

Where the method involves introduction of a transgene, a transformed plant cell, callus, tissue or plant may be identified and isolated by selecting or screening the engineered plant material for the presence of the transgene or for traits encoded by the transgene. Physical and biochemical methods may be used to identify plant or plant cell transformants containing inserted gene constructs or an endogenous DNA modification. These methods include but are not limited to 1) Southern analysis or PCR amplification for detecting and determining the structure of the recombinant DNA insert or modified endogenous genes; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct or expression is affected by the genetic modification; and 4) protein gel electrophoresis, Western blot techniques, immunoprecipitation, or enzyme-linked immunoassays, where the gene construct or endogenous gene products are proteins. Additional techniques, such as in situ hybridization, enzyme staining, and immunostaining, also may be used to detect the presence or expression of the recombinant construct or detect a modification of endogenous gene in specific plant organs and tissues. The methods for doing all these assays are well known to those skilled in the art.

In some embodiments, the expression system encoding the polynucleotide modifying agent and/or system components can be designed to comprise one or more selectable or detectable markers that provide a means to isolate or efficiently select cells that contain and/or have been modified by the system at an early stage and on a large scale.

In the case of *Agrobacterium*-mediated transformation, the marker cassette may be adjacent to or between flanking T-DNA borders and contained within a binary vector. In another embodiment, the marker cassette may be outside of the T-DNA. A selectable marker cassette may also be within or adjacent to the same T-DNA borders as the expression cassette or may be somewhere else within a second T-DNA on the binary vector (e.g., a 2 T-DNA system).

For particle bombardment or with protoplast transformation, the expression system can include one or more isolated linear fragments or may be part of a larger construct that might contain bacterial replication elements, bacterial selectable markers or other detectable elements. The expression cassette(s) comprising the polynucleotide(s) encoding the polynucleotide modifying agents(s), system component(s), or system can be physically linked to a marker cassette or may be mixed with a second nucleic acid molecule encoding a marker cassette. The marker cassette can include the necessary elements to express a detectable or selectable marker that allows for efficient selection of transformed cells. Such elements will be appreciated by one of ordinary skill in the art.

The selection procedure for the cells based on the selectable marker will depend on the nature of the marker gene. In particular embodiments, use is made of a selectable marker, i.e., a marker which allows a direct selection of the cells based on the expression of the marker. A selectable marker can confer positive or negative selection and is conditional or non-conditional on the presence of external substrates (Miki et al. 2004, 107 (3): 193-232). Most commonly, antibiotic or herbicide resistance genes are used as a marker, whereby selection is be performed by growing the engineered plant material on media containing an inhibitory amount of the antibiotic or herbicide to which the marker gene confers resistance. Examples of such genes are genes that confer resistance to antibiotics, such as hygromycin (hpt) and kanamycin (nptII), and genes that confer resistance to herbicides, such as phosphinothricin (bar) and chlorosulfuron (als).

Transformed plants and plant cells can also be identified by screening for the activities of a visible marker, typically an enzyme capable of processing a colored substrate (e.g., the β-glucuronidase, luciferase, B or C1 genes). Such selection and screening methodologies are well known to those skilled in the art.

Plant Cultures and Regeneration

In particular embodiments, plant cells which have a modified genome and that are produced or obtained by any of the methods described herein, can be cultured to regenerate a whole plant which possesses the transformed or modified genotype and thus the desired phenotype. Conventional regeneration techniques are well known to those skilled in the art. Particular examples of such regeneration techniques rely on manipulation of certain phytohormones in a tissue culture growth medium, and typically relying on a biocide and/or herbicide marker which has been introduced together with the desired nucleotide sequences. In further particular embodiments, plant regeneration is obtained from cultured protoplasts, plant callus, explants, organs, pollens, embryos or parts thereof (see e.g., Evans et al. (1983), Handbook of Plant Cell Culture, Klee et al (1987) Ann. Rev. of Plant Phys.).

In particular embodiments, transformed or improved plants as described herein can be self-pollinated to provide seed for homozygous improved plants of the invention (homozygous for the DNA modification) or crossed with non-transgenic plants or different improved plants to provide seed for heterozygous plants. Where a recombinant DNA was introduced into the plant cell, the resulting plant of such a crossing is a plant which is heterozygous for the recombinant DNA molecule. Both such homozygous and heterozygous plants obtained by crossing from the improved plants and comprising the genetic modification (which can be a recombinant DNA) are referred to herein as "progeny". Progeny plants are plants descended from the original transgenic plant and containing the genome modification or recombinant DNA molecule introduced by the methods provided herein. Alternatively, genetically modified plants can be obtained by one of the methods described supra using the Cfpl enzyme, whereby no foreign DNA is incorporated into the genome. Progeny of such plants, obtained by further breeding, may also contain the genetic modification. Breedings are performed by any breeding methods that are commonly used for different crops (e.g., Allard, Principles of Plant Breeding, John Wiley & Sons, NY, U. of CA, Davis, C A, 50-98 (1960).

Applications of the Modified Non-Animal Organisms

In some embodiments, the modified plants, algae, yeast or other non-animal organisms can be used to produce a desirable gene product. The desirable gene product can then be harvested after production and used accordingly.

In particular embodiments, the polynucleotide modifying agents and system can be used for visualization of genetic element dynamics. For example, CRISPR imaging can visualize either repetitive or non-repetitive genomic sequences, report telomere length change and telomere movements and monitor the dynamics of gene loci throughout the cell cycle (Chen et al., Cell, 2013). These methods may also be applied to plants.

Other applications of the systems, and preferably the systems described herein, are the targeted gene disruption positive-selection screening in vitro and in vivo (Malina et al., Genes and Development, 2013). These methods may also be applied to plants.

In particular embodiments, fusion of inactive Cas endonucleases with histone-modifying enzymes can introduce custom changes in the complex epigenome (Rusk et al., Nature Methods, 2014). These methods may also be applied to plants.

In particular embodiments, the systems, and preferably the systems described herein, can be used to purify a specific portion of the chromatin and identify the associated proteins, thus elucidating their regulatory roles in transcription (Waldrip et al., Epigenetics, 2014). These methods may also be applied to plants.

In particular embodiments, the present invention can be used as a therapy for virus removal in plant systems, as it is able to cleave both viral DNA and RNA. Previous studies in human systems have demonstrated the success of utilizing CRISPR in targeting the single-strand RNA virus, hepatitis C (A. Price, et al., Proc. Natl. Acad. Sci, 2015) as well as the double-stranded DNA virus, hepatitis B (V. Ramanan, et al., Sci. Rep, 2015). These methods may also be adapted for using the systems in plants.

In particular embodiments, the present invention could be used to alter genome complexity. In further particular embodiment, the systems, and preferably the systems described herein, can be used to disrupt or alter chromosome number and generate haploid plants, which only contain chromosomes from one parent. Such plants can be induced to undergo chromosome duplication and converted into diploid plants containing only homozygous alleles (Karimi-Ashtiyani et al., PNAS, 2015; Anton et al., Nucleus, 2014). These methods may also be applied to plants.

The polynucleotide modifying agent(s) and systems can be used to generate loss of function plants, algae, yeast, and other non-animal organisms, which can allow for functional analysis of genomic material. Ma et al. (Mol Plant. 2015 Aug. 3; 8 (8): 1274-84. doi: 10.1016/j.molp.2015.04.007) reports robust CRISPR-Cas9 vector system, utilizing a plant codon optimized Cas9 gene, for convenient and high-efficiency multiplex genome editing in monocot and dicot plants. Ma et al. designed PCR-based procedures to rapidly generate multiple sgRNA expression cassettes, which can be assembled into the binary CRISPR-Cas9 vectors in one round of cloning by Golden Gate ligation or Gibson Assembly. With this system, Ma et al. edited 46 target sites in rice with an average 85.4% rate of mutation, mostly in biallelic and homozygous status. Ma et al. provide examples of loss-of-function gene mutations in T0 rice and T1 *Arabidopsis* plants by simultaneous targeting of multiple (up to eight) members of a gene family, multiple genes in a biosynthetic pathway, or multiple sites in a single gene. The methods of Ma et al. can be applied to the polynucleotide modifying agent(s) and systems described herein.

In plants, pathogens are often host-specific. For example, *Fusarium oxysporum* f. sp. *lycopersici* causes tomato wilt but attacks only tomato, and *F. oxysporum* f. dianthii *Puccinia graminis* f. sp. *tritici* attacks only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible. There can also be Horizontal Resistance, e.g., partial resistance against all races of a pathogen, typically controlled by many genes and Vertical Resistance, e.g., complete resistance to some races of a pathogen but not to other races, typically controlled by a few genes. In a Gene-for-Gene level, plants and pathogens evolve together, and the genetic changes in one balance changes in other. Accordingly, using Natural Variability, breeders combine most useful genes for Yield, Quality, Uniformity, Hardiness, Resistance. The sources of resistance genes include native or foreign Varieties, Heirloom Varieties, Wild Plant Relatives, and Induced Mutations, e.g., treating plant material with mutagenic agents. The polynucleotide modifying agents and systems can be used to induce mutations, to analyze the genome of sources of resistance genes, and in varieties having desired characteristics or traits employ the present invention to induce the rise of resistance genes, with more precision than previous mutagenic agents and hence accelerate and improve plant breeding programs. Further, the modifying agents and systems described herein can be used to generate plants with one or more disease resistant genes or alleles.

Similarly, the polynucleotide modifying agents and systems described herein can be used to induce mutations to allow for genome wide screening for mutations, alleles, and variants that have a desired characteristic (e.g., heat tolerance, cold tolerance, fast growth, pest resistance, etc.) and also used to generate plants with the identified and desired allele(s).

In some embodiments, the polynucleotide modifying agents and systems described herein can be used to generate non-animal organism model systems of animals. Modified non-animal organisms or cells thereof can be modified to express one or more heterologous genes, such as genes from a human or non-human animal. Such model systems can be used to determine response to environmental toxins, pharmaceutical agents, or other stimuli. Other uses for such model systems will be appreciated by those of ordinary skill in the art.

Improved Non-Animal Organisms

The methods described herein can result in the generation of "improved plants, algae, fungi, yeast, etc." in that they have one or more desirable traits compared to the wildtype plant. In particular embodiments, the plants, algae, fungi, yeast, etc., cells or parts obtained are transgenic plants, comprising an exogenous DNA sequence incorporated into the genome of all or part of the cells. In particular embodiments, non-transgenic genetically modified plants, algae, fungi, yeast, etc., parts or cells are obtained, in that no exogenous DNA sequence is incorporated into the genome of any of the cells of the plant. In such embodiments, the improved plants, algae, fungi, yeast, etc., are non-transgenic. Where only the modification of an endogenous gene is ensured and no foreign genes are introduced or maintained in the plant, algae, fungi, yeast, etc. genome, the resulting genetically modified crops contain no foreign genes and can thus basically be considered non-transgenic. The different applications of the systems for plant, algae, fungi, yeast, etc. genome editing include, but are not limited to, introduction of one or more foreign genes to confer an agricultural trait of interest; editing of endogenous genes to confer an agricultural trait of interest; modulating of endogenous genes by the systems to confer an agricultural trait of interest. Exemplary genes conferring agronomic traits include, but are not limited to, genes that confer resistance to pests or diseases; genes involved in plant diseases, such as those listed in PCT Patent Publication WO 2013-046247; genes that confer resistance to herbicides, fungicides, or the like; genes involved in (abiotic) stress tolerance. Other aspects of the use of the systems include, but are not limited to, creating (male) sterile plants; increasing the fertility stage in plants/algae etc.; generating genetic variation in a crop of interest; affecting fruit-ripening; increasing storage life of plants/algae etc.; reducing allergen in plants/algae censuring a value-added trait (e.g., nutritional improvement); screening methods for endogenous genes of interest; biofuel, fatty acid, organic acid, etc., production.

Also described here are modified non-animal organisms (e.g., plants, algae, and yeast cells) obtainable and obtained by the methods provided herein that can be improved in at least one aspect as compared to an unmodified plant. The improved non-animal organisms obtained by the methods described herein may be useful in one or more fields (e.g., food or feed production) through expression of genes or alleles which, for instance, ensure tolerance to infectious agents, pests, herbicides, drought, low or high temperatures, excessive water, toxins, etc.

The improved plants obtained by the methods described herein, especially crops and algae may be useful in food or feed production through expression of, for instance, higher protein, carbohydrate, nutrient or vitamin levels than would normally be seen in the wildtype. In this regard, improved plants, especially pulses and tubers are preferred.

Improved algae or other plants such as rape may be particularly useful in the production of vegetable oils or biofuels such as alcohols (especially methanol and ethanol), for instance. These may be engineered to express or over-express high levels of oil or alcohols for use in the oil or biofuel industries.

Also described herein are improved parts of a plant. Plant parts include, but are not limited to, leaves, stems, roots, tubers, seeds, endosperm, ovule, and pollen. Plant parts as envisaged herein may be viable, nonviable, regeneratable, and/or non-regeneratable. The improved part of the plant can, for example, result in earlier fruit, higher content of one or more molecules involved in fruit taste, color, maturity, ripening, etc. or have other desired characteristics. In one embodiment, the method described in Soyk et al. (Nat Genet. 2017 January; 49 (1): 162-168), which used CRISPR-Cas9 mediated mutation targeting flowering repressor SP5G in tomatoes to produce early yield tomatoes, can be modified and adapted for use with the polynucleotide modifying agent(s) and systems thereof described herein.

Non-Human Animals

The systems and methods may be used to generate modified non-human animals and cells thereof. In an aspect, the invention provides a non-human eukaryotic organism, preferably a multicellular eukaryotic organism, comprising a eukaryotic host cell according to any of the described embodiments. In other aspects, the invention provides a eukaryotic organism, preferably a multicellular eukaryotic organism, comprising a eukaryotic host cell according to any of the described embodiments. The organism in some embodiments of these aspects may be an animal, for example, a mammal. Also, the organism may be an arthropod, such as an insect. The present invention may also be extended to other agricultural applications such as, for example, farm and production animals. For example, pigs have many features that make them attractive as biomedical models, especially in regenerative medicine. In particular, pigs with severe combined immunodeficiency (SCID) may provide useful models for regenerative medicine, xenotransplantation (discussed also elsewhere herein), and tumor development and will aid in developing therapies for human SCID patients. Lee et al., (Proc Natl Acad Sci USA. 2014 May 20; 111 (20): 7260-5) utilized a reporter-guided transcription activator-like effector nuclease (TALEN) system to generated targeted modifications of recombination activating gene (RAG) 2 in somatic cells at high efficiency, including some that affected both alleles. Such techniques and modifications can be adapted for and used with the modifying agent(s) and systems thereof described herein to generate a modified non-human animal or cell thereof.

The methods of Lee et al. (Proc Natl Acad Sci USA. 2014 May 20; 111 (20): 7260-5) may be applied to the present invention analogously as follows. Mutated pigs are produced by targeted insertion, for example, in RAG2 in fetal fibroblast cells followed by SCNT and embryo transfer. Constructs coding for CRISPR Cas and a reporter are electroporated into fetal-derived fibroblast cells. After 48 h, transfected cells expressing the green fluorescent protein are sorted into individual wells of a 96-well plate at an estimated dilution of a single cell per well. Targeted modification of RAG2 are screened by amplifying a genomic DNA fragment flanking any CRISPR Cas cutting sites followed by sequencing the PCR products. After screening and ensuring lack of off-site mutations, cells carrying targeted modification of RAG2 are used for SCNT. The polar body, along with a portion of the adjacent cytoplasm of oocyte, presumably containing the metaphase II plate, are removed, and a donor cell are placed in the perivitelline. The reconstructed embryos are then electrically operated to fuse the donor cell with the oocyte and then chemically activated. The activated embryos are incubated in Porcine Zygote Medium 3 (PZM3) with 0.5 µM Scriptaid (S7817; Sigma-Aldrich) for 14-16 h. Embryos are then washed to remove the Scriptaid and cultured in PZM3 until they were transferred into the oviducts of surrogate pigs. Such techniques and modifications can be adapted for and used with the modifying agent(s) and systems thereof described herein to generate a modified non-human animal or cell thereof.

The modified non-human animals described herein can be a platform to model a disease or disorder of an animal, including but not limited to mammals. In some of these embodiments, the mammal can be a human. In certain embodiments, such models and platforms are rodent based, in non-limiting examples, rat or mouse. Such models and platforms can take advantage of distinctions among and comparisons between inbred rodent strains. In certain embodiments, such models and platforms primate, horse, cattle, sheep, goat, swine, dog, cat or bird-based, for example to directly model diseases and disorders of such animals or to create modified and/or improved lines of such animals. Advantageously, in certain embodiments, an animal-based platform or model is created to mimic a human disease or disorder. For example, the similarities of swine to humans make swine an ideal platform for modeling human diseases. Compared to rodent models, development of swine models has been costly and time intensive. On the other hand, swine and other animals are much more similar to humans genetically, anatomically, physiologically and pathophysiologically. The present invention provides a high efficiency platform for targeted gene and genome editing, gene and genome modification and gene and genome regulation to be used in such animal platforms and models. Though ethical standards block development of human models and in many cases models based on non-human primates, the present invention is used with in vitro systems, including but not limited to cell culture systems, three dimensional models and systems, and organoids to mimic, model, and investigate genetics, anatomy, physiology and pathophysiology of structures, organs, and systems of humans. The platforms and models provide manipulation of single or multiple targets.

In certain embodiments, the present invention is applicable to disease models like that of Schomberg et al. (FASEB Journal, April 2016; 30 (1): Suppl 571.1). To model the inherited disease neurofibromatosis type 1 (NF-1) Schomberg used CRISPR-Cas9 to introduce mutations in the swine neurofibromin 1 gene by cytosolic microinjection of CRISPR/Cas9 components into swine embryos. CRISPR guide RNAs (gRNA) were created for regions targeting sites both upstream and downstream of an exon within the gene for targeted cleavage by Cas9 and repair was mediated by a specific single-stranded oligodeoxynucleotide (ssODN) template to introduce a 2500 bp deletion. The systems were also used to engineer swine with specific NF-1 mutations or clusters of mutations, and further can be used to engineer mutations that are specific to or representative of a given human individual. Such techniques and modifications can be adapted for and used with the modifying agent(s) and systems thereof described herein to generate a modified non-human animal or cell thereof. In some embodiments, the polynucleotide modifying agent(s) or systems thereof can be similarly used to develop animal models, including, but not limited to, swine models, of human multigenic diseases. In some embodiments, multiple genetic loci in one gene or in multiple genes are simultaneously targeted using multiplexed guides and optionally one or multiple templates.

SNPs of other animals, such as cows, can also be modified or generated using one or more polynucleotide modifying agents or systems described herien. Tan et al. (Proc Natl Acad Sci USA. 2013 Oct. 8; 110 (41): 16526-16531) expanded the livestock gene editing toolbox to include transcription activator-like (TAL) effector nuclease (TALEN)- and clustered regularly interspaced short palindromic repeats (CRISPR)/Cas9-stimulated homology-directed repair (HDR) using plasmid, rAAV, and oligonucleotide templates. Gene specific gRNA sequences were cloned into the Church lab gRNA vector (Addgene ID: 41824) according to their methods (Mali P, et al. (2013) RNA-Guided Human Genome Engineering via Cas9. Science 339 (6121): 823-826). The Cas9 nuclease was provided either by co-transfection of the hCas9 plasmid (Addgene ID: 41815) or mRNA synthesized from RCIScript-hCas9. This RCIScript-hCas9 was constructed by sub-cloning the Xbal-Agel fragment from the hCas9 plasmid (encompassing the hCas9 cDNA) into the RCIScript plasmid. Such techniques and modifications can be adapted for and used with the modifying agent(s) and systems thereof described herein to generate a modified non-human animal or cell thereof.

Heo et al. (Stem Cells Dev. 2015 Feb. 1; 24 (3): 393-402. doi: 10.1089/scd.2014.0278. Epub 2014 Nov. 3) reported highly efficient gene targeting in the bovine genome using bovine pluripotent cells and clustered regularly interspaced short palindromic repeat (CRISPR)/Cas9 nuclease. First, Heo et al. generate induced pluripotent stem cells (iPSCs) from bovine somatic fibroblasts by the ectopic expression of yamanaka factors and GSK3β and MEK inhibitor (2i) treatment. Heo et al. observed that these bovine iPSCs are highly similar to naïve pluripotent stem cells with regard to gene expression and developmental potential in teratomas. Moreover, CRISPR-Cas9 nuclease, which was specific for the bovine NANOG locus, showed highly efficient editing of the bovine genome in bovine iPSCs and embryos. Such techniques and modifications can be adapted for and used with the modifying agent(s) and systems thereof described herein to generate a modified non-human animal or cell thereof.

Igenity® provides a profile analysis of animals, such as cows, to perform and transmit traits of economic traits of economic importance, such as carcass composition, carcass quality, maternal and reproductive traits and average daily gain. The analysis of a comprehensive Igenity® profile begins with the discovery of DNA markers (most often single nucleotide polymorphisms or SNPs). All the markers behind the Igenity® profile were discovered by independent scientists at research institutions, including universities, research organizations, and government entities such as USDA. Markers are then analyzed at Igenity® in validation populations. Igenity® uses multiple resource populations that represent various production environments and biological types, often working with industry partners from the seedstock, cow-calf, feedlot and/or packing segments of the beef industry to collect phenotypes that are not commonly available. Cattle genome databases are widely available, see, e.g., the NAGRP Cattle Genome Coordination Program (www.animalgenome.org/cattle/maps/db.html). Thus, the polynucleotide modifying agent(s) and/or systems described herein can be applied to target bovine SNPs. One of skill in the art may utilize the above protocols for targeting SNPs and apply them to bovine SNPs as described, for example, by Tan et al. or Heo et al.

Qingjian Zou et al. (Journal of Molecular Cell Biology Advance Access published Oct. 12, 2015) demonstrated increased muscle mass in dogs by targeting the first exon of the dog Myostatin (MSTN) gene (a negative regulator of skeletal muscle mass). First, the efficiency of the sgRNA was validated, using cotransfection of the sgRNA targeting MSTN with a Cas9 vector into canine embryonic fibroblasts (CEFs). Thereafter, MSTN KO dogs were generated by micro-injecting embryos with normal morphology with a mixture of Cas9 mRNA and MSTN sgRNA and auto-transplantation of the zygotes into the oviduct of the same female dog. The knock-out puppies displayed an obvious muscular phenotype on thighs compared with its wild-type littermate sister. This can also be performed using the polynucleotide agent(s) and/or systems provided herein. Such techniques and modifications can be adapted for and used with the modifying agent(s) and systems thereof described herein to generate a modified non-human animal or cell thereof.

Livestock

Also described herein are modified pigs or cells that can express one or more polynucleotides, genes or alleles of interest. In some embodiments, the polynucleotide of interest is a MARC polynucleotide, such as any of those in Tables 1 or 2, or a variant thereof. In some embodiments, the MARC polynucleotide corresponds to the risk MARC variant. In some embodiments, the MARC polynucleotide corresponds to the protective MARC variant. MARC variants and polynucleotides are described in greater detail elsewhere herein. As reported by Kristin M Whitworth and Dr Randall Prather et al. (Nature Biotech 3434 published online 7 Dec. 2015) CD163 (a viral target) was targeted using CRISPR-Cas9 and the offspring of edited pigs were resistant when exposed to PRRSv. One founder male and one founder female, both of whom had mutations in exon 7 of CD163, were bred to produce offspring. The founder male possessed an 11-bp deletion in exon 7 on one allele, which results in a frameshift mutation and missense translation at amino acid 45 in domain 5 and a subsequent premature stop codon at amino acid 64. The other allele had a 2-bp addition in exon 7 and a 377-bp deletion in the preceding intron, which were predicted to result in the expression of the first 49 amino acids of domain 5, followed by a premature stop code at amino acid 85. The sow had a 7 bp addition in one allele that when translated was predicted to express the first 48 amino acids of domain 5, followed by a premature stop codon at amino acid 70. The sow's other allele was unamplifiable. Selected offspring were predicted to be a null animal (CD163−/−), i.e., a CD163 knock out. Such techniques and modifications can be adapted for and used with the modifying agent(s) and systems thereof described herein to generate a modified pig that can express a polynucleotide of interest. Thus, also described herein are modified pigs their progeny that also express one or more copies of the gene or allele of interest. This may be for livestock, breeding or modelling purposes (i.e. a porcine model). Semen comprising the modification (e.g., polynucleotide of interest) is also provided.

Other Animals

Also described herein are other non-human animals that are modified to express one or more polynucleotides, genes or alleles of interest. In some embodiments, the polynucleotide of interest is a MARC polynucleotide, such as any of those in Tables 1 or 2, or a variant thereof. In some embodiments, the MARC polynucleotide corresponds to the risk MARC variant. In some embodiments, the MARC polynucleotide corresponds to the protective MARC variant. MARC variants and polynucleotides are described in greater detail elsewhere herein. Suitable polynucleotide modifying agent(s) and/or system thereof described elsewhere herein can be used to generate other non-human animals such as non-human primates, chickens (reviewed in Sid and Schusser et al 2018. Front. Genet. Doi.org/10.3389/fgene.2018.00456) and other avians (e.g., Scott et al. 2010. ILAR J. 51 (4): 353-361), cattle (Yum et al., 2016. Scientific Reports. 6:27185 and Tait-Burkard et al. 2018. Genome Biology. 19:2014), sheep and goats (see e.g., Kalds et al., 2019. Front. Genet. Doi.org//10.3389/fgene.2019.00750), horses (see e.g., West and Gill. 2016. J. Equine Vet. Sci. 41:1-6), dogs (see e.g., D. Duan. Nature Biomedical Engineering. 2018. 2:795-796), reptiles (see e.g., Rasys et al. 2019. Cell Reports. 28:2288-2292), fish (including but not limited to zebrafish, see e.g., Datsomor et al. 2019. Scientific Reports. 9:7533, Liu et al. 2019. Front. Cell. Dev. Biol. doi.org/10.3389/fcell.2019.00013), insects (see e.g., Kotwica-Rolinska et al. 2019. Front. Physiol. doi.org/10.3389/fphys.2019.00891; Gantz and Akbari. 2018. Curr. Opin. Insect. Sci. 28:66-72), rabbits (see e.g., Kawano and Honda. 2017. Methods Mol. Biol. 4630:109-120; Liu et al., 2018. Nature Commun. 9:2717; and Liu et al. 2018. Gene. doi.org/10.1016/j.gene.2018.01.044), mice (see e.g., Hall et al. 2018. Curr Protoc Cell Biol. 81 (1): e57), rats (see e.g., Back et al. 2019. Neuron. 102 (1): 105-119), amphibians (see e.g., Nakayama et al. 2013. Genesis. 51 (12): 835-843), nematodes (see e.g., J. B. Lok. 2019. Front. Genet. doi.org/10.3389/fgene.2019.00656), molluscs (see e.g., Abe and Kuroda. 2019. Development. 146: dev175976 doi: 10.1242/dev.175976, geckos, shrimp and other crustaceans (see e.g., Gui et al. Genes Genomes Genetics: 6 (11): 3757-3764), oysters (Yu et al. 2019; Mar. Biotechnol (NY) 21 (3): 301-309. doi: 10.1007/s10126-019-09885-y), and sponges (see e.g., Revilla-i-Domingo et al. 2018. Genetics. 210 (2) 435-443), the teachings of which can be adapted for use with one or more of the modifying agent(s) and/or systems described herein to generate the modified non-human animal or cell thereof.

Pharmaceutical Formulations

Also described herein are pharmaceutical formulations that can contain an amount, effective amount, and/or least effective amount, and/or therapeutically effective amount of one or more compounds, molecules, compositions, vectors, vector systems, cells, or a combination thereof (which are also referred to as the primary active agent or ingredient elsewhere herein) described in greater detail elsewhere herein a pharmaceutically acceptable carrier. When present, the compound can optionally be present in the pharmaceutical formulation as a pharmaceutically acceptable salt. In some embodiments, the pharmaceutical formulation can include an active ingredient, such as a MARC (e.g., MARC1 and/or MARC2) modulating and/or modifying agent as described elsewhere herein, a liver disease therapeutic and/or other therapeutic as described elsewhere herein, a modified cell as described elsewhere herein, or a combination thereof.

The pharmaceutical formulations described herein can be administered via any suitable method or route to a subject in need thereof. Suitable administration routes can include, but are not limited to auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorpus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/or vaginal administration, and/or any combination of the above administration routes, which typically depends on the disease to be treated and/or the active ingredient(s).

Where appropriate, compounds, molecules, compositions, vectors, vector systems, cells, or a combination thereof, which are described in greater detail elsewhere herein, can be provided to a subject in need thereof as an ingredient, such as an active ingredient or agent, in a pharmaceutical formulation. In some embodiments, the pharmaceutical formulations contain one or more of the compounds, such as a small molecule active agent, or salt thereof, or a pharmaceutically acceptable salt thereof. Suitable salts and/or pharmaceutically acceptable salts include, hydrobromide, iodide, nitrate, bisulfate, phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, naphthalenesulfonate, propionate, malonate, mandelate, malate, phthalate, and pamoate.

In some embodiments, the subject in need thereof to which a pharmaceutical formulation can be administered has or is suspected of having a liver disease or a symptom thereof. In some embodiments, the subject in need thereof has or is suspected of having a liver disease or symptom thereof, or a combination thereof. Liver diseases and some symptoms associated therewith are described elsewhere herein in greater detail. In some embodiments, the subject has one or more biomarkers indicative of abnormal liver function and/or one or more MARC risk variant alleles and/or polypeptides. Such biomarkers and MARC variants are described in greater detail elsewhere herein. As used herein, "agent" refers to any substance, compound, molecule, and the like, which can be biologically active or otherwise can induce a biological and/or physiological effect on a subject to which it is administered to. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

Pharmaceutically Acceptable Carriers and Auxiliary Ingredients and Agents

The pharmaceutical formulation can include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active compound.

In some embodiments, the pharmaceutical formulation can also include an effective amount of auxiliary active agents, including but not limited to, biologic agents or molecules (including but not limited to, for example, polypeptides, polynucleotides, antibodies and fragments thereof, aptamers, and the like), chemotherapeutics, antineoplastic agents, hormones, antibiotics, antivirals, immunomodulating agents, anti-nausea, pain modifying compounds (such as opiates), anti-inflammatory agents, antipyretics, antibiotics, and combinations thereof.

Effective Amounts

In some embodiments, the amount of the primary active agent and/or optional auxiliary active agent can be an effective amount, least effective amount, and/or therapeutically effective amount. The effective amount, least effective amount, and/or therapeutically effective amount of the primary and optional auxiliary active agent described elsewhere herein contained in the pharmaceutical formulation can range from about 0 to 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 pg, ng, µg, mg, or g or be any numerical value with any of these ranges. In some embodiments, the effective amount, least effective amount, and/or therapeutically effective amount can be an effective concentration, least effective concentration, and/or therapeutically effective concentration, which can each range from about 0 to 10, 20, 30, 40, 50, 60, 70, 80, 90,100,110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 pM, nM, µM, mM, or M or be any numerical value with any of these ranges.

In other embodiments, the effective amount, least effective amount, and/or therapeutically effective amount of the auxiliary active agent can range from about 0 to 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 IU or be any numerical value with any of these ranges.

In some embodiments, a primary active agent can be present in the pharmaceutical formulation can range from about 0 to 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.9, to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% w/w, v/v, or w/v of the pharmaceutical formulation.

In some embodiments, the auxiliary active agent, when optionally present, can range from about 0 to 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.9, to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% w/w, v/v, or w/v of the pharmaceutical formulation.

In some embodiments where a cell population is delivered, the effective amount of cells can range from about $1\times10^1$/mL to $1\times10^{20}$/mL or more, such as about $1\times10^1$/mL, $1\times10^2$/mL, $1\times10^3$/mL, $1\times10^4$/mL, $1\times10^5$/mL, $1\times10^6$/mL, $1\times10^7$/mL, $1\times10^8$/mL, $1\times10^9$/mL, $1\times10^{10}$/mL, $1\times10^{11}$/mL, $1\times10^{12}$/mL, $1\times10^{13}$/mL, $1\times10^{14}$/mL, $1\times10^{15}$/mL, $1\times10^{16}$/mL, $1\times10^{17}$/mL, $1\times10^{18}$/mL, $1\times10^{19}$/mL, to/or about $1\times10^{20}$/mL.

In some embodiments, a dose or booster dose and/or effective amount can contain at least $1\times10^5$ particles (also referred to as particle units, pu) of virus particles or viral vector(s). In an embodiment herein, the dose and/or effective amount preferably is at least about $1\times10^6$ virus particles or viral vector(s) (for example, about $1\times10^6$-$1\times10^{12}$ virus particles or viral vector(s)), more preferably at least about $1\times10^7$ virus particles or viral vector(s), more preferably at least about $1\times10^8$ virus particles or viral vector(s) (e.g., about $1\times10^8$-$1\times10^{11}$ virus particles or viral vector(s) or about $1\times10^8$-$1\times10^{12}$ virus particles or viral vector(s)), and most preferably at least about $1\times10^{10}$ virus particles or viral vector(s) (e.g., about $1\times10^9$-$1\times10^{10}$ virus particles or viral vector(s) or about $1\times10^9$-$1\times10^{12}$ virus particles or viral vector(s)), or even at least about $1\times10^{10}$ virus particles or viral vector(s) (e.g., about $1\times10^{10}$-$1\times10^{12}$ virus particles or viral vector(s)). Alternatively, the dose comprises no more than about $1\times10^{14}$ virus particles or viral vector(s), preferably no more than about $1\times10^{13}$ virus particles or viral vector(s), even more preferably no more than about $1\times10^{12}$ virus particles or viral vector(s), even more preferably no more than about $1\times10^{11}$ virus particles or viral vector(s), and most preferably no more than about $1\times10^{10}$ virus particles or viral vector(s) (e.g., no more than about $1\times10^9$ virus particles or viral vector(s)). Thus, the dose may contain a single dose of a viral particle or viral vector with, for example, about $1\times10^6$ particle units (pu), about $2\times10^6$ pu, about $4\times10^6$ pu, about $1\times10^7$ pu, about $2\times10^7$ pu, about $4\times10^7$ pu, about $1\times10^8$ pu, about $2\times10^8$ pu, about $4\times10^8$ pu, about $1\times10^9$ pu, about $2\times10^9$ pu, about $4\times10^9$ pu, about $1\times10^{10}$ pu, about $2\times10^{10}$ pu, about $4\times10^{10}$) pu, about $1\times10^{11}$ pu, about $2\times10^{11}$ pu, about $4\times10^{11}$ pu, about $1\times10^{12}$ pu, about $2\times10^{12}$ pu, or about $4\times10^{12}$ pu of adenoviral vector. See, for example, the adenoviral vectors in U.S. Pat. No. 8,454,972 B2 to Nabel, et. al., granted on Jun. 4, 2013, incorporated by reference herein, and the dosages at column 29, lines 36-58 thereof. In an embodiment herein, the viral vector and/or virus particle is delivered via multiple doses. In some embodiments, the dosage can contain the above amounts of an adenoviral vector or adenovirus particles.

In an embodiment herein, the delivery is via a virus such as an AAV or Lentivirus. A therapeutically effective dosage for in vivo delivery of the AAV or lentivirus to a human is believed to be in the range of from about 20 to about 50 ml of saline solution containing from about $1\times10^{10}$ to about $1\times10^{10}$ functional AAV or lentivirus/ml solution. The dosage may be adjusted to balance the therapeutic benefit against any side effects. In an embodiment herein, the AAV or lentivirus dose is generally in the range of concentrations of from about $1\times10^5$ to $1\times10^{50}$ genomes AAV or lentivirus, from about $1\times10^8$ to $1\times10^{20}$ genomes AAV or lentivirus, from about $1\times10^{10}$ to about $1\times10^{16}$ genomes, or about $1\times10^{11}$ to about $1\times10^{16}$ genomes AAV or lentivirus. A human dosage may be about $1\times10^{13}$ genomes AAV or lentivirus. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at column 27, lines 45-60.

In aspects where virus particles are included in the formulation, the formulation can contain 1 to $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, $1\times10^{18}$, $1\times10^{19}$, or $1\times10^{20}$ transducing units (TU)/mL of the virus particles. In some aspects, the formulation can be 0.1 to 100 mL in volume and can contain 1 to $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, $1\times10^{18}$, $1\times10^{19}$, or $1\times10^{20}$ transducing units (TU)/mL of the virus particles.

In some embodiments, a dosage of CRISPR Cas expressed via a lentiviral vector and packaged in a lentivirus particle may be contemplated for humans in the present invention. In some of these embodiments, a dose can have about 10-50 ml of CRISPR Cas in a lentivirus having a titer of $1\times10^9$ transducing units (TU)/ml.

In embodiments where there is an auxiliary active agent contained in the pharmaceutical formulation, the effective amount of the auxiliary active agent will vary depending on the auxiliary active agent.

When optionally present in the pharmaceutical formulation, the auxiliary active agent can be included in the pharmaceutical formulation or can exist as a stand-alone compound or pharmaceutical formulation that can be administered contemporaneously or sequentially with the compound, derivative thereof, or pharmaceutical formulation thereof. In yet other embodiments, the effective amount of the auxiliary active agent can range from about 0 to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% w/w, v/v, or w/v of the total auxiliary active agent pharmaceutical formulation. In additional embodiments, the effective amount of the auxiliary active agent can range from about 0 to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% w/w, v/v, or w/v of the total pharmaceutical formulation.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20 g and from mice experiments, one can scale up to a 70 kg individual.

Dosage Forms

In some embodiments, the pharmaceutical formulations described herein can be in a dosage form. The dosage form can be administered to a subject in need thereof. The dosage form can be effective generate specific concentration, such as an effective concentration, at a given site in the subject in need thereof. In some cases, the dosage form contains a greater amount of the active ingredient than the final intended amount needed to reach a specific region or location within the subject to account for loss of the active components such as via first and second pass metabolism.

The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, parenteral, subcutaneous, intramuscular, intravenous, internasal, and intradermal. Other appropriate routes are described elsewhere herein. Such formulations can be prepared by any method known in the art.

Dosage forms adapted for oral administration can discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution. The oral dosage form can be administered to a subject in need thereof. Where appropriate, the dosage forms described herein can be microencapsulated.

The dosage form can also be prepared to prolong or sustain the release of any ingredient. In some embodiments, compounds, molecules, compositions, vectors, vector systems, cells, or a combination thereof described herein can be the ingredient whose release is delayed. In some embodiments the primary active agent is the ingredient whose release is delayed. In some embodiments, an optional auxiliary agent can be the ingredient whose release is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate, polyvinyl acetate phthalate, acrylic acid polymers and copolymers, and methacrylic resins that are commercially available under the trade name EUDRAGIT® (Roth Pharma, Weiterstadt, Germany), zein, shellac, and polysaccharides.

Coatings may be formed with a different ratio of water-soluble polymer, water insoluble polymers, and/or pH dependent polymers, with or without water insoluble/water soluble non-polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Where appropriate, the dosage forms described herein can be a liposome. In these embodiments, primary active ingredient(s), and/or optional auxiliary active ingredient(s), and/or pharmaceutically acceptable salt thereof where appropriate are incorporated into a liposome. In embodiments where the dosage form is a liposome, the pharmaceutical formulation is thus a liposomal formulation. The liposomal formulation can be administered to a subject in need thereof.

Dosage forms adapted for topical administration can be formulated as ointments, creams, suspensions, lotions, powders, solutions, pastes, gels, sprays, aerosols, or oils. In some embodiments for treatments of the eye or other external tissues, for example, the mouth or the skin, the pharmaceutical formulations are applied as a topical ointment or cream. When formulated in an ointment, a primary active ingredient, optional auxiliary active ingredient, and/or pharmaceutically acceptable salt thereof where appropriate can be formulated with a paraffinic or water-miscible ointment base. In other embodiments, the primary and/or auxiliary active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, a primary active ingredient, optional auxiliary active ingredient, and/or pharmaceutically acceptable salt thereof where appropriate can be in a dosage form adapted for inhalation is in a particle-sizereduced form that is obtained or obtainable by micronization. In some embodiments, the particle size of the size reduced (e.g., micronized) compound or salt or solvate thereof is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active (primary and/or auxiliary) ingredient, which may be generated by various types of metered dose pressurized aerosols, nebulizers, or insufflators. The nasal/inhalation formulations can be administered to a subject in need thereof.

In some embodiments, the dosage forms are aerosol formulations suitable for administration by inhalation. In some of these embodiments, the aerosol formulation contains a solution or fine suspension of a primary active ingredient, auxiliary active ingredient, and/or pharmaceutically acceptable salt thereof where appropriate and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g., metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a primary active ingredient, optional auxiliary active ingredient, and/or pharmaceutically acceptable salt thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time. The aerosol formulations can be administered to a subject in need thereof.

For some dosage forms suitable and/or adapted for inhaled administration, the pharmaceutical formulation is a dry powder inhalable-formulations. In addition to a primary active agent, optional auxiliary active ingredient, and/or pharmaceutically acceptable salt thereof where appropriate, such a dosage form can contain a powder base such as lactose, glucose, trehalose, manitol, and/or starch. In some of these embodiments, a primary active agent, auxiliary active ingredient, and/or pharmaceutically acceptable salt thereof where appropriate is in a particle-size reduced form. In further embodiments, a performance modifier, such as L-leucine or another amino acid, cellobiose octaacetate, and/or metals salts of stearic acid, such as magnesium or calcium stearate. In some embodiments, the aerosol formulations are arranged so that each metered dose of aerosol contains a predetermined amount of an active ingredient, such as the one or more of the compositions, compounds, vector(s), molecules, cells, and combinations thereof described herein.

Dosage forms adapted for vaginal administration can be presented as pessaries, tampons, creams, gels, pastes, foams, or spray formulations. Dosage forms adapted for rectal administration include suppositories or enemas. The vaginal formulations can be administered to a subject in need thereof.

Dosage forms adapted for parenteral administration and/or adapted for injection can include aqueous and/or non-aqueous sterile injection solutions, which can contain antioxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including, but not limited to, sealed ampoules or vials. The doses can be lyophilized and re-suspended in a sterile carrier to reconstitute the dose prior to administration. Extemporaneous injection solutions and suspensions can be prepared in some embodiments, from sterile powders, granules, and tablets. The parenteral formulations can be administered to a subject in need thereof.

For some embodiments, the dosage form contains a predetermined amount of a primary active agent, auxiliary active ingredient, and/or pharmaceutically acceptable salt thereof, where appropriate, per unit dose. In an embodiment, the predetermined amount of primary active agent, auxiliary active ingredient, and/or pharmaceutically acceptable salt thereof, where appropriate, can be an effective amount, a least effect amount, and/or a therapeutically effective amount. In some embodiments, the predetermined amount can be effective to modify a MARC polynucleotide and/or modulate MARC expression and/or activity. In some embodiments, the predetermined amount can be effective to reduce MARC expression and/or activity. In some embodiments, the predetermined amount can be effective to modify a MARC polynucleotide such that it is a protective MARC variant. In some embodiments, the predetermined amount can be effective to treat and/or prevent a liver disease or a symptom thereof.

In other embodiments, the predetermined amount of a primary active agent, auxiliary active agent, and/or pharmaceutically acceptable salt thereof where appropriate, can be an appropriate fraction of the effective amount of the active ingredient. Such unit doses may therefore be administered once or more than once a day, month, or year (e.g., 1, 2, 3, 4, 5, 6, or more times per day, month, or year). Such pharmaceutical formulations may be prepared by any of the methods well known in the art.

Delivery

Delivery of any of the compounds, compositions, formulations, particles, and cells described herein can be via any suitable method. In some embodiments, a compound composition, formulation, and/or particle described herein can be delivered to a cell. In some embodiments, a cell described herein can be delivered to a subject. In some embodiments, enhancing NHEJ or HR efficiency can be advantageous. In some embodiments NHEJ efficiency can be enhanced by co-expressing end-processing enzymes such as Trex2 (Dumitrache et al. Genetics. 2011 August; 188 (4): 787-797). In some embodiments, HR efficiency can be increased by transiently inhibiting NHEJ machineries such as Ku70 and Ku86. HR efficiency can also be increased by co-expressing prokaryotic or eukaryotic homologous recombination enzymes such as RecBCD, RecA.

Vector and Virus Particle Delivery

A vector (including non-viral carriers) described herein can be introduced into host cells to thereby produce transcripts, proteins, or peptides, including those encoded by nucleic acids as described herein (e.g., MARC variant polynucleotides, MARC variant polypeptides, polynucleotide modifying polynucleotides and/or polypeptides, etc.), and virus particles (such as those generated from viral vectors and systems thereof).

One or more polynucleotides described herein can be delivered using adeno associated virus (AAV), adenovirus, lentivirus, or other plasmid or viral vector types as previously described, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as described in U.S. Pat. No. 8,454,972 and as in clinical trials involving AAV. For Adenovirus, the route of administration, formulation and dose can be as described in U.S. Pat. No. 8,404,658 and as in clinical trials involving adenovirus.

For plasmid delivery, the route of administration, formulation and dose can be as described in U.S. Pat. No. 5,846,946 and as in clinical studies involving plasmids. In some aspects, doses can be based on or extrapolated to an average 70 kg individual (e.g., a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into or otherwise delivered to the tissue or cell of interest.

In terms of in vivo delivery, AAV can be advantageous over other viral vectors for a couple of reasons such as low toxicity (this may be due to the purification method not requiring ultra-centrifugation of cell particles that can activate the immune response) and a low probability of causing insertional mutagenesis because it doesn't integrate into the host genome.

The vector(s) and virus particles described herein can be delivered in to a host cell in vitro, in vivo, and/or ex vivo. Delivery can occur by any suitable method including, but not limited to, physical methods, chemical methods, and biological methods. Physical delivery methods are those methods that employ physical force to counteract the membrane barrier of the cells to facilitate intracellular delivery of the vector. Suitable physical methods include, but are not limited to, needles (e.g., injections), ballistic polynucleotides (e.g., particle bombardment, micro projectile gene transfer, and gene gun), electroporation, sonoporation, photoporation, magnetofection, hydroporation, and mechanical massage. Chemical methods are those methods that employ a chemical to elicit a change in the cells membrane permeability or other characteristic(s) to facilitate entry of the vector into the cell. For example, the environmental pH can be altered which can elicit a change in the permeability of the cell membrane. Biological methods are those that rely and capitalize on the host cell's biological processes or biological characteristics to facilitate transport of the vector (with or without a carrier) into a cell. For example, the vector and/or its carrier can stimulate an endocytosis or similar process in the cell to facilitate uptake of the vector into the cell.

In some embodiments the vectors and virus particles described herein can be delivered to one or more to cells via particles. The term "particle" as used herein, refers to any suitable sized particles for delivery of the vector or vector system components described herein. Suitable sizes include macro-, micro-, and nano-sized particles. In some aspects, any of the vector system components (e.g., polypeptides, polynucleotides, vectors and combinations thereof described herein) can be attached to, coupled to, integrated with, otherwise associated with one or more particles or component thereof as described herein. The particles described herein can then be administered to a cell or organism by an appropriate route and/or technique, including but not limited to those described elsewhere herein. In some aspects, particle delivery can be selected and be advantageous for delivery of the polynucleotide or vector components. It will be appreciated that in aspects, particle delivery can also be advantageous for other engineered capsid system molecules and formulations described elsewhere herein.

Virus Particles

Also described herein are virus particles that can contain a cargo molecule, including, but not limited to, one or more polynucleotides as described in detail elsewhere herein. It will be appreciated that the virus particles can be lentiviral particles, lentivirus helper particles, adenovirus-based particles, helper adenovirus-based particles, AAV-based particles, or hybrid adenovirus-based particles, or any other virus particle described elsewhere herein. The virus particles can include one or more cargo polynucleotides. In some aspects, the one or more cargo polynucleotides can be operably linked to a capsid polynucleotide(s) and can be part of the viral genome of the viral system of the present invention. The cargo polynucleotides can be packaged into a virus particle, which can be delivered to, e.g., a cell. In some aspects, the cargo polynucleotide can be capable of modifying a polynucleotide (e.g., gene or transcript) of a cell to which it is delivered to a cell, with or without the assistance or complexing with one or more other polynucleotides or polypeptides.

As used herein, "gene" can refer to a hereditary unit corresponding to a sequence of DNA that occupies a specific location on a chromosome and that contains the genetic instruction for a characteristic(s) or trait(s) in an organism. The term gene can refer to translated and/or untranslated regions of a genome. "Gene" can refer to the specific sequence of DNA that is transcribed into an RNA transcript that can be translated into a polypeptide or be a catalytic RNA molecule, including but not limited to, tRNA, siRNA, piRNA, miRNA, long-non-coding RNA and shRNA. Polynucleotide, gene, transcript, etc. modification includes all genetic engineering techniques including, but not limited to, gene editing as well as conventional recombinational gene modification techniques (e.g., whole or partial gene insertion, deletion, and mutagenesis, for example, insertional and deletional mutagenesis) techniques.

In some embodiments, the cargo molecule can be a polynucleotide that can encode one or more RNA or polypeptides described elsewhere herein, such as a MARC variant (e.g., a MARC protective variant or risk variant) or a CRISPR-Cas system component (e.g., one or more Cas polypeptides and/or gRNA). In some embodiments, the cargo molecule is a polynucleotide that is or can encode a vaccine. In some embodiments, the vaccine can stimulate an immune response.

In some embodiments, the cargo molecule can be a polynucleotide or polypeptide that can alone or when delivered as part of a system, whether or not delivered with other components of the system, operate to modify the genome, epigenome, and/or transcriptome of a cell to which it is delivered. Such systems include, but are not limited to, CRISPR-Cas systems. Other gene modification systems, e.g., TALENs, Zinc Finger nucleases, Cre-Lox, morpholinos, etc. are other non-limiting examples of polynucleotide modification systems whose one or more components can be delivered by the viral particles described herein.

In some embodiments, the cargo molecule is a gene editing system or component thereof. In some embodiments, the cargo molecule is a CRISPR-Cas system molecule or a component thereof. In some embodiments, the cargo molecule is a polynucleotide that encodes one or more components of a gene modification system (such as a CRISPR-Cas system). In some embodiments the cargo molecule is a gRNA. In some embodiments the cargo molecule is a polynucleotide that can encode one or more Cas polypeptides. In some embodiments the cargo molecule is a polynucleotide that can encode one or more transposase polypeptides.

In some embodiments, the cargo molecule can be a polynucleotide or polypeptide that can alone, or when delivered as part of a system, whether or not delivered with other components of the system, operate to modify the genome, epigenome, and/or transcriptome of a cell to which it is delivered, such that it treats or prevents a disease, a disorder, or a symptom thereof of a muscle or skeletal disorder, a neurologic disease or disorder, and/or viruses (such as single stranded RNA viruses). In some embodiments, the cargo molecule, whether or not delivered with other components of the system, operate to modify the genome, epigenome, and/or transcriptome of a cell to which it is delivered, such that it treats or prevents a liver disease or a symptom thereof. Exemplary liver diseases are described in greater detail elsewhere herein. In some embodiments, the delivered components operate to modify a MARC gene, transcript, and/or polypeptide. In some embodiments, the delivered components operate to modify a MARC risk variant gene, transcript, and/or polypeptide such that it is modified to a MARC protective variant gene, transcript and/or polypeptide.

In some embodiments, the cargo molecule is an antisense oligomer or RNA molecule, such as those described in US Patent Publication Nos. US20160251398, US20150267202, US20190015440, US20140287983, US20180216111, US20190177723, US20170051278, US20180271893, U.S. Pat. No. 10,076,536, and PCT Patent Publications WO 2018/00580, WO 2018/11866, WO 2017/062835, WO 2016/14965, and WO 2019/059973, the contents of which are incorporated by reference as if expressed in their entirety herein and can be adapted for use with the present invention.

RNA Delivery

The polynucleotides, polypeptides, systems and/or components thereof described elsewhere herein can also be delivered in the form of RNA. In particular embodiments, RNA based delivery is used to deliver an RNA and/or a polypeptide to a cell. In some embodiments, an RNA once delivered to a cell can be translated into a polypeptide thereby delivering the polypeptide to the cell. In some embodiments, mRNA of a protein can be delivered optionally together with other RNA molecules. In some embodiments, a Cas mRNA can be delivered optionally together with a guide RNA. In some embodiments, the protein mRNA (e.g., a Cas mRNA) and/or other RNA molecules (e.g., siRNA, guide RNA, etc.) can be an in vitro transcribed RNA. Other methods of producing RNA molecules are generally known in the art. Liang et al. describes efficient genome editing using RNA based delivery (Protein Cell. 2015 May; 6 (5): 363-372), the compositions techniques of which can be used and/or adapted for use with the present invention. In some embodiments, the RNA can include one or more modified nucleosides e.g., using pseudo-U or 5-Methyl-C. In some embodiments, the inclusion of one or more modified nucleosides can increase efficiency and/or reduce toxicity.

Where multiple components of a system are delivered by RNA, one or more of the multiple components can be delivered together or can be delivered separately. In some systems, such as CRISPR-Cas and other Cas-based systems, Cas mRNA can be delivered prior to the guide RNA (or other RNA molecule) to allow for time for components of the system(s) to be expressed and/or become active before the guide or other RNA molecule is present. In some embodiments, the Cas mRNA (or other protein mRNA) can be administered 1-12 hours prior to the administration of guide RNA (or other RNA). In some embodiments, In some embodiments, the Cas mRNA (or other protein mRNA) can be administered 2-6 hours prior to the administration of guide RNA (or other RNA).

In some systems, such as CRISPR-Cas and other Cas-based systems, Cas mRNA can and the guide RNA (or other RNA molecule) can be administered together. In some of these embodiments, a second booster dose of guide RNA (or other RNA) can be administered 1-12 hours after the initial administration of the Cas (or other protein) mRNA+guide RNA (or other RNA). In some of these embodiments, a second booster dose of guide RNA (or other RNA) can be administered 2-6 hours after the initial administration of the Cas (or other protein) mRNA+guide RNA (or other RNA).

RNPs

In particular embodiments, one or more polynucleotides, polypeptides, systems, and/or components thereof are delivered as a ribonucleoprotein (RNP). RNPs can be advantageous in some instances, as delivery by an RNP avoids the need for transcription and/or is transient, which can reduce off-target effects and/or toxicity. RNPs have been demonstrated to deliver gene editing systems and lead to efficient genome editing in different cell types. See e.g., Kim et al. (2014, Genome Res. 24 (6): 1012-9), Paix et al. (2015, Genetics 204 (1): 47-54), Chu et al. (2016, BMC Biotechnol. 16:4), and Wang et al. (2013, Cell. 9; 153 (4): 910-8), the compositions of techniques of which can be used with and/or adapted for use with the compositions described herein.

In particular embodiments, the ribonucleoprotein is delivered by way of a polypeptide-based shuttle agent, such as any of those described in PCT Patent Publication WO 2016/161516. In some embodiments, one or more polypeptide-based shuttle agent can be composed of one or more synthetic peptides that have an endosome leakage domain (ELD) operably linked to a cell penetrating domain (CPD), to a histidine-rich domain, and a CPD.

Delivery via Particles

Any of the systems or components thereof, complexes, polypeptides, polynucleotides, vectors, virus particles, cells and combinations thereof described herein can be delivered via particles or vesicles. The term "particle" as used herein, refers to any suitable sized particles for delivery of the systems or components thereof, complexes, polypeptides, polynucleotides, vectors, virus particles, and combinations thereof described herein. Suitable sizes include macro-, micro-, and nano-sized particles. In some aspects, any of the systems or components thereof, complexes, polypeptides, polynucleotides, vectors, virus particles, cells and combinations thereof described herein can be attached to, coupled to, integrated with, otherwise associated with one or more particles or component thereof as described herein. The particles described herein can then be administered to a cell or organism by an appropriate route and/or technique. In some aspects, particle delivery can be selected and be advantageous for delivery of RNA and/or protein components. It will be appreciated that in aspects, particle delivery can be advantageous for other CRISPR-Cas system molecules and formulations.

In some embodiments, the delivery particles can be micelles. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase.

It will be understood that the size of the particle will differ depending as to whether it is measured before or after loading. Accordingly, in particular embodiments, the term "nanoparticles" may apply only to the particles pre-loading.

Nanoparticles can be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

In some embodiments, the nanoparticles can be semi-solid or soft nanoparticles. An example of a nanoparticle of semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. In some embodiments, nanoparticles, such as liposomes, can self-assemble at water/oil interfaces and act as solid surfactants.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843, 6,007,845, 5,855,913, 5,985,309, 5,543, 158; and the publication by James E. Dahlman and Carmen Barnes et al. Nature Nanotechnology (2014) published online 11 May 2014, doi: 10.1038/nnano.2014.84, concerning particles, methods of making and using them and measurements thereof.

Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

In some embodiments, a particle is any entity having a greatest dimension (e.g., diameter) of less than 100 microns (µm). In some embodiments, a particle can have a greatest dimension of less than 10 µm. In some embodiments, a particle can have a greatest dimension of less than 2000 nanometers (nm). In some embodiments, a particle can have a greatest dimension of less than 1000 nanometers (nm). In some embodiments, a particle can have a greatest dimension of less than 900 nm, 800 nm, 700 nm, 600 nm, 500 nm, 400 nm, 300 nm, 200 nm, or 100 nm. In some embodiments, a particle can have a greatest dimension (e.g., diameter) of 500 nm or less. In some embodiments, a particle can have a greatest dimension (e.g., diameter) of 250 nm or less. In some embodiments, a particle can have a greatest dimension (e.g., diameter) of 200 nm or less. In some embodiments, a particle can have a greatest dimension (e.g., diameter) of 150 nm or less. In some embodiments, a particle can have a greatest dimension (e.g., diameter) of 100 nm or less. Smaller particles, e.g., having a greatest dimension of 50 nm or less are used in some embodiments of the invention. In some embodiments, a particle can have a greatest dimension ranging between 25 nm and 200 nm.

In some embodiments, the size of a particle with in a group of particles can be represented as the average of the greatest dimension of the particles in a population or a representative and/or statistically relevant subpopulation thereof.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, nanoparticles of the invention have a greatest dimension ranging between 35 nm and 60 nm. It will be appreciated that reference made herein to particles or nanoparticles can be interchangeable, where appropriate.

In some embodiments, delivery of one or more systems or components thereof, complexes, polypeptides, polynucleotides, vectors, virus particles, cells and combinations thereof described herein can be via nanoparticles, including, but not limited to, any of those as described in, e.g., Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19:3112-3118, 2010), the compositions and techniques of which can be used with and/or adapted for use with the present invention.

In some embodiments, one or more systems or components thereof, complexes, polypeptides, polynucleotides, vectors, virus particles, cells and combinations thereof described herein can be delivered to a cell by a composition, such as any of those described by US Patent Publication No. US20160367686. In some embodiments, one or more systems or components thereof, complexes, polypeptides, polynucleotides, vectors, virus particles, cells and combinations thereof described herein can form a complex with a composition described by US Patent Publication No. US20160367686. In some embodiments, the composition described by US Patent Publication No. US20160367686 can include a cholesterol, a PEGylated lipid, a phospholipid, an apolipoprotein, or a combination thereof.

In some embodiments, one or more systems or components thereof, complexes, polypeptides, polynucleotides, vectors, virus particles, cells and combinations thereof described herein can be delivered to a cell by a microparticle, such as any of those described by US Patent Publication No. US20050123596, which describes microparticles that can release their payload when exposed to acidic conditions. In some embodiments, such microparticles can include one or more RNA molecules, such as any of those described herein, a pH triggering agent, and a polymer. In some embodiments, the polymer is a polymethacrylate or a polyacrylate.

Methods of producing and/or assembling particles are generally known in the art and can include methods and techniques, such as those set forth in US Patent Publication Nos. US 20150105538, US20150250725, and US20100129793.

Lipid-Based Particles

In some embodiments, the delivery particle comprises a lipid-based particle, optionally a lipid nanoparticle, or cationic lipid and optionally biodegradable polymer. Methods of preparing liposomes, lipid discs, and other lipid nanoparticles and the like are generally known in the art, such as by methods described by Zhu et al. (U.S. Pat. No. 1,403,489 P200), Cullis et al. (US20140328759), See Wang et al., ACS Synthetic Biology, 1, 403-07 (2012); Wang et al., PNAS, 113 (11) 2868-2873 (2016); Spuch and Navarro, Journal of Drug Delivery, vol. 2011, Article ID 469679, 12 pages, 2011. doi: 10.1155/2011/469679; PCT Patent Publication WO 2008/042973; U.S. Pat. No. 8,071,082; and PCT Patent Publication WO 2014/186366 A1 (US Patent Publication No. US20160082126), the compositions and techniques of which can be used with and/or adapted for use with the present invention.

In some embodiments, the cationic lipid comprises 1,2-dioleoyl-3-trimethylammonium-propane (DOTAP). In some embodiments, the hydrophilic polymer comprises ethylene glycol or polyethylene glycol. In some embodiments, the delivery particle further comprises a lipoprotein, preferably cholesterol.

In some embodiments, one or more systems or components thereof, complexes, polypeptides, polynucleotides, vectors, virus particles, cells and combinations thereof described herein can be delivered to a cell by a particle or other composition, such as any of those described by US Patent Publication No. US20150232883. In some embodiments, the particle or other composition described by US Patent Publication No. US2015023288 can include a surfactant, a lipid, a protein, or a combination thereof. In some embodiments the surfactant can be a cationic lipid.

In some embodiments, the polynucleotides, polypeptides, systems thereof, complexes thereof, etc. can be delivered by a particle, including but not limited to, liposomes, exosomes, micelles, microparticles, nanoparticles, and the like. In some embodiments, Cas (or other) protein(s) mRNA and/or gRNA (or other RNA) (and, for instance, HR repair template) can be delivered into cells using liposomes, microvesicles, or other particles. For example, Cas protein mRNA and gRNA can be packaged into liposomal particles for delivery in vivo. Liposomal transfection reagents, such as lipofectamine from Life Technologies, and other reagents commercially available and generally known in the art can effectively deliver RNA molecules to a cell. In some embodiments, such reagents can be particularly effective for delivery into the liver.

In some embodiments, the polynucleotides, polypeptides, systems thereof, complexes thereof, etc. can be delivered by a particle as in Dahlman et al., WO2015089419 A2 and documents cited therein, such as 7C1 (see, e.g., James E. Dahlman and Carmen Barnes et al. Nature Nanotechnology (2014) published online 11 May 2014, doi: 10.1038/nnano.2014.84).

In some embodiments, the polynucleotides, polypeptides, systems thereof, complexes thereof, etc. can be delivered by a particle, such as any as set forth in U.S. Pat. No. 9,301,923.

In some embodiments, the polynucleotides, polypeptides, systems thereof, complexes thereof, etc. can be delivered by a particle, such as any as set forth in US Patent Publication No. US20160174546, which describes at least nanolipid delivery particles and systems.

In some embodiments, the polynucleotides, polypeptides, systems thereof, complexes thereof, etc. can be delivered by a particle, such as any as set forth in US Patent Publication No. US20140301951, which describes at least a protocell nanostructure composed of a porous particle core comprising a plurality of pores and at least one lipid bilayer surrounding the porous particle core to form a protocell, wherein the protocell is capable of loading one or more cargo components to the plurality of pores of the porous particle core and releasing the one or more cargo components from the porous particle core across the surrounding lipid bilayer.

In some embodiments, the lipid particles as described in, e.g., Wang et al., *J. Control Release,* 2017 Jan. 31. pii: S0168-3659 (17) 30038-X. doi: 10.1016/j.jconrel.2017.01.037. [Epub ahead of print]; Altmoğlu et al., *Biomater Sci.,* 4 (12): 1773-80, Nov. 15, 2016; Wang et al., *PNAS,* 113 (11): 2868-73 Mar. 15, 2016; Wang et al., *PloS One,* 10 (11): e0141860. doi: 10.1371/journal.pone.0141860. eCollection 2015 Nov. 3, 2015; Takeda et al., *Neural Regen Res.* 10 (5): 689-90, May 2015; Wang et al., *Adv. Healthc Mater.,* 3 (9): 1398-403, September 2014; and Wang et al., *Agnew Chem Int Ed Engl.,* 53 (11): 2893-8, Mar. 10, 2014, can be used/adapted to deliver one or more of the systems or components thereof, complexes, polynucleotides, polypeptides, vectors, virus particles, etc. described elsewhere herein.

In some embodiments, the polynucleotides, polypeptides, systems thereof, complexes thereof, etc. can be delivered by a particle, such as any as set forth in US Patent Publication No. US20110293703, which can describe at least lipidoid compounds, including aminoalcohol lipidoid compounds.

In some embodiments, the polynucleotides, polypeptides, systems thereof, complexes thereof, etc. can be delivered by a particle, such as any as set forth in U.S. Pat. No. 5,985,309.

In some embodiments, the polynucleotides, polypeptides, systems thereof, complexes thereof, etc. can be delivered by a particle or complex, such as any as set forth in PCT Patent Publication WO 2012/135025, which at least describes conjugated lipomers.

In some embodiments, the polynucleotides, polypeptides, systems thereof, complexes thereof, etc. can be delivered by a particle or complex, such as any as set forth in any of PCT Patent Publications WO 2005/105152 (PCT/EP2005/004920), WO 2006/069782 (PCT/EP2005/014074), WO 2007/121947 (PCT/EP2007/003496), and WO 2015/082080 (PCT/EP2014/003274).

In some embodiments, the polynucleotides, polypeptides, systems thereof, complexes thereof, etc. can be delivered by a particle that contains a lipid, such as any as set forth in US Patent Publication Nos. US20140308304, US20150140070, US20160200779, US20150118216, US 20150071903, and US20150071903, and PCT Patent Publication WO 2013/093648.

In some embodiments, the liposome can be a Trojan Horse liposome. See e.g., cshprotocols.cshlp.org/content/2010/4/pdb.prot5407.long.

In some embodiments, the lipid particle can be a stable nucleic-acid-lipid particle (SNALP). See, e.g., Morrissey et al., Nature Biotechnology, Vol. 23, No. 8, August 2005, the teachings of which can be applied and/or adapted to the present invention.

Polymer-Based Particles

The systems and compositions described herein may be delivered using polymer-based particles (e.g., nanoparticles). In some embodiments, the polymer-based particles may mimic a viral mechanism of membrane fusion. The polymer-based particles may be a synthetic copy of Influenza virus machinery and form transfection complexes with various types of nucleic acids (siRNA, miRNA, plasmid DNA or shRNA, mRNA) that cells take up via the endocytosis pathway, a process that involves the formation of an acidic compartment. The low pH in late endosomes acts as a chemical switch that renders the particle surface hydrophobic and facilitates membrane crossing. Once into the cytosol, the particle can release its payload for cellular action. This active endosome escape technology is safe and can maximize transfection efficiency, as it uses a natural uptake pathway. In some embodiments, the polymer-based particles may comprise alkylated and carboxyalkylated branched polyethylenimine. In some examples, the polymer-based particles are VIROMER, e.g., VIROMER RNAi, VIROMER RED, VIROMER mRNA, VIROMER CRISPR.

Example methods of delivering the systems and compositions herein include those described in Bawage S S et al., Synthetic mRNA expressed Cas13a mitigates RNA virus infections, www.biorxiv.org/content/10.1101/370460v1.full doi: doi.org/10.1101/370460, Viromer® RED, a powerful tool for transfection of keratinocytes. doi: 10.13140/RG.2.2.16993.61281, Viromer® Transfection-Factbook 2018: technology, product overview, users' data, doi: 10.13140/RG.2.2.23912.16642.

In some embodiments, the polynucleotides, polypeptides, systems thereof, complexes thereof, etc. can be delivered by a particle, such as any as set forth in US Patent Publication No. US20110212179, which at least provides bimodal porous polymer microspheres.

In some embodiments, the polynucleotides, polypeptides, systems thereof, complexes thereof, etc. can be delivered by a particle or complex, such as any as set forth in US Patent Publication No. US20130302401, which describes at least a class of poly (beta-amino alcohols.

In some embodiments, the polynucleotides, polypeptides, systems thereof, complexes thereof, etc. can be delivered by a particle or complex, such as any as set forth in U.S. Pat. No. 8,709,843, which describes at least targeted lipo-polymeric particles.

In some embodiments, the polynucleotides, polypeptides, systems thereof, complexes thereof, etc. can be delivered by a particle or complex, such as any as set forth in U.S. Pat. No. 6,007,845, which describes at least particles composed of multiblock copolymers.

In some embodiments, the polynucleotides, polypeptides, systems thereof, complexes thereof, etc. can be delivered by a particle or complex, such as any as set forth in U.S. Pat. No. 5,543,158, which describes at least biodegradable injectable particles having a biodegradable solid core containing a biologically active material and poly (alkylene glycol) moieties on the surface.

In some embodiments, the polynucleotides, polypeptides, systems thereof, complexes thereof, etc. can be delivered by a particle or complex, such as any as set forth in any of US Patent Publication Nos. US20130252281, US20130245107, and US20130244279, which describe at least PLGA microparticles.

Dendrimers

In some embodiments, of one or more systems or components thereof, complexes, polypeptides, polynucleotides, vectors, virus particles, and combinations thereof described herein can be delivered via a dendrimer nanoparticle or a modified dendrimer nanoparticle, such as those described in US Patent Publication Nos. US20170079916, US20050019923, and US 20080267903. Dendrimers are synthetic 3-dimensional macromolecules that are prepared in a step-wise fashion from simple branched monomer units, the nature and functionality of which can be easily controlled and varied. Dendrimers are synthesised from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers.

Sugar-Based Particles

In some embodiments, the particle for delivery of the one or more systems or components thereof, complexes, polypeptides, polynucleotides, vectors, virus particles, and combinations thereof described herein can be a sugar-based particle.

In some embodiments, sugar-based particles may be used, for example GalNAc, as described herein and with reference to PCT Patent Publication WO 2014/118272 (incorporated herein by reference) and Nair, J K et al., 2014, Journal of the American Chemical Society 136 (49), 16958-16961).

In some embodiments, one or more systems or components thereof, complexes, polypeptides, polynucleotides, vectors, virus particles, and combinations thereof described herein can be delivered by any lipid-protein-sugar particle, such as by any of those described in US Patent Publication No. US20020150626. In some embodiments, the lipid-protein-sugar particle can encapsulate the one or more RNA molecules. Encapsulation can be accomplished by contacting the polynucleotide with a lipid, a protein, and a sugar; and spray drying mixture of the polynucleotide, the lipid, the protein, and the sugar to make microparticles.

Spherical Nucleic Acid (SNA)

In some embodiments, the particle for delivery of one or more systems or components thereof, complexes, polypeptides, polynucleotides, vectors, virus particles, and combinations thereof described herein can be a SNA. SNAs are three dimensional nanostructures that can be composed of densely functionalized and highly oriented nucleic acids that can be covalently attached to the surface of spherical nanoparticle cores. The core of the spherical nucleic acid can impart the conjugate with specific chemical and physical properties, and it can act as a scaffold for assembling and orienting the oligonucleotides into a dense spherical arrangement that gives rise to many of their functional properties, distinguishing them from all other forms of matter.

In some embodiments, the SNA can be any of those set forth in Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem.

Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495: S14-S16, Choi et al., Proc. Natl. Acad. Sci. USA. 2013 110 (19): 7625-7630, Jensen et al., Sci. Transl. Med. 5, 209ra152 (2013) and Mirkin, et al., Small, 10:186-192, which can be applied and/or adapted for generation of and delivery of one or more systems or components thereof, complexes, polypeptides, polynucleotides, vectors, virus particles, and combinations thereof described herein.

Self-Assembling Nanoparticles

In some embodiments, the particle for delivery of one or more systems or components thereof, complexes, polypeptides, polynucleotides, vectors, virus particles, and combinations thereof described herein can be a self-assembling nanoparticle or nanoplex.

In some embodiments, the self-assembling nanoparticle can be any of those described elsewhere herein. In some embodiments, the self-assembling nanoparticle or nanoplex can be an of those set forth in Bartlett et al. PNAS, Sep. 25, 2007, vol. 104, no. 39; Schiffelers et al., Nucleic Acids Research, 2004, Vol. 32, No. 19; and Nature, Vol 464, 15 Apr. 2010.

Nanoclews

In some embodiments, the particle for delivery of one or more systems or components thereof, complexes, polypeptides, polynucleotides, vectors, virus particles, and combinations thereof described herein can be a nanoclew. In some embodiments, the nanoclew can be any of those described by Sun W et al, *Cocoon-like self-degradable DNA nanoclew for anticancer drug delivery*, J Am Chem Soc. 2014 Oct. 22; 136 (42): 14722-5. doi: 10.1021/ja5088024. Epub 2014 Oct. 13; or in Sun W et al, *Self-Assembled DNA Nanoclews for the Efficient Delivery of CRISPR-Cas9 for Genome Editing*, Angew Chem Int Ed Engl. 2015 Oct. 5; 54 (41): 12029-33. doi: 10.1002/anie.201506030. Epub 2015 Aug. 27.

Exosomes

Exosomes are endogenous nano-vesicles that transport RNAs and proteins, and which can deliver a cargo to a cell, tissue, organ, etc.

In some embodiments, delivery of systems or components thereof, complexes, polypeptides, polynucleotides, vectors, virus particles, and combinations thereof described herein can be via exosomes, including, but not limited to, any of those described in Schroeder, A., Levins, C., Cortez, C., Langer, R., and Anderson, D., Lipid-based nanotherapeutics for siRNA delivery, Journal of Internal Medicine, 267:9-21, 2010, PMID: 20059641, the compositions and techniques of which can be used with and/or adapted for use with the present invention. Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7 (12): 2112-26. doi: 10.1038/nprot.2012.131. Epub 2012 Nov. 15) describe how exosomes are promising tools for drug delivery across different biological barriers and can be harnessed for delivery of siRNA in vitro and in vivo, which can be adapted for use with and delivery of the compositions and systems described herein. In some embodiments, exosomes can be generated via transfection of an expression vector, that contains an exosomal protein fused with a peptide ligand. The exosomes are then purified and characterized from transfected cell supernatant, then cargo RNA is loaded into the exosomes, which can subsequently be delivered to a cell or subject. In some embodiments, the RNA can be a mRNA, an RNAi molecule (e.g., an siRNA etc.) or other RNA molecule (e.g., gRNA etc.)

In some embodiments, delivery of one or more of the systems or components thereof, complexes, polypeptides, polynucleotides, vectors, virus particles, and combinations thereof described herein can be via exosomes, including, but not limited to, any of those described in Wahlgren et al. (Nucleic Acids Research, 2012, Vol. 40, No. 17 e130).

Delivery by Supercharged Proteins

Supercharged proteins are a class of engineered or naturally occurring proteins with unusually high positive or negative net theoretical charge. In some embodiments, delivery of systems or components thereof, complexes, polypeptides, polynucleotides, vectors, virus particles, and combinations thereof described herein can be via a supercharged protein(s).

Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo. The creation and characterization of supercharged proteins has been described and can applied and/or adapted for delivery of the systems or components thereof, complexes, polypeptides, polynucleotides, vectors, virus particles, and combinations thereof elsewhere herein. See e.g., Lawrence et al., 2007, Journal of the American Chemical Society 129, 10110-10112; cNaughton et al., 2009, Proc. Natl. Acad. Sci. USA 106, 6111-6116; Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012), the teachings of which can be adapted for and/or applied for generation and/or delivery of one or more of the systems or components thereof, complexes, polypeptides, polynucleotides, vectors, virus particles, and combinations thereof described herein.

Cell Penetrating Peptides

Cell Penetrating Peptides (CPPs) are short peptides that facilitate cellular uptake of various molecular cargo, such as the systems or components thereof, complexes, polypeptides, polynucleotides, vectors, virus particles, and combinations thereof described The function of the CPPs are to deliver the cargo into cells, a process that commonly occurs through endocytosis with the cargo delivered to the endosomes of cells. Cell-penetrating peptides are of different sizes, amino acid sequences, and charges, but all CPPs have one distinct characteristic, which is the ability to translocate the plasma membrane and facilitate the delivery of various molecular cargoes to the cytoplasm or an organelle. CPP translocation may be classified into three main entry mechanisms: direct penetration in the membrane, endocytosis-mediated entry, and translocation through the formation of a transitory structure.

In some embodiments, the CPP can have a have an amino acid composition that contains a high relative abundance of positively charged amino acids such as lysine or arginine. In some embodiments, the CPP can have an amino acid composition that contains sequences that contain an alternating pattern of polar/charged amino acids and non-polar, hydrophobic amino acids. In some embodiments, the CPP can have an amino acid composition that contains only apolar residues with low net charge or have hydrophobic amino acid groups.

Suitable CPPs that can be used with some embodiments described herein, include but are not limited to Penetratin, Tat (48-60), Transportan, and (R-AhX-R4) (Ahx-aminohexanoyl), any of those described in U.S. Pat. Nos. 8,372,951, 8,575,305, 614,194 and 8,044,019.

Implantable Devices

In yet another embodiment, implantable devices coated with or otherwise incorporated with or including one or more of the systems or components thereof, complexes, polypeptides, polynucleotides, vectors, virus particles, cells, and combinations thereof described or formulations thereof (e.g., any delivery composition or formulation described herein) can be used to deliver one or more components of the systems or components thereof, complexes, polypeptides, polynucleotides, vectors, virus particles, cells, and combinations thereof described herein. Implantable devices include any device, graft, or other composition that can be implanted into a subject. Implantable devices can be natural, synthetic, or a be combination of both types of materials. Many such implantable devices are known in the art.

Targeted Delivery

Delivery of any of the systems or components thereof, complexes, polypeptides, polynucleotides, vectors, virus particles, cells and combinations thereof described herein can be targeted to one or more spatial locations within a cell and/or organism. As discussed elsewhere herein, this can provide an aspect of spatial and/or temporal control over expression and/or activity of the systems or components thereof, complexes, polypeptides, polynucleotides, vectors, virus particles, cells and combinations thereof described herein. In some embodiments, the delivery system (such as any of those described above) can include a targeting moiety. Many suitable targeting moieties are described in the art, and can include, without limitation, those described in Nanomedicine (Lond). 8 (9), doi: 10.2217/nnm.13.118 (2013), and the documents it cites, WO/2016/027264, and the documents it cites, and Lorenzer et al, Journal of Controlled Release, 203:1-15 (2015).

In some embodiments, the targeting moiety is specific for a protein, sugar, or other molecule present on the surface of a cell. In some embodiments, the targeting moiety is a substrate for a receptor or enzyme on the surface of a cell. In some embodiments, the targeting moiety is an antibody or aptamer specific for a protein, sugar, or other molecule present on the surface of a cell. In some embodiments, the targeting moiety can recognize a single target. In some embodiments, the targeting moiety is bivalent and is specific for more than on target on the surface of one or more cells. In some embodiments, each of the two targets for a bivalent targeting moiety are on different cells. In some embodiments, each of the two targets for a bivalent targeting moiety are on the same cell. In some embodiments, the targeting moiety can be multi-valent and can recognize more than two different targets, each of which can be on the same or different cells.

In some embodiments, targeting moiety can be stimuli-sensitive, e.g., sensitive to an externally applied or environmentally native stimuli, such as magnetic fields, heat/cold, ultrasound, light; osmolarity, enzymes (catalysis), and pH-triggering can also be used, e.g., a labile linkage can be used between a hydrophilic moiety such as PEG and a hydrophobic moiety such as a lipid entity of the invention, which is cleaved only upon exposure to the relatively acidic conditions characteristic of a particular environment or microenvironments. For example, inflamed tissues can have a differential temperature gradient redox potential, osmolarity, pH, etc, which can direct delivery of a cargo to the inflamed tissue by a delivery system with a targeting moiety that is sensitive/responsive to such stimuli.

Kits

Any of the compounds, compositions, formulations, particles, cells, described herein or a combination thereof can be presented as a combination kit. As used herein, the terms "combination kit" or "kit of parts" refers to the compounds, compositions, formulations, particles, cells and any additional components that are used to package, sell, market, deliver, and/or administer the combination of elements or a single element, such as the active ingredient, contained therein. Such additional components include, but are not limited to, packaging, syringes, blister packages, bottles, and the like. When one or more of the compounds, compositions, formulations, particles, cells, described herein or a combination thereof (e.g., agents) contained in the kit are administered simultaneously, the combination kit can contain the active agents in a single formulation, such as a pharmaceutical formulation, (e.g., a tablet) or in separate formulations. When the compounds, compositions, formulations, particles, and cells described herein or a combination thereof and/or kit components are not administered simultaneously, the combination kit can contain each agent or other component in separate pharmaceutical formulations. The separate kit components can be contained in a single package or in separate packages within the kit.

In some embodiments, the combination kit also includes instructions printed on or otherwise contained in a tangible medium of expression. The instructions can provide information regarding the content of the compounds, compositions, formulations, particles, cells, described herein or a combination thereof contained therein, safety information regarding the content of the compounds, compositions, formulations (e.g., pharmaceutical formulations), particles, and cells described herein or a combination thereof contained therein, information regarding the dosages, indications for use, and/or recommended treatment regimen(s) for the compound(s) and/or pharmaceutical formulations contained therein. In some embodiments, the instructions can provide directions for administering the compounds, compositions, formulations, particles, and cells described herein or a combination thereof to a subject in need thereof. In some embodiments, the subject in need thereof can be in need of a treatment or prevention for a liver disease or a symptom thereof. In some embodiments, the liver disease can be or include as a symptom or as part of the pathology, cirrhosis. Such liver diseases or causes can include, but are not limited to, alcoholic cirrhosis (also referred to as alcoholic liver disease), non-alcoholic fatty liver disease (NAFLD) and NAFLD subtypes, viral hepatitis (e.g., chronic viral hepatitis caused by hepatitis B, C, and/or D), hemochromatosis, cystic fibrosis, liver fibrosis, Wilson's disease, biliary atresia, alpha-1 antitrypsin deficiency, inherited disorders of sugar metabolism (e.g., galactosemia or glycogen storage disease), Alagille syndrome, autoimmune hepatitis, primary biliary cirrhosis, primary sclerosing cholangitis, syphilis, brucellosis, medications (e.g., methotrexate and isoniazids). In some embodiments, the instructions provide that the subject in need thereof to which the compounds, compositions, formulations, particles, cells, described herein or a combination thereof can be administered has one or more copies of a MARC risk variant, or expresses a MARC variant, expresses MARC (even if not a MARC risk variant) at a level that is about the same as would be expected from a MARC risk variant, and/or has MARC activity that is at a level that is about the same as would be expected from a MARC risk variant.

Methods of Modulating Marc and Treating Liver Disease

Also described herein are methods of modulating MARC. Modulation includes both methods of modulating MARC activity, function, expression, gene product production, and the like that do not employ alteration of the gene or protein sequence, as well as those methods of modifying the sequence of a gene or gene product (e.g., an RNA transcript). In this context herein, the term "modifying" only relates to repentantly altering the nucleotide sequence of the polynucleotide and/or translated amino acid sequence. Non-modifying modulating methods and compositions can alter the expression or activity level without making a permeant change to the underlying genomic and/or RNA polynucleotide sequence. Such methods can include exposure to inhibitors, such as small molecule inhibitors or MARC-specific antibodies. It will be appreciated that the term "modulating" as used in this specific context herein encompasses both methods that modify a MARC gene/protein sequence as well as those that do not. MARC modulators are described in greater detail elsewhere herein.

In some embodiments, the method of modulating MARC can include modifying a MARC gene and/or gene product. In some embodiments, a MARC gene can be modified such that the modified MARC is a protective variant and/or has a MARC expression and/or activity level that is comparable or the equivalent as a MARC protective variant. Any suitable gene modification technique can be used to modify the MARC. Such techniques include traditional modification techniques that rely on homologous recombination as well as programmable nuclease-based systems and methods. Such programmable nuclease-based methods include, but are not limited to, CRISPR-Cas and Cas-based systems, TALE nuclease systems, meganuclease systems, Zinc finger proteins, all of which are described in greater detail elsewhere herein. MARC modification can be carried out in vivo, ex vivo, or in vitro. Methods of generating modified cells and organisms are also described in further detail elsewhere herein.

In some embodiments, mARC1 activity and/or substrate interactions is modulated. In this regard, the structure indicates molybdenum cofactor (Moco) coordination by C273, forming a slightly distorted coordination geometry (neither ideal square pyramidal nor trigonal bipyramidal). This cysteine residue is highly conserved among all mARC proteins throughout all species and is part of a common CxxC motif. Another Moco-coordinating side chain is R92, which interacts with several atoms of the cofactor via polar and ionic interactions, keeping it strictly in place. The pterin ring system is further bound by residues T210, S211, P212, R238, N240, and Y317, while the phosphate moiety is coordinated by K67, S68, R92, and R238. The active site and substrate binding area is mainly composed of residues C273, D209, R272, S271, R107, Y317, T210, H152, and S311, most of which are highly conserved throughout mARC proteins from different organisms. Any one or more of these interactions may be disrupted to reduce mARC1 activity, for example by DNA or RNA editing in appropriate cells resulting in a proportion of mARC1 proteins being mutated. Another approach is to reduce mARC1 activity by siRNA or other RNAi approach. In certain embodiments, it is desirable to reduce mARC1 activity but not to the point of complete inhibition.

In methods of the invention, it is appropriate to modulate MARC-related activity by modulating MARC expression and/or mARC protein activity or by modulating cellular components that regulate MARC expression and/or mARC activity. While the participation of mARC in liver disease is hereby established, mARC is an important drug metabolising enzyme which reduces N-hydroxylated compounds such as amidoximes to amidines and likely participates in other unknown processes. Accordingly, in certain embodiments, mARC is partially suppressed while in other embodiments, mARC is completely inhibited. In certain embodiments, mARC activity is inhibited or suppressed at a level effective for treatment or prophylaxis of a liver disease or disorder while maintaining an effective level of drug metabolising activity. In certain embodiments, mARC activity is inhibited or suppressed with respect to treatment or prophylaxis of a liver disorder by selectively blocking interaction with another cellular component while drug metabolising activity or other activity is maintained. In certain embodiments, mARC is inhibited or suppressed with respect to treatment or prophylaxis of a liver disorder in certain cell types but not others. For example, MacParland describes 20 discrete cell populations of hepatocytes, endothelial cells, cholangiocytes, hepatic stellate cells, B cells, conventional and non-conventional T cells, NK-like cells, and distinct intrahepatic monocyte/macrophage populations. (MacParland et al., "Single cell RNA sequencing of human liver reveals distinct intrahepatic macrophage populations," Nature Communications 9, Article number: 4383 (2018)). In certain embodiments, mARC inhibition or suppression is accompanied by modulation of a second target, such as, but not limited to, liver disease targets linked to PNPLA3, TM6SF2, and rs72613567 in HSD17B13.

In some embodiments, a method of modifying MARC can include exposing a MARC polynucleotide to a polynucleotide modifying agent or system. In some embodiments the gene modifying agent can be a programmable nuclease-based system. In some embodiments, the method can include delivering a gene modifying agent to a cell. Compositions and techniques for delivering a gene modifying agent, such as a programmable nuclease-based system described in greater detail elsewhere herein.

Without being bound by theory, modification of a risk MARC variant to a protective MARC variant can result in decreased MARC expression (as compared to the unmodified risk MARC variant) and a protective effect on the liver. In some embodiments, modification of a risk MARC variant to a protective MARC variant can result in an improvement in a liver disease or a symptom thereof in a subject or a cell thereof.

In some embodiments, the expression and/or activity of MARC can be modulated by being knocked-down or inhibited without polynucleotide modification. In some embodiments, the expression of MARC can be knocked-down using an RNAi or antisense RNA approach or by a small molecule agent that can reduce the transcription of a MARC gene (e.g., a histone modulating agent or DNA methylation modulating agent). In some embodiments, MARC activity can be inhibited by an inhibitor, which can be a small molecule agent or other molecule such as an antibody or a fragment thereof. Such agents are described, without limitation, elsewhere herein.

Also described herein are methods of treating a liver disease or a symptom thereof in a subject. The method of treating a liver disease or symptom thereof can include modulating expression and/or activity of MARC in the subject in need thereof. In some embodiments, modulating the expression and/or activity of MARC activity of MARC can include administering an agent capable of modulating MARC expression and/or activity to the subject in need thereof. The effect of the MARC modulation can be evaluated by monitoring liver function, disease progression and/or regression, and/or disease symptom progression and/or regression. In some embodiments, biomarkers of disease and/or liver function can be used. These are described elsewhere herein and/or will be appreciated by those of ordinary skill in the art in view of the description here and elsewhere herein.

As used herein, "treatment" or "treating," or "palliating" or "ameliorating" are used interchangeably. These terms refer to an approach for obtaining beneficial or desired results including, but not limited to, a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

In some embodiments, modulating the expression and/or activity of MARC can include modifying a MARC polynucleotide in the subject. In some embodiments, the MARC being modified is a risk MARC variant. In some embodiments, the MARC polynucleotide can be modified to a protective variant of the MARC polynucleotide. In some embodiments, the subject has a risk MARC polynucleotide. In some embodiments, the method of treating a liver disease or a symptom thereof in a subject can include administering a suitable polynucleotide modifying agent(s) and/or system (or components thereof) capable of modifying a risk MARC variant into a protective MARC variant in the subject or in cell(s) thereof. Suitable polynucleotide modifying agent(s) and/or systems are described in greater detail herein. In some embodiments, one or both copies of the MARC gene are modified in the subject or cell thereof. In some embodiments, only an RNA transcript is modified. In some embodiments, the suitable polynucleotide modifying agent(s) and/or system thereof is a CRISPR-Cas based system. Formulations and methods of delivery of the suitable polynucleotide modifying agent(s), systems thereof, and/or components thereof are described in greater detail elsewhere herein and/or will be appreciated by those of ordinary skill in the art in view of the description herein.

In some embodiments, modulating the expression and/or activity of MARC activity of MARC can include administering, to the subject, a non-polynucleotide modifying agent capable of modulating MARC expression and/or activity. In some of these embodiments, the modulating agent can be an inhibitor of a MARC protein. In some of these embodiments, the modulating agent can be an inhibitor of a MARC risk variant protein. In some of these embodiments, the inhibitor can be a small molecule agent or a biomolecule. In some embodiments, the biomolecule can be an antibody or a fragment thereof. In some of these embodiments, the modulating agent can be an inhibitor of MARC transcription or translation. In some embodiments, the inhibitor of MARC transcription or translation can be an RNAi molecule or system thereof. In some embodiments, the inhibitor of MARC transcription or translation can be an antisense RNA molecule or system thereof. In some embodiments, the inhibitor of MARC can be a small molecule epigenetic modulator. Epigenetic modulators include, without limitation, histone acetylases and deactylases, and DNA methylases and methyl transferases. In some embodiments, the small molecule epigenetic modulator can be decitabine, azacytidine, vorinostat, romidespin, GSK126, C646, JQ1, UNC669, TSA, Valproic Acid, EGCG, zebularine, hydralazine, procainamide, curcumin, givinostat, panobinostat, belinostat, entinostat, CG-1521, romidespin, ITF-A, ITF—B, OSU-HDAC-44, HC-toxin, magnesium valproate, plitidespin, tasquinimod, sodium butyrate, mocetinostat, carbamazepine, SB939, CHR-2845, CHR-3996, JNJ-26481585, sodium phenylbutyrate, pivanex, resveratrol, abexinostat, resminostat, dacinostat, droxinostat, paragyline, clorgyline, bixin, GSK2879552, GSKJ4, KDM5-C70, JIB-04, tranylcypromine, EPZ-6438, GSK-126, CPI360, DZNep, GSK343, EI1, BIX-01294, UNC0638, EPZ004777, UNC0224, CPI203, RVX-208, U-BET151, I-BET762, i-BET-726, UNC1215, combinations thereof, variants thereof, and/or analogs thereof.

In an aspect, the invention provides a method of prophylaxis against a liver disease or a method of treating a liver disease or a method of reducing cholesterol or a method of reducing LDL cholesterol or a method of reducing triglycerides in a subject in need thereof which comprises modulating a component of a mitochondrial amidoxime reductase enzyme system. In certain embodiments, the liver disease comprises cirrhosis, alcoholic cirrhosis, non-alcoholic cirrhosis, hepatitis-related cirrhosis, hepatic steatosis, alcohol-related fatty liver disease (ALD), or nonalcoholic fatty liver disease (NAFLD). In certain embodiments, prophylactic treatment is administered to a subject that exhibits one or more of elevated alanine aminotransferase (ALT), triglyceride (TG), alkaline phosphatase (ALP), total cholesterol, and LDL cholesterol. In certain embodiments, the method is used when a subject is homozygous for a high-risk allele of MARC1 or MARC2. In other embodiments, the method is used when a subject is heterozygous for a high-risk allele of MARC1 or MARC2. In still other embodiments, the method is used when a subject is homozygous for a low risk allele of MARC1 or MARC2.

In certain embodiments of the method, the component of the mitochondrial amidoxime reductase enzyme system comprises mitochondrial reducing component 1 (mARC1) or mitochondrial reducing component 2 (mARC2). In certain embodiments, the modulating comprises modulating the level or modulating the activity of mARC1 or mARC2. In certain embodiments, the level of mARC1 or mARC2 in a cell is modulated by administration of an inhibitory RNA. In certain embodiments, the modulating comprises modulating expression of MARC1 or MARC2 or editing of MARC1 or MARC2. In certain embodiments, the editing comprises DNA editing. In certain embodiments, the editing comprises RNA editing.

In embodiments of the invention, editing may comprise mutating, truncating, or deleting a MARC1 or MARC2 nucleotide sequence or substituting a sequence of one MARC1 or MARC2 allele with a sequence of another, for example, lower risk MARC1 or MARC2 allele. In certain embodiments, editing may comprises mutating a MARC1 or MARC2 nucleotide sequence such that the interaction of the encoded mARC1 or mARC2 protein with a cofactor is modified. In certain embodiments, binding or complex formation of the mARC1 or mARC2 protein with a molybdenum cofactor is modified.

In an aspect, there is provided a method of modulating activity of mARC1 or mARC2 which comprises contacting the mARC1 or mARC2 with an inhibitor or other MARC modulator. In certain embodiments, the inhibitor is administered to a subject. In certain embodiments, the inhibitor is formulated or engineered for delivery to liver cells and/or hepatic tissue.

Diagnosing Liver Disease or Risk Thereof

In some embodiments, liver disease or risk of developing a liver disease can be determined by detecting a MARC variant, such as a MARC risk variant and/or a MARC protective variant in a subject. Subjects having one or more MARC risk variant alleles or polypeptides can be at a higher risk for development of a liver disease as compared to subjects that do not contain one or more MARC risk variant alleles or polypeptides and/or have one or more MARC protective variant alleles or polypeptides. In some embodiments, liver disease can be diagnosed and/or prognosed, at least in part, by detecting a MARC variant, such as a MARC risk variant and/or a MARC protective variant in a subject. In some embodiments, the subject has one or more symptoms of liver disease. In some embodiments, the symptom is cirrhosis. Subjects with symptoms of liver disease not carrying a MARC risk variant allele and/or polypeptide and/or having a MARC protective variant allele and/or polypeptide can have a better prognosis than subjects identified as having a MARC risk variant allele and/or polypeptide. The methods herein can also be used to determine efficacy of a treatment or treatment outcome.

In an aspect, the invention provides a method for evaluating risk of developing liver disease in a subject. In one embodiment, the method comprises detecting whether a MARC1 or MARC2 risk allele is present in the subject, wherein the presence of a MARC1 or MARC2 risk allele indicates that the subject has an increased risk of liver disease, and identifying the subject as having an elevated level of risk for a liver disease if a risk allele of MARC1 or MARC2 is present.

In certain embodiments, the liver disease comprises one or more of alcoholic cirrhosis, non-alcoholic cirrhosis, hepatitis C-related cirrhosis, alcohol-related fatty liver disease (ALD), or nonalcoholic fatty liver disease (NAFLD). In certain embodiments, the method further comprises administering a treatment for the liver disease. In certain embodiments, the method is used to evaluate one or more treatment outcomes in an individual suffering from a liver disease. In other embodiments, the method is used to identify subjects for prophylactic treatment against a liver disease.

In some embodiments, the invention provides a method of evaluating a test candidate or subject for treatment or prophylactic treatment of a liver disorder, which comprises determining the level in the candidate of one or more plasma biomarkers selected from alanine transaminase (ALT), aspartate transaminase (AST), alkaline phosphatase (ALP), total cholesterol, LDL cholesterol, HDL cholesterol, and triglycerides as compared with the level of the one or more plasma biomarkers in control population comprising homozygotes for a low risk MARC1 allele, and/or a control population comprising MARC1 heterozygotes, and/or a control population comprising homozygotes for a high risk MARC1 allele and treating the test subject if the level of the one or more of the biomarkers is present at a level consistent with the level of the one or more biomarker in subject having a MARC1 risk allele. In certain embodiments, the level of ALT and ALP is determined.

The invention provides biomarkers (e.g., phenotype specific or cell type) for the identification, diagnosis, prognosis and manipulation of cell properties, for use in a variety of diagnostic and/or therapeutic indications. Biomarkers in the context of the present invention encompasses, without limitation nucleic acids, proteins, reaction products, and metabolites, together with their polymorphisms, mutations, variants, modifications, subunits, fragments, and other analytes or sample-derived measures. In certain embodiments, biomarkers include those indicative of liver function and MARC variants (e.g., MARC risk variants and MARC protective variants). Such biomarkers are described in greater detail elsewhere herein.

Biomarkers are useful in methods of diagnosing, prognosing and/or staging an immune response in a subject by detecting a first level of expression, activity and/or function of one or more biomarker and comparing the detected level to a control of level, wherein a difference in the detected level and the control level indicates that the presence of an immune response in the subject.

The terms "diagnosis" and "monitoring" are commonplace and well-understood in medical practice. By means of further explanation and without limitation the term "diagnosis" generally refers to the process or act of recognising, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The biomarkers of the present invention are useful in methods of identifying patient populations at risk or suffering from an immune response based on a detected level of expression, activity and/or function of one or more biomarkers. These biomarkers are also useful in monitoring subjects undergoing treatments and therapies for suitable or aberrant response(s) to determine efficaciousness of the treatment or therapy and for selecting or modifying therapies and treatments that would be efficacious in treating, delaying the progression of or otherwise ameliorating a symptom. The biomarkers provided herein are useful for selecting a group of patients at a specific state of a disease with accuracy that facilitates selection of treatments.

The term "monitoring" generally refers to the follow-up of a disease or a condition in a subject for any changes which may occur over time.

The terms also encompass prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a "negative" prediction of such, i.e., that the subject's risk of having such is not significantly increased vis-à-vis a control subject or subject population.

Reference values may be established according to known procedures previously employed for other cell populations, biomarkers and gene or gene product signatures. For example, a reference value may be established in an individual or a population of individuals characterised by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

A "deviation" of a first value from a second value may generally encompass any direction (e.g., increase: first value>second value; or decrease: first value<second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., $\pm 1 \times SD$ or $\pm 2 \times SD$ or $\pm 3 \times SD$, or $\pm 1 \times SE$ or $\pm 2 \times SE$ or $\pm 3 \times SE$). Deviation may also refer to a value falling outside of a reference range defined by values in a given population (for example, outside of a range which comprises $\geq 40\%$, $\geq 50\%$, $\geq 60\%$, $\geq 70\%$, $\geq 75\%$ or $\geq 80\%$ or $\geq 85\%$ or $\geq 90\%$ or $\geq 95\%$ or even $\geq 100\%$ of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

Biomarkers can be evaluated using any suitable technique for a respective biomarker, including, but not limited to, mass spectrometry, immunoassays, hybridization assays, sequencing methods, and combinations thereof. Such techniques are generally known in the art and will be appreciated by those of ordinary skill in the art.

Biomarkers can be evaluated in a sample obtained from a subject. In some embodiments, the sample can be a biological fluid. In some embodiments, the biological fluid is blood or a fraction thereof (e.g., plasma, serum, buffy coat, etc.).

Liver Diseases

In some embodiments, the MARC variant is associated with and/or can result in (directly or indirectly) a reduced risk of a liver disease. In some embodiments, modulating the MARC in a subject can be effective to treat a liver disease or a symptom thereof. In some embodiments, the liver disease is a disease where a symptom or result of the underlying pathological condition or disease is cirrhosis. Such liver diseases or causes can include, but are not limited to, alcoholic cirrhosis (also referred to as alcoholic liver disease), non-alcoholic fatty liver disease (NAFLD) and NAFLD subtypes, viral hepatitis (e.g., chronic viral hepatitis caused by hepatitis B, C, and/or D), hemochromatosis, cystic fibrosis, liver fibrosis, Wilson's disease, biliary atresia, alpha-1 antitrypsin deficiency, inherited disorders of sugar metabolism (e.g., galactosemia or glycogen storage disease), Alagille syndrome, autoimmune hepatitis, primary biliary cirrhosis, primary sclerosing cholangitis, syphilis, brucellosis, medications (e.g., methotrexate and isoniazids).

As the term is used herein "cirrhosis" refers to cirrhosis of the liver and refers to refers to scarring of the liver which results in abnormal liver function as a consequence of chronic liver injury. In some embodiments, described herein are compositions and methods for treatment, prophylaxis, and evaluating risk of cirrhosis.

NAFLD and its subtype, Non-Alcoholic Steatohepatitis, or NASH, are usually seen in individuals with metabolic syndrome (MS) or its components such as obesity, type-2 diabetes (DM), dyslipidemia, and insulin resistance. NASH rarely manifests as inflammation and/or apoptosis/necrosis only, more often than not it is also accompanied by liver fibrosis. It refers to the accumulation of fat, mainly triglycerides, in hepatocytes so that it exceeds 5% of the liver weight. Treatment strategies for NAFLD have revolved around identification and treatment of associated metabolic conditions such as diabetes and hyperlipidemia; improving insulin resistance by weight loss, exercise, or pharmacotherapy; and use of hepatoprotective agents such as antioxidants to protect the liver from secondary insults. In some embodiments, described herein are compositions and methods for treatment, prophylaxis, and evaluating risk of non-alcoholic fatty liver disease.

Alcoholic liver disease (or alcoholic cirrhosis) can be the result of excessive and/or chronic alcoholic consumption. Indeed, excessive and chronic alcohol consumption is an important causal factor of liver fibrosis and/or cirrhosis. The process of the breakdown of ethanol produces two profibrotic agents, acetaldehyde and reactive oxygen species (ROS). Alcoholic liver diseases are often grouped into three histological stages of ALD: fatty liver or simple steatosis, alcoholic hepatitis, and chronic hepatitis with hepatic fibrosis or cirrhosis. These latter stages may also be associated with a number of histological changes including the presence of Mallory's hyaline, mega mitochondria, or perivenular and perisinusoidal fibrosis. Fatty liver develops in about 90% of individuals who drink more than 60 g/day of alcohol, but may also occur in individuals who drink less. Treatment approaches includes inhibition of tumor necrosis factor, antioxidant therapy, stimulation of liver regeneration, and stimulation of collagen degradation. In some embodiments, described herein are compositions and methods for treatment, prophylaxis, and evaluating risk of non-alcoholic fatty liver disease.

Hepatic steatosis results from an imbalance between the uptake of fat and its oxidation and export. Insulin resistance, predisposing to lipolysis of peripheral fat with mobilization to and uptake of fatty acids by the liver, is the most consistent underlying pathogenic factor. Steatosis is observed in alcohol and non-alcohol fatty liver disease. In the context of non-alcoholic fatty liver disease, common causes and conditions associated with steatosis include obesity, insulin resistance, and dyslipidemia. Other factors include starvation, inflammatory bowel disease, and drugs such as glucocorticoids, tamoxifen, amiodarone, valproic acid, zidovudine, didanosine, and halogenated hydrocarbons, and toxic mushrooms. See, e.g., Tolman et al., "Treatment of non-alcoholic fatty liver disease," Therapeutics and Clinical Risk Management, 2007, Vol. 3, pp. 1153-63. Mutations in PNPLA3 (e.g., PNPLA3 p.148M) and TM6SF2 (e.g., Tm6SF2. p.E40K) associated with hepatic steatosis and strongly predispose to the development of alcoholic cirrhosis, non-alcoholic cirrhosis, and hepatitis C-related cirrhosis. Current treatments include pharmacologic therapy targeted toward insulin resistance or dyslipidemia and weight loss as well as physical intervention via bariatric surgery.

As used herein "liver fibrosis" is defined as the building up of excessive amount of extracellular matrix, also known as scar tissue, in the liver parenchyma. Liver fibrosis is the final pathway for most chronic liver disease and is the main reason for increased mortality in affected patients. The extent of liver fibrosis displays great individual variation, even after controlling for age (at infection), gender & exogenous factors. Thus, host genetic factors are likely to play an important role in the process of liver scarring. Loss of hepatic functions, ascites, portal hypertension with an increased risk for esophageal varices and HCC are among the most serious complications that are often fatal. As activation of the hepatic stellate cells (HSCs) is the central event in fibrogenesis, various candidate drugs including rennin-angiotensin system inhibitors, IFN-γ, peroxisomal proliferator activated receptor (PPAR)-γ ligands, pirfenidone, colchicine and herbal medicines that have demonstrated potential in inhibiting HSC activation, proliferation and collagen synthesis have been proposed for the treatment of liver fibrosis. In addition, antioxidants such as vitamin E, silymarin, phosphatidylcholine and S-adenosyl-L-methionine have also been investigated for protection against oxidative stress that may induce hepatic injury and fibrogenesis.

Cholestasis (reduced bile duct excretion) is another well-known cause of liver fibrosis. Cholestasis triggers the proliferation of the cholangiocyte lining of the intrahepatic and extrahepatic bile duct systems through a complex regulatory milieu that involves both autocrine and paracrine factors. Cholestasis i.e., blockage of bile flow, is due to either intrahepatic disorders such as cystic fibrosis, granulomatosis or drug side effects. In Cholestasis, the bile canaliculi are enlarged, the fluidity of the canalicular cell membrane is decreased (cholesterol embedding, bile salt effect), their brush border is deformed (or totally absent) and the function of the cytoskeleton, including canalicular motility, is disrupted. The dihydroxy bile acid, ursodeoxycholic acid (UDCA), is increasingly used for the treatment of chronic cholestatic liver diseases.

Inherited liver diseases are a group of metabolic and genetic defects that typically cause early chronic liver involvement. Most are due to a defect of an enzyme/transport protein that alters a metabolic pathway and exerts a pathogenic role mainly in the liver. Alpha-1 antitrypsin deficiency (AAT) is an autosomal recessive (codominant) disease due to mutations in the SERPINA1 gene that encodes the serine protease inhibitor AAT. The protein, mainly synthesized by liver cells, inhibits proinflammatory proteases such as neutrophil elastase, thus, protecting the lung from proteolytic damage. AAT deficiency has an incidence of 1:2,000-5,000 but the number of diagnosed patients is underestimated. Cystic fibrosis (CF) is a lethal autosomal recessive disease characterized by pancreatic insufficiency in more than 90% of cases and pulmonary disease. Liver disease in CF appears mainly in the first decade of life. It is observed in up to 30% of patients and depends on the altered activity of cystic fibrosis transmembrane regulator (CFTR) chloride channel on the apical membrane of cholangiocytes. Altered activity of CFTR results in increased bile flow leading to cholangitis and fibrosis. Wilson's disease is a genetic condition that causes the build-up of copper in the body, and more particularly the organs including the liver. Mutations of the ATP7B gene, which encodes a copper transporting ATPase, are associated with and/or result in Wilson's disease. There are about 300 known mutations in the ATP7B gene; severe mutations (nonsense, frameshift) are associated with liver disease.

Hereditary hemochromatosis is characterized by iron-induced lipid peroxidation, enhanced serum ferritin and high transferrin saturation. An exemplary mutation is p.C282Y in the HFE gene which is associated with liver cirrhosis.

Type I tyrosinemia is the result of an accumulation of the metabolite succinylacetone, resulting in toxicity to liver. The most frequent mutations resulting in this disease are in the FAH gene.

In some embodiments, the allele encoding threonine is the "risk" allele or the allele associated with increased risk of cirrhosis. The less common allele encoding alanine, which is also referred to in Example 1 as the "effect" or "protective" allele, is associated with reduced risk of cirrhosis and/or liver disease. These MARC variants are described in greater detail elsewhere herein.

Evaluating Liver Function

Some embodiments described throughout will include the evaluation or measurement of liver function. Liver function can be used to diagnose and/or prognose disease and can also be used to determine the efficacy of any treatments or preventatives. Provided herein is a discussion of some normal and abnormal liver values of typically measured parameters that can be used or applied in the evaluation or measurement of liver function as it pertains to the instant invention. Others will be appreciated by those of ordinary skill in the art and will appreciated to be within the scope of the present disclosure. Thus, in some embodiments, the method can include measuring and/or detecting a liver function biomarker, such as any of those described herein, comparing it to a reference value, wherein a value measured falling within the normal reference value(s) can indicate that liver function as measured by that characteristic is normal, wherein a value measured falling outside of the normal reference value(s) can indicate that liver function is abnormal as measured by that characteristic.

Albumin (ALB) is a protein made by the liver. ALB is used to diagnose disease, to monitor changes in health status with treatment, or with disease progression. It can be used to evaluate liver function, and optionally in conjunction with a creatinine or BUN test to evaluate kidney function, or along with prealbumin to evaluate a person's nutritional status. In some embodiments, ALB and/or creatinine values can be determined and similarly used to determine liver function or status in a subject. Normal reference range values for circulating albumin in the blood of humans are about 3.5 to about 5.5 g/dL. In some embodiments, the normal range for albumin can be about 4 to about 6 g/dL/. Normal reference range values for circulating creatinine in the blood of humans are about 0.6 to about 1.2 mg/dL in males and about 0.5 to about 1.1 mg/dl in females. Elevated levels of these can indicate dehydration. Below normal levels can indicate liver disease, insufficient protein intake and can be observed in inflammation, shock, malnutrition, and with conditions where the body does not properly absorb protein (e.g., Crohn's disease and celiac disease). Drugs that can increase albumin levels in the blood include, but are not limited to, anabolic steroids, androgens, growth hormones, and insulin.

Alkaline Phosphatase (ALK PHOS or ALP) is an enzyme found in many organs in the body, including the liver. In conditions that affect the liver, damaged liver cells release increased amounts of ALP into the blood. With some forms of liver disease, such as hepatitis, ALP is often much less elevated than AST and ALT. This test is also used to detect blocked bile ducts. A normal reference range of values for an adult human can be about 30 to 120 IU/L. Children typically have higher normal values. Elevated ALP levels can be a warning sign that there is some type of liver dysfunction resulting in liver tissue damage. Drugs that can increase ALP include, but are not limited to, anti-epileptics. Drugs that can lower ALP include, but are not limited to, oral contraceptives.

Alanine Aminotransferase (ALT or SGPT is a protein found primarily in the liver. ALT is used to detect liver injury and can be used in conjunction with AST to for and/or help diagnose liver disease. AST and ALT are considered to be two of the most important tests to detect liver injury. Sometimes AST is compared directly to ALT and AST/ALT ratio is calculated. The ratio may then be used to distinguish between different causes of liver damage. Very high levels of AT (more than 10 times the highest normal level) are usually due to acute hepatitis. In acute hepatitis, ALT levels usually stay high for 1-2 months but can take much longer to return to normal. ALT levels may also be greatly elevated by exposure to drugs or other substances that are toxic to the liver as well as conditions that cause decreased blood flow to the liver. ALT levels are not usually as high in chronic hepatitis and are often less than 4 times normal range. Other causes of moderate increases in ALT include obstruction of bile ducts, cirrhosis, and tumors in the liver. In most types of liver disease, the ALT level is higher than the AST level, and the AST/ALT ratio will be low. A normal reference ranged for ALT values in blood is less than about 35 U/L. Elevated ALT can indicates that liver tissue damage has occurred as a result of infection, medications, obstruction, cirrhosis or injury to the liver. Drugs that can increase ALT include, but are not limited to, acetaminophen, ampicillin, codeine, dicumarol, indomethacin, methotrexate, oral contraceptives, tetracyclines, and verapamil. Previous intramuscular injections may cause elevated levels. There is no known disease process that results in a low ALT level.

Ammonia levels in the blood can be used in the diagnosis of severe liver diseases and helps to monitor the course of these diseases. It helps to investigate the cause of changes in behavior and consciousness. Ammonia levels are also helpful in the diagnosis and treatment of hepatic encephalopathy, which is a condition caused by the accumulated toxins that result from liver disease and liver failure. Normal values for this test vary widely, depending upon the age of the patient and the type of specimen. A normal reference value can range, for example, from about 10-70 micrograms per dL (heparinized plasma). Drugs that may cause increased levels include alcohol, barbiturates, narcotics, and diuretics. Increased levels may also be seen with GI bleeding, muscular exertion, and tourniquet use. Drugs that may decrease levels include broad-spectrum antibiotics, levodopa, *lactobacillus*, and potassium salts.

Aspartate Aminotransferase (AST or SGOT) is a protein that is found primarily in the liver. It is released into the blood when there has been some sort of liver tissue damage. Elevated levels can indicate tissue damage as a result of such things as obstruction, hepatitis, or cirrhosis. Below normal levels are usually not significant. Things that can increase levels include a shot or injection into the muscle tissue and even strenuous exercise.

Total Bilirubin (TBIL) blood levels can be used to evaluate liver function. Bilirubin is a normal component of red blood cells. When these cells break down, free bilirubin is released in the blood. Bilirubin is then carried to the liver where it is broken down and excreted. When the liver is not functioning properly, bilirubin builds up in the body, causing jaundice (yellowing of the skin and eyes and darkening of the urine). Normal reference values for total bilirubin in the blood can be less than about 1.0 mg/dL. Normal values of direct bilirubin can range from about 0 to about 0.4 mg/dL. Elevated levels can usually be caused by a dysfunction of the system that breaks down bilirubin which includes the liver. Such an elevation can be caused by an obstruction or liver failure. Drugs that may cause increased blood levels of total bilirubin include anabolic steroids, antibiotics, antimalarials, ascorbic acid, diabinese, codeine, diuretics, epinephrine, oral contraceptives, and vitamin A.

5'N'Tase (5'nucleotidase), also known as 5'NT, levels in the blood can be used to evaluate liver function. 5'NT is an intrinsic membrane glycoprotein that is present as an enzyme in a wide variety of mammalian cells. It facilitates the hydrolysis of the phosphate group from 5'-nucleotides, resulting in corresponding nucleosides. A normal reference range can be about 2-15 U/L in the blood. Higher blood levels of the enzyme 5'N'Tase can indicate a problem with bile secretion. Diseases such as hepatitis or cirrhosis can cause a blockage of bile flow.

GGT refers to gamma-glutamyl transferase, but it's also called gamma-glutamyl transpeptidase (GGTP) or Gamma-GT. GGT is an enzyme that is found in many organs throughout the body, with the highest concentrations found in the liver. High levels of GGT are found in the liver, bile ducts, and the kidney. Bloodstream GGT levels will be higher in people with diseases of the liver and bile ducts. A normal reference range for blood GGT levels can be 2-30 U/L in males and 1-24 U/L in females. Drugs that may cause increased GGT levels include, but are not limited to, alcohol, phenytoin, and phenobarbital. Drugs that may cause decreased levels include, but are not limited to, oral contraceptives.

PT (prothrombin time) test measures how quickly the blood clots, which is dependent on clotting factors (proteins) that are made by the liver. The PT test is used as a marker of advanced liver disease and can indicate blood-clotting problems where it takes one longer to stop bleeding. PT results that can be provided as a value that has been to an internationally recognized and easily comparable value that is referred to as the International Normalized Ratio (INR). The INR is one of the three factors used to determine wait time for a liver transplant. The normal reference range for prothrombin time is 11.0-12.5 seconds; 85%-100% (although the normal range can depend on reagents used for PT). If under full anticoagulant therapy the value can be >1.5-2 times control value; 20%-30%. The reference range for the international normalized ratio (INR) is 0.8-1.1.

Further embodiments are illustrated in the following examples which are given for illustrative purposes only and are not intended to limit the scope of the invention.

EXAMPLES

Example 1—Association of Known Alcoholic and Non-Alcoholic Cirrhosis Variants with All-Cause Cirrhosis in UK Biobank To examine whether known alcoholic and non-alcoholic cirrhosis variants associate with all-cause cirrhosis, the association of six known cirrhosis variants (PNPLA3 I48M, TM6SF2 E167K, MBOAT7 rs641738, HSD) 17B13 rs72613567, HFE C282Y and SERPINA1 E366K[4,9,11,12]) with all-cause cirrhosis in UK Biobank (ICD codes K70.2 (alcoholic fibrosis and sclerosis of the liver), K70.3 (alcoholic cirrhosis of the liver), K70.4 (alcoholic hepatic failure), K74.0 (hepatic fibrosis), K74.1 (hepatic sclerosis), K74.2 (hepatic fibrosis with hypertension), K74.6 (other and unspecified cirrhosis of liver), K76.6 (portal hypertension), or 185 (esophageal varices)) was tested. Whether this approach increased power relative to examining subtypes of alcoholic and non-alcoholic cirrhosis was tested by comparing the significance of the association of these variants with all-cause cirrhosis (their Z-scores) to the significance of the association of these variants with alcoholic cirrhosis and with non-alcoholic cirrhosis. Alcoholic cirrhosis was defined as physician-diagnosed alcoholic cirrhosis or alcoholic liver failure (ICD codes K70.2, K70.3 or K70.4). Non-alcoholic cirrhosis was defined as non-alcoholic cirrhosis (ICD codes K74.0, K74.1, K74.2, K74.6, K76.6 or 185) that occurred among individuals who drank less than fourteen alcoholic drinks per week. Former drinkers (individuals who previously consumed alcohol but stopped) were excluded from analysis of non-alcoholic cirrhosis, as these individuals may have previously consumed alcohol but quit due to adverse effects.[23] The association of each of the six variants with all-cause cirrhosis, alcoholic cirrhosis, and non-alcoholic cirrhosis in UK Biobank was tested using logistic regression adjusted for age, sex, ten principal components of ancestry and a dummy variable for array type.

Example 2—Genome Wide Association Study for All-Cause Cirrhosis

A genome wide association study was conducted for all-cause cirrhosis using five cohorts: UK Biobank, Partners Biobank, Atherosclerosis Risk in Communities study (ARIC), and summary statistics from two cohorts from a prior genome wide association study of alcoholic cirrhosis.[4] Definitions of cirrhosis used in each of the five cohorts are provided (Table 7). Cases of cirrhosis secondary to primary biliary cholangitis and primary sclerosis cholangitis were excluded as these autoimmune disorders are directed against the biliary (and not hepatic) parenchyma.[24,25]

For UK Biobank, genotyping was performed using either the UK BiLEVE Axiom array or the UK Biobank Axiom array. Phasing and imputation were performed centrally, by UK Biobank, using the Haplotype Reference Consortium and a reference panel of UK 10K merged with the 1000 Genomes phase 3 panel. One related individual of each related pair of individuals, individuals whose genetic sex did not match self-reported sex and individuals with an excess of missing genotype calls or more heterozygosity than expected were excluded from analysis. For Partners Biobank, genotyping was performed using Illumina MEGA array. Variants were imputed to the HapRef consortium using the Michigan Imputation Server.[26] For ARIC, genotyping was performed using the Affymetrix 6.0 array. Variants were imputed to the HapRef consortium using the Michigan Imputation Server. Any variants with an imputation quality <0.3 were excluded.

Figure 2:
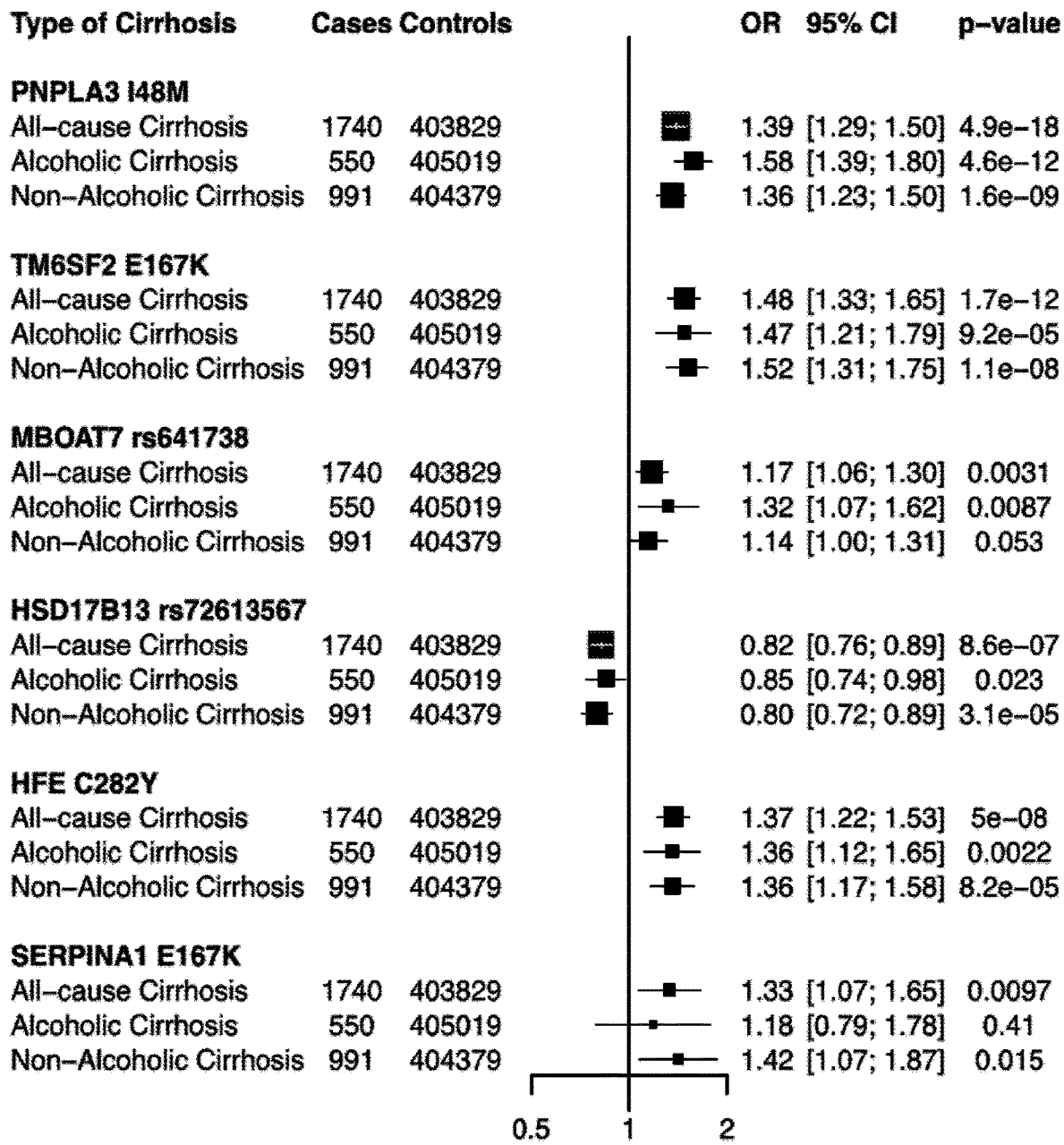
FIG. 2—Association of known alcoholic and non-alcoholic cirrhosis variants with all-cause cirrhosis in UK Biobank.

Genome wide association study in each cohort was performed using logistic regression with adjustment for age, sex and ten principal components of ancestry. The association of fourteen million variants with minor allele frequency of greater than 0.1% with cirrhosis in each cohort was tested. PLINK was used for all analyses.[27] To combine estimates across cohorts, inverse variance fixed effects meta-analysis, as implemented by METAL, was used.[28] Quantile-quantile analysis was used to examine for the presence of population stratification. No evidence of inflation was observed (lambda 1.02; FIG. 2). Both additive and recessive analyses were performed.

Example 3—Replication of the Association of MARC1 p·A165T with Cirrhosis and Fatty Liver The association of MARC1 p·A165T with all-cause cirrhosis was replicated in two cohorts. MARC1 p·A165T associates with physician-diagnosed all-cause cirrhosis in the Vanderbilt BioVU, a DNA databank linked to de-identified electronic health records. 46,328 individuals of European ancestry were identified with genome-wide genotyping as either cases or controls for all-cause cirrhosis. Using ICD-9 (571.2, 571.5, 572.3, 456.0, 456.1, 456.2) or ICD-10 codes (K70.2, K70.3, K70.4, K74.0, K74.1, K74.2, K74.6, K76.6, 185) to define all-cause cirrhosis, 1,328 cases were identified. 45,000 controls were identified using the EHR-based PheWAS approach, which excludes related diseases based on ICD codes.[29] Logistic regression, with adjustment for age, sex and principal components of ancestry, was used to estimate the association of MARC1 p·A165T with cirrhosis in this dataset. Second, 688 cases of all-cause cirrhosis (ICD-10 K70.2, K70.3, K70.4, K74.0, K74.1, K74.2, K74.6, K76.6, 185), and 8,3020 controls were identified in FinnGen. Logistic regression, as implemented in SAIGE30, was used to test the association of MARC1 p·A165T with cirrhosis in this dataset while controlling for age, sex and relatedness within the sample.

To examine whether MARC1 p·A165T associates with fatty liver, the association of this variant with fatty liver in five cohorts was tested. In the Framingham cohort (Offspring Cohort and Third Generation Cohort), association of MARC1 p·A165T with hepatic steatosis on CT imaging was examined. 3,284 individuals in Framingham with genotype data available underwent multidetector abdominal CT.[31] Hepatic steatosis was measured by computing the liver-tophantom ratio of the average Hounsfield units of three liver measurements to average Hounsfield units of three phantom measurements (to correct for inter-individual differences in penetration), as previously described.[31] Association of the p·A165T variant with liver-to-phantom ratio with adjustment for age, sex and ten principal components of ancestry was tested using a linear mixed model to control for relatedness among individuals. In the Multi-Ethnic Study of Atherosclerosis cohort (MESA), 4195 individuals underwent multidetector CT. Hepatic steatosis was measured as the mean of three attenuation measurements (two in the right lobe of the liver and one in the left lobe). No phantom measurement was available for standardization. Therefore the association of the p·A165T variant with mean liver attenuation with adjustment for age, sex and ten principal components of ancestry was tested. Individuals with higher liver fat have lower liver-to-phantom ratios and liver attenuation measurements. Therefore, for interpretability, all estimates are reported in units of standard deviation increases in liver fat, with a one standard deviation increase in liver fat corresponding to a one standard deviation decrease in the liver-to-phantom ratio or mean liver attenuation.

Three cohorts (Partners Biobank, UK Biobank, BioVU) lacked CT imaging data to measure hepatic steatosis. Therefore, the association of the MARC1 p·A165T variant with physician-diagnosed fatty liver in these cohorts (ICD codes K76.0 fatty change of liver, K76.5 non-alcoholic steatohepatitis) was tested using logistic regression, adjusted for age, sex and ten principal components of ancestry. Estimates of the association of MARC1 p·A165T with fatty liver across all five cohorts were pooled using fixed effects meta-analysis.[28]

Example 4—Association of MARC1 p·A165T with Liver Enzyme Levels, Metabolic Traits and Disease The association of p·A165T with metabolic traits was tested using four different datasets. For serum levels of liver enzymes, Data from Partners Biobank (n=26471), Framingham (n=3288), LOLIPOP (n=54857) 32 and BioBank Japan (n=134182) 33 where measures of serum alanine transaminase (ALT), aspartate transaminase (AST) and alkaline phosphatase (ALP) were available, were used. ALT, AST and ALP were log transformed, and a linear regression analysis was conducted with adjustment for age, sex and ten principal components of ancestry. Estimates were pooled across cohorts using inverse variance weighted fixed effects meta-analysis. For lipids (LDL cholesterol, HDL cholesterol, triglycerides and total cholesterol), data from the Global Lipids Genetics Consortium, a meta-analysis of 188,587 individuals of European descent13 was used. This GWAS included 37 studies genotyped using the Illumina Metabochip array as well as an additional 23 studies genotyped using a variety of arrays. For BMI and WHRadjBMI data were used from the Genetic Investigation of ANthropometric Traits (GIANT) consortium.[34,35] For WHRadjBMI, data from 210,088 individuals of European ancestry were included. For BMI, data for 322,154 individuals of European ancestry were included. Individuals were genotyped using various arrays and imputed with the HapMap reference panel to 2.5 million SNPs. Data from UK Biobank were used for blood pressure. The association of p·A165T with systolic blood pressure and diastolic blood pressure was tested using linear regression with adjustment for age, sex and ten principal components of ancestry.

Example 5—Phenome-Wide Association Study for MARC1 p·A165T in UK Biobank

A phenome-wide association study of MARC1 p·A165T in UK Biobank was performed. 36.37 The association of MARC1 p·A165T with diseases with more than one thousand cases in UK Biobank was tested. Definitions for 31 different diseases analyzed in the phenome-wide association study are provided (Table 6). The association of p·A165T with each disease was estimated using logistic regression with adjustment for age, sex, ten principal components of ancestry and a dummy variable for array type. A Bonferroni adjusted significance level of p<0.0016 (0.05/31) was used.

TABLE 6

| Definition of outcomes in phenome wide association study in UK Biobank. | |
|---|---|
| Outcome | Definition (UK Biobank unless otherwise specified) |
| Coronary artery disease | (1) Myocardial infarction (MI), coronary artery bypass grafting, or coronary artery angioplasty documented in medical history at time of enrollment by a trained nurse or (2) Hospitalization for ICD-10 code for acute myocardial infarction (I21.0, I21.1, I21.2, I21.4, I21.9) or (3) Hospitalization for OPCS-4 coded procedure: coronary artery bypass grafting (K40.1-40.4, K41.1-41.4, K45.1-45.5) or (4) Hospitalization for OPCS-4 coded procedure: coronary angioplasty ± stenting (K49.1-49.2, K49.8-49.9, K50.2, K75.1-75.4, K75.8-75.9) |
| Atrial fibrillation/flutter | History of atrial fibrillation or flutter during verbal interview with trained nurse or hospitalization for or death due to ICD code I48 |
| Heart failure | History of heart failure during verbal interview with trained nurse or hospitalization for or death due to ICD code I11.0, I13.0, I13.2, I125.5, I42, I50 |
| Stroke | History of stroke, adjudicated by UK Biobank centrally as report of stroke during verbal interview with trained nurse or hospitalization for or death due to ICD code I60-64 (http://biobank.ctsu.ox.ac.uk/crystal/refer.cgi?id=462) |
| Peripheral vascular disease | History of peripheral vascular disease or intermittent claudication during verbal interview with trained nurse or hospitalization for or death due to ICD code I70, I73.8 or I73.9 |
| Venous thromboembolism | History of venous thromboembolism, deep vein thrombosis or pulmonary embolism during verbal interview with trained nurse or hospitalization for death due to I26, I80.1, I80.2, I81, or I82.0 |

TABLE 6-continued

Definition of outcomes in phenome wide association study in UK Biobank.

| Outcome | Definition (UK Biobank unless otherwise specified) |
| --- | --- |
| Aortic stenosis | History of aortic stenosis during verbal interview with trained nurse or hospitalization for ICD code I06.0, I06.2 I35.0 or I35.2 |
| Inflammatory bowel disease | History of inflammatory bowel disease, Crohn's disease or ulcerative colitis during verbal interview with trained nurse or hospitalization for or death due to ICD code K50 or K51 |
| Gastric reflux | History of gastric reflux during verbal interview with trained nurse or hospitalization for or death due to ICD code K21 |
| Gallstone | History of gallstones during verbal interview with trained nurse or hospitalization for or death due to ICD code K56.3 or K80 |
| Type 2 Diabetes | History of diabetes unspecified, type 2 diabetes during verbal interview with trained nurse or hospitalization for or death due to ICD code E11 |
| Hyperthyroidism | History of hyperthyroidism during verbal interview with trained nurse or hospitalization for or death due to ICD code E05 |
| Hypothyroidism | History of hypothyroidism during verbal interview with trained nurse or hospitalization for or death due to ICD code E03 |
| Gout | History of gout during verbal interview with trained nurse or hospitalization for or death due to ICD code M10 |
| Enlarged prostate | History of enlarged prostate during verbal interview with trained nurse or hospitalization for or death due to ICD code N40 |
| Uterine fibroids | History of uterine fibroids during verbal interview with trained nurse or hospitalization for or death due to ICD code D25 |
| Migraine | History of migraine during verbal interview with trained nurse or hospitalization for or death due to ICD code G43 |
| Depression | History of depression during verbal interview with trained nurse or hospitalization for or death due to ICD code F32 |
| Anxiety | History of anxiety/panic attacks during verbal interview with trained nurse or hospitalization for or death due to ICD code F41 |
| Osteoporosis | History of osteoporosis during verbal interview with trained nurse or hospitalization for or death due to ICD code M80 or M81 |
| Osteoarthritis | History of osteoarthritis during verbal interview with trained nurse or hospitalization for or death due to ICD code M15-19 |
| Sciatica | History of sciatica during verbal interview with trained nurse or hospitalization for or death due to ICD code M54.3 |
| Prolapsed disc | History of prolapsed disc/slipped disc during verbal interview with trained nurse or hospitalization for or death due to ICD code M50.2 or M51.2 |
| Asthma | History of asthma during verbal interview with trained nurse or hospitalization for or death due to ICD code J45 or J46 |
| COPD/Emphysema | History of chronic obstructive airways disease, emphysema/chronic bronchitis or emphysema during verbal interview with trained nurse or hospitalization for or death due to ICD code J41-44 |
| Pneumonia | History of pneumonia during verbal interview with trained nurse or hospitalization for or death due to ICD code J12-18 |
| Hayfever | History of hayfever during verbal interview with trained nurse or hospitalization for or death due to ICD code J30 |
| Lung cancer | History of breast cancer during verbal interview with trained nurse or hospitalization for or death due to ICD code C34 |
| Colorectal cancer | History of large bowel cancer/colorectal cancer, colon cancer/sigmoid cancer or rectal cancer during verbal interview with trained nurse or hospitalization for or death due to ICD code C18 |
| Skin cancer | History of skin cancer, malignant melanoma, non-melanoma skin cancer, basal cell carcinoma or squamous cell carcinoma during verbal interview with trained nurse or hospitalization for or death due to ICD code C43-44 |
| Prostate cancer | History of prostate cancer during verbal interview with trained nurse or hospitalization for or death due to ICD code C61 |
| Cervical cancer | History of cervical cancer or CIN cells at the cervix during verbal interview with trained nurse or hospitalization for or death due to ICD code C53 |

Example 5—Phenome-Wide Association Study for MARC1 p·A165T in UK Biobank

MARC1 p·A165T associated with reduced total cholesterol levels, LDL cholesterol levels, alanine transaminase levels and alkaline phosphatase levels. To examine whether MARC1 deficiency may therefore protect against elevated cholesterol levels and liver enzyme levels, the association of rare predicted loss of function variants in MARC1 with these phenotypes was estimated using five data sources. The association of a rare genotyped stop codon in MARC1 (Arg200Ter, rs139321832) with total and LDL cholesterol in the Global Lipids Genetics Consortium exome chip analysis of 283,474 individuals[14] was examined. Also examined, the association of rare predicted loss of function variants with cholesterol in two exome sequence datasets: the Myocardial Infarction Genetics consortium (n=27034) and the T2D Genes consortium (n=18456). Sequence data for MARC1 were extracted from exome sequencing performed in the MIGen Consortium as previously described.[38,39] The Burrows-Wheeler Aligner algorithm was used to align reads from participants to the reference genome (hg19). The GATK HaploTypeCaller was used to jointly call variants. Metrics including Variant Quality Score Recalibration (VQSR), quality over depth, and strand bias were then used to filter variants. The Jackson Heart Study was excluded from analysis of MIGen as it was included in the T2D Genes consortium. Exome sequencing was performed in the T2D Genes consortium as previously described.[40] To analyze exome sequences from the T2D Genes consortium, the online Genetic Association Interactive Test in the T2D Knowledge portal was used.[40]

Predicted loss of function variants in MARC1 were defined as those which resulted in loss-of-function of the protein (nonsense mutations that resulted in early termination of MARC1, frameshift mutations due to insertions or deletions of DNA, or splice-site mutations which result in an incorrectly spliced protein), as previously described.[41] The Variant Effect Predictor algorithm was used to annotate predicted damaging variants.[42] The variant Arg200Ter was excluded from analysis in MIGEN and T2D Genes to prevent overlap between samples. Estimates were adjusted for age, sex and five principle components of ancestry. Estimates were pooled from all three data sources using inverse variance weighted fixed effects meta-analysis.

Third, the association of the genotyped Arg200Ter variant with log-transformed ALT and ALP levels was also examined using data from the Partners Biobank cohort. The association of this variant with log-transformed ALT and ALP levels was tested using linear regression with adjustment for age, sex and ten principal components of ancestry.

Example 6—Discussion of Examples 1-6

To test the hypothesis that some genetic variants may predispose to all-cause cirrhosis through pathways common to alcoholic and non-alcoholic cirrhosis, an all-cause liver cirrhosis phenotype was created in UK Biobank, combining the following ICD10 diagnostic codes: K70.2 (alcoholic fibrosis and sclerosis of the liver), K70.3 (alcoholic cirrhosis of the liver), K70.4 (alcoholic hepatic failure), K74.0 (hepatic fibrosis), K74.1 (hepatic sclerosis), K74.2 (hepatic fibrosis with hepatic sclerosis), K74.6 (other and unspecified cirrhosis of liver), K76.6 (portal hypertension), or 185 (esophageal varices). Using this definition, 1,740 cases of cirrhosis were identified in UK Biobank. The association of all-cause cirrhosis with six genetic variants previously reported to be associated with alcoholic or non-alcoholic cirrhosis was examined: PNPLA3 I48M, TM6SF2 E167K, MBOAT7 rs641738, HSD17B13 rs72613567, HFE C282Y and SERPINAI E366K.[4,9,11,12] All six variants associated with all-cause cirrhosis in UK Biobank (FIG. 2). Each variant exhibited greater statistical significance with all-cause cirrhosis than with alcoholic or non-alcoholic subtypes in UK Biobank, with an average 30% gain in power by analyzing all-cause cirrhosis compared to non-alcoholic cirrhosis and an 87% gain in power compared to analyzing alcoholic cirrhosis.

Figure 3:
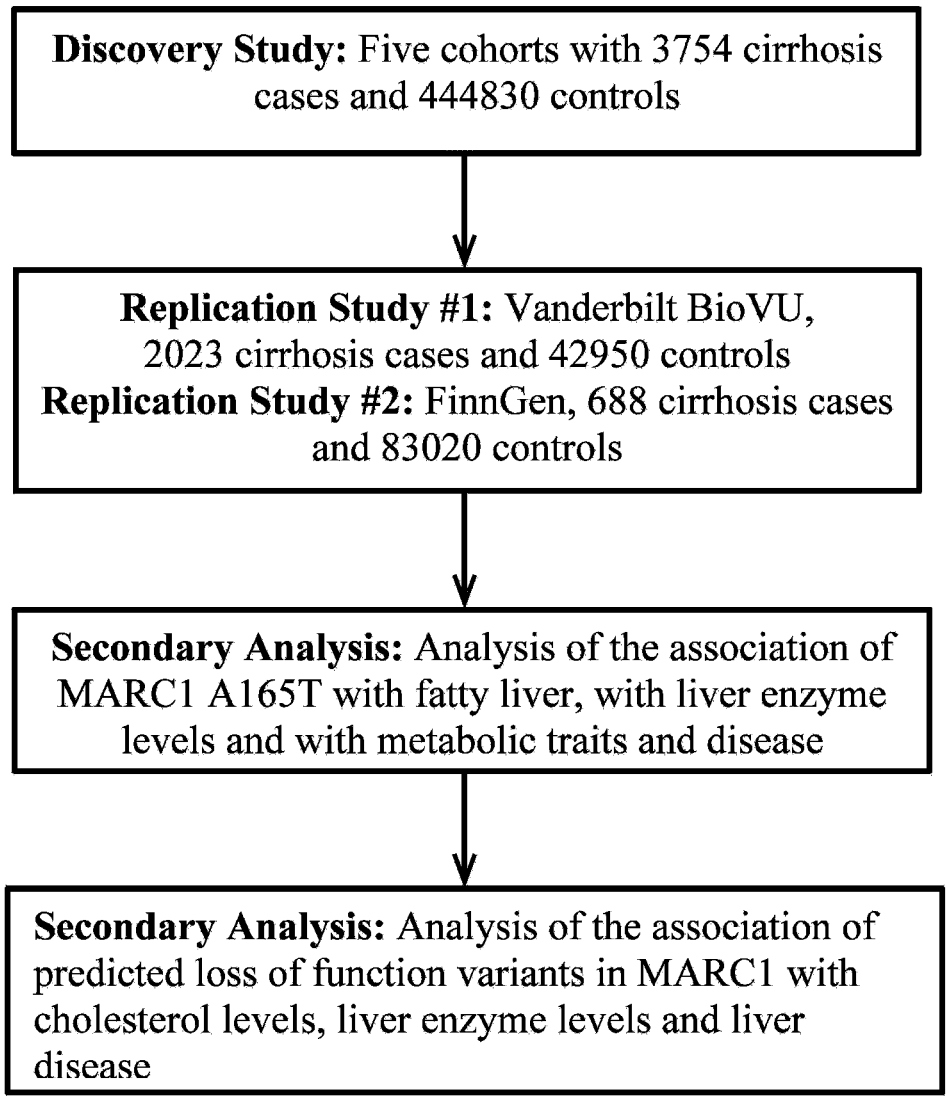
FIG. 3—A schematic of experimental design.
Figure 4:
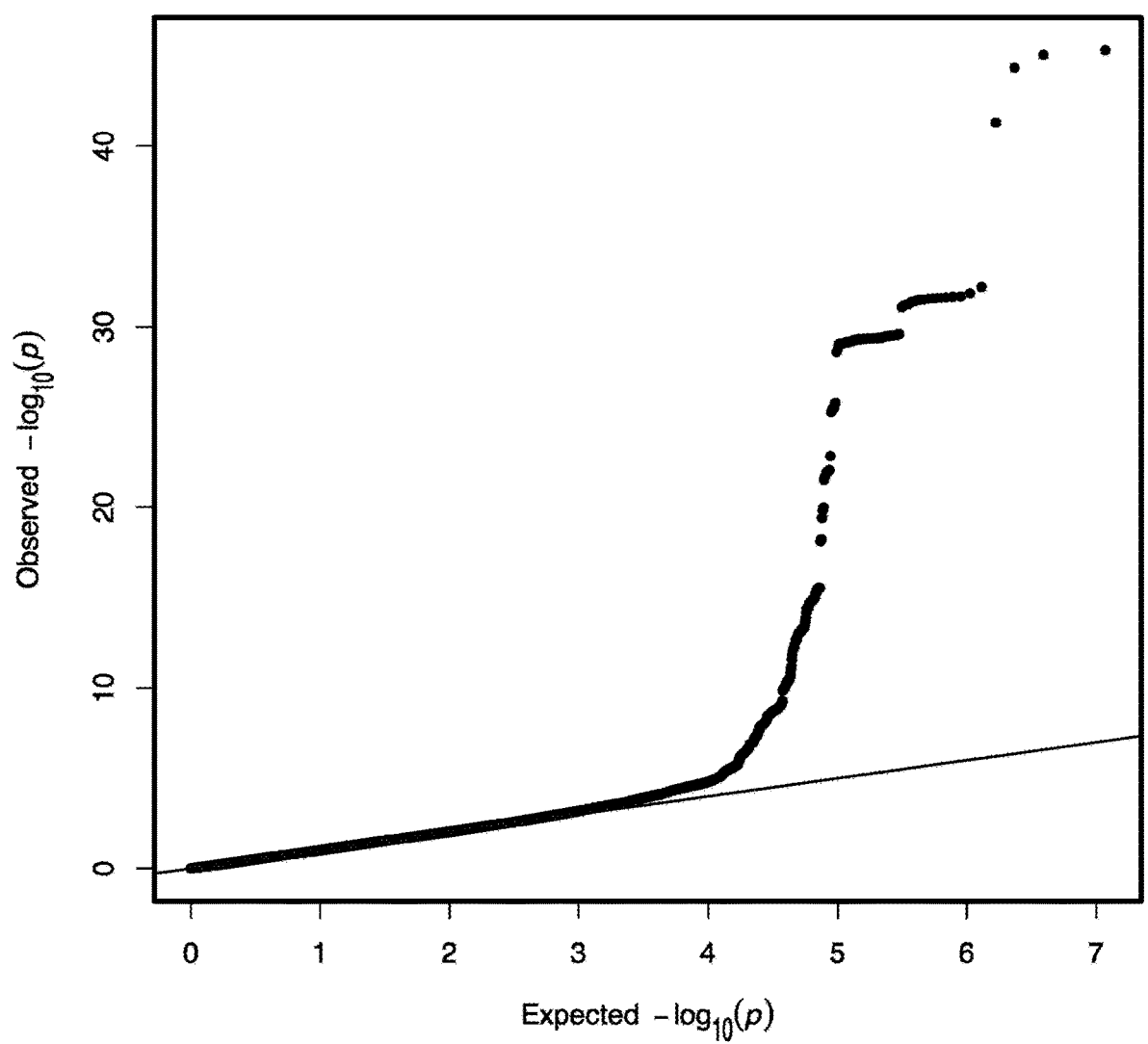
FIG. 4—A QQ plot for genome wide analysis of cirrhosis. Lambda=1.02.

Having established that an analysis of all-cause cirrhosis would provide improved statistical power, novel genetic determinants of all-cause cirrhosis were identified through a discovery genome-wide association analysis followed by replication (FIG. 3). In the discovery analysis, 3,754 all-cause cirrhosis cases and 444,830 controls from five cohorts were analyzed (Table 7).

TABLE 7

Definition of cirrhosis in each cohort.

| Cohort | Definition of cirrhosis | Cases | Controls | Individual-level data |
|---|---|---|---|---|
| UK Biobank | Hospitalization or death due to physician diagnosed cirrhosis: K70.2 (alcoholic fibrosis and sclerosis of the liver), K70.3 (alcoholic cirrhosis), K70.4 (alcoholic hepatic failure), K74.0 (hepatic fibrosis), K74.1 (hepatic sclerosis), K74.2 (hepatic fibrosis with hepatic sclerosis), K74.6 (other and unspecific cirrhosis of liver), K76.6 (portal hypertension), or 185 (esophageal varices) | 1,740 | 403,829 | Yes |
| Partners Biobank | Hospitalization or death due to physician diagnosed cirrhosis: K70.2 (alcoholic fibrosis and sclerosis of the liver), K70.3 (alcoholic cirrhosis), K70.4 (alcoholic hepatic failure), K74.0 (hepatic fibrosis), K74.1 (hepatic sclerosis), K74.2 (hepatic fibrosis with hepatic sclerosis), K74.6 (other and unspecific cirrhosis of liver), K76.6 (portal hypertension), or 185 (esophageal varices) | 1,214 | 29,502 | Yes |
| ARIC | Hospitalization or death due to physician diagnosed cirrhosis: K70.2 (alcoholic fibrosis and sclerosis of the liver), K70.3 (alcoholic cirrhosis), K70.4 (alcoholic hepatic failure), K74.0 (hepatic fibrosis), K74.1 (hepatic sclerosis), K74.2 (hepatic fibrosis with hepatic sclerosis), K74.6 (other and unspecific cirrhosis of liver), K76.6 (portal hypertension), or 185 (esophageal varices) | 88 | 1,0034 | Yes |
| Alcoholic cirrhosis | Presence of cirrhosis on liver biopsy (fibrosis stage 5 or 6) or unequivocal clinical and | 410 | 1,119 | No |

TABLE 7-continued

Definition of cirrhosis in each cohort.

| Cohort | Definition of cirrhosis | Cases | Controls | Individual-level data |
|---|---|---|---|---|
| GWAS: German Cohort | laboratory evidence for the presence of cirrhosis | | | |
| Alcoholic cirrhosis GWAS: UK Cohort | Histological examination of liver tissue or compatible historical, clinical, laboratory, radiological and endoscopic features | 302 | 346 | No |
| Total | | 3,754 | 444,830 | |

Figure 5:
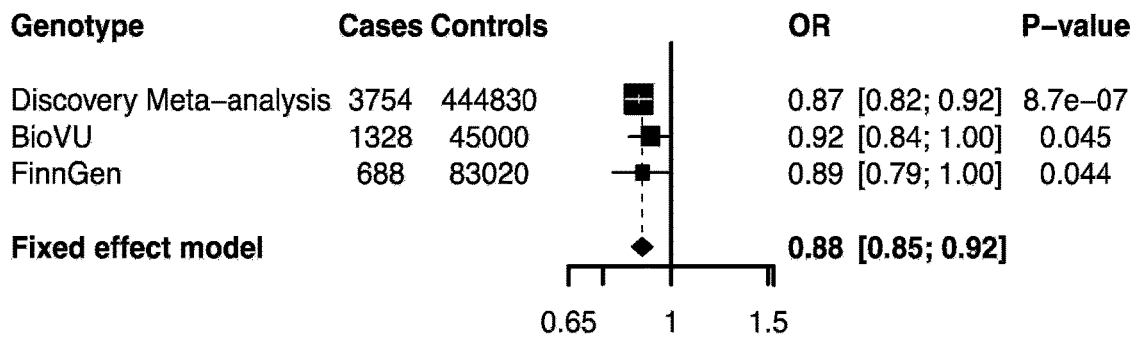
FIG. 5—Association of MARC1 p·A165T with cirrhosis and fatty liver in discovery and replication datasets.
Figure 5:
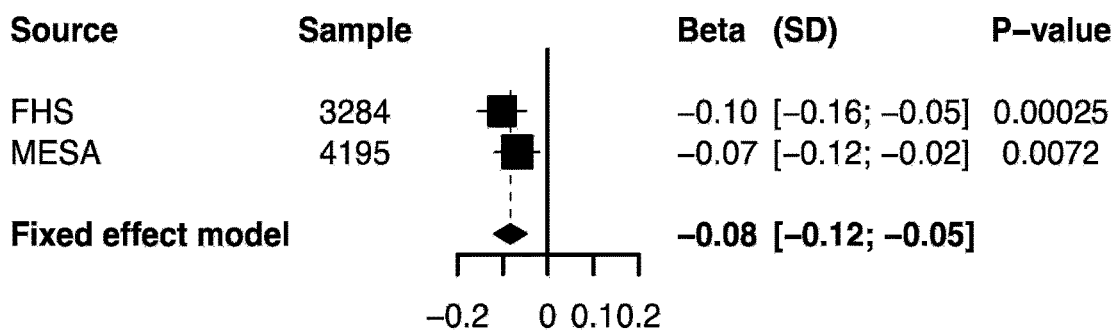
Figure 5:
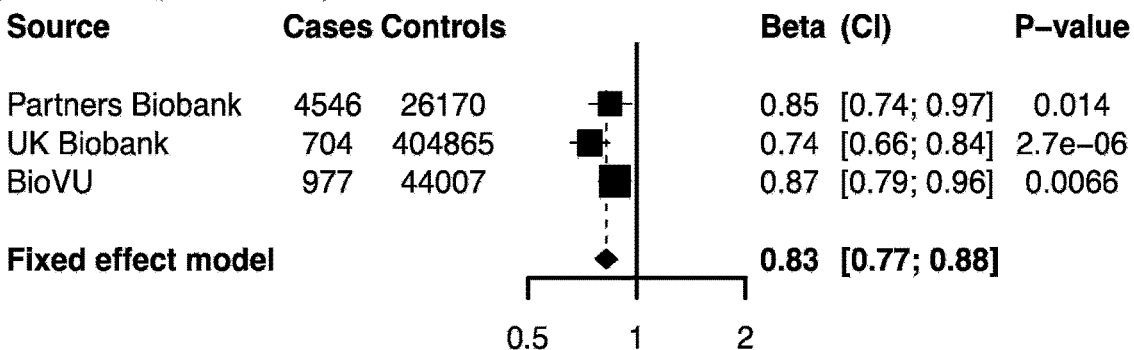

The association of 14 million genetic variants with minor allele frequency >0.1% with all-cause cirrhosis in both additive and recessive models was tested. No evidence of genomic inflation was observed (lambda 1.02, FIG. 4). Known associations of PNPLA3, TM6SF2 and HDS17B13 variants with cirrhosis were replicated at genome-wide significance (Table 8) and the HFE p.C282Y variant (the most cause of hemochromatosis in populations of European ancestry) was identified as associated with all-cause cirrhosis in a recessive model (OR 3.2, p=$1.3*10^{-14}$).[11] No other variants were associated with all-cause cirrhosis at genome-wide significance.

from the discovery and replication studies are combined, MARC1 p·A165T associated with protection from cirrhosis at a significance level exceeding genome wide significance (OR 0.88, p=$2*10^{-8}$, FIG. 5). No evidence of heterogeneity in the association of MARC1 p·A165T with all-cause cirrhosis in the discovery analysis and replication analyses was observed (p=0.64).

The association of MARC1 p·A165T with fatty liver (definitions provided in Table 9) was examined. MARC1 p·A165T was associated with reduced hepatic fat on computed tomographic imaging in both the Framingham Heart Study and Multi-ethnic Study of Atherosclerosis cohorts

TABLE 8

DNA sequence variants associated with all-cause cirrhosis in the discovery analysis

| Model | Variant | CHR | EA | EAF | Gene | Annotation | OR | p-value |
|---|---|---|---|---|---|---|---|---|
| Additive | rs2642438 | 1 | A | 25% | MARC1 | Missense: p.A165T | 0.87 | $8.7 * 10^{-7}$ |
| Additive | rs72613567 | 4 | TA | 22% | HSD17B13 | Splice Variant | 0.82 | $4.5 * 10^{-8}$ |
| Additive | rs58542926 | 19 | T | 7% | TM6SF2 | Missense: p.E167K | 1.42 | $9.7 * 10^{-24}$ |
| Additive | rs738409 | 22 | G | 26% | PNPLA3 | Missense: p.148M | 1.47 | $2.2 * 10^{-67}$ |
| Recessive | rs1800562 | 6 | A | 3% | HFE | Missense: p.C282Y | 3.2 | $1.3 * 10^{-14}$ |

CHR: chromosome,
EA: effect allele,
EAF: effect allele frequency

The lead coding variant at sub-genome wide significance was a missense variant in MARC1 (p·A165T) that was associated with lower risk of all-cause cirrhosis (OR 0.87, p=$8.7*10^{-7}$, minor allele frequency 25%). This observation was replicated in two independent studies-BioVU and the FinnGen Consortium. MARC1 p·A165T associated with protection from cirrhosis in BioVU (OR 0.92, p=0.045) and in FinnGen (0.89, p=0.044). When the statistical evidence ($-0.08$ SD, p=$8.2*10^{-6}$). MARC1 p·A165T also associated with reduced risk of physician-diagnosed fatty liver in three biobank studies (OR 0.83, p=$1.90*10^{-8}$). In UK Biobank, a similar association of MARC1 p·A165T with all-cause cirrhosis (OR 0.84, p=$1.0*10^{-5}$) and fatty liver (OR 0.74, p=$2.3*10^{-6}$) was observed when number of medications taken by each participant was adjusted for.

TABLE 9

Definition of fatty liver in each cohort

| Cohort | Definition of cirrhosis | Cases | Controls | Individual-level data |
|---|---|---|---|---|
| Framingham | CT: Ratio of mean of liver attenuation measurements to phantom measurement | 3,284 | | Yes |
| MESA | CT: Mean of three liver attenuation measurements | 4,195 | | Yes |
| UK Biobank | Physician diagnosed: K76.0 (fatty change of liver), K76.5 (non-alcoholic steatohepatitis) | 704 | 40,4865 | Yes |

TABLE 9-continued

Definition of fatty liver in each cohort

| Cohort | Definition of cirrhosis | Cases | Controls | Individual-level data |
|---|---|---|---|---|
| Partners Biobank | Physician diagnosed: K76.0 (fatty change of liver), K76.5 (non-alcoholic steatohepatitis) | 4,546 | 26,170 | Yes |
| BioVU | Physician diagnosed: K76.0 (fatty change of liver), K76.5 (non-alcoholic steatohepatitis) | 977 | 44,007 | Yes |
| Total | | | 488748 | |

Having established that MARC1 p·A165T associates with protection from all-cause cirrhosis as well as fatty liver, the association of this variant with plasma biomarkers-alanine transaminase (ALT), aspartate transaminase (AST), alkaline phosphatase (ALP), total cholesterol, LDL cholesterol, HDL cholesterol, and triglycerides—was tested. MARC1 p·A165T associated with lower ALT levels (−0.012 SD, p=$1.4*10^{-8}$) and ALP levels (−0.019 SD, p=$6.6*10^{-9}$) but was not associated with AST levels (−0.005 SD, p=0.12).

In previously published work from the Global Lipids Genetics Consortium, MARC1 p·A165T associated with lower total cholesterol (−0.037, p=$1.3*10^{-18}$) and low-density lipoprotein (LDL) cholesterol (−0.035, p=$7.3*10^{-16}$) 13. MARC1 p·A165T associated with higher triglyceride levels (0.017 SD, p=$5*10^{-6}$) and lower HDL levels (−0.030 SD, p=$7.8*10^{-14}$, Table 10) but did not associate with blood pressure, body mass index or waist-to-hip ratio.

TABLE 10

Association of MARC1 A165T with metabolic traits

| Outcome | Source | n | Beta | SE | p-value |
|---|---|---|---|---|---|
| Liver enzymes | | | | | |
| ALT | Partners Biobank, Framingham, LOLIPOP, BioBank Japan, BioVU | 261614 | −0.012 | 0.003 | $1.4 * 10^{-8}$ |
| AST | Partners Biobank, Framingham, LOLIPOP, BioBank Japan | 221662 | −0.005 | 0.003 | 0.12 |
| AP | Partners Biobank, Framingham, LOLIPOP, BioBank Japan | 164664 | −0.019 | 0.003 | $6.6 * 10^{-9}$ |
| Blood lipids | | | | | |
| Total Cholesterol | GLGC | 188577 | −0.037 SD | 0.004 | $1.3 * 10^{-18}$ |
| LDL Cholesterol | GLGC | 188577 | −0.035 SD | 0.004 | $7.3 * 10^{-16}$ |
| HDL Cholesterol | GLGC | 188577 | −0.030 SD | 0.004 | $7.8 * 10^{-14}$ |
| Triglycerides | GLGC | 188577 | 0.017 SD | 0.004 | $5.3 * 10^{-6}$ |
| Blood pressure | | | | | |
| Systolic blood pressure | UK Biobank | 379771 | 0.001 SD | 0.002 | 0.55 |
| Diastolic blood pressure | UK Biobank | 379782 | 0.003 SD | 0.003 | 0.19 |
| Anthropometric measurements | | | | | |
| Body mass index | GIANT | 325053 | 0.005 SD | 0.003 | 0.17 |
| Waist to hip ratio adjusted for body mass index | GIANT | 211816 | 0.006 SD | 0.004 | 0.15 |

Figure 6:
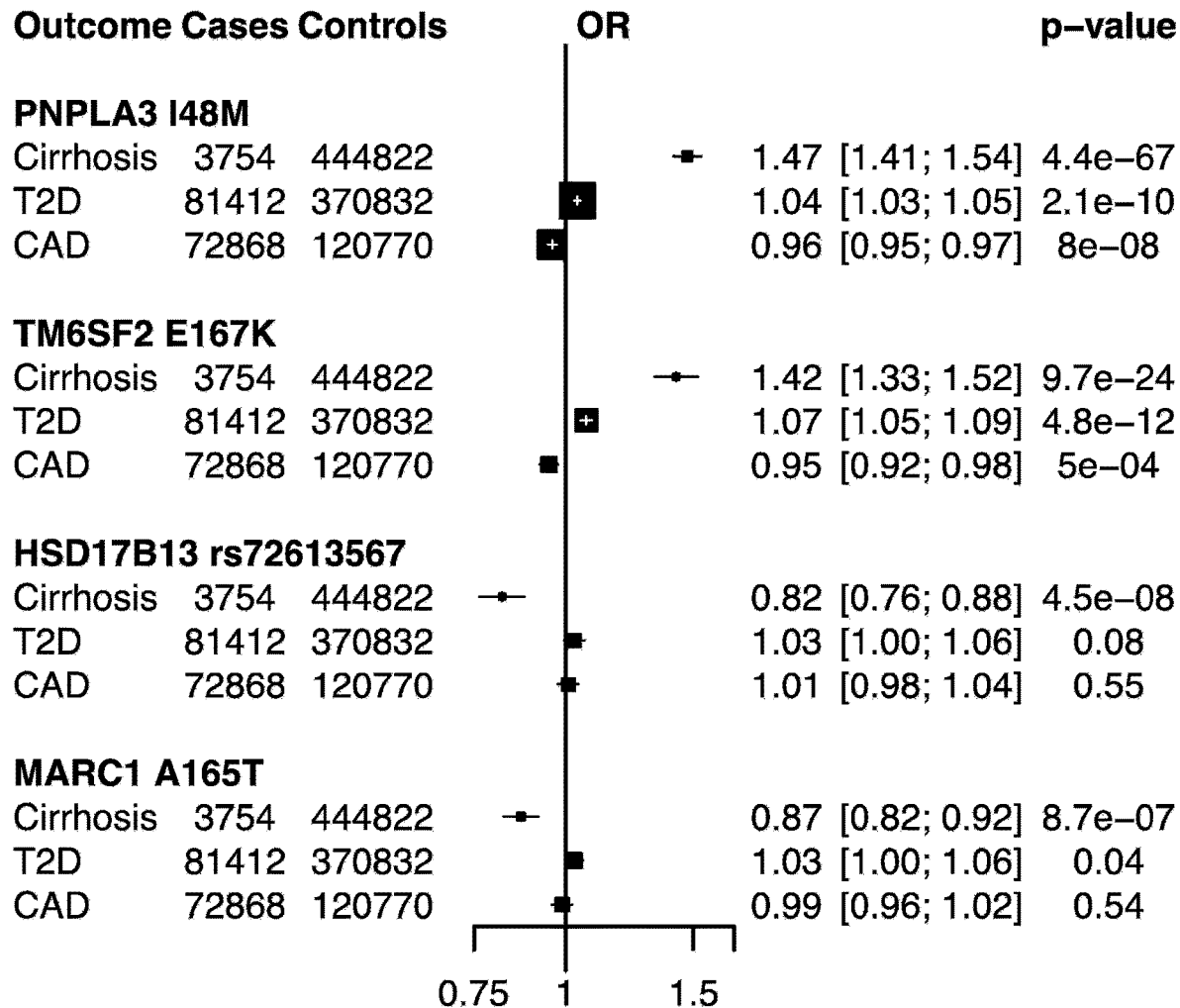
FIG. 6—Association of cirrhosis variants with type 2 diabetes, coronary artery disease and cirrhosis.
Figure 7:
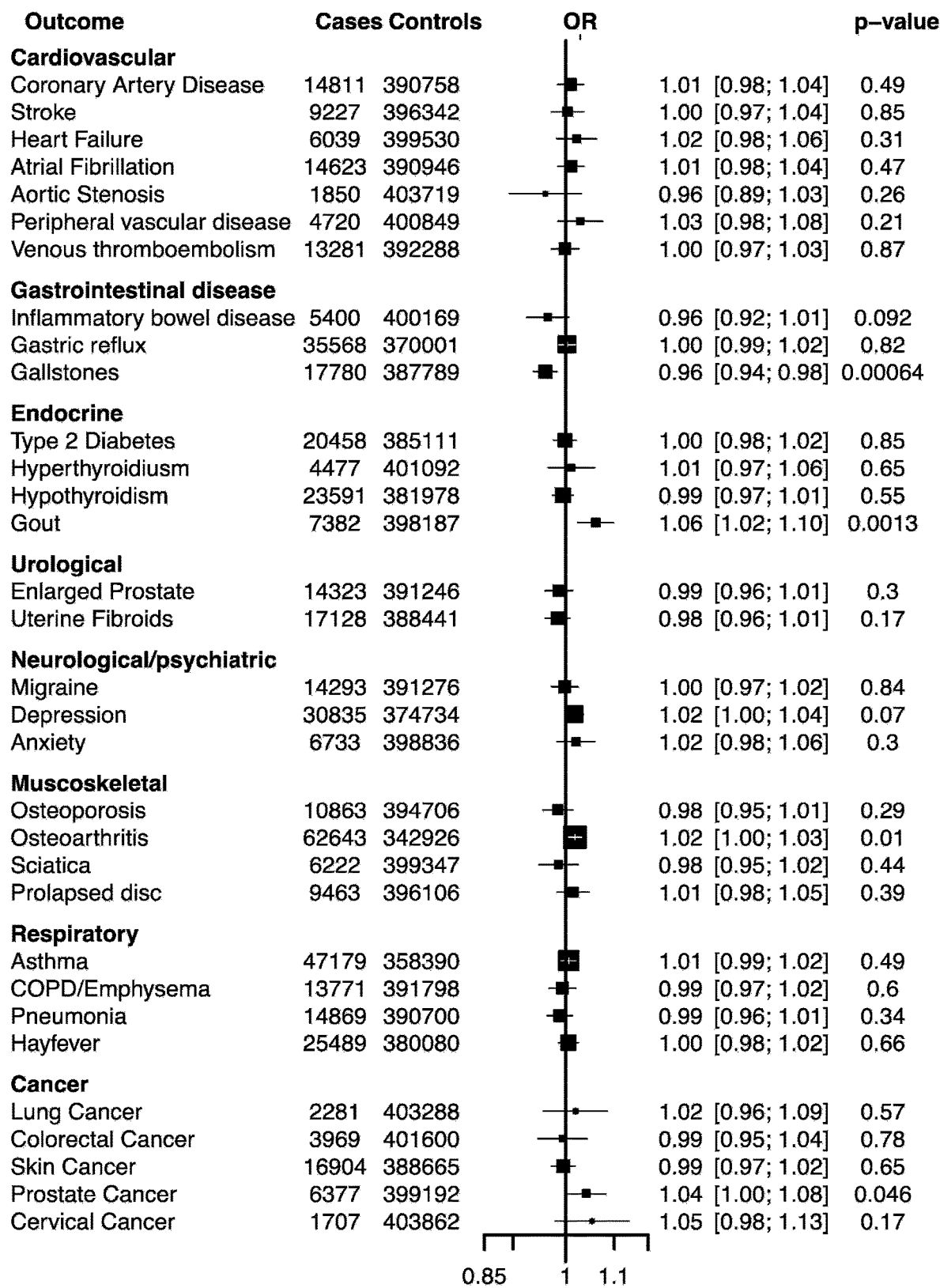
FIG. 7—Association of MARC p·A165T with other diseases in a phenome wide association study.

GLGC: Global lipids genetics consortium, GIANT: Genetic investigation of anthropometric traits consortium, SD: standard deviations Variants in PNPLA3 and TM6SF2 that decrease risk of cirrhosis have been reported to increase risk for coronary artery disease (CAD).[14] This raises the possibility that treatment of cirrhosis (e.g., through MARC1 or HSD17B13 inhibition) may have adverse cardiovascular effects. Therefore, whether MARC1 p·A165T increases CAD risk was examined. In contrast to PNPLA3 and TM6SF2, neither MARC1 p·A165T nor HSD17B13 rs72613567 associated with risk of CAD (FIG. 6).[15] In a phenome wide association study in UK Biobank, MARC1 p·A165T associated with a lower risk of gallstones (OR 0.96, p=0.0006) and an elevated risk of gout (OR 1.06, p=0.001, FIG. 7).

Figure 8:
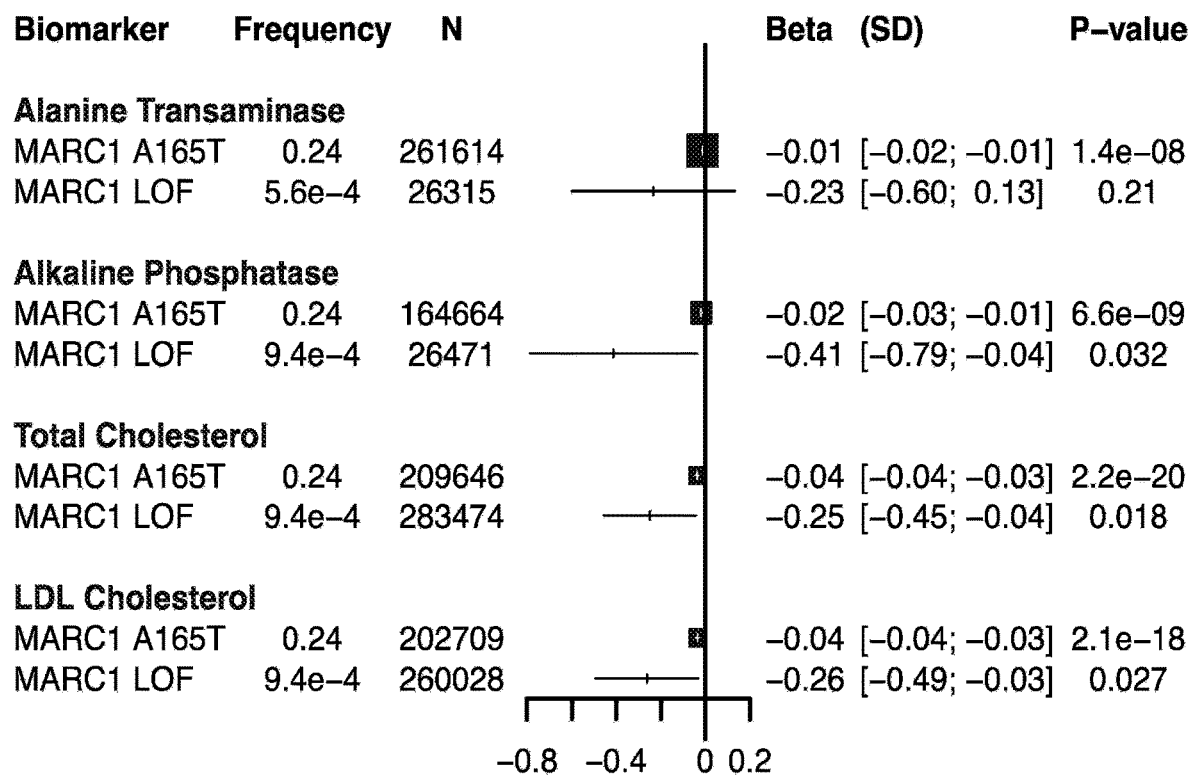
FIG. 8—Association of MARC1 p·A165T and predicted loss of function variants in MARC1 with alanine transaminase, alkaline phosphatase, total cholesterol and LDL cholesterol.

Finally, using two approaches, it was determined whether loss or gain of MARC1 function might be responsible for the protection from cirrhosis and the reduced levels of ALT, ALP, total cholesterol, and LDL cholesterol. In the first approach, a rare nonsense mutation observed early in the MARC1 gene (p·R200Ter) was leveraged. In a combined analysis of UK Biobank, Partners Biobank, MESA and Framingham, one case of liver disease (either fatty liver or cirrhosis) was observed among 110 carriers of MARC1 R200Ter compared to 7,629 cases of liver disease among 446,965 non-carriers (adjusted odds ratio 0.19, p=0.04). Second, sequence data was assembled for MARC1 in 45,493 individuals and identified 22 carriers of MARC1 p·R200Ter and 21 carriers of other predicted loss of function variants (Tables 11 and 12). Carriers of predicted loss of function variants in MARC1 (early truncation, splice site and frameshift variants) had lower ALP levels (−0.41 SD, p=0.032), total cholesterol levels (−0.25 SD, p=0.018) and LDL cholesterol levels (−0.26 SD, p=0.027, FIG. 8) and had non-significantly lower ALT levels (−0.23 SD, p=0.21, FIG. 8).

Combined, these findings indicate that MARC1 loss of function protects against cirrhosis.

TABLE 11

Rare predicted loss of function variants in MIGEN

| CHR:POS_REF/ALT | Consequence | Amino Acid Change | Individuals With Variant |
|---|---|---|---|
| 1:220970148_G/A | Splice Donor | | 2 |
| 1:220970148_G/C | Splice Donor | | 1 |
| 1:220971357_G/A | Splice Donor | | 1 |
| 1:220978456_G/A | Splice Donor | | 2 |
| 1:220978457_T/C | Splice Donor | | 1 |
| 1:220986659_C/T | Stop Gained | Arg305Ter | 2 |
| 1:220986755_C/T | Stop Gained | Gln337Ter | 3 |
| Total | | | 12 |

TABLE 12

Rare predicted loss of function variants in T2D Genes

| CHR:POS_REF/ALT | Consequence | Amino Acid Change | Individuals With Variant |
|---|---|---|---|
| 1:220960469_TG/T | Frameshift | Trp62fs | 2 |
| 1:220960562_G/A | Splice Donor | | 1 |
| 1:220970097_C/T | Stop Gained | Arg188Ter | 1 |
| 1:220978402_G/A | Stop Gained | Trp254Ter | 2 |
| 1:220986659_C/T | Stop Gained | Arg305Ter | 2 |
| 1:220986728_TG/T | Frameshift | Val328fs | 1 |
| Total | | | 9 |

In summary, MARC1 is identified as a novel genetic determinant of fatty liver and all-cause cirrhosis and suggest that MARC1 deficiency protects against liver disease and reduces blood levels of several biomarkers-ALT, ALP, total cholesterol, and LDL cholesterol. MARC1 encodes mitochondrial amidoxime-reducing component, a molybdenum-containing enzyme that is involved in metabolizing prodrugs in the liver.[16] It contains an N-terminal transmembrane helix that anchors the protein to the outer mitochondrial membrane, with the enzymatic domain of MARC1 located in the cytosol.[17] The crystal structure of MARC1 was recently described.[18] The molybdenum cofactor is coordinated in a solvent exposed center by predominantly positively charged amino acids. The A165 residue lies within an alpha helix in the N-terminal domain of MARC1. The function of MARC1 is unknown, however, it has been reported to activate N-hydroxylated prodrugs[19], reduce nitrite to produce nitric oxide[20] and detoxify trimethylamine N-oxide.[21] The mechanism by which MARC1 may contribute to liver damage and cirrhosis is unclear. The lack of association of MARC1 p·A165T and HSD17B13 rs72613567 with CAD (in contrast to PNPLA3 and TM6SF2) suggests that pharmacologic treatment of cirrhosis and hepatic steatosis may not universally cause excess cardiovascular risk.

Despite the substantial burden of disease posed by cirrhosis worldwide[22], identification of genetic risk factors has been limited relative to other common diseases such as type 2 diabetes, coronary artery disease or inflammatory bowel disease. In addition to targeted analyses of cirrhosis subtypes[4], joint analysis of alcoholic and non-alcoholic cirrhosis cases from multiple cohorts can increase power to identify genetic variants that influence cirrhosis through pathways common to alcoholic and non-alcoholic disease, identify therapeutic targets, and improve understanding of this disease.

REFERENCES FOR EXAMPLES 1-6

1. Schuppan, D. & Afdhal, N. H. Liver cirrhosis. Lancet 371, 838-851 (2008).
2. Romeo, S. et al. Genetic variation in PNPLA3 confers susceptibility to nonalcoholic fatty liver disease. Nat. Genet. 40, 1461-1465 (2008).
3. Kozlitina, J. et al. Exome-wide association study identifies a TM6SF2 variant that confers susceptibility to non-alcoholic fatty liver disease. Nat. Genet. 46, 352-356 (2014).
4. Buch, S. et al. A genome-wide association study confirms PNPLA3 and identifies TM6SF2 and MBOAT7 as risk loci for alcohol-related cirrhosis. Nat. Genet. 47, 1443-1448 (2015).
5. Speliotes, E. K. et al. PNPLA3 variants specifically confer increased risk for histologic nonalcoholic fatty liver disease but not metabolic disease. Hepatology 52, 904-912 (2010).
6. Liu, Y.-L. et al. TM6SF2 rs58542926 influences hepatic fibrosis progression in patients with non-alcoholic fatty liver disease. Nat Commun 5, 4309 (2014).
7. Valenti, L. et al. Patatin-like phospholipase domain-containing 3 I148M polymorphism, steatosis, and liver damage in chronic hepatitis C. Hepatology 53, 791-799 (2011).
8 Liu, Z. et al. The effect of the TM6SF2 E167K variant on liver steatosis and fibrosis in patients with chronic hepatitis C: a meta-analysis. Sci Rep 7, 9273 (2017).
9. Abul-Husn, N. S. et al. A Protein-Truncating HSD17B13 Variant and Protection from Chronic Liver Disease. N. Engl. J. Med. 378, 1096-1106 (2018).
10. About, F., Abel, L. & Cobat, A. HCV-Associated Liver Fibrosis and HSD17B13. N. Engl. J. Med. 379, 1875-1876 (2018).
11. Bacon, B. R. et al. Diagnosis and management of hemochromatosis: 2011 practice guideline by the American Association for the Study of Liver Diseases. Hepatology (Baltimore, Md.) 54, 328-343 (2011).
12. Dürr, R. & Caselmann, W. H. Carcinogenesis of primary liver malignancies. Langenbecks Arch Surg 385, 154-161 (2000).
13. Global Lipids Genetics Consortium et al. Discovery and refinement of loci associated with lipid levels. Nat. Genet. 45, 1274-1283 (2013).
14. Liu, D. J. et al. Exome-wide association study of plasma lipids in >300,000 individuals. Nat. Genet. 49, 1758-1766 (2017).
15. Myocardial Infarction Genetics and CARDIOGRAM Exome Consortia Investigators. Coding Variation in ANGPTL4, LPL, and SVEP1 and the Risk of Coronary Disease. N.

Engl. J. Med. 374, 1134-1144 (2016).
16. Havemeyer, A. et al. Identification of the missing component in the mitochondrial benzamidoxime prodrug-converting system as a novel molybdenum enzyme. J. Biol. Chem. 281, 34796-34802 (2006).
17. Klein, J. M. et al. The mitochondrial amidoxime-reducing component (mARC1) is a novel signal-anchored protein of the outer mitochondrial membrane. J. Biol. Chem. 287, 42795-42803 (2012).

18. Kubitza, C. et al. Crystal structure of human mARC1 reveals its exceptional position among eukaryotic molybdenum enzymes. Proc. Natl. Acad. Sci. U.S.A. 34, 201808576 (2018).
19. Gruenewald, S. et al. The fourth molybdenum containing enzyme mARC: cloning and involvement in the activation of N-hydroxylated prodrugs. J Med Chem 51, 8173-8177 (2008).
20. Sparacino-Watkins, C. E. et al. Nitrite reductase and nitric-oxide synthase activity of the mitochondrial molybdopterin enzymes mARC1 and mARC2. J. Biol. Chem. 289, 10345-10358 (2014).
21. Schneider, J., Girreser, U., Havemeyer, A., Bittner, F. & Clement, B. Detoxification of Trimethylamine N-Oxide by the Mitochondrial Amidoxime Reducing Component mARC. Chem. Res. Toxicol. 31, 447-453 (2018).
22. Lozano, R. et al. Global and regional mortality from 235 causes of death for 20 age groups in 1990 and 2010: a systematic analysis for the Global Burden of Disease Study 2010. 380, 2095-2128 (2012).
23. Roerecke, M. & Rehm, J. Ischemic heart disease mortality and morbidity rates in former drinkers: a meta-analysis. American journal of epidemiology 173, 245-258 (2011).
24. Qiu, F. et al. A genome-wide association study identifies six novel risk loci for primary biliary cholangitis. Nat Commun 8, 14828 (2017).
25. Ji, S.-G. et al. Genome-wide association study of primary sclerosing cholangitis identifies new risk loci and quantifies the genetic relationship with inflammatory bowel disease. Nat. Genet. 49, 269-273 (2017).
26. McCarthy, S. et al. A reference panel of 64,976 haplotypes for genotype imputation. Nat. Genet. 48, 1279-1283 (2016).
27. Chang, C. C. et al. Second-generation PLINK: rising to the challenge of larger and richer datasets. Gigascience 4, 7 (2015).
28. Willer, C. J., Li, Y. & Abecasis, G. R. METAL: fast and efficient meta-analysis of genomewide association scans. Bioinformatics 26, 2190-2191 (2010).
29. Denny, J. C. et al. PheWAS: demonstrating the feasibility of a phenome-wide scan to discover gene-disease associations. Bioinformatics 26, 1205-1210 (2010).
30. Zhou, W. et al. Efficiently controlling for case-control imbalance and sample relatedness in large-scale genetic association studies. Nat. Genet. 50, 1335-1341 (2018).
31. Speliotes, E. K. et al. Liver fat is reproducibly measured using computed tomography in the Framingham Heart Study. J. Gastroenterol. Hepatol. 23, 894-899 (2008).
32. Chambers, J. C. et al. Genome-wide association study identifies loci influencing concentrations of liver enzymes in plasma. Nat. Genet. 43, 1131-1138 (2011).
33. Kanai, M. et al. Genetic analysis of quantitative traits in the Japanese population links cell types to complex human diseases. Nat. Genet. 50, 390-400 (2018).
34. Shungin, D. et al. New genetic loci link adipose and insulin biology to body fat distribution. Nature 518, 187-196 (2015).
35. Locke, A. E. et al. Genetic studies of body mass index yield new insights for obesity biology. Nature 518, 197-206 (2015).
36. Emdin, C. et al. Phenotypic Consequences of a Genetic Predisposition to Enhanced Nitric Oxide Signaling. Circulation 137, 222-232 (2018).
37. Emdin, C. et al. Analysis of predicted loss-of-function variants in U K Biobank identifies variants protective for disease. Nat Commun 9, 1613 (2018).
38. Do, R. et al. Exome sequencing identifies rare LDLR and APOA5 alleles conferring risk for myocardial infarction. Nature 518, 102-106 (2015).
39. Khera, A. V. et al. Diagnostic Yield of Sequencing Familial Hypercholesterolemia Genes in Patients with Severe Hypercholesterolemia. J. Am. Coll. Cardiol. (2016). doi: 10.1016/j.jacc.2016.03.520.
40. Fuchsberger, C. et al. The genetic architecture of type 2 diabetes. Nature 536, 41-47 (2016).
41. Khera, A. V. et al. Association of Rare and Common Variation in the Lipoprotein Lipase Gene With Coronary Artery Disease. JAMA: the journal of the American Medical Association 317, 937-946 (2017).
42. McLaren, W. et al. Deriving the consequences of genomic variants with the Ensembl API and SNP Effect Predictor. Bioinformatics 26, 2069-2070 (2010).
43. Buch S, Stickel F, Trépo E, et al. A genome-wide association study confirms PNPLA3 and identifies TM6SF2 and MBOAT7 as risk loci for alcohol-related cirrhosis. Nat Genet. 2015; 47 (12): 1443-1448. doi: 10.1038/ng.3417.
44. Speliotes E K, Butler J L, Palmer C D, et al. PNPLA3 variants specifically confer increased risk for histologic nonalcoholic fatty liver disease but not metabolic disease. Hepatology. 2010; 52 (3): 904-912. doi: 10.1002/hep.23768.
45. Valenti L, Rumi M, Galmozzi E, et al. Patatin-like phospholipase domain-containing 3 I148M polymorphism, steatosis, and liver damage in chronic hepatitis C. Hepatology. 2011; 53 (3): 791-799. doi: 10.1002/hep.24123.
46. Liu Y-L, Reeves H L, Burt A D, et al. TM6SF2 rs58542926 influences hepatic fibrosis progression in patients with non-alcoholic fatty liver disease. Nat Commun. 2014; 5 (1): 4309. doi: 10.1038/ncomms5309.
47. Liu Z, Que S, Zhou L, et al. The effect of the TM6SF2 E167K variant on liver steatosis and fibrosis in patients with chronic hepatitis C: a meta-analysis. Sci Rep. 2017; 7 (1): 9273. doi: 10.1038/s41598-017-09548-9.
48. Abul-Husn N S, Cheng X, Li A H, et al. A Protein-Truncating HSD17B13 Variant and Protection from Chronic Liver Disease. N Engl J Med. 2018; 378 (12): 1096-1106. doi: 10.1056/NEJMoa1712191.
49. About F, Abel L, Cobat A. HCV-Associated Liver Fibrosis and HSD17B13. N Engl J Med. 2018; 379 (19): 1875-1876. doi: 10.1056/NEJMc1804638.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of making a protective modification of a MARC1 gene in a subject comprising:

detecting a MARC1 protein variant or a MARC1 protein variant-encoding polynucleotide in the subject, wherein the MARC1 protein variant comprises alanine at a position in the MARC1 protein of the subject corresponding to position 165 of SEQ ID NO: 1; and administering, to the subject thereof having the MARC1 protein variant or the MARC1 protein variant-encoding polynucleotide, a programmable nuclease-based system comprising a nuclease or a guide polynucleotide each configured to bind a target polynucleotide, wherein the target polynucleotide is the MARC1 protein variant-encoding polynucleotide, and wherein the programmable nuclease-based system is configured to modify the MARC1 protein variant-encoding polynucleotide from the alanine at the position in the MARC1 protein of the subject corresponding to position 165 of SEQ ID NO: 1 to a threonine, thereby making a protective modification of the MARC1 gene in the subject.

2. The method of claim 1, wherein the subject has a liver disease or symptom thereof.

3. The method of claim 2, wherein the liver disease or symptom thereof comprises alcoholic cirrhosis, non-alcoholic cirrhosis, a hepatitis-related cirrhosis, hepatic steatosis, alcohol-related fatty liver disease (ALD), or nonalcoholic fatty liver disease (NAFLD).

4. The method of claim 1, wherein the subject has an elevated amount, activity of, or both of or one or more of aminotransferase (ALT), alkaline phosphatase (ALP), total cholesterol, low-density lipoprotein (LDL) cholesterol, or a combination thereof as compared to a subject having threonine at position 165 of MARC1 prior to administration.

5. The method of claim 1, wherein the protective modification of the MARC1 gene produces in the subject a decrease in:

(a) an amount of, activity of, or both of aminotransferase (ALT), alkaline phosphatase (ALP), or any combination thereof in the subject;

(b) an amount of total cholesterol, low-density lipoprotein (LDL) cholesterol, triglycerides, or any combination thereof in the subject; or (c) both (a) and (b).

6. The method of claim 1, wherein the subject is a) heterozygous for a MARC1 variant allele comprising alanine at a position in the MARC1 protein of the subject corresponding to position 165 of SEQ ID NO: 1; or b) homozygous for the MARC1 variant allele comprising alanine at a position in the MARC1 protein of the subject corresponding to position 165 of SEQ ID NO: 1.

7. A method of reducing total cholesterol, low-density lipoprotein, or a combination thereof in a subject thereof, comprising:

detecting a MARC1 protein variant or a MARC1 protein variant-encoding polynucleotide in the subject, wherein the MARC1 protein variant comprises alanine at a position in the MARC1 protein of the subject corresponding to position 165 of SEQ ID NO: 1; and administering to the subject having the MARC1 protein variant or the MARC1 protein variant-encoding polynucleotide a programmable nuclease-based system comprising a nuclease or a guide polynucleotide each configured to bind a target polynucleotide, wherein the target polynucleotide is the MARC1 protein variant-encoding polynucleotide, wherein the programmable nuclease-based system is configured to modify the MARC1 protein variant-encoding polynucleotide, wherein the modification comprises modifying the alanine at the position in the MARC1 protein of the subject corresponding to position 165 of SEQ ID NO: 1 to a threonine, thereby reducing total cholesterol, low-density lipoprotein, or a combination thereof in the subject.

8. The method of claim 7, wherein the subject is a) heterozygous for a MARC1 variant allele comprising alanine at a position in the MARC1 protein of the subject corresponding to position 165 of SEQ ID NO: 1; or b) homozygous for the MARC1 variant allele comprising alanine at a position in the MARC1 protein of the subject corresponding to position 165 of SEQ ID NO: 1.

9. The method of claim 8, wherein the MARC1 protein variant is SEQ ID NO: 22.

10. The method of claim 7, wherein the subject has an elevated amount, activity of, or both of or one or more of aminotransferase (ALT), alkaline phosphatase (ALP), or a combination thereof prior to administration.

11. The method of claim 7, wherein the subject has a liver disease or a symptom thereof, wherein the liver disease is selected from the group consisting of: alcoholic cirrhosis, non-alcoholic cirrhosis, a hepatitis-related cirrhosis, hepatic steatosis, alcohol-related fatty liver disease (ALD), and nonalcoholic fatty liver disease (NAFLD).

12. The method of claim 1, wherein the MARC1 protein variant is SEQ ID NO: 22.

\* \* \* \* \*